(12) United States Patent
Xu et al.

(10) Patent No.: US 10,919,911 B2
(45) Date of Patent: Feb. 16, 2021

(54) TRICYCLIC ASK1 INHIBITORS

(71) Applicant: Terns, Inc., San Mateo, CA (US)

(72) Inventors: Yingzi Xu, Palo Alto, CA (US); Randall Halcomb, Foster City, CA (US); Thorsten A. Kirschberg, San Carlos, CA (US); F. Anthony Romero, Redwood City, CA (US)

(73) Assignee: TERNS, INC., Foster City, CA (US)

( * ) Notice: Subject to any disclaimer, the term of this patent is extended or adjusted under 35 U.S.C. 154(b) by 0 days.

(21) Appl. No.: 16/382,936

(22) Filed: Apr. 12, 2019

(65) Prior Publication Data

US 2019/0315767 A1  Oct. 17, 2019

Related U.S. Application Data

(60) Provisional application No. 62/720,863, filed on Aug. 21, 2018, provisional application No. 62/656,764, filed on Apr. 12, 2018.

(51) Int. Cl.
| | | |
|---|---|---|
| *C07D 498/04* | (2006.01) | |
| *A61P 9/12* | (2006.01) | |
| *A61P 1/16* | (2006.01) | |
| *A61P 25/28* | (2006.01) | |
| *A61P 13/12* | (2006.01) | |
| *A61P 9/04* | (2006.01) | |
| *A61P 29/00* | (2006.01) | |

(52) U.S. Cl.
CPC .............. *C07D 498/04* (2013.01); *A61P 1/16* (2018.01); *A61P 9/04* (2018.01); *A61P 9/12* (2018.01); *A61P 13/12* (2018.01); *A61P 25/28* (2018.01); *A61P 29/00* (2018.01)

(58) Field of Classification Search
CPC .. C07D 401/14; C07D 403/14; A61K 31/444; A61K 31/506
USPC ...................... 540/546, 547, 548; 514/214.02
See application file for complete search history.

(56) References Cited

U.S. PATENT DOCUMENTS

| | | |
|---|---|---|
| 2007/0032488 A1 | 2/2007 | Botyanszki et al. |
| 2012/0004267 A1 | 1/2012 | Corkey et al. |
| 2014/0228411 A1 | 8/2014 | Notte |
| 2016/0304523 A1 | 10/2016 | Alexander et al. |
| 2017/0196844 A1 | 7/2017 | Xu et al. |

FOREIGN PATENT DOCUMENTS

| | | |
|---|---|---|
| WO | WO-2004/002481 A1 | 1/2004 |
| WO | WO-2012/129562 A2 | 9/2012 |
| WO | WO-2017/161028 A1 | 9/2017 |
| WO | WO-2018/106818 A1 | 6/2018 |
| WO | WO-2018/106820 A1 | 6/2018 |
| WO | WO-2018/157856 A1 | 9/2018 |
| WO | WO-2018/157857 A1 | 9/2018 |
| WO | WO-2019/015559 A1 | 1/2019 |

OTHER PUBLICATIONS

Damasio, Alzheimer's Disease and related dementias, Cecil Textbook of Medicine, 20th Edition, vol. 2, pp. 1992-1996, 1996.*
Layzer, Degenerative diseases of the nervous system, Cecil Textbook of Medicine, 20th Edition, vol. 2, pp. 2050-2057, 1996.*
Brownlee, M. (Dec. 13, 2001). "Biochemistry and Molecular Cell Biology of Diabetic Complications," *Nature* 414(6865):813-820.
Hattori, K. et al. (Apr. 24, 2009). "The Roles of ASK Family Proteins in Stress Responses and Diseases," *Cell Commun. Signal* 7(9):1-10.
Hung, K. et al. (2009, e-pub. Sep. 15, 2008). "N-Acetylcysteine-Mediated Antioxidation Prevents Hyperglycemia-Induced Apoptosis and Collagen Synthesis in Rat Mesangial Cells," *Am. J. Nephrol.* 29(3):192-202.
Ichijo, H. et al. (Jan. 3, 1997). "Induction of Apoptosis by ASK1, a Mammalian MAPKKK that Activates SAPK/JNK and p38 Signaling Pathways," *Science* 275(5296):90-94.
Mimura, I. et al. (Nov. 2010, Sep. 28, 2010). "The Suffocating Kidney: Tubulointerstitial Hypoxia in End-Stage Renal Disease," Nat. Rev. Nephrol. 6(11):667-678.
Nagai, H. et al. (Jan. 31, 2007). "Pathophysiological Roles of ASK1-MAP Kinase Signaling Pathways," *J. Biochem. Mol. Biol.* 40(1):1-6.
Singh, D.K. et al. (Mar. 2011, e-pub. Dec. 14, 2010). "Oxidative Stress in Early Diabetic Nephropathy: Fueling the Fire," Nat. Rev. Endocrinol. 7(3):176-184.
Takeda, K. et al. (2008). "Apoptosis Signal-Regulating Kinase 1 in Stress and Immune Response," Annu. Rev. PharmacoL Toxicol. 48:199-225.
Terada, Y. et al. (Dec. 28, 2007, e-pub. Oct. 29, 2007). "Important Role of Apoptosis Signal-Regulating Kinase 1 in Ischemic Acute Kidney Injury," *Biochem. Biophys. Res. Commun.* 364(4):1043-1049.
Watanabe, T. et al. (Jul. 29, 2005, e-pub. Jun. 6, 2005). "Apoptosis Signal-Regulating Kinase 1 is Involved Not Only in Apoptosis but also in Non-Apoptotic Cardiomyocyte Death," Biochem Biophys. Res. Commun. 333(2):562-567.
Zhang, X-F. et al. (Oct. 2014, Oct. 16, 2014). "TRAF1 is a Key Mediator for Hepatic Ischemia/Reperfusion Injury," *Cell Death Dis.* 5(10):e1467, 17 pages.
International Search Report and Written Opinion of the International Searching Authority dated Jun. 11, 2019 for PCT Patent Application No. PCT/US2019/027236, filed Apr. 12, 2019, 9 pages.

* cited by examiner

*Primary Examiner* — Deepak R Rao
(74) *Attorney, Agent, or Firm* — Morrison & Foerster LLP

(57) ABSTRACT

Provided herein are compounds, preferably ASK1 inhibitor compounds, compositions thereof, and methods of their preparation, and methods of inhibiting ASK1 and methods for treating disorders mediated by ASK1.

20 Claims, No Drawings

TRICYCLIC ASK1 INHIBITORS

CROSS-REFERENCE TO RELATED APPLICATIONS

This application claims priority to U.S. Provisional Application No. 62/656,764, filed Apr. 12, 2018, and U.S. Provisional Application No. 62/720,863, filed Aug. 21, 2018, the disclosures of each of which are hereby incorporated by reference in their entireties for all purposes.

FIELD OF THE INVENTION

This invention relates to compounds, preferably apoptosis signal-regulating kinase 1 (ASK1) inhibitor compounds, compositions thereof, and methods of their preparation, and to methods of inhibiting ASK1 and treating disorders mediated by ASK1.

STATE OF THE ART

ASK1, also known as mitogen-activated protein kinase kinase kinase 5 (MAP3K5), is a member of the MAP kinase kinase kinase ("MAP3K") family and, as such, a part of the mitogen-activated protein kinase pathway. ASK1 can play an important role in many stress-related disorders, including cardiovascular and neurodegenerative disorders.

The MAP3K family activates c-Jun N-terminal protein kinase ("JNK") and p38 MAP kinase (Ichijo et al. (1997) *Science*, 275, 90-94). ASK1 is activated by a variety of stimuli including oxidative stress, reactive oxygen species (ROS), LPS, TNF-α, FasL, ER stress, and increased intracellular calcium concentrations (Hattori et al. (2009) *Cell Comm. Signal.* 7:1-10; Takeda et al. (2007) *Annu. Rev. Pharmacol. Toxicol.* 48: 1-8.27; Nagai et al. (2007) *J. Biochem. Mol. Biol.* 40:1-6). Phosphorylation of ASK1 can lead to apoptosis or other cellular responses depending on the cell type. ASK1 activation and signaling have been reported to play an important role in a broad range of diseases including neurodegenerative, cardiovascular, inflammatory, autoimmune, and metabolic disorders. In addition, ASK1 has been implicated in mediating organ damage following ischemia and reperfusion of the heart, brain, and kidney (Watanabe et al. (2005) *BBRC* 333, 562-567; Zhang et al. (2014) *Cell Death Dis.* 5(10): e1467; Terada et al. (2007) *BBRC* 364: 1043-49).

ROS are reported be associated with increases of inflammatory cytokine production, fibrosis, apoptosis, and necrosis in the kidney (Singh et al. (2011) *Nat. Rev. Endocrinol.* 7(3):176-184; Brownlee M. (2001) *Nature* 414(6865):813-820; Mimura et al. (2010) *Nat. Rev. Nephrol.* 6(11):667-678). Moreover, oxidative stress facilitates the formation of advanced glycation end-products (AGEs) that cause further renal injury and production of ROS (Hung et al. (2009) *Am. J. Nephrol.* 29(3):192-202).

Thus, therapeutic agents that function as inhibitors of ASK1 signaling have the potential to remedy or improve the lives of patients in need of treatment for diseases or conditions such as neurodegenerative, cardiovascular, inflammatory, autoimmune, and metabolic disorders. In particular, ASK1 inhibitors have the potential to treat cardio-renal diseases, including kidney disease, diabetic kidney disease, chronic kidney disease, fibrotic diseases (including lung and kidney fibrosis), respiratory diseases (including chronic obstructive pulmonary disease (COPD) and acute lung injury), acute and chronic liver diseases (including nonalcoholic steatohepatitis (NASH)).

Provided herein are compounds and compositions that inhibit ASK1 and are useful for treating disorders mediated by ASK1.

SUMMARY

Disclosed herein is a compound of formula (IA):

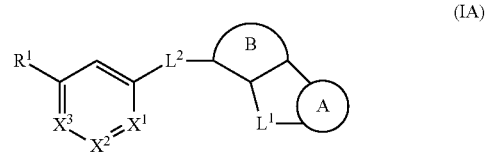

(IA)

or a pharmaceutically acceptable salt thereof, wherein:

ring A is an optionally substituted 5-membered heteroaryl ring;

ring B is $C_6$-$C_{10}$ aryl or 5- to 10-membered heteroaryl;

$L^1$ is optionally substituted $C_2$-$C_6$ alkylene or optionally substituted $C_2$-$C_6$ heteroalkylene;

$L^2$ is —CO—NH—, —NH—CO—, —$SO_2$—NH—, or —NH—$SO_2$—;

$R^1$ is optionally substituted $C_3$-$C_8$ cycloalkyl, optionally substituted 6-membered aryl, optionally substituted 5- to 6-membered heteroaryl, optionally substituted 4- to 6-membered heterocyclyl, —$CONR^{11}R^{12}$ or —$SO_2NR^{11}R^{12}$;

$R^{11}$ and $R^{12}$ are independently selected from the group consisting of hydrogen, optionally substituted $C_1$-$C_6$ alkyl, and optionally substituted $C_3$-$C_8$ cycloalkyl;

or $R^{11}$ and $R^{12}$ are taken together with the nitrogen atom to which they are attached to form a 4- to 7-membered heterocyclyl;

$X^1$, $X^2$, and $X^3$ are independently $CR^2$ or N;

each $R^2$ is independently hydrogen, optionally substituted $C_1$-$C_6$ alkyl, optionally substituted $C_1$-$C_6$ alkoxy, optionally substituted $C_3$-$C_8$ cycloalkyl, optionally substituted 6-membered aryl, optionally substituted 5- to 10-membered heteroaryl, optionally substituted 4- to 10-membered heterocyclyl, halo, —$NO_2$, haloalkyl, haloalkoxy, —CN, —O—$R^3$, —S—$R^3$, —N($R^3$)($R^4$), —S(=O)—$R^3$, —S(=O)$_2R^3$, —S(=O)$_2$—N($R^3$)($R^4$), —S(=O)$_2$—O—$R^3$, —N($R^3$)—C(O)—$R^4$, —N($R^3$)—C(O)—O—$R^4$, —N($R^3$)—C(O)—N($R^3$)($R^4$), —C(O)—$R^3$, —C(O)—O—$R^3$, —C(O)—N($R^3$)($R^4$), or —N($R^3$)—S(=O)$_2$—$R^4$; and $R^3$ and $R^4$ are independently selected from the group consisting of hydrogen, optionally substituted $C_1$-$C_6$ alkyl, optionally substituted $C_1$-$C_6$ alkoxy, optionally substituted $C_3$-$C_8$ cycloalkyl, optionally substituted 6-membered aryl, optionally substituted 5- to 10-membered heteroaryl, and optionally substituted 5- to 10-membered heterocyclyl;

or $R^3$ and $R^4$ are taken together with the nitrogen atom or with the intervening atoms to which they are attached to form an optionally substituted 4- to 10-membered heterocyclyl.

In some embodiments, ring B is phenyl.

In some embodiments, ring A is:

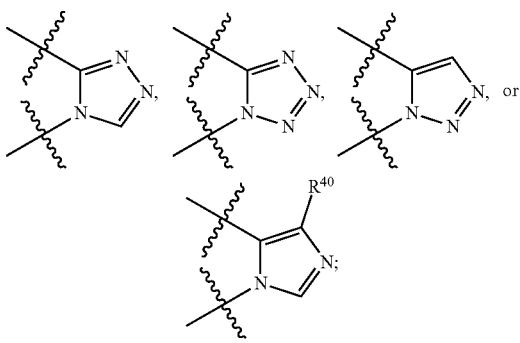

and $R^{40}$ is H, $C_1$-$C_6$ alkyl, or halo.

In some embodiments, $L^1$ is —O-$L^{10}$-; and $L^{10}$ is optionally substituted $C_1$-$C_5$ alkylene or optionally substituted $C_1$-$C_5$ heteroalkylene.

In some embodiments, $L^1$ is:

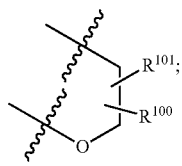

and
$R^{100}$ and $R^{101}$ are independently H, optionally substituted $C_1$-$C_6$ alkyl, halo, optionally substituted $C_3$-$C_5$ cycloalkyl, optionally substituted 4- to 5-membered heterocyclyl, or optionally substituted 5-membered heteroaryl;
or $R^{100}$ and $R^{101}$ are taken together with the carbon atom or carbon atoms to which they are attached to form a $C_3$-$C_5$ cycloalkyl.

In some embodiments, $R^{100}$ and $R^{101}$ are independently H; $C_1$-$C_6$ alkyl optionally substituted with 1-3 hydroxyl or halo; halo; $C_3$-$C_5$ cycloalkyl optionally substituted with 1-3 $C_1$-$C_6$ alkyl, hydroxyl, or halo; 4- to 5-membered heterocyclyl optionally substituted with 1-3 $C_1$-$C_6$ alkyl, hydroxyl, or halo; or 5-membered heteroaryl optionally substituted with 1-3 $C_1$-$C_6$ alkyl, hydroxyl, or halo; or $R^{100}$ and $R^{101}$ are taken together with the carbon atom or carbon atoms to which they are attached to form a $C_3$-$C_5$ cycloalkyl.

In some embodiments, $L^1$ is —O—$CH_2$—$CH_2$—, —O—$CH_2$—CH(Me)-, —O—$CH_2$—C(Me)$_2$-, —O—CH(Me)-$CH_2$—, —O—$CH_2$—CH($CH_2$OH)—, —O—$CH_2$—CH($CH_2$F)—,

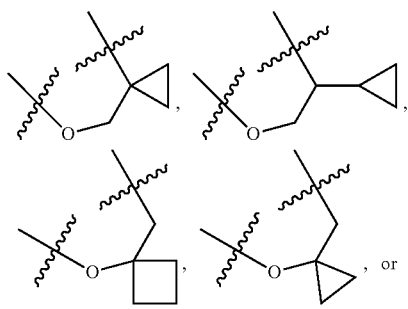

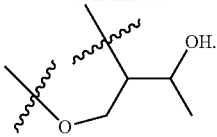

In some embodiments, $L^2$ is —CO—NH—.

In some embodiments, $R^1$ is $C_3$-$C_8$ cycloalkyl, 6-membered aryl, 5- to 6-membered heteroaryl, or 4- to 6-membered heterocyclyl, each of which is optionally substituted with 1-2 $C_1$-$C_6$ alkyl or with one $C_3$-$C_6$ cycloalkyl which is optionally substituted with 1-2 substituents selected from the group consisting of $C_1$-$C_6$ alkyl, $C_2$-$C_6$ alkenyl, and $C_2$-$C_6$ alkynyl; —CONR$^{11}$R$^{12}$; or —SO$_2$NR$^{11}$R$^{12}$.

In some embodiments, $R^1$ is:

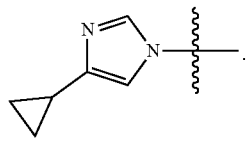

In some embodiments, $R^2$ is hydrogen; $C_1$-$C_6$ alkyl optionally substituted with 1-3 halo, —CF$_3$, —OCF$_3$, hydroxyl, —CN or —N(R$^3$)(R$^4$); $C_1$-$C_6$ alkoxy optionally substituted with 1-3 halo, —CF$_3$, —OCF$_3$, hydroxyl, —CN or —N(R$^3$)(R$^4$); $C_3$-$C_8$ cycloalkyl optionally substituted with 1-3 halo, $C_1$-$C_6$ alkyl, —CF$_3$, —OCF$_3$, hydroxyl, —CN or —N(R$^3$)(R$^4$); 6-membered aryl optionally substituted with 1-3 halo, $C_1$-$C_6$ alkyl, —CF$_3$, —OCF$_3$, hydroxy, —CN or —N(R$^3$)(R$^4$); 5- to 10-membered heteroaryl optionally substituted with 1-3 halo, $C_1$-$C_6$ alkyl, —CF$_3$, —OCF$_3$, hydroxyl, —CN or —N(R$^3$)(R$^4$); 5- to 10-membered heterocyclyl optionally substituted with 1-3 halo, $C_1$-$C_6$ alkyl, —CF$_3$, —OCF$_3$, hydroxyl, —CN or —N(R$^3$)(R$^4$); or halo; and
$R^3$ and $R^4$ are independently selected from the group consisting of hydrogen; $C_1$-$C_6$ alkyl optionally substituted with 1-3 halo, —CF$_3$, —OCF$_3$, hydroxyl, or —CN; $C_3$-$C_8$ cycloalkyl optionally substituted with 1-3 halo, $C_1$-$C_6$ alkyl, —CF$_3$, —OCF$_3$, hydroxyl, or —CN; 6-membered aryl optionally substituted with 1-3 halo, $C_1$-$C_6$ alkyl, —CF$_3$, —OCF$_3$, hydroxyl, or —CN; 5- to 10-membered heteroaryl optionally substituted with 1-3 halo, $C_1$-$C_6$ alkyl, —CF$_3$, —OCF$_3$, hydroxyl, or —CN; or 5- to 10-membered heterocyclyl optionally substituted with 1-3 halo, $C_1$-$C_6$ alkyl, —CF$_3$, —OCF$_3$, hydroxyl, or —CN;
or $R^3$ and $R^4$ are taken together with the nitrogen atom or with the intervening atoms to which they are attached to form a 4- to 10-membered heterocyclyl optionally substituted with 1-3 halo, $C_1$-$C_6$ alkyl, —CF$_3$, —OCF$_3$, hydroxyl, or —CN.

In some embodiments, $X^1$ is N or CR$^2$; and $R^2$ is halo.
In some embodiments, $X^2$ is CH.
In some embodiments, $X^3$ is CR$^2$;
$R^2$ is hydrogen; $C_1$-$C_6$ alkyl optionally substituted with 1-2 halo or hydroxyl; $C_1$-$C_6$ alkoxy optionally substituted with 1-2 halo or hydroxyl; 4-10 membered heterocyclyl optionally substituted with 1-2 $C_1$-$C_6$ alkyl or hydroxyl; —O—R$^3$; or —N(R$^3$)(R$^4$); and
$R^3$ and $R^4$ are independently hydrogen or $C_1$-$C_6$ alkyl;
or $R^3$ and $R^4$ are taken together with the nitrogen atom or with the intervening atoms to which they are attached to form a 4- to 7-membered heterocyclyl optionally substituted with 1-2 $C_1$-$C_6$ alkyl or hydroxyl.

In some embodiments, $X^3$ is $CR^2$; and $R^2$ is H, —$CH_3$, —$OCH(CH_3)_2$, —$N(CH_3)_2$,

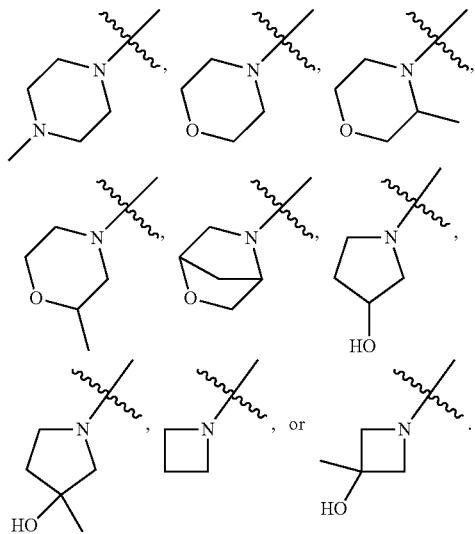

In some embodiments, disclosed herein is a compound of formula (5A) or (5B):

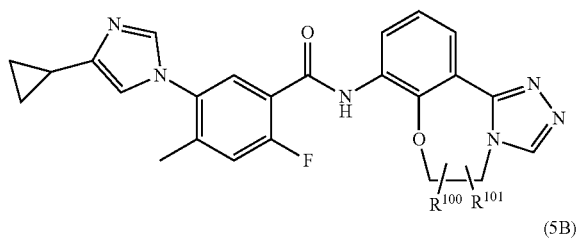

(5A)

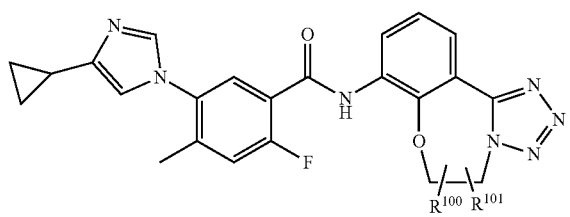

(5B)

wherein:
$R^{100}$ and $R^{101}$ are independently H; $C_1$-$C_6$ alkyl optionally substituted with 1-3 hydroxyl or halo; halo; $C_3$-$C_5$ cycloalkyl optionally substituted with 1-3 $C_1$-$C_6$ alkyl, hydroxyl, or halo; 4- to 5-membered heterocyclyl optionally substituted with 1-3 $C_1$-$C_6$ alkyl, hydroxyl, or halo; or 5-membered heteroaryl optionally substituted with 1-3 $C_1$-$C_6$ alkyl, hydroxyl, or halo;
or $R^{100}$ and $R^{101}$ are taken together with the carbon atom or carbon atoms to which they are attached to form a $C_3$-$C_5$ cycloalkyl.

Also disclosed herein is a compound selected from Table 1 or a pharmaceutically acceptable salt thereof.

In addition, disclosed herein is a pharmaceutical composition comprising any compound disclosed herein, or a pharmaceutically acceptable salt thereof, and at least one pharmaceutically acceptable excipient.

Also disclosed herein is a method of inhibiting ASK1, comprising contacting ASK1 with an effective amount of any compound disclosed herein, or a pharmaceutically acceptable salt thereof, or a pharmaceutical composition thereof.

Also disclosed herein is a method of treating a disorder which is mediated by ASK1, comprising administering to a patient in need thereof a therapeutically effective amount of any compound disclosed herein, or a pharmaceutically acceptable salt thereof, or a pharmaceutical composition thereof.

In some embodiments, the disorder which is mediated by ASK1 is pulmonary arterial hypertension (PAH), diabetic kidney disease, heart failure, a vascular disease, a neurodegenerative disorder, an inflammatory disease, or liver disease. In some embodiments, the disorder is liver disease. In some embodiments, the liver disease is a chronic liver disease. In some embodiments, the liver disease is nonalcoholic steatohepatitis (NASH).

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the compounds, compositions, treatment methods, and/or processes described herein, as defined by the claims, will become apparent in the detailed description set forth herein.

DETAILED DESCRIPTION

Definitions

As used herein, the following definitions shall apply unless otherwise indicated. Further, if any term or symbol used herein is not defined as set forth below, it shall have its ordinary meaning in the art.

"Comprising" is intended to mean that the compositions and methods include the recited elements, but not excluding others. "Consisting essentially of" when used to define compositions and methods, shall mean excluding other elements of any essential significance to the combination. For example, a composition consisting essentially of the elements as defined herein would not exclude other elements that do not materially affect the basic and novel characteristic(s) of the claimed invention. "Consisting of" shall mean excluding more than trace amount of, e.g., other ingredients and substantial method steps recited. Embodiments defined by each of these transition terms are within the scope of this invention.

"Disorder mediated by ASK1" includes without limitation non-alcoholic steatohepatitis (NASH); a liver disease, including chronic liver disease; pulmonary arterial hypertension (PAH); diabetic kidney disease; heart failure; vascular diseases such as ischemia/reperfusion injury (cardiac muscle), ischemia/reperfusion injury (kidney), ischemia/reperfusion injury (other tissues), cardiac remodeling, vascular injury, atherosclerosis, and brain ischemia; neurodegenerative disorders such as polyQ disease, amyotrophic lateral sclerosis (ALS), Alzheimer's disease (AD), Parkinson's disorder (PD), normal tension glaucoma, mesial temporal lobe epilepsy, progressive cervical cord compression, and sensorineural deafness/retinal dystrophy; inflammatory diseases such as multiple sclerosis, rheumatoid arthritis (RA); cancers/tumors such as skin cancer, colon cancer, gastric cancer, breast cancer, liver cancer, melanoma and the like.

"Effective amount" or dose of a compound or a composition, refers to that amount of the compound or the composition that results in an intended result as desired based on the disclosure herein. Effective amounts can be determined by standard pharmaceutical procedures in cell cultures or experimental animals, e.g., and without limitation, by determining the $LD_{50}$ (the dose lethal to 50% of the population) and the $ED_{50}$ (the dose therapeutically effective in 50% of the population).

The term "excipient" as used herein means an inert or inactive substance that may be used in the production of a drug or pharmaceutical, such as a tablet containing a compound of the invention as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

"Patient" refers to mammals and includes humans and non-human mammals. Examples of patients include, but are not limited to mice, rats, hamsters, guinea pigs, pigs, rabbits, cats, dogs, goats, sheep, cows, and humans. In some embodiments, patient refers to a human.

"Pharmaceutically acceptable" refers to safe and non-toxic, preferably for in vivo, more preferably, for human administration.

"Pharmaceutically acceptable salt" refers to a salt that is pharmaceutically acceptable. A compound described herein may be administered as a pharmaceutically acceptable salt.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than employing the corresponding drug. For illustration and without limitation, prodrugs include, carboxy esters, linear and cyclic phosphate esters and phosphoramide and phosphoramidates, carbamates, preferably phenolic carbamates (i.e., carbamates where the hydroxy group is part of an aryl or heteroaryl moiety, where the aryl and heteroaryl may be optionally substituted), and the like.

"Salt" refers to an ionic compound formed between an acid and a base. When the compound provided herein contains an acidic functionality, such salts include, without limitation, alkali metal, alkaline earth metal, and ammonium salts. As used herein, ammonium salts include, salts containing protonated nitrogen bases and alkylated nitrogen bases. Exemplary and non-limiting cations useful in pharmaceutically acceptable salts include Na, K, Rb, Cs, $NH_4$, Ca, Ba, imidazolium, and ammonium cations based on naturally occurring amino acids. When the compounds utilized herein contain basic functionality, such salts include, without limitation, salts of organic acids, such as carboxylic acids and sulfonic acids, and mineral acids, such as hydrogen halides, sulfuric acid, phosphoric acid, and the like. Exemplary and non-limiting anions useful in pharmaceutically acceptable salts include oxalate, maleate, acetate, propionate, succinate, tartrate, chloride, sulfate, bisulfate, mono-, di-, and tribasic phosphate, mesylate, tosylate, and the like.

"Therapeutically effective amount" or dose of a compound or a composition refers to that amount of the compound or the composition that results in reduction or inhibition of symptoms or a prolongation of survival in a patient. The results may require multiple doses of the compound or the composition.

"Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease. As used herein, "treatment" or "treating" is an approach for obtaining beneficial or desired results including clinical results. For purposes of this disclosure, beneficial or desired results include, but are not limited to, one or more of the following: decreasing one more symptoms resulting from the disease or disorder, diminishing the extent of the disease or disorder, stabilizing the disease or disorder (e.g., preventing or delaying the worsening of the disease or disorder), delaying the occurrence or recurrence of the disease or disorder, delay or slowing the progression of the disease or disorder, ameliorating the disease or disorder state, providing a remission (whether partial or total) of the disease or disorder, decreasing the dose of one or more other medications required to treat the disease or disorder, enhancing the effect of another medication used to treat the disease or disorder, delaying the progression of the disease or disorder, increasing the quality of life, and/or prolonging survival of a patient. Also encompassed by "treatment" is a reduction of pathological consequence of the disease or disorder. The methods of the invention contemplate any one or more of these aspects of treatment.

An "isotopomer" of a compound is a compound in which one or more atoms of the compound have been replaced with isotopes of those same atoms. For example, where H has been replaced by D or T, or $^{12}C$ has been replaced by $^{11}C$ or $^{14}N$ has been replaced by $^{15}N$. For example, and without limitation, replacement of with D can in some instances lead to reduced rates of metabolism and therefore longer half-lives. Replacement of H with T can provide radioligands potentially useful in binding studies. Replacement of $^{12}$C with the short-lived isotope $^{11}$C can provide ligands useful in Positron Emission Tomography (PET) scanning. Replacement of $^{14}$N with $^{15}$N provides compounds that can be detected/monitored by $^{15}$N NMR spectroscopy. For example, and without limitation, an isotopomer of a compound containing —CH$_2$CH$_3$ is that compound but containing —CD$_2$CD$_3$ instead of the —CH$_2$CH$_3$.

"Stereoisomer" or "stereoisomers" refer to compounds that differ in the stereogenicity of the constituent atoms such as, without limitation, in the chirality of one or more stereocenters or related to the cis or trans configuration of a carbon-carbon or carbon-nitrogen double bond. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

"Alkyl" refers to monovalent saturated aliphatic hydrocarbyl groups having from 1 to 12 carbon atoms, preferably from 1 to 10 carbon atoms, and more preferably from 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—). C$_x$ alkyl refers to an alkyl group having x number of carbon atoms.

"Alkylene" refers to a divalent saturated aliphatic hydrocarbyl group having from 1 to 12 carbon atoms, preferably from 1 to 10 carbon atoms, and more preferably from 1 to 6 carbon atoms. This term includes, by way of example, linear and branched hydrocarbyl groups such as methylene (—CH$_2$—), ethylene (—CH$_2$CH$_2$— or —CH(Me)-), propylene (—CH$_2$CH$_2$CH$_2$— or —CH(Me)CH$_2$—, or —CH(Et)-) and the like.

"Alkenyl" refers to straight or branched monovalent hydrocarbyl groups having from 2 to 6 carbon atoms and preferably 2 to 4 carbon atoms and having at least 1 and preferably from 1 to 2 sites of vinyl (>C=C<) unsaturation. Such groups are exemplified, for example, by vinyl, allyl, and but-3-en-1-yl. Included within this term are the cis and trans isomers or mixtures of these isomers. C$_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH). C$_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein.

"Substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein and with the proviso that any hydroxyl or thiol substitution is not attached to an acetylenic carbon atom.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{30}C(O)$alkyl, —$NR^{30}C(O)$substituted alkyl, —$NR^{30}C(O)$cycloalkyl, —$NR^{30}C(O)$substituted cycloalkyl, —$NR^{30}C(O)$alkenyl, —$NR^{30}C(O)$substituted alkenyl, alkoxy, substituted alkoxy-$NR^{30}C(O)$alkynyl, —$NR^{30}C(O)$substituted alkynyl, —$NR^{30}C(O)$aryl, —$NR^{30}C(O)$substituted aryl, —$NR^{30}C(O)$heteroaryl, —$NR^{30}C(O)$substituted heteroaryl, —$NR^{30}C(O)$heterocyclic, and —$NR^{30}C(O)$substituted heterocyclic wherein $R^{30}$ is hydrogen, alkyl, substituted alkyl, aryl, substituted aryl, heteroaryl, substituted heteroaryl, cycloalkyl, or substituted cycloalkyl; and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, arylamino, substituted arylamino, heteroarylamino, substituted heteroarylamino, cycloalkylamino, substituted cycloalkylamino, heterocloalkylamino, substituted heterocyclylamino, sulfonylamino, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —$C(O)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —$C(S)NR^{33}R^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —$NR^{30}C(O)NR^{33}R^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —$NR^{30}C(S)NR^{33}R^{34}$ where $R^{30}$ is hydrogen, alkyl, substituted alkyl, aryl, substituted aryl, heteroaryl, substituted heteroaryl, cycloalkyl, or substituted cycloalkyl, and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where R$^{30}$ is hydrogen, alkyl, substituted alkyl, aryl, substituted aryl, heteroaryl, substituted heteroaryl, cycloalkyl, or substituted cycloalkyl, and R$^{33}$ and R$^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 14 carbon atoms having a single ring (e.g., phenyl (Ph)) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, arylamino, substituted arylamino, heteroarylamino, substituted heteroarylamino, cycloalkylamino, substituted cycloalkylamino, heterocycloalkylamino, substituted heterocyclylamino carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, sulfonylamino, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Arylamino" refers to the group —NR$^{37}$(aryl), where aryl is as defined herein and R$^{37}$ is hydrogen, alkyl, or substituted alkyl.

"Substituted arylamino" refers to the group —NR$^{37}$(substituted aryl), where R$^{37}$ is hydrogen, alkyl, or substituted alkyl where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to saturated or unsaturated but non-aromatic cyclic alkyl groups of from 3 to 10 carbon atoms, preferably from 3 to 8 carbon atoms, and more preferably from 3 to 6 carbon atoms, having single or multiple cyclic rings including fused, bridged, and spiro ring systems. $C_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more of the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylamino" refers to the group —NR$^{37}$(cycloalkyl) where R$^{37}$ is hydrogen, alkyl, or substituted alkyl.

"Substituted cycloalkylamino" refers to the group —NR$^{37}$(substituted cycloalkyl) where R$^{37}$ is hydrogen, alkyl, or substituted alkyl and substituted cycloalkyl is as defined herein.

"Cycloalkylthio" refers to —S-cycloalkyl.

"Substituted cycloalkylthio" refers to —S-(substituted cycloalkyl).

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two R$^{36}$ groups attached to a common guanidino nitrogen atom are optionally joined together with the nitrogen bound thereto to form a heterocyclic or substituted heterocyclic group, provided that at least one R$^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroalkylene" refers to an alkylene group wherein one or more carbons is replaced with —O—, —S—, SO$_2$, —NR$^Q$—,

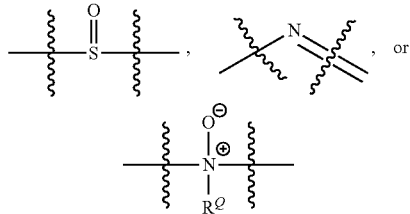

moieties where R$^Q$ is H or C$_1$-C$_6$ alkyl. "Substituted heteroalkylene" refers to heteroalkylene groups having from 1 to 3 substituents, and preferably 1 to 2 substituents, selected from the substituents disclosed for substituted alkylene. "C$_x$ heteroalkylene" refers to a heteroalkylene group having x number of atoms in the alkylene chain including the heteroatoms in the chain. For example, C$_3$ heteroalkylene includes "Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, thiophenyl, and furanyl. Other preferred heteroaryls include 9 or 10 membered heteroaryls, such as indolyl, quinolinyl, quinolonyl, isoquinolinyl, and isoquinolonyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heteroarylamino" refers to the group —NR$^{37}$(heteroaryl) where R$^{37}$ is hydrogen, alkyl, or substituted alkyl.

"Substituted heteroarylamino" refers to the group —NR$^{37}$(substituted heteroaryl), where R$^{37}$ is hydrogen, alkyl, or substituted alkyl and substituted heteroaryl is defined as herein.

"Heterocycle" or "heterocyclic" or "heterocycloalkyl" or "heterocyclyl" refers to a saturated or partially saturated, but not aromatic, group having from 1 to 10 ring carbon atoms, preferably from 1 to 8 carbon atoms, and more preferably from 1 to 6 carbon atoms, and from 1 to 4 ring heteroatoms, preferably from 1 to 3 heteroatoms, and more preferably from 1 to 2 heteroatoms selected from the group consisting of nitrogen, sulfur, or oxygen. "C$_x$ heterocycloalkyl" refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, or sulfonyl moieties.

"Heterocyclylene" refers to a divalent saturated or partially saturated, but not aromatic, group having from 1 to 10 ring carbon atoms and from 1 to 4 ring heteroatoms selected from the group consisting of nitrogen, sulfur, or oxygen. "Substituted heterocyclylene" refers to heterocyclylene groups that are substituted with from 1 to 5 or preferably 1 to 3 of the same substituents as defined for substituted cycloalkyl.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

"Heterocyclylamino" refers to the group —NR$^{37}$(heterocyclyl) where R$^{37}$ is hydrogen, alkyl, or substituted alkyl.

"Substituted heterocyclylamino" refers to the group —NR$^{37}$(substituted heterocyclyl), where R$^{37}$ is hydrogen, alkyl, or substituted alkyl and substituted heterocyclyl is defined as herein.

Examples of heterocyclyl and heteroaryl include, but are not limited to, azetidinyl, pyrrolyl, imidazolyl, pyrazolyl, pyridyl, pyrazyl, pyrimidyl, pyridazyl, indolizyl, isoindolyl, indolyl, dihydroindolyl, indazolyl, purinyl, quinolizinyl, isoquinolinyl, quinolinyl, phthalazinyl, naphthylpyridinyl, quinoxalinyl, quinazolinyl, cinnolinyl, pteridinyl, carbazolyl, carbolinyl, phenanthridinyl, acridinyl, phenanthrolinyl, isothiazolyl, phenazinyl, isoxazolyl, phenoxazinyl, phenothiazinyl, imidazolidinyl, imidazolinyl, piperidinyl, piperazinyl, indolinyl, phthalimidyl, 1,2,3,4-tetrahydroisoquinolinyl, 4,5,6,7-tetrahydrobenzo[b]thiophenyl, thiazolyl, thiazolidinyl, thiophenyl, benzo[b]thiophenyl, morpholinyl, thiomorpholinyl (also referred to as thiamorpholinyl), 1,1-dioxothiomorpholinyl, piperidinyl, pyrrolidinyl, and tetrahydrofuranyl.

"Nitro" refers to the group —NO$_2$.

"Oxo" refers to the atom (=O) or (O).

"Spiro ring systems" refers to bicyclic ring systems that have a single ring carbon atom common to both rings.

"Sulfinyl" refers to the divalent group —S(O)— or —S(=O)—.

"Sulfonyl" refers to the divalent group —S(O)$_2$— or —S(=O)$_2$—.

"Substituted sulfonyl" refers to the group —SO$_2$-alkyl, —SO$_2$-substituted alkyl, —SO$_2$—OH, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—. Preferred substituted alkyl groups on the substituted alkyl-SO$_2$— include halogenated alkyl groups and particularly halogenated methyl groups such as trifluoromethyl, difluromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cycloalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cycloalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the group —NR$^{37}$(substituted sulfonyl) where R$^{37}$ is hydrogen, alkyl, or substituted alkyl and substituted sulfonyl is as defined here.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluromethyl, fluoromethyl and the like.

"Vinyl" refers to unsaturated hydrocarbon radical —CH=CH$_2$, derived from ethylene.

The terms "optional" or "optionally" as used throughout the specification means that the subsequently described event or circumstance may but need not occur, and that the description includes instances where the event or circumstance occurs and instances in which it does not. For example, "the nitrogen atom is optionally oxidized to provide for the N-oxide (N→O) moiety" means that the nitrogen atom may but need not be oxidized, and the description includes situations where the nitrogen atom is not oxidized and situations where the nitrogen atom is oxidized.

The term "optionally substituted" refers to a substituted or unsubstituted group. The substituted group may be substituted with one or more substituents, such as e.g., 1, 2, 3, 4 or 5 substituents. Preferably, the substituents are selected from the functional groups provided herein. In certain more preferred embodiments, the substituents are selected from oxo, halo, —CN, NO$_2$, —CO$_2$R$^{50}$, —OR$^{50}$, —SR$^{50}$, —SOR$^{50}$, —SO$_2$R$^{50}$, —NR$^{51}$R$^{52}$, —CONR$^{51}$R$^{52}$, —SO$_2$NR$^{51}$R$^{52}$, C$_1$-C$_6$ alkyl, C$_1$-C$_6$ alkoxy, —CR$^{50}$=C(R$^{50}$)$_2$, —CCR$^{50}$, C$_3$-C$_{10}$ cycloalkyl, C$_4$-C$_{10}$ heterocyclyl, C$_6$-C$_{14}$ aryl and C$_5$-C$_{12}$ heteroaryl, wherein each R$^{50}$ independently is hydrogen or C$_1$-C$_8$ alkyl; C$_3$-C$_{12}$ cycloalkyl; C$_4$-C$_{10}$ heterocyclyl; C$_6$-C$_{14}$ aryl; or C$_2$-C$_{12}$ heteroaryl; wherein each alkyl, cycloalkyl, heterocyclyl, aryl, or heteroaryl is optionally substituted with 1-3 halo, 1-3 C$_1$-C$_6$ alkyl, 1-3 C$_1$-C$_6$ haloalkyl or 1-3 C$_1$-C$_6$ alkoxy groups. More preferably, the substituents are selected from the group consisting of chloro, fluoro, —OCH$_3$, methyl, ethyl, isopropyl, cyclopropyl, —OCF$_3$, —CF$_3$ and —OCHF$_2$.

R$^{51}$ and R$^{52}$ independently are hydrogen; C$_1$-C$_8$ alkyl, optionally substituted with —CO$_2$H or an ester thereof, C$_1$-C$_6$ alkoxy, oxo, —CR$^{53}$=C(R$^{53}$)$_2$, —CCR, C$_3$-C$_{10}$ cycloalkyl, C$_3$-C$_{10}$ heterocyclyl, C$_6$-C$_{14}$ aryl or C$_2$-C$_{12}$ heteroaryl, wherein each R$^{53}$ independently is hydrogen or C$_1$-C$_8$ alkyl; C$_3$-C$_{12}$ cycloalkyl; C$_4$-C$_{10}$ heterocyclyl; C$_6$-C$_{14}$ aryl; or C$_2$-C$_{12}$ heteroaryl; wherein each cycloalkyl, heterocyclyl, aryl, or heteroaryl is optionally substituted with 1-3 alkyl groups or 1-3 halo groups, or R$^{51}$ and R$^{52}$ together with the nitrogen atom they are attached to form a 5-7 membered heterocycle.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

In some embodiments of a substituted moiety, the moiety is substituted with a group that may also be substituted with a further group, but the further group cannot be additionally substituted. For example, in some embodiments of "substituted alkyl", the alkyl moiety is substituted with a group that may be further substituted (e.g., substituted alkoxy, substituted amino, substituted aryl, substituted aryloxy, substituted arylthio, substituted arylamino, substituted heteroarylamino, substituted cycloalkylamino, substituted heterocyclylamino, substituted cycloalkyl, substituted cycloalkyloxy, substituted cycloalkylthio, substituted guanidino, substituted heteroaryl, substituted heteroaryloxy, substituted heteroarylthio, substituted heterocyclic, substituted heterocyclyloxy, substituted heterocyclylthio, substituted sulfonyl, substituted alkylthio), but the substituted alkoxy, substituted amino, substituted aryl, substituted aryloxy, substituted arylthio, substituted arylamino, substituted heteroarylamino, substituted cycloalkylamino, substituted heterocyclylamino, substituted cycloalkyl, substituted cycloalkyloxy, substituted cycloalkylthio, substituted guanidino, substituted heteroaryl, substituted heteroaryloxy, substituted heteroarylthio, substituted heterocyclic, substituted heterocyclyloxy, substituted heterocyclylthio, substituted sulfonyl or substituted alkylthio on the alkyl moiety is not substituted with a moiety that is itself further substituted. Although "substituted alkyl" is provided as an example, such an embodiment is intended for each substituted moiety described herein.

In some embodiments of a substituted moiety, the moiety is substituted with a group that is not further substituted. Thus, in some embodiments, "substituted alkyl" is an alkyl moiety substituted with one or more, and in some aspects, 1 or 2 or 3 or 4 or 5 moieties independently selected from the group consisting of alkoxy, acyl, acylamino, acyloxy, amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, aryloxy, arylthio, arylamino, heteroarylamino, cycloalkylamino, heterocycloalkylamino, carboxyl, carboxyl ester, (carboxyl ester)amino, (carboxyl ester)oxy, cyano, cycloalkyl, cycloalkyloxy, cycloalkylthio, guanidino, halo, hydroxy, heteroaryl, heteroaryloxy, heteroarylthio, heterocyclic, heterocyclyloxy, heterocyclylthio, nitro, SO$_3$H, sulfonyloxy, sulfonylamino, thioacyl, thiol, and alkylthio. Although "substituted alkyl" is provided as an example, such an embodiment is intended for each substituted moiety described herein.

It is understood that the above definitions are not intended to include impermissible substitution patterns (e.g., methyl substituted with 4 fluoro groups). Such impermissible substitution patterns are well known to the skilled artisan.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

Compounds

In one aspect, provided herein are compounds of formula (IA):

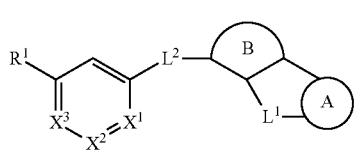

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:

ring A is an optionally substituted 5-membered heteroaryl ring, preferably containing heteroatoms selected from N, O, and S, more preferably, containing one or more, such as 1-4 ring N atoms;

ring B is aryl, preferably $C_6$-$C_{10}$ aryl, more preferably phenyl, or is heteroaryl, preferably 5-10 membered heteroaryl, more preferably, 6 membered heteroaryl containing 1-2 ring nitrogen atoms;

$L^1$ is optionally substituted $C_2$-$C_6$ alkylene or optionally substituted $C_2$-$C_6$ heteroalkylene;

$L^2$ is —CO—NH—, —NH—CO—, —SO$_2$—NH—, or —NH—SO$_2$—;

$R^1$ is optionally substituted $C_3$-$C_8$ cycloalkyl, optionally substituted $C_6$-$C_{10}$ aryl, optionally substituted 5-10 membered heteroaryl, optionally substituted 4-10 membered heterocyclyl, —CONR$^{11}$R$^{12}$, or —SO$_2$NR$^{11}$R$^{12}$, preferably, when substituted, the cycloalkyl, aryl, heteroaryl, or heterocyclyl is substituted with a $C_3$-$C_6$ cycloalkyl optionally substituted with one or more, preferably 1-2 substituents selected from $C_1$-$C_6$ alkyl, $C_2$-$C_6$ alkenyl, and $C_2$-$C_6$ alkynyl or, the cycloalkyl, aryl, heteroaryl, or heterocyclyl is substituted with 1-2 $C_1$-$C_6$ alkyl;

each of $R^{11}$ and $R^{12}$ is independently selected from hydrogen, optionally substituted $C_1$-$C_6$ alkyl, and optionally substituted $C_3$-$C_8$ cycloalkyl, preferably optionally substituted $C_3$-$C_5$ cycloalkyl; or $R^{11}$ and $R^{12}$, together with the nitrogen atom they are attached to form a 4-7 membered heterocycle;

$X^1$, $X^2$, and $X^3$ are independently optionally substituted CH, preferably, —CR$^2$; or N;

each $R^2$ is independently hydrogen, optionally substituted alkyl preferably optionally substituted $C_1$-$C_6$ alkyl, optionally substituted alkoxy preferably optionally substituted $C_1$-$C_6$ alkoxy, optionally substituted cycloalkyl preferably optionally substituted $C_3$-$C_8$ cycloalkyl, optionally substituted aryl preferably optionally substituted 6 membered aryl, optionally substituted heteroaryl preferably optionally substituted 5-10 membered heteroaryl, optionally substituted heterocyclyl preferably optionally substituted 5-10 membered heterocyclyl, halo, —NO$_2$, haloalkyl, haloalkoxy, —CN, —O—R$^3$, —S—R$^3$, —N(R$^3$)(R$^4$), —S(=O)—R$^3$, —S(=O)$_2$R$^3$, —S(=O)$_2$—N(R$^3$)(R$^4$), —S(=O)$_2$—O—R$^3$, —N(R$^3$)—C(O)—R$^4$, —N(R$^3$)—C(O)—O—R$^4$, —N(R$^3$)—C(O)—N(R$^3$)(R$^4$), —C(O)—R$^3$, —C(O)—O—R$^3$, —C(O)—N(R$^3$)(R$^4$), or —N(R$^3$)—S(=O)$_2$—R$^4$; and $R^3$ and $R^4$ are independently selected from the group consisting of hydrogen, optionally substituted alkyl preferably optionally substituted $C_1$-$C_6$ alkyl, optionally substituted alkoxy preferably optionally substituted $C_1$-$C_6$ alkoxy, optionally substituted cycloalkyl preferably optionally substituted $C_3$-$C_8$ cycloalkyl, optionally substituted aryl preferably optionally substituted 6 membered aryl, optionally substituted heteroaryl preferably optionally substituted 5-10 membered heteroaryl, optionally substituted heterocyclyl preferably optionally substituted 5-10 membered heterocyclyl; or $R^3$ and $R^4$ when taken together with the nitrogen, or with the intervening atoms to which they are attached form an optionally substituted heterocycle preferably an optionally substituted 4-10 membered heterocycle.

In some embodiments, provided herein is a compound of formula (IA) or a pharmaceutically acceptable salt thereof.

In certain variations of formula (IA), $L^1$ is optionally substituted $C_2$-$C_6$ alkylene or optionally substituted $C_3$-$C_6$ heteroalkylene. In one variation of formula (IA), $L^1$ is optionally substituted $C_3$-$C_6$ heteroalkylene. In another variation of formula (IA), $L^1$ is optionally substituted $C_3$-$C_6$ alkylene.

In one embodiment, the compound provided is of formula (IB):

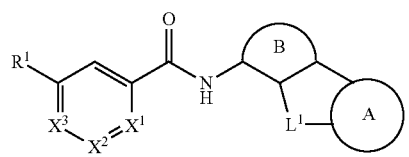

or a pharmaceutically acceptable salt thereof, wherein the variables are defined as herein.

In another embodiment, the compound provided is of formula (IC):

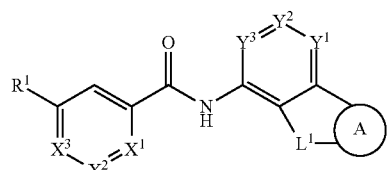

or a pharmaceutically acceptable salt thereof,
wherein $Y^1$, $Y^2$, and $Y^3$ independently are CH or N; and
the remaining variables are defined as herein.

In another embodiment, the compound provided is of formula (ID):

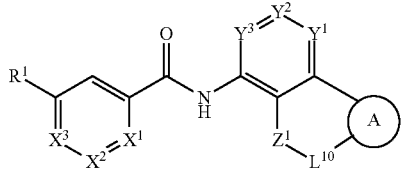
(ID)

or a pharmaceutically acceptable salt thereof,
wherein $Y^1$, $Y^2$, and $Y^3$ independently are CH or N;
$Z^1$ is O, S(O)n, or $NR^{15}$;
n is 0, 1, or 2;
$R^{15}$ is H or $C_1$-$C_3$ alkyl;
$L^{10}$ is optionally substituted $C_1$-$C_5$ alkylene or optionally substituted $C_1$-$C_5$ heteroalkylene; and
the remaining variables are defined as herein.

In another embodiment, the compound provided is of formula (IE) or (IF):

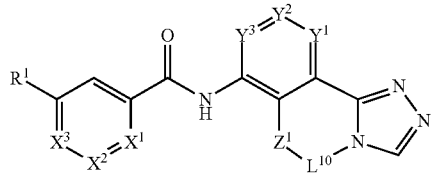
(IE)

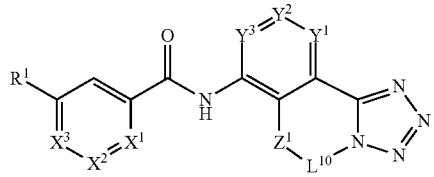
(IF)

or a pharmaceutically acceptable salt thereof,
wherein $Y^1$, $Y^2$, and $Y^3$ independently are CH or N;
$Z^1$ is O, S(O)$_n$, or $NR^{15}$;
n is 0, 1, or 2;
$R^{15}$ is H or $C_1$-$C_3$ alkyl;
$L^{10}$ is optionally substituted $C_1$-$C_5$ alkylene or optionally substituted $C_1$-$C_5$ heteroalkylene; and
the remaining variables are defined as herein.

In another embodiment, the compound provided is of formula (IE). In another embodiment, the compound provided is of formula (IF).

In another embodiment, the compound provided is of formula (IG) or (IH):

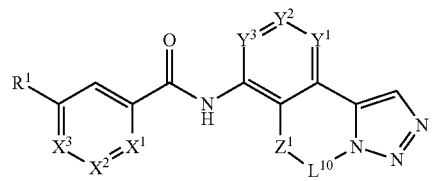
(IG)

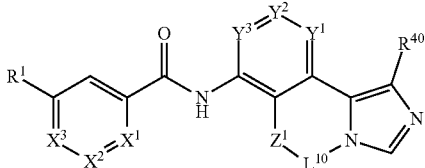
(IH)

or a pharmaceutically acceptable salt thereof,
wherein $Y^1$, $Y^2$, and $Y^3$ independently are CH or N;
$Z^1$ is O, S(O)$_n$, or $NR^{15}$;
n is 0, 1, or 2;
$R^{15}$ is H or $C_1$-$C_3$ alkyl;
$L^{10}$ is optionally substituted $C_1$-$C_5$ alkylene or optionally substituted $C_1$-$C_5$ heteroalkylene;
$R^{40}$ is H, $C_1$-$C_6$ alkyl, or halo; and
the remaining variables are defined as herein.

In another embodiment, the compound provided is of formula (IG). In another embodiment, the compound provided is of formula (IH).

In another embodiment, the compound provided is of formula (2A) or (2B):

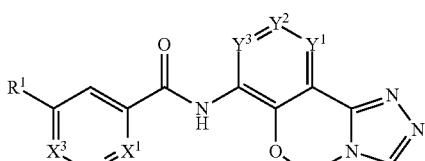
(2A)

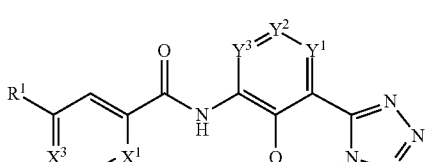
(2B)

or a pharmaceutically acceptable salt thereof,
wherein $Y^1$, $Y^2$, and $Y^3$ independently are CH or N;
$L^{10}$ is optionally substituted $C_1$-$C_5$ alkylene or optionally substituted $C_1$-$C_5$ heteroalkylene; and
the remaining variables are defined as herein.

In another embodiment, the compound provided is of formula (2A). In another embodiment, the compound provided is of formula (2B).

In another embodiment, the compound provided is of formula (2C) or (2D):

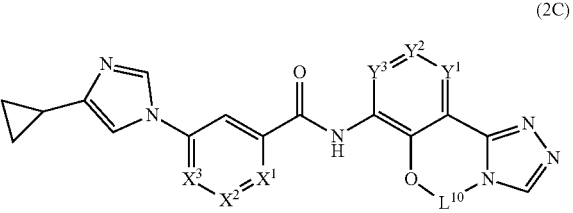
(2C)

-continued (2D)
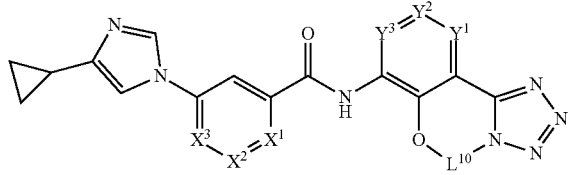

or a pharmaceutically acceptable salt thereof,
wherein $Y^1$, $Y^2$, and $Y^3$ independently are CH or N;
$L^{10}$ is optionally substituted $C_1$-$C_5$ alkylene or optionally substituted $C_1$-$C_5$ heteroalkylene; and
the remaining variables are defined as herein.

In another embodiment, the compound provided is of formula (2C). In another embodiment, the compound provided is of formula (2D).

In another embodiment, the compound provided is of formula (2E) or (2F):

(2E)
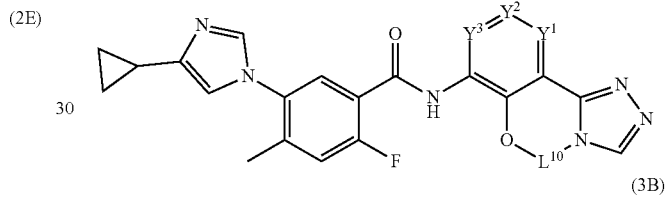

(2F)

or a pharmaceutically acceptable salt thereof,
wherein $Y^1$, $Y^2$, and $Y^3$ independently are CH or N;
$L^{10}$ is optionally substituted $C_1$-$C_5$ alkylene or optionally substituted $C_1$-$C_5$ heteroalkylene;
$R^{40}$ is H, $C_1$-$C_6$ alkyl, or halo; and
the remaining variables are defined as herein.

In another embodiment, the compound provided is of formula (2E). In another embodiment, the compound provided is of formula (2F).

In another embodiment, the compound provided is of formula (2G) or (2H):

(2G)
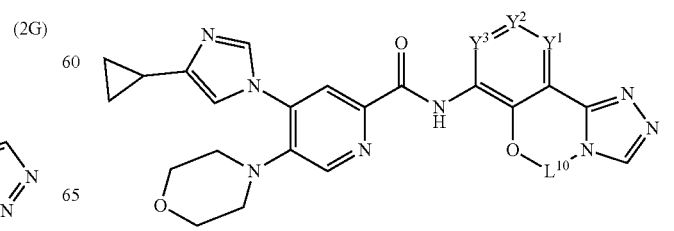

-continued (2H)
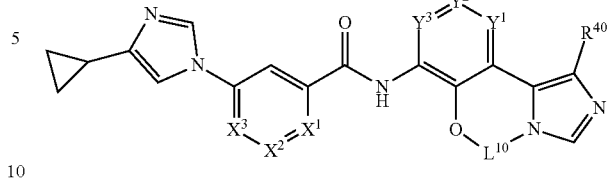

or a pharmaceutically acceptable salt thereof,
wherein $Y^1$, $Y^2$, and $Y^3$ independently are CH or N;
$L^{10}$ is optionally substituted $C_1$-$C_5$ alkylene or optionally substituted $C_1$-$C_5$ heteroalkylene;
$R^{40}$ is H, $C_1$-$C_6$ alkyl, or halo; and
the remaining variables are defined as herein.

In another embodiment, the compound provided is of formula (2G). In another embodiment, the compound provided is of formula (2H).

In another embodiment, the compound provided is of formula (3A), (3B), (3C), (3D), (3E), or (3F):

(3A)
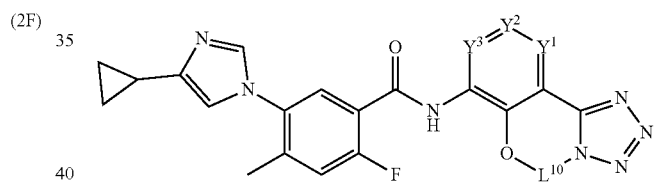

(3B)
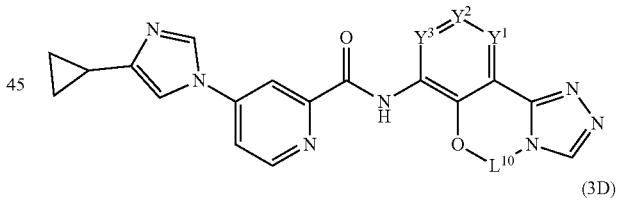

(3C)
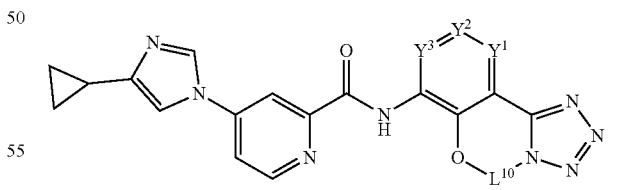

(3D)

(3E)

-continued (3F)

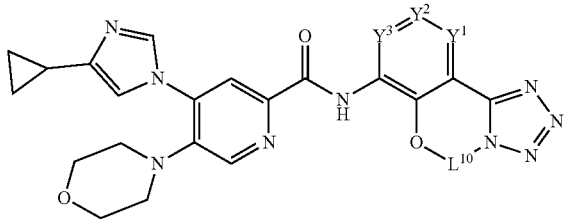

or a pharmaceutically acceptable salt thereof, wherein $Y^1$, $Y^2$, and $Y^3$ independently are CH or N; and $L^{10}$ is optionally substituted $C_1$-$C_5$ alkylene or optionally substituted $C_1$-$C_5$ heteroalkylene.

In another embodiment, the compound provided is of formula (3A). In another embodiment, the compound provided is of formula (3B). In another embodiment, the compound provided is of formula (3C). In another embodiment, the compound provided is of formula (3D). In another embodiment, the compound provided is of formula (3E). In another embodiment, the compound provided is of formula (3F).

In another embodiment, the compound provided is of formula (3G), (3H), (3I), or (3J):

(3G)

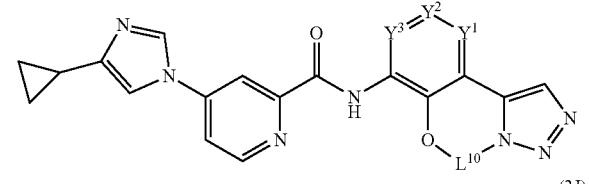

(3H)

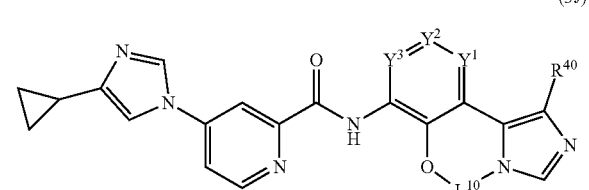

(3I)

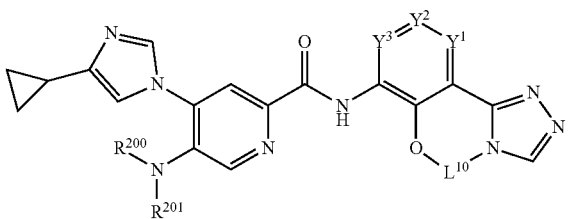

(3J)

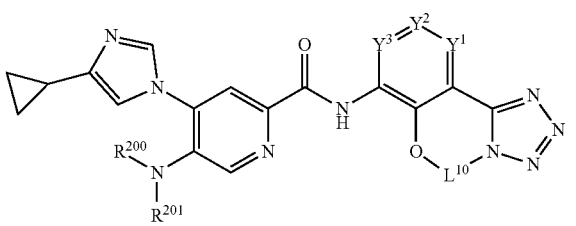

or a pharmaceutically acceptable salt thereof,
wherein $Y^1$, $Y^2$, and $Y^3$ independently are CH or N;

$L^{10}$ is optionally substituted $C_1$-$C_5$ alkylene or optionally substituted $C_1$-$C_5$ heteroalkylene; and $R^{40}$ is H, $C_1$-$C_6$ alkyl, or halo.

In another embodiment, the compound provided is of formula (3G). In another embodiment, the compound provided is of formula (3H). In another embodiment, the compound provided is of formula (3I). In another embodiment, the compound provided is of formula (3J).

In another embodiment, the compound provided is of formula (3K), (3L), (3M), or (3N):

(3K)

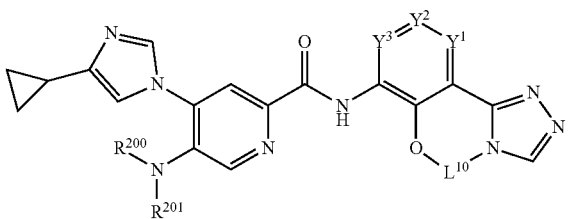

(3L)

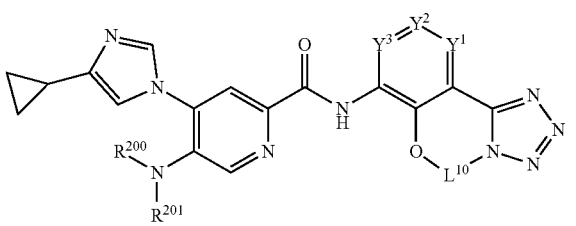

(3M)

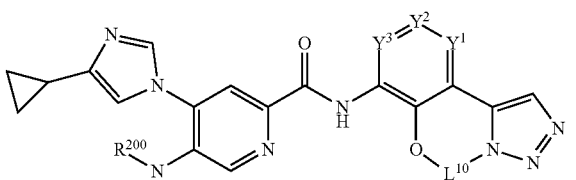

(3N)

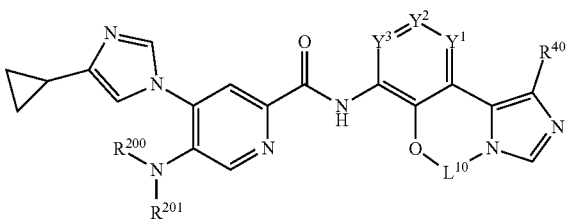

or a pharmaceutically acceptable salt thereof,
wherein $Y^1$, $Y^2$, and $Y^3$ independently are CH or N;
$L^{10}$ is optionally substituted $C_1$-$C_5$ alkylene or optionally substituted $C_1$-$C_5$ heteroalkylene;
$R^{40}$ is H, $C_1$-$C_6$ alkyl, or halo;
$R^{200}$ and $R^{201}$ are independently H or $C_1$-$C_6$ alkyl, or $R^{200}$ and $R^{201}$ are taken together with the nitrogen atom to which they are attached to form an optionally substituted 4- to 7-membered heterocyclyl.

In another embodiment, the compound provided is of formula (3K). In another embodiment, the compound provided is of formula (3L). In another embodiment, the compound provided is of formula (3M). In another embodiment, the compound provided is of formula (3N).

In another embodiment, the compound provided is of formula (3O), (3P), (3Q), or (3R):

(3O)
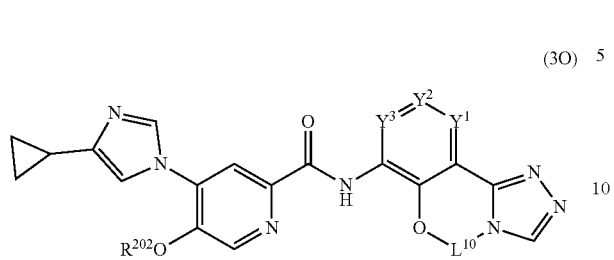

(3P)
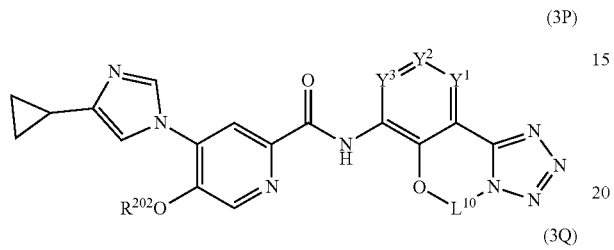

(3Q)
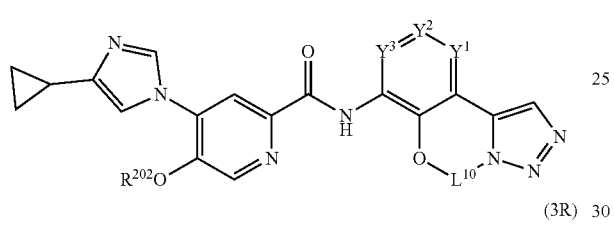

(3R)
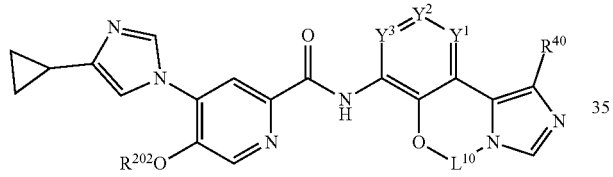

or a pharmaceutically acceptable salt thereof, wherein $Y^1$, $Y^2$, and $Y^3$ independently are CH or N;

$L^{10}$ is optionally substituted $C_1$-$C_5$ alkylene or optionally substituted $C_1$-$C_5$ heteroalkylene;

$R^{40}$ is H, $C_1$-$C_6$ alkyl, or halo; and $R^{202}$ is $C_1$-$C_6$ alkyl.

In another embodiment, the compound provided is of formula (3O). In another embodiment, the compound provided is of formula (3P). In another embodiment, the compound provided is of formula (3Q). In another embodiment, the compound provided is of formula (3R).

In another embodiment, the compound provided is of formula (4A), (4B), (4C), (4D), (4E), or (4F):

(4A)
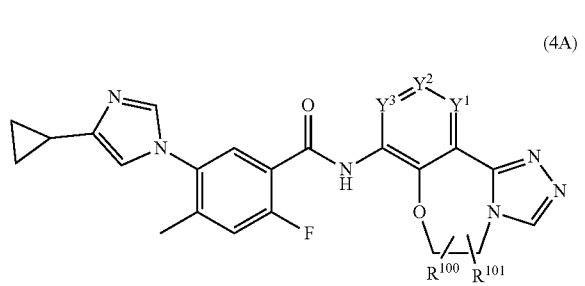

(4B)
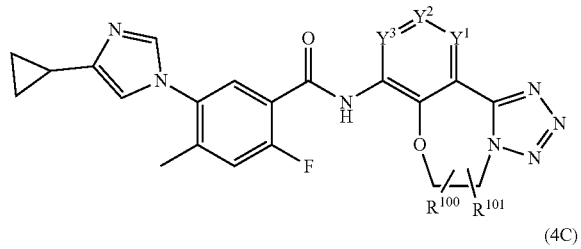

(4C)
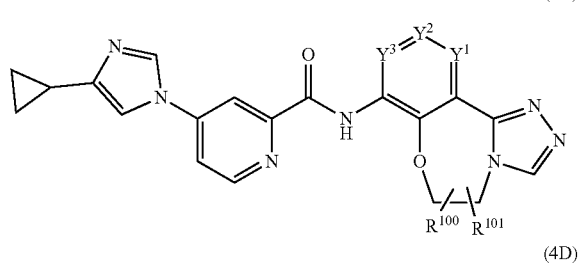

(4D)
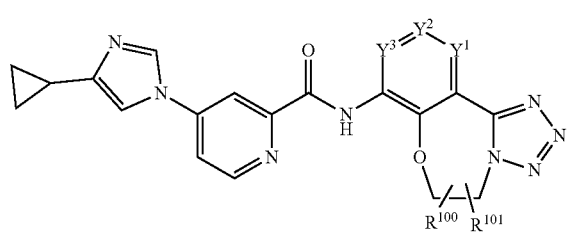

(4E)
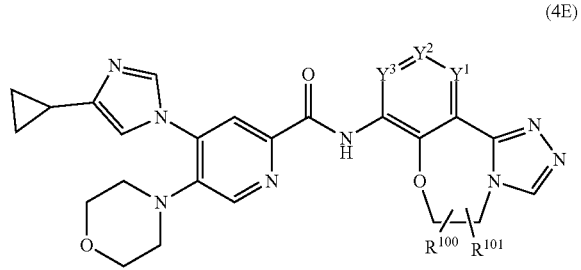

(4F)
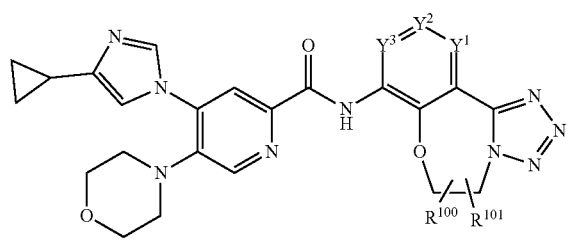

or a pharmaceutically acceptable salt thereof, wherein $Y^1$, $Y^2$, and $Y^3$ independently are CH or N; and $R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, or optionally substituted 5 membered heteroaryl; or $R^{100}$ and $R^{101}$ together with the carbon atom or carbon atoms they are attached to form a $C_3$-$C_5$ cycloalkyl.

In another embodiment, the compound provided is of formula (4A). In another embodiment, the compound provided is of formula (4B). In another embodiment, the compound provided is of formula (4C). In another embodiment, the compound provided is of formula (4D). In another embodiment, the compound provided is of formula (4E). In another embodiment, the compound provided is of formula (4F).

In another embodiment, the compound provided is of formula (4G), (4H), (4I), (4J), (4K), or (4L):

(4G)

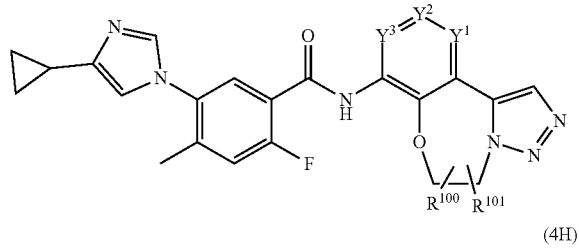

(4H)

(4I)

(4J)

(4K)

-continued (4L)

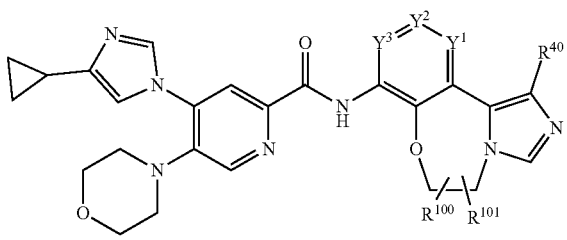

or a pharmaceutically acceptable salt thereof, wherein $Y^1$, $Y^2$, and $Y^3$ independently are CH or N;

$R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, or optionally substituted 5 membered heteroaryl; or $R^{100}$ and $R^{101}$ together with the carbon atom or carbon atoms they are attached to form a $C_3$-$C_5$ cycloalkyl; and $R^{40}$ is H, $C_1$-$C_6$ alkyl, or halo.

In another embodiment, the compound provided is of formula (4G). In another embodiment, the compound provided is of formula (4H). In another embodiment, the compound provided is of formula (4I). In another embodiment, the compound provided is of formula (4J). In another embodiment, the compound provided is of formula (4K). In another embodiment, the compound provided is of formula (4L).

In another embodiment, the compound provided is of formula (4M), (4N), (4O), or (4P):

(4M)

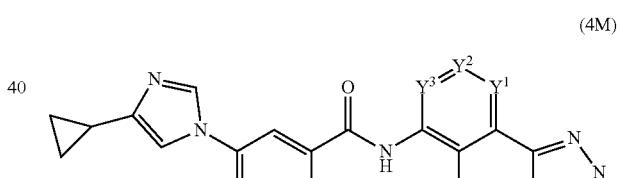

(4N)

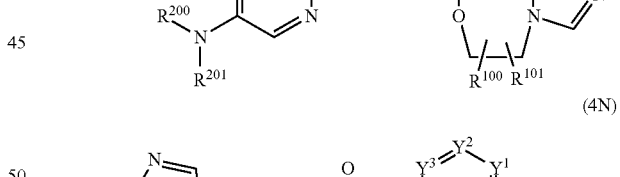

(4O)

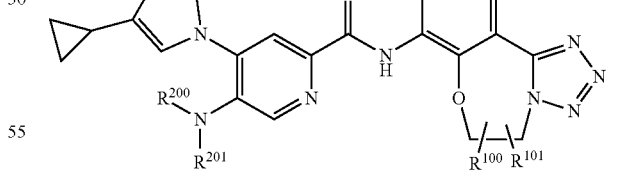

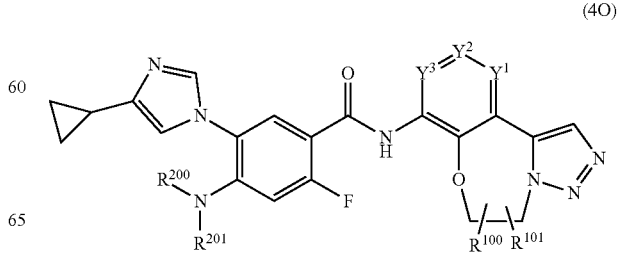

-continued (4P)

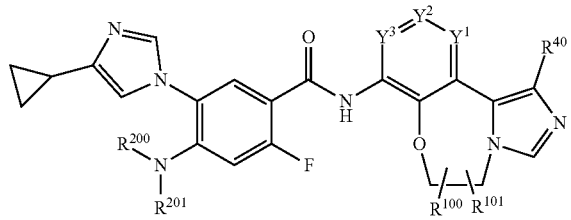

(4T)

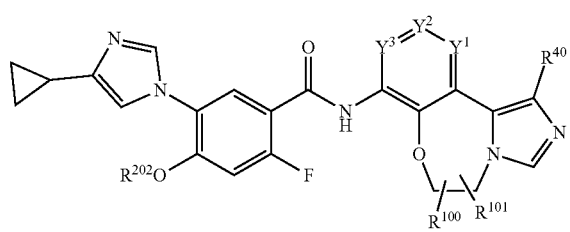

or a pharmaceutically acceptable salt thereof, wherein $Y^1$, $Y^2$, and $Y^3$ independently are CH or N;

$R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, or optionally substituted 5 membered heteroaryl; or $R^{100}$ and $R^{101}$ together with the carbon atom or carbon atoms they are attached to form a $C_3$-$C_5$ cycloalkyl;

$R^{40}$ is H, $C_1$-$C_6$ alkyl, or halo; and $R^{200}$ and $R^{201}$ are independently H or $C_1$-$C_6$ alkyl; or $R^{200}$ and $R^{201}$ are taken together with the nitrogen atom to which they are attached to form an optionally substituted 4- to 7-membered heterocyclyl.

In another embodiment, the compound provided is of formula (4M). In another embodiment, the compound provided is of formula (4N). In another embodiment, the compound provided is of formula (4O). In another embodiment, the compound provided is of formula (4P).

In another embodiment, the compound provided is of formula (4Q), (4R), (4S), or (4T):

or a pharmaceutically acceptable salt thereof, wherein $Y^1$, $Y^2$, and $Y^3$ independently are CH or N; and $R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, or optionally substituted 5 membered heteroaryl; or $R^{100}$ and $R^{101}$ together with the carbon atom or carbon atoms they are attached to form a $C_3$-$C_5$ cycloalkyl;

$R^{40}$ is H, $C_1$-$C_6$ alkyl, or halo; and $R^{202}$ is $C_1$-$C_6$ alkyl.

In another embodiment, the compound provided is of formula (4Q). In another embodiment, the compound provided is of formula (4R). In another embodiment, the compound provided is of formula (4S). In another embodiment, the compound provided is of formula (4T).

In another embodiment, the compound provided is of formula (4U):

(4U)

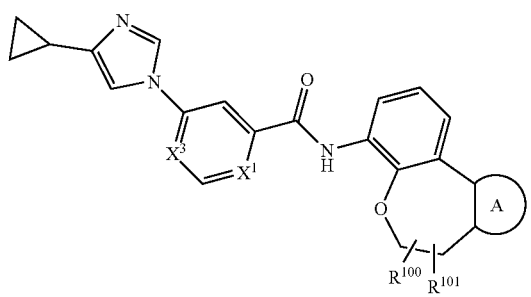

(4Q)

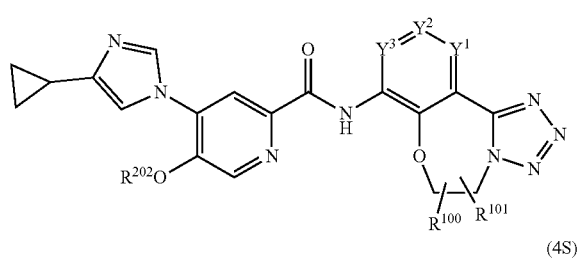

(4R)

or a pharmaceutically acceptable salt thereof, wherein the variables are defined as herein.

In another embodiment, the compound provided is of formula (5A), (5B), (5C), (5D), (5E), or (5F):

(5A)

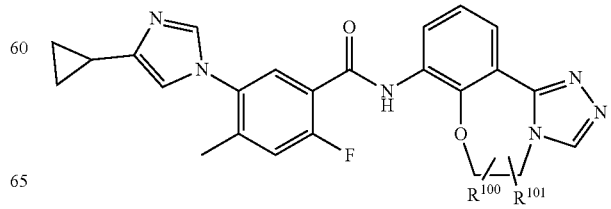

(4S)

-continued (5B)
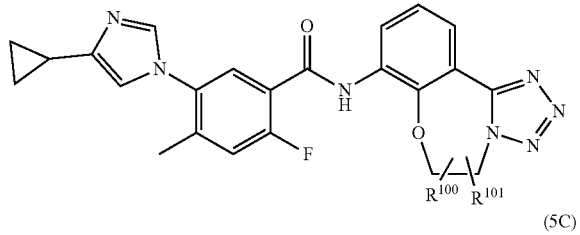

(5C)

(5D)
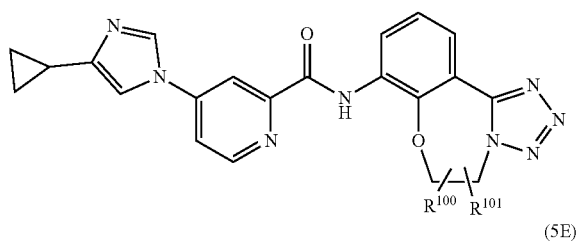

(5E)
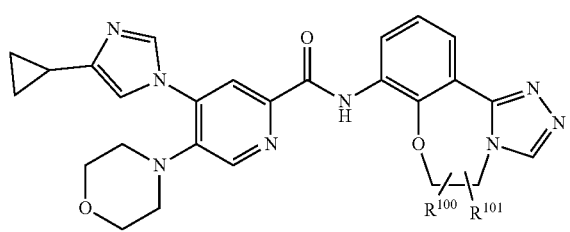

(5F)
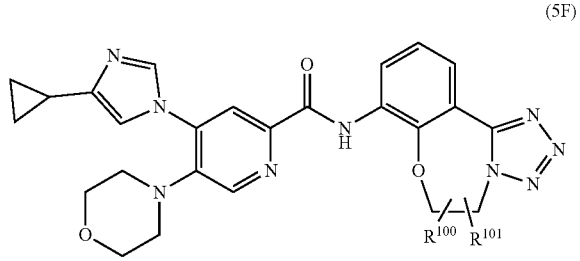

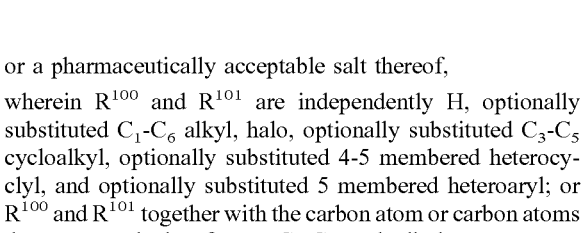

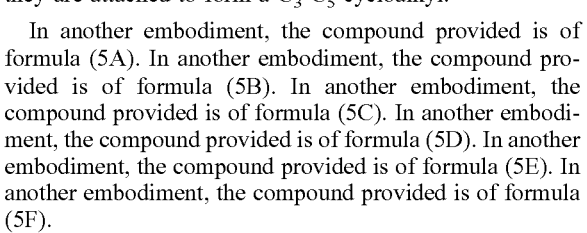

or a pharmaceutically acceptable salt thereof,
wherein $R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, and optionally substituted 5 membered heteroaryl; or $R^{100}$ and $R^{101}$ together with the carbon atom or carbon atoms they are attached to form a $C_3$-$C_5$ cycloalkyl.

In another embodiment, the compound provided is of formula (5A). In another embodiment, the compound provided is of formula (5B). In another embodiment, the compound provided is of formula (5C). In another embodiment, the compound provided is of formula (5D). In another embodiment, the compound provided is of formula (5E). In another embodiment, the compound provided is of formula (5F).

In another embodiment, the compound provided is of formula (5G), (5H), (5I), (5J), (5K), or (5L):

(5G)
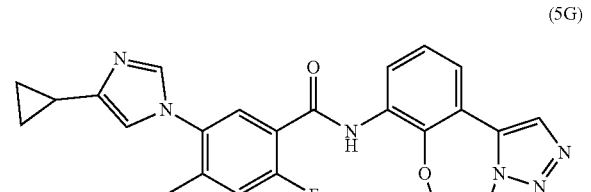

(5H)
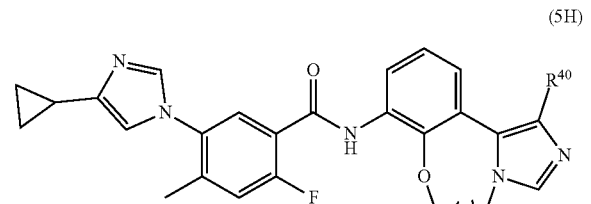

(5I)
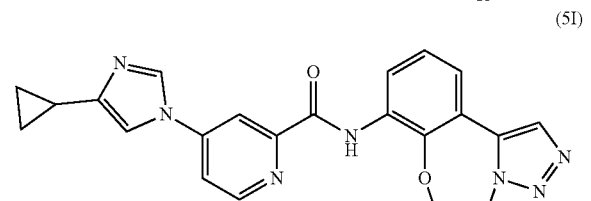

(5J)
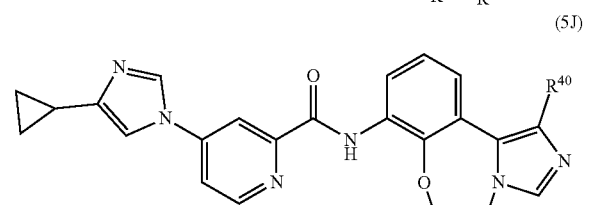

(5K)
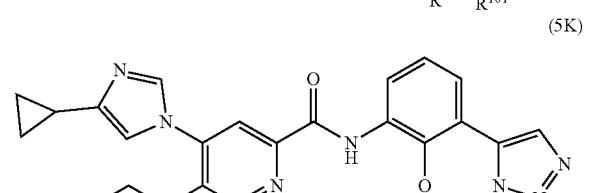

(5L)
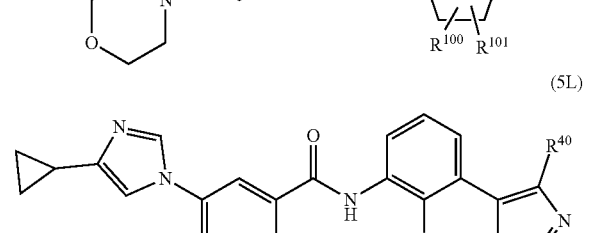

or a pharmaceutically acceptable salt thereof,
wherein $R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, and optionally substituted 5 membered heteroaryl; or $R^{100}$ and $R^{101}$ together with the carbon atom or carbon atoms they are attached to form a $C_3$-$C_5$ cycloalkyl; and $R^{40}$ is H, $C_1$-$C_6$ alkyl, or halo.

In another embodiment, the compound provided is of formula (5G). In another embodiment, the compound provided is of formula (5H). In another embodiment, the compound provided is of formula (5I). In another embodiment, the compound provided is of formula (5J). In another embodiment, the compound provided is of formula (5K). In another embodiment, the compound provided is of formula (5L).

In another embodiment, the compound provided is of formula (5M), (5N), (5O), (5P), (5Q), (5R), (5S), or (5T):

(5M)
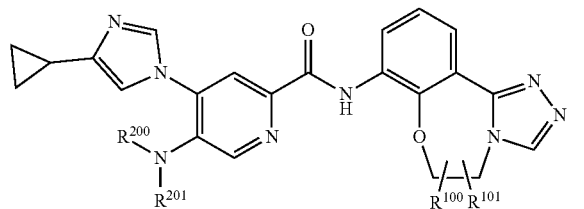

(5N)
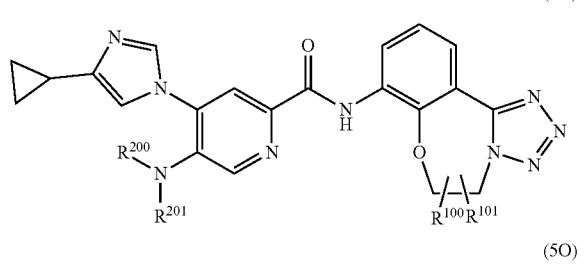

(5O)
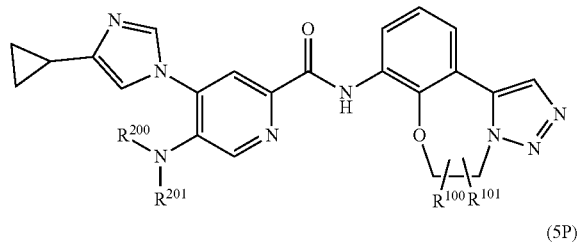

(5P)
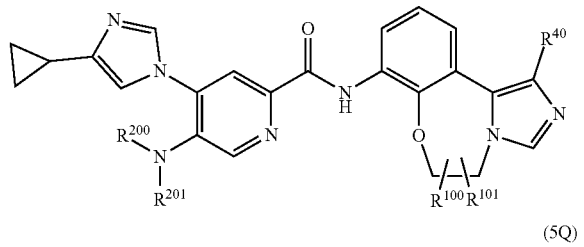

(5Q)
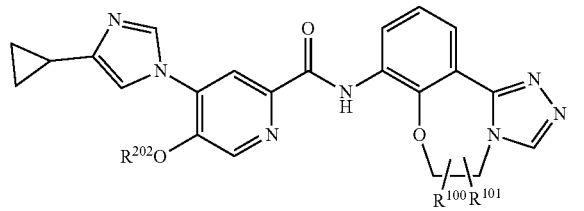

(5R)
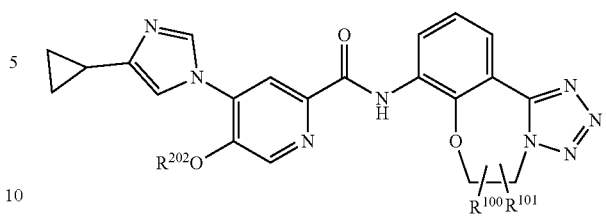

(5S)
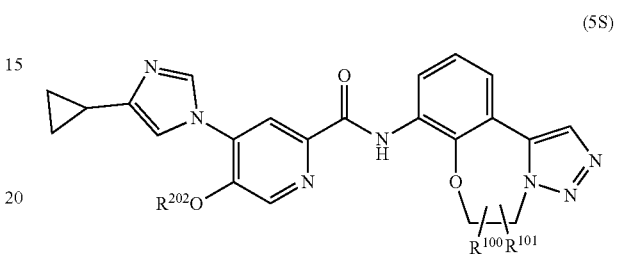

(5T)
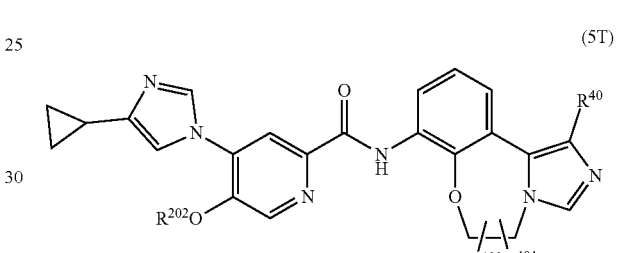

or a pharmaceutically acceptable salt thereof, wherein $R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, and optionally substituted 5 membered heteroaryl; or $R^{100}$ and $R^{101}$ together with the carbon atom or carbon atoms they are attached to form a $C_3$-$C_5$ cycloalkyl;

$R^{40}$ is H, $C_1$-$C_6$ alkyl, or halo; and $R^{200}$ and $R^{201}$ are independently H or $C_1$-$C_6$ alkyl; or $R^{200}$ and $R^{201}$ are taken together with the nitrogen atom to which they are attached to form an optionally substituted 4- to 7-membered heterocyclyl; and $R^{202}$ is $C_1$-$C_6$ alkyl.

In another embodiment, the compound provided is of formula (5M). In another embodiment, the compound provided is of formula (5N). In another embodiment, the compound provided is of formula (5O). In another embodiment, the compound provided is of formula (5P). In another embodiment, the compound provided is of formula (5Q). In another embodiment, the compound provided is of formula (5R). In another embodiment, the compound provided is of formula (5S). In another embodiment, the compound provided is of formula (5T).

In another embodiment, ring A is a triazole. In another embodiment, ring A is a tetrazole. In another embodiment, ring A is an optionally substituted imidazole. In some embodiments, ring A is imidazole optionally substituted with $C_1$-$C_6$ alkyl or halo. In some embodiments, ring A is selected from the group consisting of:

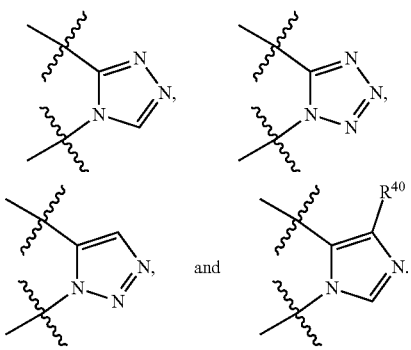

In some embodiments, ring A is

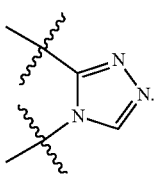 [SMILES: *c1nncn1*]

In some embodiments, ring A is

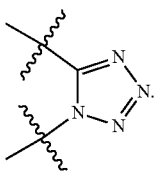 [SMILES: *c1nnnn1*]

In some embodiments, ring A is

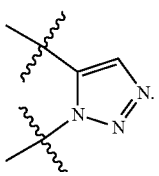 [SMILES: *c1cnnn1*]

In some embodiments, ring A is

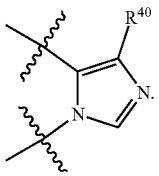

In another embodiment, ring B is phenyl. In another embodiment, ring B is pyridyl.

In another embodiment, $L^1$ is optionally substituted $C_2$-$C_6$ alkylene. In another embodiment, $L^1$ is optionally substituted $C_2$-$C_6$ heteroalkylene. In some embodiments, $L^1$ is optionally substituted $C_3$-$C_6$ heteroalkylene. In another embodiment, $L^1$ is —$Z^1$-$L^{10}$-, wherein $Z^1$ and $L^{10}$ are defined as herein. In another embodiment, $L^1$ is —O-$L^{10}$-, wherein $L^{10}$ is defined as herein. In another embodiment, $L^1$ is:

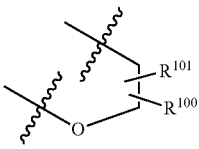

wherein $R^{100}$ and $R^{101}$ are defined as herein.

In another embodiment, -$L^1$- is: —O—CH$_2$—CH$_2$—. In another embodiment, -$L^1$- is: —O—CH$_2$—CH(Me)-. In another embodiment, -$L^1$- is: —O—CH$_2$—C(Me)$_2$-. In another embodiment, -$L^1$- is: —O—CH(Me)-CH$_2$—. In another embodiment, -$L^1$- is: —O—CH$_2$—CH(CH$_2$OH)—. In another embodiment, -$L^1$- is —O—CH$_2$—CH(CH$_2$F)—. In another embodiment, -$L^1$- is:

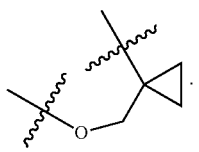

In another embodiment, -$L^1$- is:

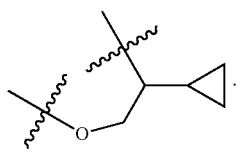 [SMILES: *OCC(*)C1CC1]

In another embodiment, -$L^1$- is:

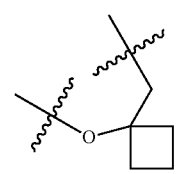

In another embodiment, -$L^1$- is:

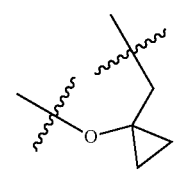

In another embodiment, -L¹- is:

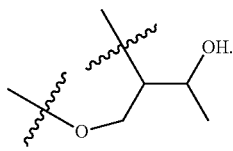 [SMILES: *OCC(*)C(C)O]

In another embodiment, L² is —CO—NH—. In another embodiment, L² is —NH—CO—. In another embodiment, L² is —SO₂—NH—. In another embodiment, L² is —NH—SO₂—.

In another embodiment, $X^1$ is optionally substituted —CH=. In another embodiment, $X^1$ is —CH=. In another embodiment, $X^1$ is substituted —CH=. In another embodiment, $X^1$ is $CR^3$, wherein $R^3$ is as defined herein. In another embodiment, $X^1$ is $CR^2$, wherein $R^2$ is as defined herein. In some embodiments, $X^1$ is C—F. In another embodiment, $X^1$ is N.

In another embodiment, $X^2$ is optionally substituted —CH=. In another embodiment, $X^2$ is —CH=. In another embodiment, $X^2$ is substituted —CH=. In another embodiment, $X^2$ is $CR^3$, wherein $R^3$ is as defined herein. In another embodiment, $X^2$ is $CR^2$, wherein $R^2$ is as defined herein. In another embodiment, $X^2$ is N.

In another embodiment, $X^3$ is optionally substituted —CH=. In another embodiment, $X^3$ is —CH=. In another embodiment, $X^3$ is substituted —CH=. In another embodiment, $X^3$ is $CR^3$, wherein $R^3$ is as defined herein. In another embodiment, $X^3$ is $CR^2$, wherein $R^2$ is as defined herein. In another embodiment, $X^3$ is N.

In another embodiment, $X^2$ is C—H, $X^1$ is C—F, and $X^3$ is C-Me. In another embodiment, $X^2$ is C—H, $X^1$ is C—F, and $X^3$ is C—H. In another embodiment, $X^2$ is C—H, $X^1$ is —N=, and $X^3$ is C—H. In another embodiment, $X^2$ is C—H, $X^1$ is N and $X^3$ is C-Me. In another embodiment, $X^2$ is C—H, $X^1$ is N and $X^3$ is C-morpholinyl, preferably, C-morpholin-1-yl. In another embodiment, $X^2$ is C—H, $X^1$ is N and $X^3$ is C-(optionally substituted 4- to 7-membered heterocyclyl). In some embodiments, $X^2$ is C—H, $X^1$ is N and $X^3$ is optionally substituted C-morpholinyl, C-piperazinyl, C-(2-oxa-5-azabicyclo[2.2.1]heptanyl), C-pyrrolidinyl, or C-azetidinyl. In some embodiments, $X^2$ is C—H, $X^1$ is N and $X^3$ is C-morpholinyl, C-piperazinyl, C-(2-oxa-5-azabicyclo[2.2.1]heptanyl), C-pyrrolidinyl, or C-azetidinyl, the heterocyclyl of each of which is optionally substituted by 1-2 substituents independently selected from the group consisting of $C_1$-$C_6$ alkyl and hydroxyl. In some embodiments, $X^2$ is C—H, $X^1$ is N and $X^3$ is —N($C_1$-$C_6$ alkyl)₂. In some embodiments, $X^2$ is C—H, $X^1$ is N and $X^3$ is —N(CH₃)₂. In some embodiments, $X^2$ is C—H, $X^1$ is N and $X^3$ is —O($C_1$-$C_6$ alkyl). In some embodiments, $X^2$ is C—H, $X^1$ is N and $X^3$ is —OCH(CH₃)₂.

In some embodiments, $R^1$ is $C_3$-$C_8$ cycloalkyl, 6-membered aryl, 5- to 6-membered heteroaryl, or 4- to 6-membered heterocyclyl, each of which is optionally substituted with 1-2 $C_1$-$C_6$ alkyl or with one $C_3$-$C_6$ cycloalkyl which is optionally substituted with 1-2 substituents selected from the group consisting of $C_1$-$C_6$ alkyl, $C_2$-$C_6$ alkenyl, and $C_2$-$C_6$ alkynyl; —CONR¹¹R¹² or —SO₂N¹¹R¹².

In another embodiment, $R^1$ is optionally substituted cycloalkyl, preferably, $C_3$-$C_8$ cycloalkyl. In another embodiment, the $C_3$-$C_8$ cycloalkyl is unsubstituted. In another embodiment, the $C_3$-$C_8$ cycloalkyl is substituted with a $C_3$-$C_6$ cycloalkyl. In another embodiment, the $C_3$-$C_8$ cycloalkyl is substituted with a $C_3$-$C_6$ cycloalkyl substituted with one or more, preferably 1-2 substituents selected from: $C_1$-$C_6$ alkyl, $C_2$-$C_6$ alkenyl, and $C_2$-$C_6$ alkynyl.

In another embodiment, $R^1$ is optionally substituted aryl. In another embodiment, the aryl is unsubstituted. In another embodiment, the aryl is substituted with a $C_3$-$C_6$ cycloalkyl. In another embodiment, the aryl is substituted with a $C_3$-$C_6$ cycloalkyl, which cycloalkyl is substituted with one or more, preferably 1-2 substituents selected from: $C_1$-$C_6$ alkyl, $C_2$-$C_6$ alkenyl, and $C_2$-$C_6$ alkynyl. In another embodiment, the aryl in a 6-membered aryl.

In another embodiment, $R^1$ is optionally substituted heteroaryl. In another embodiment, the heteroaryl is unsubstituted. In another embodiment, the heteroaryl is substituted with a $C_3$-$C_6$ cycloalkyl. In another embodiment, the heteroaryl is substituted with a $C_1$-$C_6$ alkyl. In another embodiment, the heteroaryl is substituted with a methyl. In another embodiment, the heteroaryl is substituted with a $C_3$-$C_6$ cycloalkyl, which cycloalkyl is substituted with one or more, preferably 1-2 substituents selected from: $C_1$-$C_6$ alkyl, $C_2$-$C_6$ alkenyl, and $C_2$-$C_6$ alkynyl. In another embodiment, the heteroaryl is 5-6 membered heteroaryl.

In another embodiment, $R^1$ is optionally substituted heterocyclyl. In another embodiment, the heterocyclyl is unsubstituted. In another embodiment, the heterocyclyl is substituted with a $C_3$-$C_6$ cycloalkyl. In another embodiment, the heterocyclyl is substituted with a $C_3$-$C_6$ cycloalkyl, which cycloalkyl is substituted with one or more, preferably 1-2 substituents selected from: $C_1$-$C_6$ alkyl, $C_2$-$C_6$ alkenyl, or $C_2$-$C_6$ alkynyl. In another embodiment, the heterocyclyl is a 4-6 membered heterocycle.

In some embodiments, the cycloalkyl, aryl, heteroaryl, and heterocyclyl groups are optionally substituted with one to five substituents selected from $C_1$-$C_6$ alkyl, $C_1$-$C_6$ alkoxy, $C_3$-$C_8$ cycloalkyl, cycloalkylalkyl, 6 membered aryl, arylalkyl, 5-6 membered heteroaryl, heteroarylalkyl, 4-6 membered heterocyclyl, heterocyclylalkyl, halo, oxo, —NO₂, haloalkyl, haloalkoxy, —CN, —O—$R^3$, —O—C(O)—$R^3$, —O—C(O)—N($R^3$)($R^4$), —S—$R^3$, —N($R^3$)($R^4$), —S(=O)—$R^3$, —S(=O)₂$R^3$, —S(=O)₂—N($R^3$)($R^4$), —S(=O)₂—O—$R^3$, —N($R^3$)—C(O)—$R^4$, —N($R^3$)—C(O)—O—$R^4$, —N($R^3$)—C(O)—N($R^3$)($R^4$), —C(O)—$R^3$, —C(O)—O—$R^3$, —C(O)—N($R^3$)($R^4$), and —N($R^3$)—S(=O)₂—$R^4$, wherein the substituent alkyl, alkoxy, cycloalkyl, aryl, heteroaryl or heterocyclyl is further optionally substituted with from one to five substituents selected from halo, oxo, —NO₂, alkyl, haloalkyl, haloalkoxy, —N($R^3$)($R^4$), —C(O)—$R^3$, —C(O)—O—$R^3$, —C(O)—N($R^3$)($R^4$), —CN, —O—$R^3$, cycloalkyl, aryl, heteroaryl and heterocyclyl, and $R^3$ and $R^4$ are as defined herein.

As used herein, a functional group composed of two functional groups, such as, e.g. and without limitation, cycloalkylalkyl refers to alkyl substituted with cycloalkyl, or arylalkyl refers to alkyl substituted with aryl, and the like.

In another embodiment, $R^1$ is 5-6 membered heteroaryl, wherein the heteroaryl is optionally substituted with a substituent selected from a $C_3$-$C_5$ cycloalkyl, preferably cyclopropyl; an $SO_2R^{10}$ wherein $R^{10}$ is optionally substituted $C_1$-$C_6$ alkyl; optionally substituted amino, preferably monosubstituted amino; or a $C_1$-$C_6$ alkyl optionally substituted with 1-5 fluoro groups, preferably with 1-3 fluoro groups.

In another embodiment, $R^1$ is phenyl, wherein the phenyl is optionally substituted with a substituent selected from a $C_3$-$C_5$ cycloalkyl, preferably cyclopropyl; an $SO_2R^{10}$ wherein $R^{10}$ is optionally substituted $C_1$-$C_6$ alkyl; optionally substituted amino, preferably monosubstituted amino; or a $C_1$-$C_6$ alkyl optionally substituted with 1-5 fluoro groups, preferably with 1-3 fluoro groups.

In another embodiment, $R^1$ is 4-6 membered heterocyclyl, wherein the heterocyclyl is optionally substituted with a substituent selected from a $C_3$-$C_5$ cycloalkyl, preferably cyclopropyl; an $SO_2R^{10}$ wherein $R^{10}$ is optionally substituted $C_1$-$C_6$ alkyl; optionally substituted amino, preferably monosubstituted amino; or a $C_1$-$C_6$ alkyl optionally substituted with 1-5 fluoro groups, preferably with 1-3 fluoro groups.

In one embodiment, $R^1$ is;

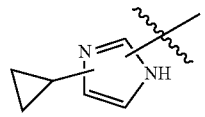

In another embodiment, $R^1$ is:

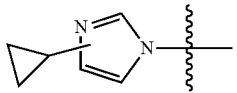

In one embodiment, $R^1$ is:

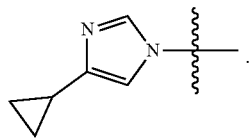 [SMILES: *n1cnc(C2CC2)c1]

In one embodiment, $R^1$ is

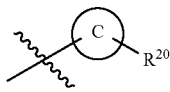

wherein ring C is a 5-6 membered heteroaryl, preferably a 5 membered heteroaryl, or a phenyl; and $R^{20}$ is $C_3$-$C_5$ cycloalkyl, preferably, cyclobutyl or cyclopropyl, more preferably, cyclopropyl; $C_1$-$C_6$ alkyl, preferably $C_1$-$C_3$ alkyl; or hydrogen.

In another embodiment, ring C is a 5-6 membered heteroaryl. In another embodiment, ring C is a 5 membered heteroaryl. In another embodiment, ring C is pyridyl. In another embodiment, ring C is imidazolyl. In another embodiment, ring C is phenyl.

In another embodiment, $R^{20}$ is $C_3$-$C_5$ cycloalkyl. In another embodiment, $R^{20}$ is cyclobutyl. In another embodiment, $R^{20}$ is cyclopropyl. In another embodiment, $R^{20}$ is $C_1$-$C_6$ alkyl. In another embodiment, $R^{20}$ is $C_1$-$C_3$ alkyl. In another embodiment, $R^{20}$ is methyl. In another embodiment, $R^{20}$ is hydrogen.

In one embodiment, $R^1$ is

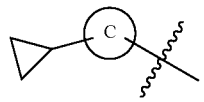

wherein ring C is a 5-6 membered heteroaryl, preferably a 5 membered heteroaryl, or a phenyl.

In one embodiment, $R^1$ is:

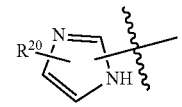

wherein $R^{20}$ is $C_3$-$C_5$ cycloalkyl. In one embodiment, $R^{20}$ is cyclobutyl. In one embodiment, $R^{20}$ is cyclopropyl.

In one embodiment, $R^1$ is:

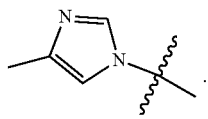 [SMILES: *n1cnc(C)c1]

In one embodiment, $R^1$ is:

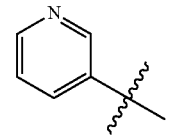

In one embodiment, $R^1$ is:

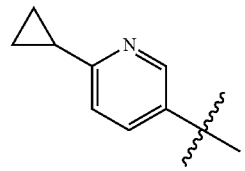

In one embodiment, $R^1$ is —$CONR^{11}R^{12}$ or —$SO_2NR^{11}R^{12}$, wherein each of $R^{11}$ and $R^{12}$ is independently selected from hydrogen, optionally substituted $C_1$-$C_6$ alkyl, and optionally substituted $C_3$-$C_8$ cycloalkyl, preferably optionally substituted $C_3$-$C_5$ cycloalkyl. In another embodiment, $R^1$ is —$CONR^{11}R^{12}$ or —$SO_2NR^{11}R^{12}$, wherein $R^{11}$ and $R^{12}$ together with the nitrogen atom they are attached to forms a heterocycle, preferably a 4-6 membered heterocycle. In one embodiment, $R^1$ is —$CONR^{11}R^{12}$. In another embodiment, $R^1$ is or —$SO_2NR^{11}R^{12}$.

In one embodiment, $R^{11}$ is hydrogen. In another embodiment, $R^{11}$ is optionally substituted $C_1$-$C_6$ alkyl. In another embodiment, $R^{11}$ is substituted $C_1$-$C_6$ alkyl. In another embodiment, $R^{11}$ is $C_1$-$C_6$ alkyl. In another embodiment, $R^{11}$ is methyl. In another embodiment, $R^{11}$ is optionally substituted $C_3$-$C_8$ cycloalkyl. In another embodiment, $R^{11}$ is $C_3$-$C_8$ cycloalkyl. In another embodiment, $R^{11}$ is substituted $C_3$-$C_8$ cycloalkyl. In another embodiment, $R^{11}$ is optionally substituted $C_3$-$C_5$ cycloalkyl. In another embodiment, $R^{11}$ is $C_3$-$C_5$ cycloalkyl. In another embodiment, $R^{11}$ is substituted $C_3$-$C_5$ cycloalkyl. In another embodiment, $R^{11}$ is cyclopropyl.

In one embodiment, $R^{12}$ is hydrogen. In another embodiment, $R^{12}$ is optionally substituted $C_1$-$C_6$ alkyl. In another embodiment, $R^{12}$ is substituted $C_1$-$C_6$ alkyl. In another embodiment, $R^{12}$ is $C_1$-$C_6$ alkyl. In another embodiment, $R^{12}$ is methyl. In another embodiment, $R^{12}$ is optionally substituted $C_3$-$C_8$ cycloalkyl. In another embodiment, $R^{12}$ is $C_3$-$C_8$ cycloalkyl. In another embodiment, $R^{12}$ is substituted $C_3$-$C_8$ cycloalkyl. In another embodiment, $R^{12}$ is optionally substituted $C_3$-$C_5$ cycloalkyl. In another embodiment, $R^{12}$ is $C_3$-$C_5$ cycloalkyl. In another embodiment, $R^{12}$ is substituted $C_3$-$C_5$ cycloalkyl. In another embodiment, $R^{12}$ is cyclopropyl.

In one embodiment, $R^1$ is —$CONH_2$. In one embodiment, $R^1$ is CONHMe. In one embodiment, $R^1$ is $CONMe_2$. In one embodiment, $R^1$ is:

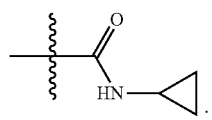 [SMILES: *C(=O)NC1CC1]

In one embodiment, $R^2$ is hydrogen. In one embodiment, $R^2$ is optionally substituted alkyl preferably optionally substituted $C_1$-$C_6$ alkyl. In one embodiment, $R^2$ is optionally substituted alkoxy preferably optionally substituted $C_1$-$C_6$ alkoxy. In one embodiment, $R^2$ is optionally substituted cycloalkyl preferably optionally substituted $C_3$-$C_8$ cycloalkyl. In one embodiment, $R^2$ is optionally substituted aryl preferably optionally substituted 6 membered aryl. In one embodiment, $R^2$ is optionally substituted heteroaryl preferably optionally substituted 5-10 membered heteroaryl. In one embodiment, $R^2$ is optionally substituted heterocyclyl preferably optionally substituted 5-10 membered heterocyclyl. In certain embodiments, the alkyl, cycloalkyl, aryl, heteroaryl, and heterocyclyl group is optionally substituted with from one to five substituents selected from halo, oxo, —$NO_2$, —$CF_3$, —O—$CF_3$, —$N(R^3)(R^4)$, —C(O)—$R^3$, —C(O)—O—$R^3$, —C(O)—$N(R^3)(R^4)$, —CN, and —O—$R^3$.

In some embodiments, $R^2$ is hydrogen; $C_1$-$C_6$ alkyl optionally substituted with 1-3 halo, —$CF_3$, —$OCF_3$, hydroxy, —CN or —$N(R^3)(R^4)$; $C_1$-$C_6$ alkoxy optionally substituted with 1-3 halo, —$CF_3$, —$OCF_3$, hydroxy, —CN or —$N(R^3)(R^4)$; $C_3$-$C_8$ cycloalkyl optionally substituted with 1-3 halo, $C_1$-$C_6$ alkyl, —$CF_3$, —$OCF_3$, hydroxy, —CN or —$N(R^3)(R^4)$; 6-membered aryl optionally substituted with 1-3 halo, $C_1$-$C_6$ alkyl, —$CF_3$, —$OCF_3$, hydroxy, —CN or —$N(R^3)(R^4)$; 5- to 10-membered heteroaryl optionally substituted with 1-3 halo, $C_1$-$C_6$ alkyl, —$CF_3$, —$OCF_3$, hydroxy, —CN or —$N(R^3)(R^4)$; 4-10 membered heterocyclyl optionally substituted with 1-3 halo, $C_1$-$C_6$ alkyl, —$CF_3$, —$OCF_3$, hydroxy, —CN or —$N(R^3)(R^4)$; or halo.

In some embodiments, $R^2$ is an optionally substituted 4- to 7-membered heterocyclyl. In some embodiments, $R^2$ is a 4- to 7-membered heterocyclyl optionally substituted with 1-2 substituents which are selected from the group consisting of $C_1$-$C_6$ alkyl and hydroxyl. In some embodiments, $R^2$ is a 4- to 7-membered heterocyclyl optionally substituted with 1-2 substituents which are independently selected from the group consisting of $C_1$-$C_3$ alkyl and hydroxyl. In some embodiments, $R^2$ is an unsubstituted 4- to 7-membered heterocyclyl. In some embodiments, $R^2$ is selected from the group consisting of:

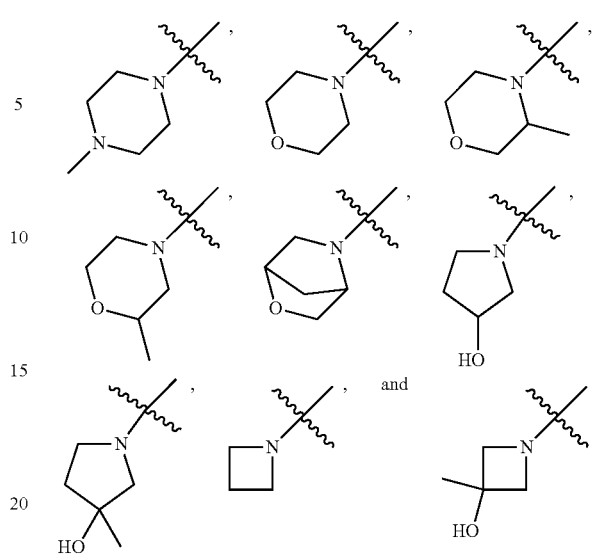

In one embodiment, $R^2$ is halo. In some embodiments, $R^2$ is fluoro. In one embodiment, $R^2$ is —$NO_2$. In one embodiment, $R^2$ is haloalkyl. In one embodiment, $R^2$ is haloalkoxy. In one embodiment, $R^2$ is —CN. In one embodiment, $R^2$ is —O—$R^3$. In some embodiments, $R^2$ is —O—$R^3$, wherein $R^3$ is $C_1$-$C_6$ alkyl. In some embodiments, $R^2$ is —O—$R^3$, where in $R^3$ is $C_1$-$C_3$ alkyl. In some embodiments, $R^2$ is —O—$R^3$, where in $R^3$ is methyl, ethyl, n-propyl, or isopropyl. In some embodiments, $R^2$ is —O—$R^3$, where in $R^3$ is isopropyl. In one embodiment, $R^2$ is —S—$R^3$. In one embodiment, $R^2$ is —$N(R^3)(R^4)$. In some embodiments, $R^2$ is —$N(R^3)(R^4)$, wherein $R^3$ and $R^4$ are independently H or $C_1$-$C_6$ alkyl. In some embodiments, $R^2$ is —$N(R^3)(R^4)$, wherein $R^3$ and $R^4$ are independently H or $C_1$-$C_3$ alkyl. In some embodiments, $R^2$ is —$N(R^3)(R^4)$, wherein $R^3$ and $R^4$ are independently H or methyl. In some embodiments, $R^2$ is —$N(R^3)(R^4)$, wherein $R^3$ and $R^4$ are both H. In some embodiments, $R^2$ is —$N(R^3)(R^4)$, wherein $R^3$ and $R^4$ are both methyl. In some embodiments, $R^2$ is —$N(R^3)(R^4)$, wherein $R^3$ is H and $R^4$ is methyl. In one embodiment, $R^2$ is —S(=O)—$R^3$. In one embodiment, $R^2$ is $S(=O)_2R^3$. In one embodiment, $R^2$ is —$S(=O)_2$—$N(R^3)(R^4)$. In one embodiment, $R^2$ is —$S(=O)_2$—O—$R^3$. In one embodiment, $R^2$ is —$N(R^3)$—C(O)—$R^4$. In one embodiment, $R^2$ is —$N(R^3)$—C(O)—O—$R^4$. In one embodiment, $R^2$ is —$N(R^3)$—C(O)—$N(R^3)(R^4)$. In one embodiment, $R^2$ is —C(O)—$R^3$. In one embodiment, $R^2$ is —C(O)—O—$R^3$. In one embodiment, $R^2$ is —C(O)—$N(R^3)(R^4)$. In one embodiment, $R^2$ is or —$N(R^3)$—$S(=O)_2$—$R^4$.

$R^3$ and $R^4$ are independently selected from the group consisting of hydrogen, optionally substituted alkyl preferably optionally substituted $C_1$-$C_6$ alkyl, optionally substituted alkoxy preferably optionally substituted $C_1$-$C_6$ alkoxy, optionally substituted cycloalkyl preferably optionally substituted $C_3$-$C_8$ cycloalkyl, optionally substituted aryl preferably optionally substituted 6 membered aryl, optionally substituted heteroaryl preferably optionally substituted 5-10 membered heteroaryl, optionally substituted heterocyclyl preferably optionally substituted 5-10 membered heterocyclyl; or $R^3$ and $R^4$ when taken together with the nitrogen, or with the intervening atoms to which they are attached form an optionally substituted heterocycle preferably an optionally substituted 4-10 membered heterocycle.

In some embodiments, $R^3$ and $R^4$ are independently H or $C_1$-$C_6$ alkyl. In some embodiments, $R^3$ and $R^4$ are independently H or $C_1$-$C_3$ alkyl. In some embodiments, $R^3$ and $R^4$ are both H. In some embodiments, one of $R^3$ and $R^4$ is H, and the other is $C_1$-$C_6$ alkyl. In some embodiments, $R^3$ and $R^4$ are both independently $C_1$-$C_6$ alkyl. In some embodiments, $R^3$ and $R^4$ are independently methyl, ethyl, n-propyl, or isopropyl. In some embodiments, $R^3$ and $R^4$ are independently H, methyl, or isopropyl.

In certain embodiments, each of alkyl, $C_1$-$C_6$ alkyl, alkoxy, $C_1$-$C_6$ alkoxy, cycloalkyl, $C_3$-$C_8$ cycloalkyl, aryl, 6 membered aryl, heteroaryl, 5-10 membered heteroaryl, heterocyclyl, substituted 5-10 membered heterocycly, is independently optionally substituted with from one to three substituents selected from halo, alkyl, monoalkylamino, dialkylamino, alkyl amide, aryl amide, heteroaryl amide, —CN, lower alkoxy, —$CF_3$, aryl, and heteroaryl.

In some embodiments, $R^3$ and $R^4$ are independently selected from the group consisting of hydrogen; $C_1$-$C_6$ alkyl optionally substituted with 1-3 halo, —$CF_3$, —$OCF_3$, hydroxyl, or —CN; $C_3$-$C_8$ cycloalkyl optionally substituted with 1-3 halo, $C_1$-$C_6$ alkyl, —$CF_3$, —$OCF_3$, hydroxy, or —CN; 6-membered aryl optionally substituted with 1-3 halo, $C_1$-$C_6$ alkyl, —$CF_3$, —$OCF_3$, hydroxyl, or —CN; 5-10 membered heteroaryl optionally substituted with 1-3 halo, $C_1$-$C_6$ alkyl, —$CF_3$, —$OCF_3$, hydroxyl, or —CN; or 5-10 membered heterocyclyl optionally substituted with 1-3 halo, $C_1$-$C_6$ alkyl, —$CF_3$, —$OCF_3$, hydroxyl, or —CN. In some embodiments, $R^3$ and $R^4$ are taken together with the nitrogen, or with the intervening atoms to which they are attached to form a 4- to 10-membered heterocycle optionally substituted with 1-3 halo, $C_1$-$C_6$ alkyl, —$CF_3$, —$OCF_3$, hydroxyl, or —CN.

In some embodiments, $R^2$ is —$N(R^3)(R^4)$. In some embodiments, $R^3$ and $R^4$ are independently selected from the group consisting of H and $C_1$-$C_6$ alkyl. In some embodiments, $R^3$ is H, and $R^4$ is $C_1$-$C_6$. In some embodiments, $R^3$ and $R^4$ are independently $C_1$-$C_6$ alkyl. In some embodiments, $R^3$ and $R^4$ are both methyl. In some embodiments, $R^3$ and $R^4$ are taken together with the nitrogen atom to which they are attached to form a 4- to 7-membered heterocycle optionally independently substituted with 1-2 $C_1$-$C_6$ alkyl or hydroxyl. In some embodiments, $R^3$ and $R^4$ are taken together with the nitrogen atom to which they are attached to form:

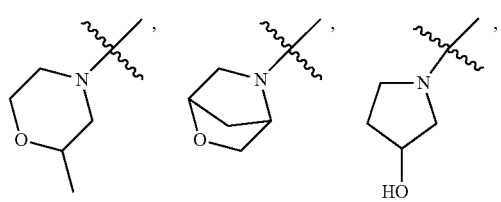

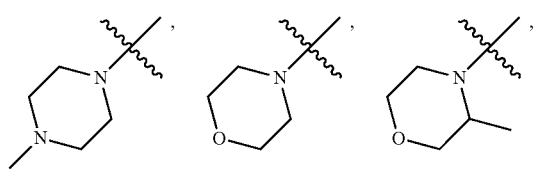

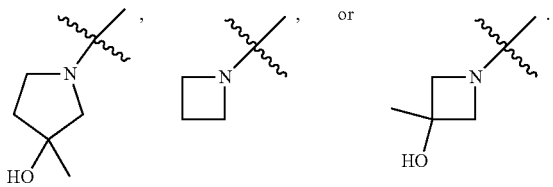

In another embodiment, $Y^1$ is CH. In another embodiment, $Y^1$ is N. In another embodiment, $Y^2$ is CH. In another embodiment, $Y^2$ is N. In another embodiment, $Y^3$ is CH. In another embodiment, $Y^3$ is N. In another embodiment, $Y^1$, $Y^2$, and $Y^3$ are CH. In another embodiment, one of $Y^1$, $Y^2$, and $Y^3$ is N.

In another embodiment, $Z^1$ is O. In another embodiment, $Z^1$ is $S(O)_n$. In another embodiment, n is 0. In another embodiment, n is 1. In another embodiment, n is 2. In another embodiment, $Z^1$ is $NR^{15}$. In another embodiment, $R^{15}$ is H or $C_1$-$C_3$ alkyl. In another embodiment, $R^{15}$ is $C_1$-$C_3$ alkyl.

In another embodiment, $L^{10}$ is optionally substituted $C_1$-$C_5$ alkylene. In another embodiment, $L^{10}$ is optionally substituted $C_1$-$C_5$ heteroalkylene. In another embodiment, $L^{10}$ is:

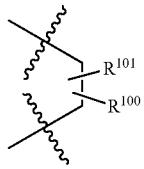

wherein $R^{100}$ and $R^{101}$ are defined as herein.

In another embodiment, -$L^{10}$- is —$CH_2$—$CH_2$—. In another embodiment, -$L^{10}$- is —$CH_2$—CH(Me)-. In another embodiment, -$L^{10}$- is —$CH_2$—$C(Me)_2$-. In another embodiment, -$L^{10}$- is —CH(Me)-$CH_2$—. In another embodiment, -$L^{10}$- is —$CH_2$—CH($CH_2OH$)—. In another embodiment, -$L^{10}$- is —$CH_2$—CH($CH_2F$)—. In another embodiment, -$L^{10}$- is:

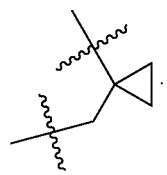 [SMILES: *CC1(*)CC1]

In another embodiment, -$L^1$- is:

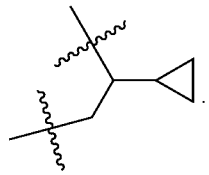 [SMILES: *CC(*)C1CC1]

In another embodiment, -L$^{10}$- is:

In another embodiment, -L$^{10}$- is:

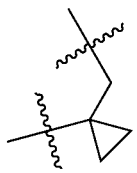

In another embodiment, -L$^{10}$- is:

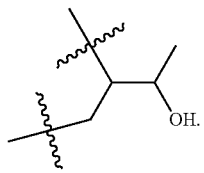 [SMILES: *CC(*)C(C)O]

In another embodiment, R$^{100}$ is optionally substituted C$_1$-C$_6$ alkyl. In another embodiment, R$^{100}$ is halo. In another embodiment, R$^{100}$ is optionally substituted C$_3$-C$_5$ cycloalkyl. In another embodiment, R$^{100}$ is C$_3$-C$_5$ cycloalkyl optionally substituted with 1-3 C$_1$-C$_6$ alkyl, hydroxy, or halo. In another embodiment, R$^{100}$ is optionally substituted 4-5 membered heterocyclyl. In another embodiment, R$^{100}$ is 4-5 membered heterocyclyl optionally substituted with 1-3 C$_1$-C$_6$ alkyl, hydroxyl, or halo. In another embodiment, R$^{100}$ is optionally substituted 5 membered heteroaryl. In another embodiment, R$^{100}$ is 5 membered heteroaryl optionally substituted with 1-3 C$_1$-C$_6$ alkyl, hydroxyl, or halo.

In another embodiment, R$^{101}$ is optionally substituted C$_1$-C$_6$ alkyl. In another embodiment, R$^{101}$ is halo. In another embodiment, R$^{101}$ is optionally substituted C$_3$-C$_5$ cycloalkyl. In another embodiment, R$^{101}$ is C$_3$-C$_5$ cycloalkyl optionally substituted with 1-3 C$_1$-C$_6$ alkyl, hydroxy, or halo. In another embodiment, R$^{101}$ is optionally substituted 4-5 membered heterocyclyl. In another embodiment, R$^{101}$ is 4-5 membered heterocyclyl optionally substituted with 1-3 C$_1$-C$_6$ alkyl, hydroxyl, or halo. In another embodiment, R$^{101}$ is optionally substituted 5 membered heteroaryl. In another embodiment, R$^{101}$ is 5 membered heteroaryl optionally substituted with 1-3 C$_1$-C$_6$ alkyl, hydroxyl, or halo.

In another embodiment, R$^{100}$ and R$^{101}$ together with the carbon atom or carbon atoms they are attached to form a C$_3$-C$_5$ cycloalkyl. In some embodiments, R$^{100}$ and R$^{101}$ together with the carbon atom or carbon atoms they are attached to form cyclopropyl or cyclobutyl.

In another embodiment, R$^{100}$ is H. In another embodiment, R$^{100}$ is C$_1$-C$_6$ alkyl optionally substituted with 1-3 hydroxy or halo, such as fluoro. In another embodiment, R$^{100}$ is optionally substituted C$_1$-C$_3$ alkyl. In another embodiment, R$^{100}$ is C$_1$-C$_3$ alkyl optionally substituted with 1-3 hydroxy or halo, such as fluoro, or is C$_3$-C$_5$ cyclopropyl group. In another embodiment, R$^{100}$ is C$_3$-C$_5$ cycloalkyl optionally substituted with 1-3 C$_1$-C$_6$ alkyl, halo, or hydroxyl groups. In some embodiments, R$^{100}$ is methyl, ethyl, n-propyl, or isopropyl. In some embodiments, R$^{100}$ is methyl. In some embodiments, R$^{100}$ is —CH(OH)—CH$_3$.

In another embodiment, R$^{101}$ is H. In another embodiment, R$^{101}$ is C$_1$-C$_6$ alkyl optionally substituted with 1-3 hydroxy or halo, such as fluoro. In another embodiment, R$^{101}$ is optionally substituted C$_1$-C$_3$ alkyl. In another embodiment, R$^{101}$ is C$_1$-C$_3$ alkyl optionally substituted with 1-3 hydroxy or halo, such as fluoro, or is C$_3$-C$_5$ cyclopropyl group. In another embodiment, R$^{101}$ is C$_3$-C$_5$ cycloalkyl optionally substituted with 1-3 C$_1$-C$_6$ alkyl, halo, or hydroxyl groups. In some embodiments, R$^{101}$ is methyl, ethyl, n-propyl, or isopropyl. In some embodiments, R$^{101}$ is methyl. In some embodiments, R$^{101}$ is —CH(OH)—CH$_3$.

In another embodiment, R$^{100}$ is H, and R$^{101}$ is C$_1$-C$_3$ alkyl optionally substituted with 1-3 hydroxy or halo, such as fluoro, or is C$_3$-C$_5$ cyclopropyl group. In another embodiment, R$^{100}$ is H, and R$^{101}$ is C$_1$-C$_3$ alkyl optionally substituted with 1-3 hydroxy or halo, such as fluoro, or is C$_3$-C$_5$ cycloalkyl group optionally substituted with 1-3 C$_1$-C$_6$ alkyl, hydroxy, or halo. In another embodiment, each R$^{100}$ and R$^{101}$ are independently C$_1$-C$_3$ alkyl. In another embodiment, R$^{100}$ and R$^{101}$ together with the carbon atom they are attached to form a C$_3$-C$_5$ cycloalkyl group. In some embodiments, R$^{100}$ and R$^{101}$ together with the carbon atom or carbon atoms they are attached to form cyclopropyl or cyclobutyl.

In another embodiment, R$^{100}$ is H, and R$^{101}$ is methyl, hydroxymethyl, fluoromethyl, or cyclopropyl. In another embodiment, each R$^{100}$ and R$^{101}$ are independently methyl or ethyl. In another embodiment, R$^{100}$ and R$^{101}$ together with the carbon atom they are attached to form a cyclopropyl group. In another embodiment, R$^{100}$ and R$^{101}$ together with the carbon atom they are attached to form a cyclobutyl group.

In another embodiment,

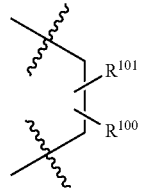

is —CH$_2$—CH$_2$—. In another embodiment,

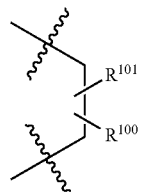

is: —CH₂—CH(Me)-. In another embodiment,
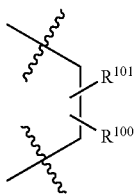
is: —CH₂—C(Me)₂-. In another embodiment,
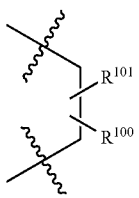
is: —CH(Me)-CH₂—. In another embodiment,
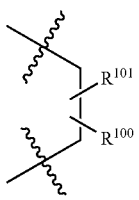
is: —CH₂—CH(CH₂OH)—. In another embodiment,
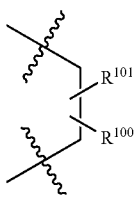
is —CH₂—CH(CH₂F)—. In another embodiment,
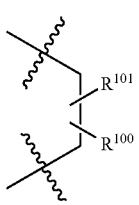
is:
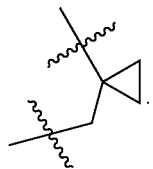
In another embodiment,
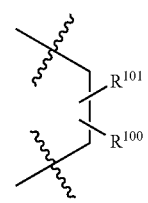
is:
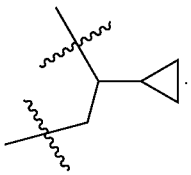 [SMILES: *CC(*)C1CC1]
In another embodiment,
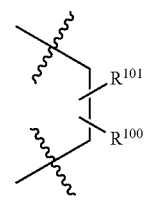
is:
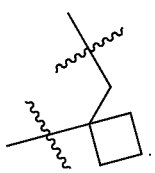 [SMILES: *CC1(*)CCC1]
In another embodiment,
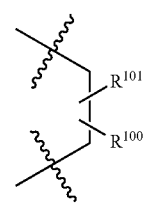

is:

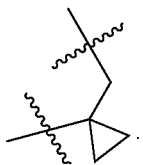 [SMILES: *CC1(*)CC1]

In another embodiment,

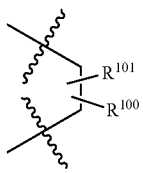

is:

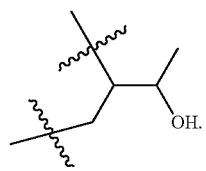 [SMILES: *CC(*)C(C)O]

In another embodiment, -L$^1$-, —Z$^1$-L$^{10}$-, —O-L$^{10}$-, or

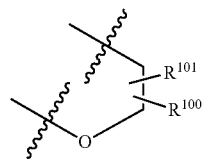

is: —O—CH$_2$—CH$_2$—, —O—CH$_2$—CH(Me)-, —O—CH(Me)-CH$_2$—, —O—CH$_2$—C(Me)$_2$-, —O—CH$_2$—CH(CH$_2$OH)—, —O—CH$_2$—CH(CH$_2$F)—,

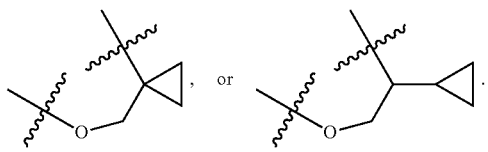 [SMILES: *OCC1(*)CC1 ; *OCC(*)C1CC1]

In another embodiment, -L$^1$-, —Z$^1$-L$^{10}$-, —O-L$^{10}$-, or

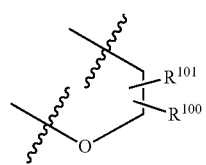

is:

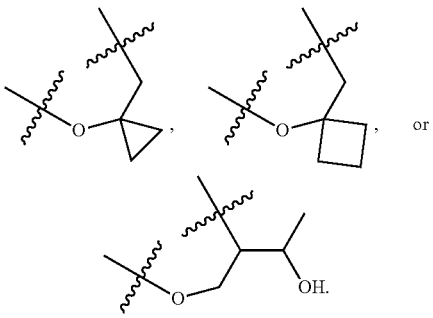

In some embodiments, R$^{200}$ and R$^{201}$ are independently C$_1$-C$_6$ alkyl. In some embodiments, R$^{200}$ and R$^{201}$ are independently C$_1$-C$_3$ alkyl. In some embodiments, R$^{200}$ and R$^{201}$ are independently methyl, ethyl, n-propyl, or isopropyl. In some embodiments, R$^{200}$ and R$^{201}$ are both methyl.

In some embodiments, R$^{200}$ and R$^{201}$ are taken together with the nitrogen atom to which they are attached to form an optionally substituted 4- to 7-membered heterocyclyl. In some embodiments, the optionally substituted 4- to 7-membered heterocyclyl is a monocyclic heterocyclyl. In some embodiments, the optionally substituted 4- to 7-membered heterocyclyl is a bicyclic heterocyclyl. In some embodiments, the optionally substituted 4- to 7-membered heterocyclyl further contains a heteroatom selected from the group consisting of nitrogen and oxygen. In some embodiments, the optionally substituted 4- to 7-membered heterocyclyl contains a second nitrogen atom. In some embodiments, the optionally substituted 4- to 7-membered heterocyclyl further contains an oxygen atom. In some embodiments, the 4- to 7-membered heterocyclyl is unsubstituted. In some embodiments, the 4- to 7-membered heterocyclyl is substituted by 1-2 substituents selected from the group consisting of C$_1$-C$_3$ alkyl and —OH. In some embodiments, the 4- to 7-membered heterocyclyl is substituted by 1-2 substituents selected from the group consisting of methyl and —OH. In some embodiments, the optionally substituted 4- to 7-membered heterocyclyl is selected from the group consisting of:

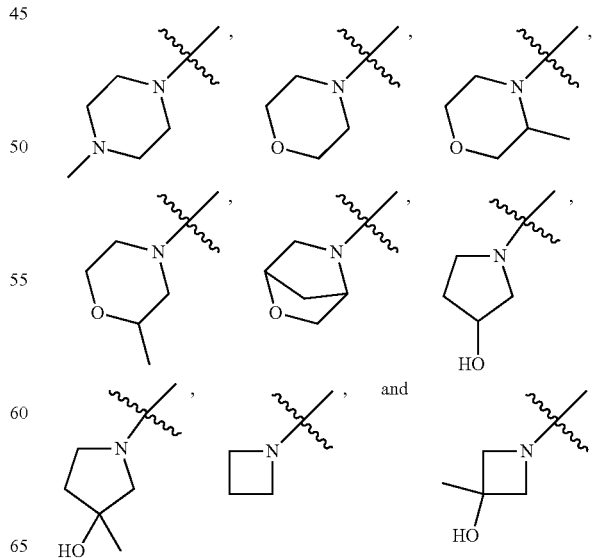

In some embodiments, $R^{202}$ is $C_1$-$C_6$ alkyl. In some embodiments, $R^{202}$ is methyl, ethyl, n-propyl, or isopropyl. In some embodiments, $R^{202}$ is isopropyl.

In some embodiments, $R^{40}$ is H, $C_1$-$C_6$ alkyl, or halo. In some embodiments, $R^{40}$ is H. In some embodiments, $R^{40}$ is halo, such as chloro, fluoro or bromo. In some embodiments, $R^{40}$ is bromo. In some embodiments, $R^{40}$ is $C_1$-$C_6$ alkyl. In some embodiments, $R^{40}$ is methyl, ethyl, n-propyl, or isopropyl. In some embodiments, $R^{40}$ is methyl.

In some embodiments, the compound of formula (IA) disclosed herein, or any embodiment, variation, or aspect thereof, excludes the compound 5-(4-cyclopropyl-1H-imidazol-1-yl)-2-fluoro-4-methyl-N-(5-methyl-5,6-dihydrobenzo[f][1,2,4]triazolo[4,3-d][1,4]oxazepin-8-yl)benzamide, or a pharmaceutically acceptable salt thereof.

In one aspect, provided is a compound of formula (IA), wherein the compound has one or more of the following features:

(I) Ring A is:
  (i) a triazole;
  (ii) a tetrazole; or
  (iii) an imidazole optionally substituted with halo or $C_1$-$C_6$ alkyl;
(II) Ring B is phenyl;
(III) $L^2$ is —C(O)—NH—;
(IV) $R^1$ is:

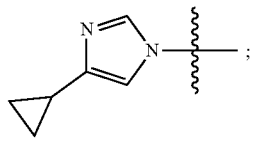 [SMILES: *n1cnc(C2CC2)c1]

;

(V) $X^1$ is:
  (iv) N; or
  (v) C—F;
(VI) $X^2$ is CH;
(VII) $X^3$ is $CR^2$, wherein $R^2$ is:
  (vi) H;
  (vii) $C_1$-$C_6$ alkyl;
  (viii) 4- to 7-membered heterocyclyl optionally substituted by 1-2 substituents selected from the group consisting of $C_1$-$C_6$ alkyl and hydroxyl;
  (ix) —N($C_1$-$C_6$ alkyl)$_2$;
  (x) —O—($C_1$-$C_6$ alkyl);
(VIII) $L^1$ is:

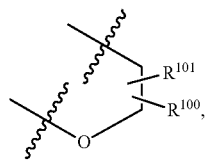

wherein $R^{100}$ and $R^{101}$ are independently H; $C_1$-$C_6$ alkyl or $C_3$-$C_6$ cycloalkyl, each of which is optionally substituted by one or more of halo, $C_1$-$C_6$ alkyl, or hydroxyl; or $R^{100}$ and $R^{101}$ together with the carbon atom or carbon atoms they are attached to form a $C_3$-$C_5$ cycloalkyl.

In one variation, (I) applies. In one variation, (II) applies. In one variation, (III) applies. In one variation, (IV) applies. In one variation, (V) applies. In one variation, (VI) applies. In one variation, (VII) applies. In one variation, (VIII) applies. In one aspect of this variation, (I), (II), (III), (IV), (V), (VI), (VII), and (VIII) apply. In one variation, (i), (v), and (vii) apply. In one variation, (ii), (v), and (vii) apply. In one variation, (iii), (v), and (vii) apply. In one variation, (i), (iv), and (viii) apply. In one variation, (ii), (iv), and (vi) apply. In one variation, (i), (iv), and (vi) apply. In one variation, (ii), (iv), and (viii) apply. In one variation, (ii), (iv), and (ix) apply. In one variation, (ii), (iv), and (x) apply. In one variation, (ii), (iv), and (ix) apply. In one variation, (i), (iv), and (x) apply.

In another aspect, provided herein are compounds selected from Table 1.

TABLE 1

| Example | Structure |
| --- | --- |
| 1 | ![structure] $C_{25}H_{23}FN_6O_2$ |
| 2 | ![structure] $C_{25}H_{23}FN_6O_2$ |
| 3 | ![structure] $C_{24}H_{22}FN_7O_2$ |
| 4 | ![structure] $C_{22}H_{20}N_8O_2$ |
| 5 | ![structure] $C_{24}H_{22}FN_7O_2$ |

TABLE 1-continued
| Example | Structure |
|---|---|
| 6 | 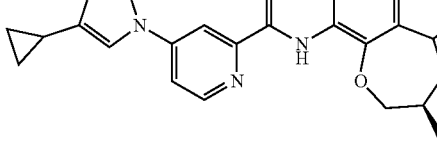 C₂₂H₂₀N₈O₂ |
| 7 | C₂₄H₂₁FN₆O₂ |
| 8 | C₂₇H₂₅FN₆O₂ |
| 9 | C₂₆H₂₅FN₆O₂ |
| 10 | C₂₆H₂₃FN₆O₂ |
| 11 | C₂₃H₂₁N₇O₂ |
| 12 | 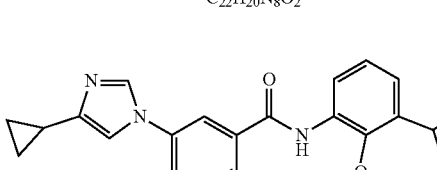 C₂₆H₂₄FN₇O₂ |
| 13 | C₂₅H₂₄FN₇O₂ |
| 14 | C₂₅H₂₂FN₇O₂ |
| 15 | C₂₃H₂₁N₇O₃ |
| 16 | C₂₅H₂₃FN₆O₃ |
| 17 | C₂₄H₂₂FN₇O₃ |

TABLE 1-continued

| Example | Structure |
|---|---|
| 18 | C₂₂H₂₀N₈O₃ |
| 19 | C₂₆H₂₇N₉O₃ |
| 20 | C₂₇H₂₇N₉O₃ |
| 21 | C₂₅H₂₅N₉O₃ |
| 22 | C₂₆H₂₇N₉O₃ |
| 23 | C₂₄H₂₂FN₇O₃ |
| 24 | C₂₂H₂₀N₈O₃ |
| 25 | C₂₈H₂₈N₈O₃ |
| 26 | C₂₄H₂₁F₂N₇O₂ |
| 27 | C₂₂H₁₉FN₈O₂ |
| 28 | C₂₅H₂₂F₂N₆O₂ |
| 29 | C₂₃H₂₀FN₇O₂ |

TABLE 1-continued
| Example | Structure |
|---|---|
| 30 | 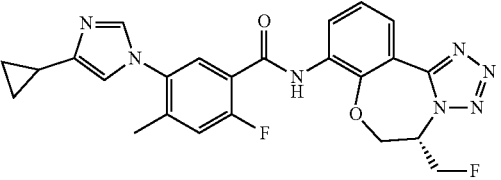 C24H21F2N7O2 |
| 31 | 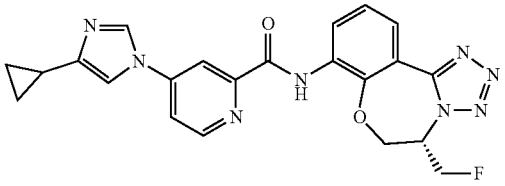 C22H19FN8O2 |
| 32 | 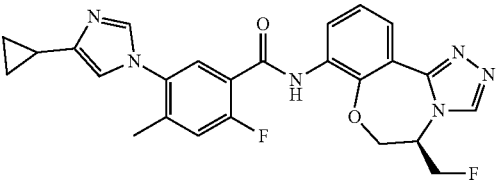 C25H22F2N6O2 |
| 33 | 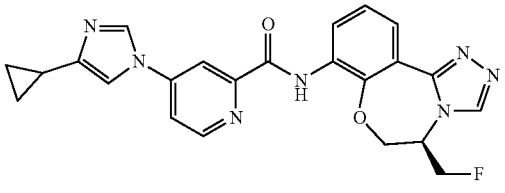 C23H20FN7O2 |
| 34 | 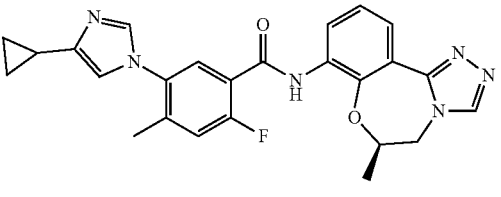 C25H23FN6O2 |
| 35 | 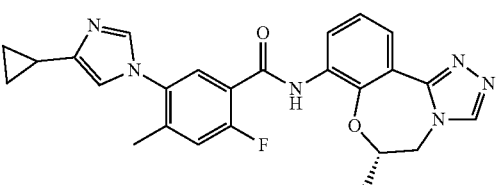 C25H23FN6O2 |
| 36 | 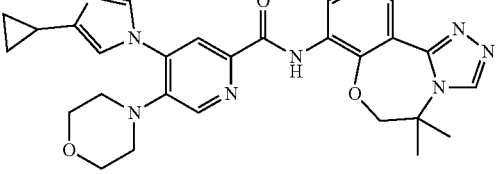 C28H30N8O3 |
| 37 | 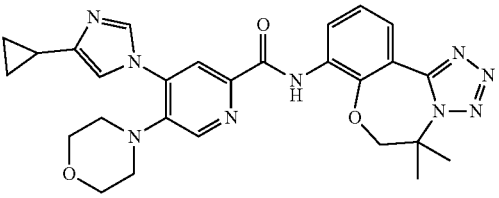 C27H29N9O3 |
| 38 | 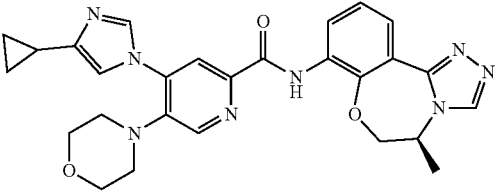 C27H28N8O3 |
| 39 | 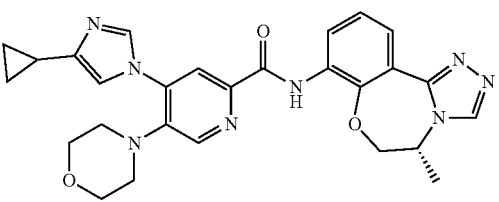 C27H28N8O3 |
| 40 | 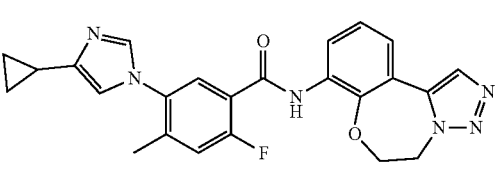 C24H21FN6O2 |
| 41 | 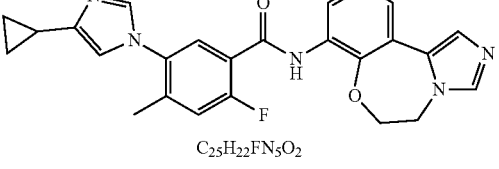 C25H22FN5O2 |
| 42 | 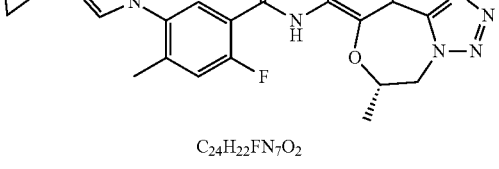 C24H22FN7O2 |

TABLE 1-continued
| Example | Structure |
|---|---|
| 43 | 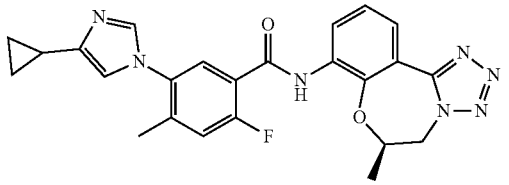<br>C$_{24}$H$_{22}$FN$_7$O$_2$ |
| 44 | 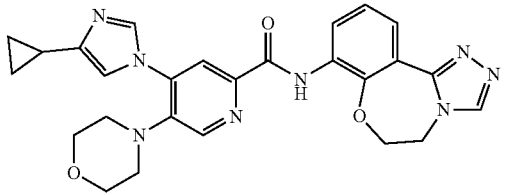<br>C$_{26}$H$_{26}$N$_8$O$_3$ |
| 45 | 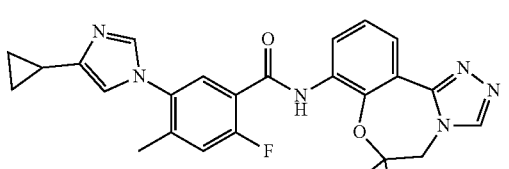<br>C$_{26}$H$_{23}$FN$_6$O$_2$ |
| 46 | 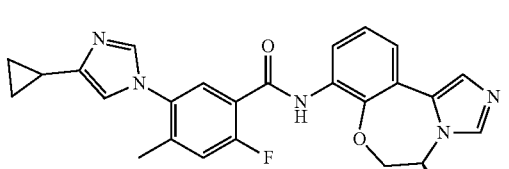<br>C$_{26}$H$_{24}$FN$_5$O$_2$ |
| 47 | 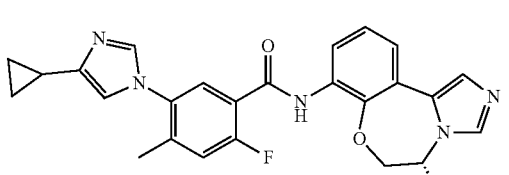<br>C$_{26}$H$_{24}$FN$_5$O$_2$ |
| 48 | 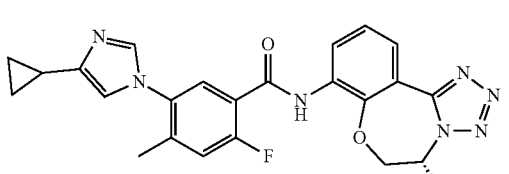<br>C$_{25}$H$_{24}$FN$_7$O$_3$ |
| 49 | 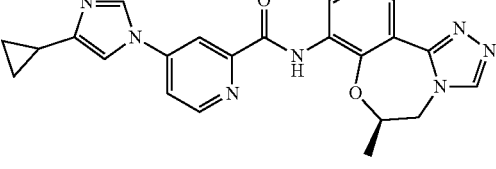<br>C$_{22}$H$_{20}$N$_8$O$_2$ |
| 50 | <br>C$_{21}$H$_{18}$N$_8$O$_2$ |
| 51 | 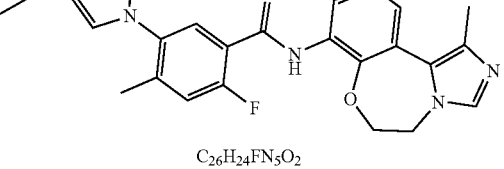<br>C$_{26}$H$_{24}$FN$_5$O$_2$ |
| 52 | 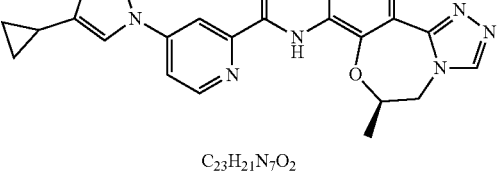<br>C$_{23}$H$_{21}$N$_7$O$_2$ |
| 53 | 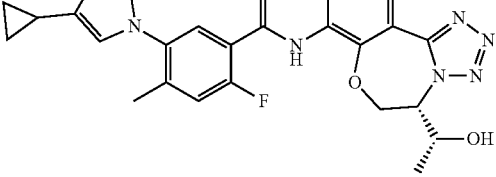<br>C$_{25}$H$_{24}$FN$_7$O$_3$ |
| 54 | 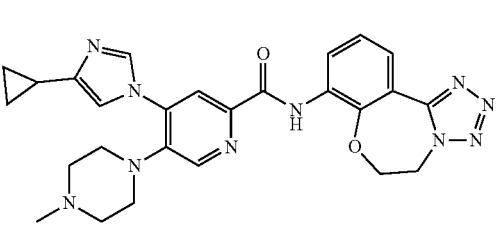<br>C$_{26}$H$_{28}$N$_{10}$O$_2$ |

TABLE 1-continued
| Example | Structure |
|---|---|
| 55 | 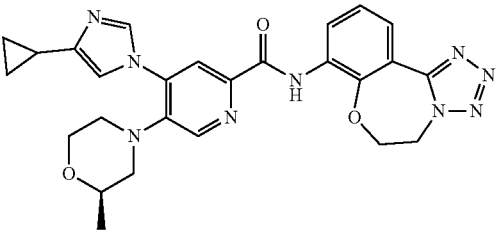 C26H27N9O3 |
| 56 | 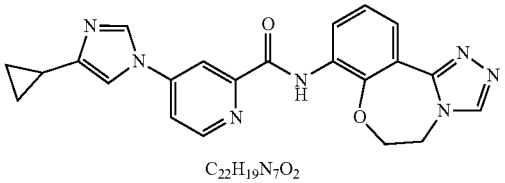 C22H19N7O2 |
| 57 | 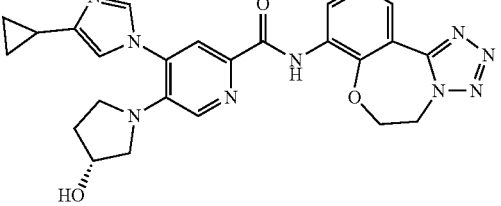 C25H25N9O3 |
| 58 | 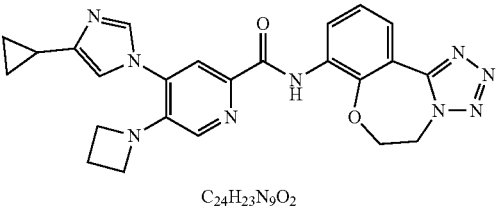 C24H23N9O2 |
| 59 | 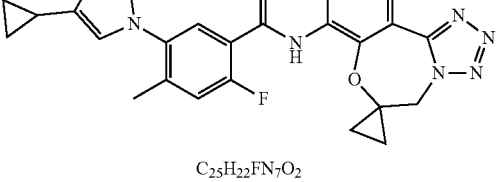 C25H22FN7O2 |
| 60 | 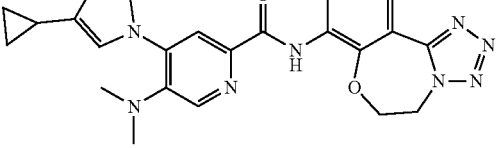 C23H23N9O2 |
| 61 | 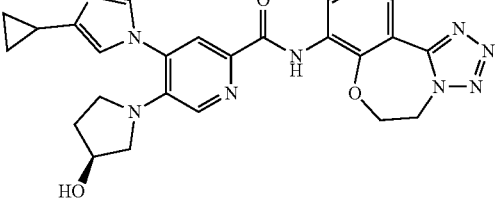 C25H25N9O3 |
| 62 | 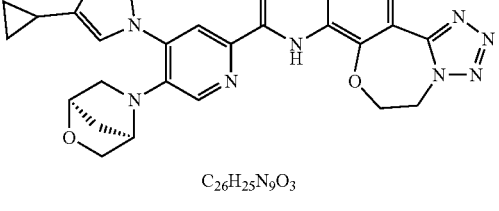 C26H25N9O3 |
| 63 | 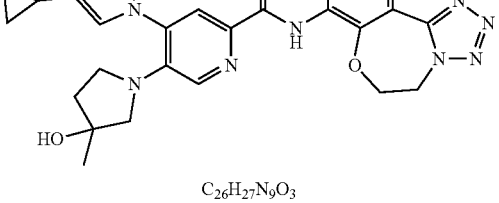 C26H27N9O3 |
| 64 | 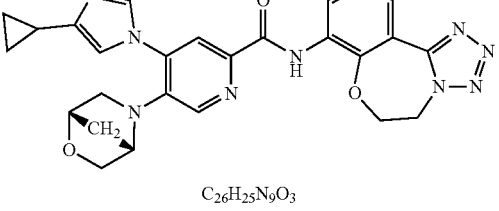 C26H25N9O3 |
| 65 | 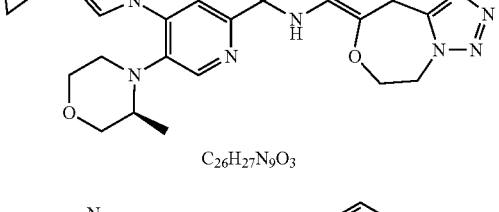 C26H27N9O3 |
| 66 | 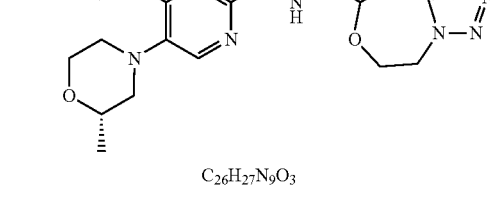 C26H27N9O3 |

TABLE 1-continued

| Example | Structure |
|---|---|
| 67 | $C_{25}H_{25}N_9O_3$ |
| 68 | $C_{24}H_{24}N_8O_3$ |
| 69 | $C_{25}H_{26}N_8O_3$ |
| 70 | $C_{26}H_{27}N_9O_3$ |
| 71 | $C_{25}H_{26}N_8O_3$ |
| 72 | $C_{26}H_{24}FN_7O_2$ |
| 73 | $C_{25}H_{25}N_7O_3$ |
| 74 | $C_{25}H_{21}BrFN_5O_2$ |
| 75 | $C_{27}H_{29}N_9O_3$ |
| 76 | $C_{27}H_{29}N_9O_3$ |
| 77 | $C_{26}H_{27}N_9O_3$ |
| 78 | $C_{26}H_{27}N_9O_3$ |

US 10,919,911 B2

TABLE 1-continued

| Example | Structure |
|---|---|
| 79 | 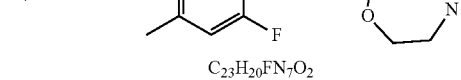<br>C₂₃H₂₀FN₇O₂ |
| 80 | C₂₃H₂₁N₇O₂ |
| 81 | C₂₅H₂₃FN₆O₃ |
| 82 | C₂₅H₂₃FN₆O₂ |
| 83 | C₂₄H₂₂FN₇O₂ |
| 84 | C₂₄H₂₂FN₇O₂ |
| 85 | C₂₄H₂₂FN₇O₂ |

TABLE 1-continued

| Example | Structure |
|---|---|
| 86 | C₂₅H₂₃FN₆O₃ |
| 87 | C₂₆H₂₄FN₅O₂ | or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding. In some embodiments, provided herein are compounds selected from Table 1 or a pharmaceutically acceptable salt thereof.

Methods of Synthesis

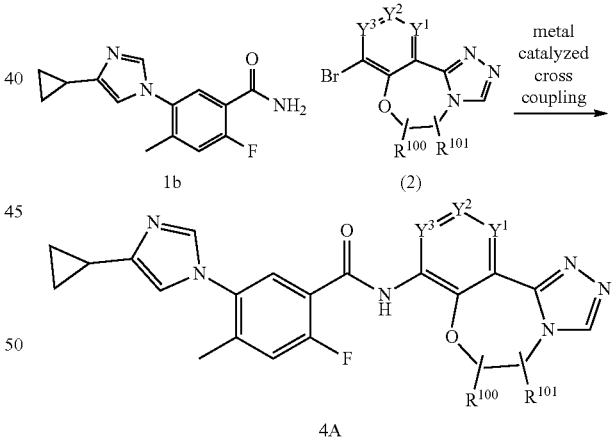

Reaction Scheme I wherein $Y^1$, $Y^2$, $Y^3$, $R^{100}$, and $R^{101}$ are as defined herein for any embodiment or variation of the compound of formula (IA).

Reaction Scheme I shows the synthesis of compounds of general formula 4A. Coupling of compound 1b with compounds of formula (2) using a metal catalyst, for example a palladium-based catalyst such as Pd₂(dba)₃ with Xantphos and a base such as t-BuOK in an aprotic solvent such as dioxane under elevated temperature, provides compounds of general formula 4A which can be isolated by conventional means.

Scheme IA

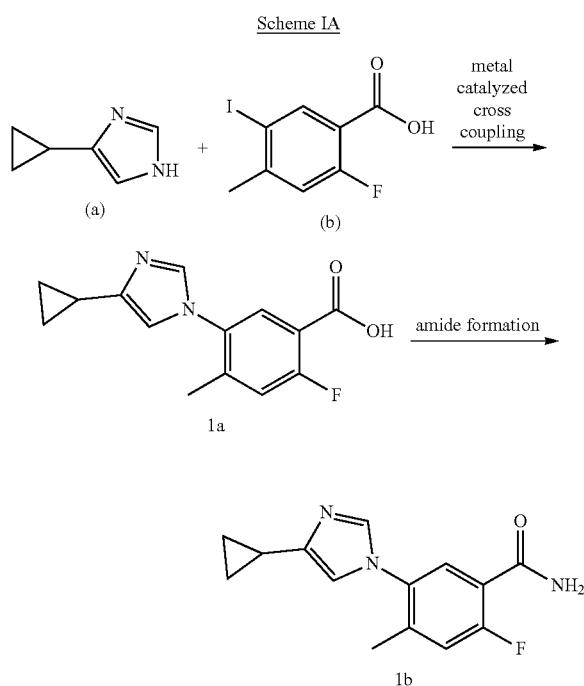

Scheme 1A outlines a synthesis of compound 1b. Metal-catalyzed cross-coupling, for example with $Cu_2O$, $CsCO_3$ and 8-hydroxyquinoline in a solvent such as DMSO, of compounds (a) and (b) under elevated temperature affords compound 1a. Subsequent treatment of 1a under conditions such as reaction of compound 1a with thionyl chloride followed by ammonia affords compound 1b. Compounds 1a and 1b can be isolated by conventional means.

Scheme IB

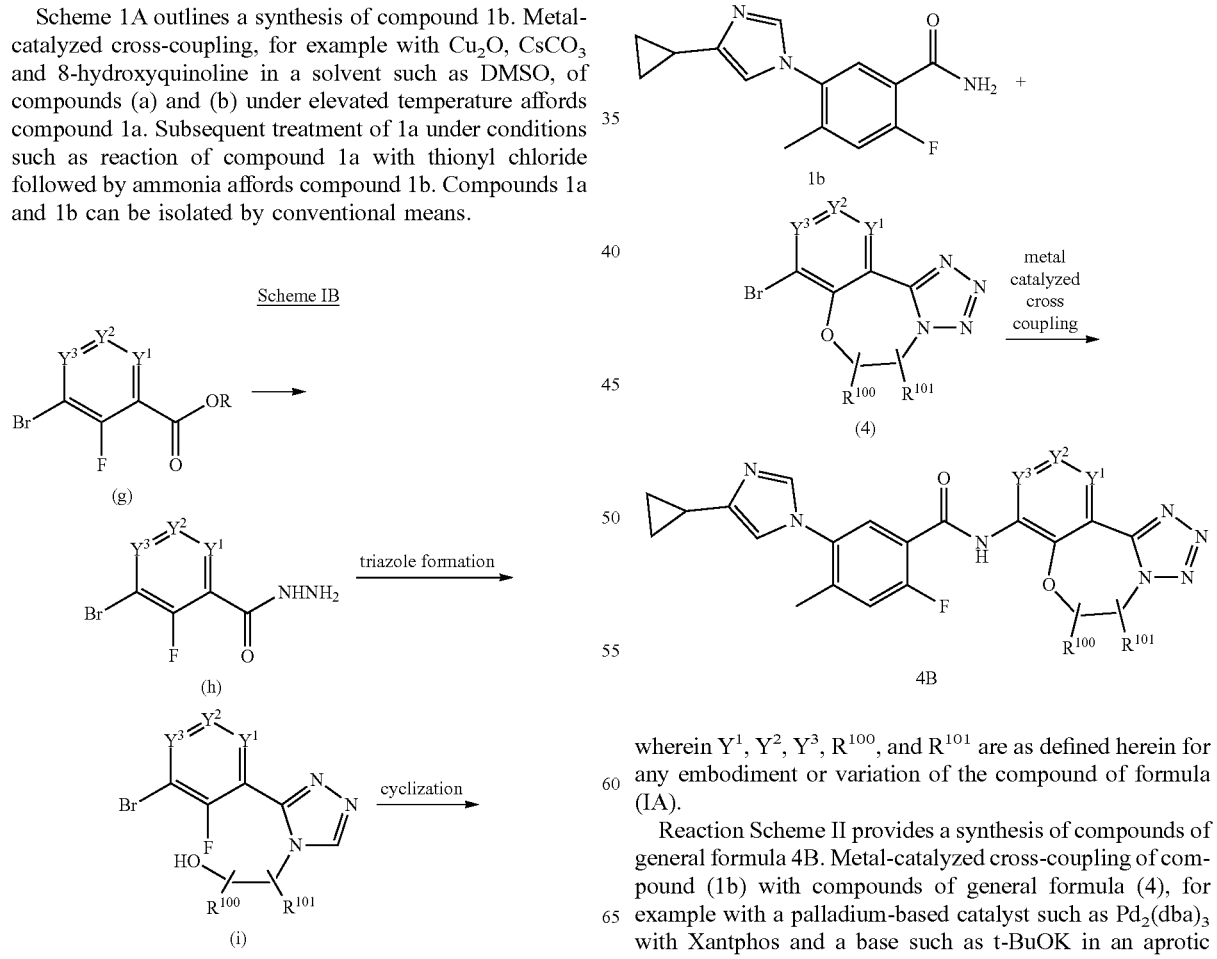

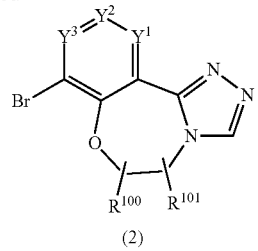

wherein $Y^1$, $Y^2$, $Y^3$, $R^{100}$, and $R^{101}$ are as defined herein for any embodiment or variation of the compound of formula (IA), and R is an alkyl group such as a methyl group.

Scheme 1B shows a synthesis of compounds of general formula (2). Esters of general formula (g) are reacted with hydrazine in a solvent, for example methanol, to form compounds of formula (h). Subsequent conversion of the compounds of formula (g) to triazoles of formula (i), for example by treating (g) stepwise with DMF-DMA and then condensation with optionally substituted ethyl amine under elevated temperature, followed by intramolecular cyclization of (i) with treatment of a base such as NaH in an inert solvent affords compounds of formula (2) which can be isolated by conventional means.

Reaction Scheme II wherein $Y^1$, $Y^2$, $Y^3$, $R^{100}$, and $R^{101}$ are as defined herein for any embodiment or variation of the compound of formula (IA).

Reaction Scheme II provides a synthesis of compounds of general formula 4B. Metal-catalyzed cross-coupling of compound (1b) with compounds of general formula (4), for example with a palladium-based catalyst such as $Pd_2(dba)_3$ with Xantphos and a base such as t-BuOK in an aprotic solvent such as dioxane under elevated temperature, provides compounds of general formula 4B which can be isolated by conventional means.

Scheme IIA

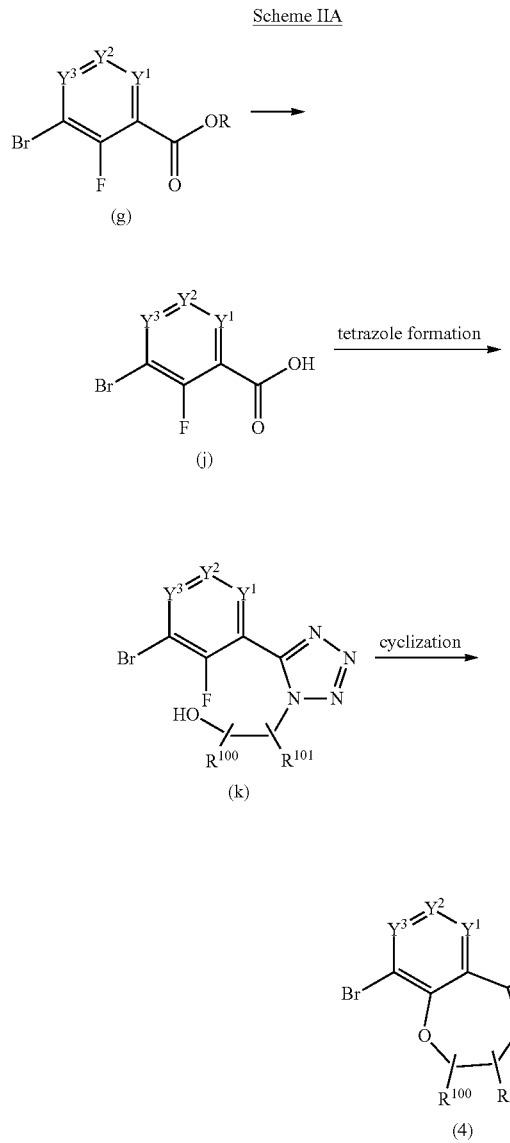

wherein $Y^1$, $Y^2$, $Y^3$, $R^{100}$, and $R^{101}$ are as defined herein for any embodiment or variation of the compound of formula (IA), and R is an alkyl group such as a methyl group.

Scheme IIA provides a general synthesis for compounds of general formula (4). Esters of formula (g) are converted to carboxylic acids of formula (j), for example by ester hydrolysis with a base such as LiOH in the presence of $H_2O$, which are then converted to tetrazoles of formula (k), for example by treatment of (j) with oxalyl chloride with a catalytic amount of DMF in an inert solvent such as DCM, to form acid chloride intermediates. The intermediates then react with optionally substituted ethyl amines followed by reaction with an azide such as $NaN_3$ or $TMSN_3$. Subsequent intramolecular cyclization of (k), for example with a base such as NaH in an inert solvent such as THF, affords compounds of formula (4) which can be isolated by conventional methods.

Reaction Scheme III

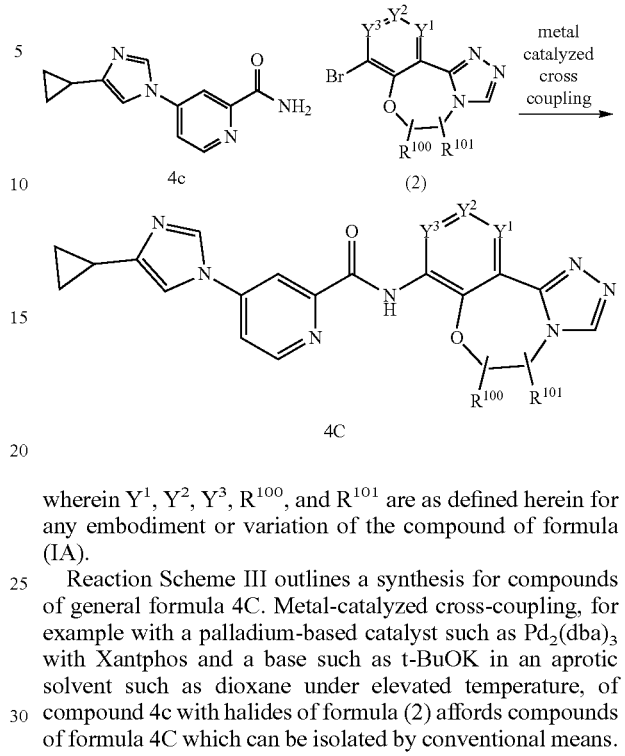

wherein $Y^1$, $Y^2$, $Y^3$, $R^{100}$, and $R^{101}$ are as defined herein for any embodiment or variation of the compound of formula (IA).

Reaction Scheme III outlines a synthesis for compounds of general formula 4C. Metal-catalyzed cross-coupling, for example with a palladium-based catalyst such as $Pd_2(dba)_3$ with Xantphos and a base such as t-BuOK in an aprotic solvent such as dioxane under elevated temperature, of compound 4c with halides of formula (2) affords compounds of formula 4C which can be isolated by conventional means.

Scheme IIIA

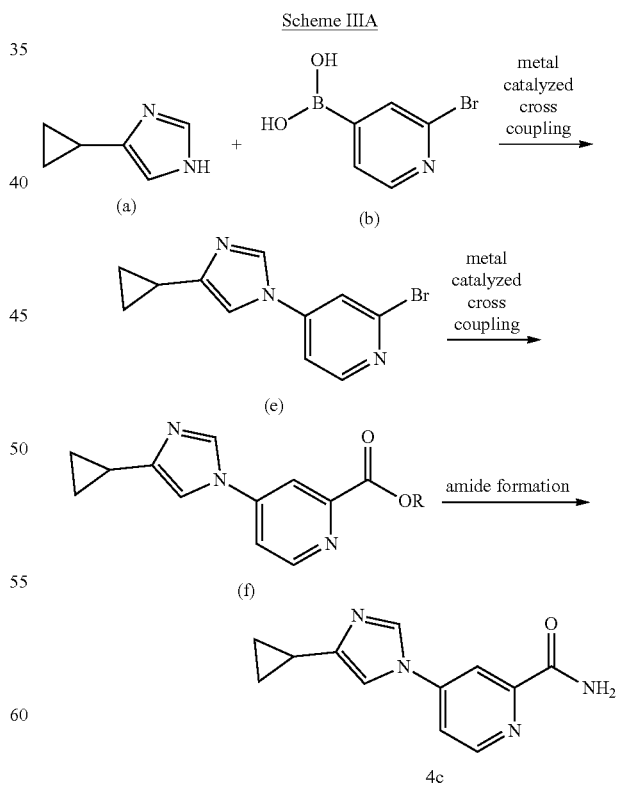

Scheme IIIA outlines a synthesis of compound (4c). Metal-catalyzed cross-coupling, for example with $Cu_2O$ in a solvent such as MeOH under $O_2$, of (a) and (d) affords compound (e) which can be isolated by conventional methods. A second metal-catalyzed cross-coupling reaction, for example with Pd(OAc)$_2$ and DPPF in MeOH with CO, converts compound (e) to compound (f), which is then converted to 4c under conditions such as NH$_3$.H$_2$O in a solvent such as MeOH.

Reaction Scheme IV

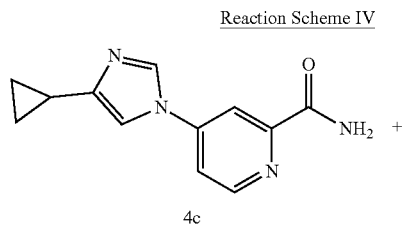

4c

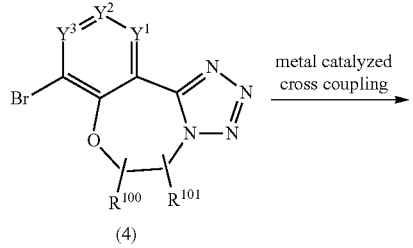

(4)

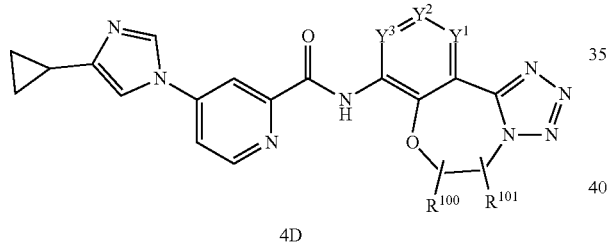

4D wherein Y$^1$, Y$^2$, Y$^3$, R$^{100}$, and R$^{101}$ are as defined herein for any embodiment or variation of the compound of formula (IA).

Reaction Scheme IV shows a general synthesis for compounds of formula 4D. Metal-catalyzed cross-coupling, for example with a palladium-based catalyst such as Pd$_2$(dba)$_3$ with Xantphos and a base such as t-BuOK in an aprotic solvent such as dioxane under elevated temperature, of compound 4c with compounds of formula (4) yields compounds of formula 4D which can be isolated by conventional means.

Reaction Scheme V

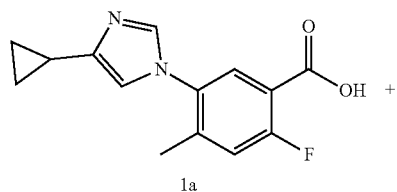

1a

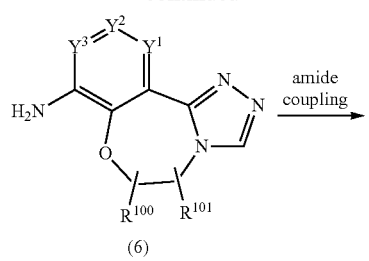

(6)

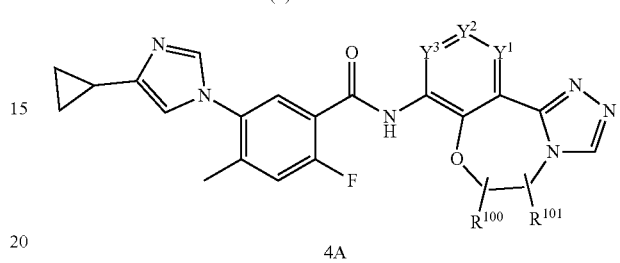

4A wherein Y$^1$, Y$^2$, Y$^3$, R$^{100}$, and R$^{101}$ are as defined herein for any embodiment or variation of the compound of formula (IA).

Reaction Scheme V shows an alternative general synthesis for compounds of formula 4A. Amide coupling, for example using coupling reagents such as HATU with a base such as NMM in solvents such as DMF, of 1a with compounds of formula (6) yields compounds of formula 4A.

Scheme VA

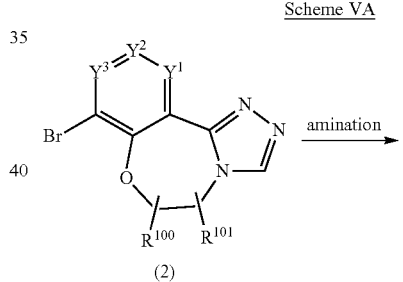

(2)

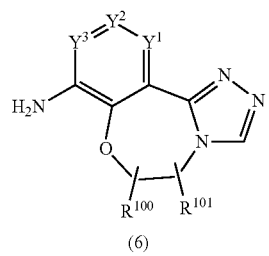

(6)

wherein Y$_1$, Y$^2$, Y$^3$, R$^{101}$, and R$^{101}$ are as defined herein for any embodiment or variation of the compound of formula (IA).

Scheme VA outlines a synthesis of compounds of general formula (6). Amination of compounds of general formula (2), for example with CuI, L-proline and NH$_3$.H$_2$O in a solvent such as DMSO under elevated temperature, affords (6) which can be isolated by conventional means.

Scheme VB

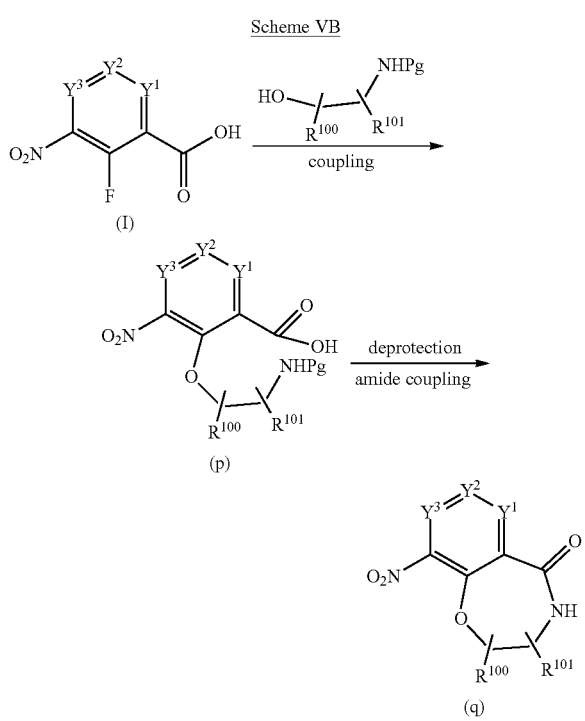

Scheme VC outlines an alternative synthesis of compounds of general formula (q). Acids of general formula (l) can form amide (t) by reaction with an optionally substituted amino alcohol under coupling conditions, for example with HATU and DIPEA in an aprotic solvent such as DMF. The resulting alcohol of general formula (t) can undergo intramolecular cyclization in the presence of a base such as t-BuOK to form compounds of general formula (q) which can be isolated by conventional means.

Scheme VD

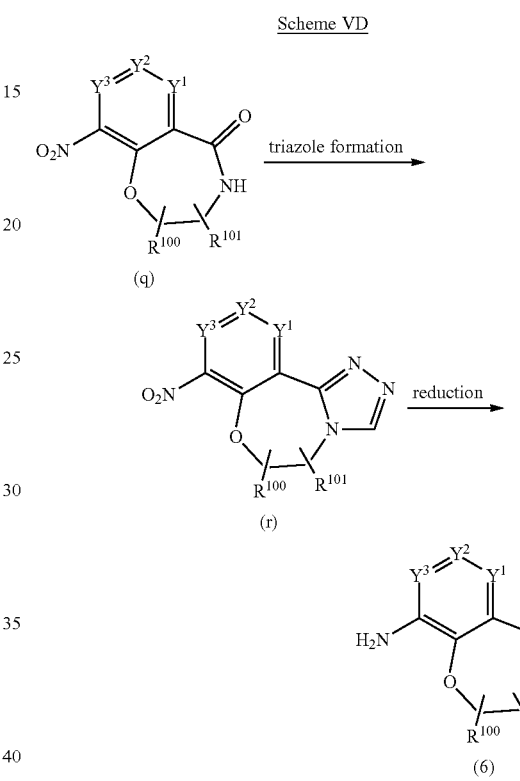

wherein $Y^1$, $Y^2$, $Y^3$, $R^{100}$, and $R^{101}$ are as defined herein for any embodiment or variation of the compound of formula (IA), and Pg is a suitable protecting group.

Scheme VB outlines a synthesis of compounds of general formula (q). Acids of general formula (l) can be treated with a base such as NaH in an aprotic solvent such as DME and an optionally substituted N-protected amino alcohol to form compounds of general formula (p). After deprotection of (p), a lactam forms through intramolecular amide bond formation with coupling reagents such as HATU with NMM in an aprotic solvent such as DMF to form compounds of general formula (q).

Scheme VC

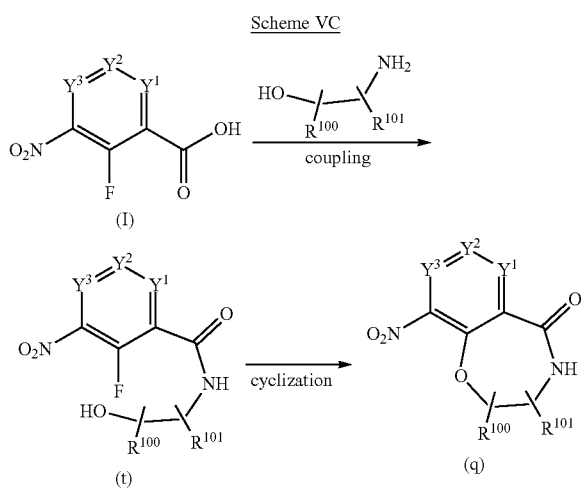

wherein $Y^1$, $Y^2$, $Y^3$, $R^{100}$, and $R^{101}$ are as defined herein for any embodiment or variation of the compound of formula (IA).

wherein $Y^1$, $Y^2$, $Y^3$, $R^{100}$, and $R^{101}$ are as defined herein for any embodiment or variation of the compound of formula (IA).

Scheme VD outlines an alternative synthesis of compounds of general formula (6). Compounds of general formula (q) can be transformed to triazole (r) through activation using reagents such as $PCl_5$ followed by cyclization with reagents such as formohydrazide under elevated temperature. Reduction of (r) with reducing agents such as Fe, $NH_4Cl$ or $H_2$ in the presence of a catalyst such as Pd/C affords compounds of general formula (6) which can be isolated by conventional methods.

Reaction Scheme VI

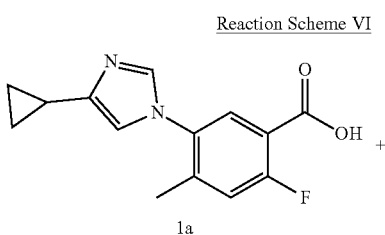

1a

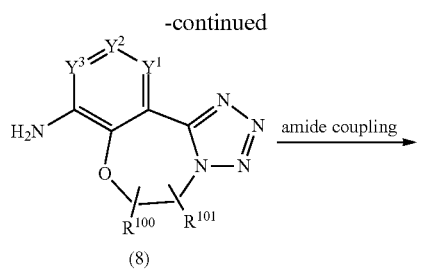

(8)

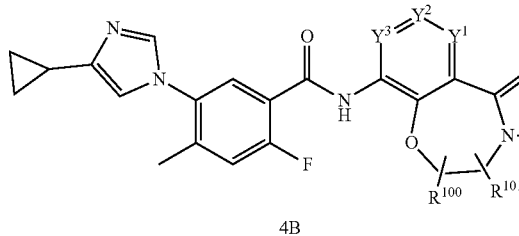

4B wherein $Y^1$, $Y^2$, $Y^3$, $R^{100}$, and $R^{101}$ are as defined herein for any embodiment or variation of the compound of formula (IA).

Reaction Scheme VI shows an alternative general synthesis for compounds of formula 4B. Amide coupling, for example using coupling reagents such as HATU with a base such as NMM in a solvent such as DMF, of 1a with compounds of formula (8) yields compounds of formula 4B.

Scheme VIA

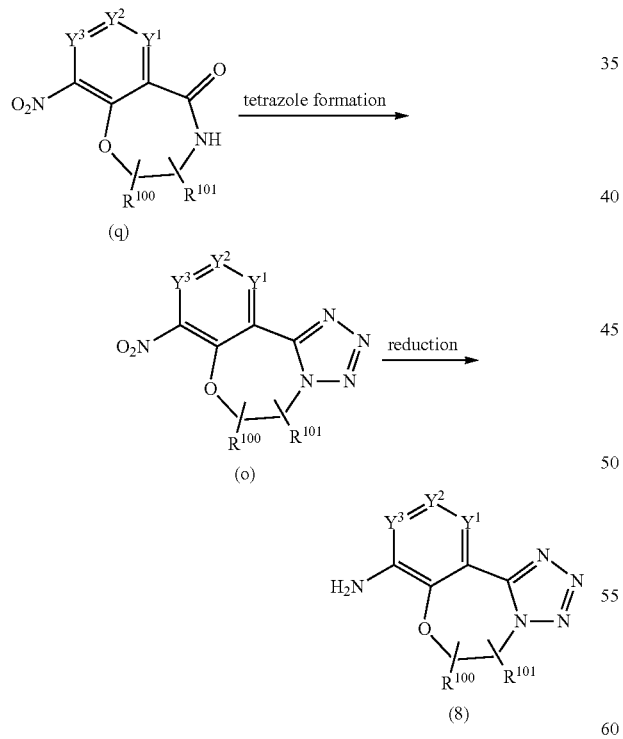

wherein $Y^1$, $Y^2$, $Y^3$, $R^{100}$, and $R^{101}$ are as defined herein for any embodiment or variation of the compound of formula (IA).

Scheme VIA outlines the synthesis of compounds of general formula (8). Compounds of general formula (q) can be transformed to tetrazole (o) through activation with reagents such as $PCl_5$ or Lawesson's reagent followed by cyclization with reagents such as $NaN_3$ or $TMSN_3$. Reduction of (o) with reducing agents such as Fe, $NH_4Cl$ or $H_2$ in the presence of a catalyst such as Pd/C affords compounds of general formula (8) which can be isolated by conventional methods.

Scheme VIB

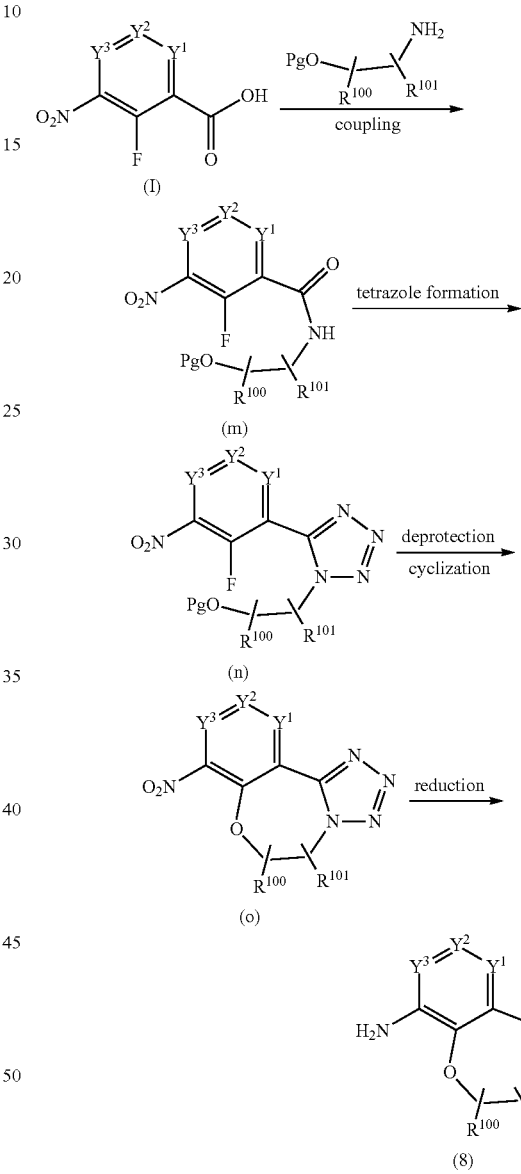

wherein $Y^1$, $Y^2$, $Y^3$, $R^{100}$, and $R^{101}$ are as defined herein for any embodiment or variation of the compound of formula (IA), and Pg is a suitable protecting group.

Scheme VIB shows an alternative synthesis of compounds of general formula (8). Acids of general formula (l) react with an optionally substituted O-protected amino alcohol using amide coupling reagents such as HATU with a base such as DIPEA in an aprotic solvent such as DMF to afford compounds of general formula (m). Using similar reactions as outlined above for conversion of (q) to (o) (Scheme VIA), (m) can be transformed to tetrazole (n). After deprotection of (n), intramolecular cyclization can occur spontaneously or by use of a base such as NaH or t-BuOK. Compounds of general formula (o) can be reduced to (8) in the same manner as shown in Scheme VIA.

Reaction Scheme VII

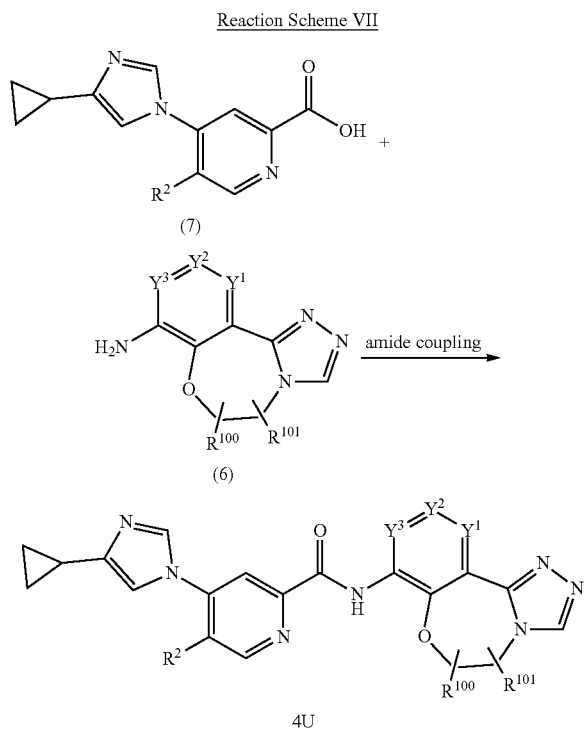

(7)

(6)

4U wherein $Y^1$, $Y^2$, $Y^3$, $R^2$, $R^{100}$, and $R^{101}$ are as defined herein for any embodiment or variation of the compound of formula (IA).

Scheme VII shows a synthesis of compounds of general formula 4U. Compounds of formula 4U can be assembled from acid (7) and amine (6) through amide coupling, for example with HATU, NMM in DMF.

Scheme VIIA

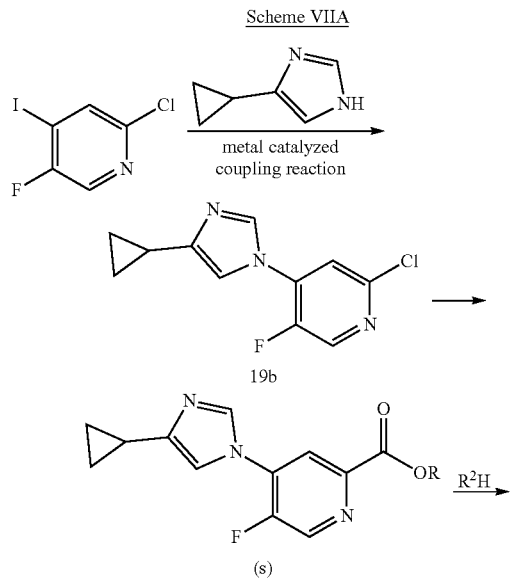

19b (s)

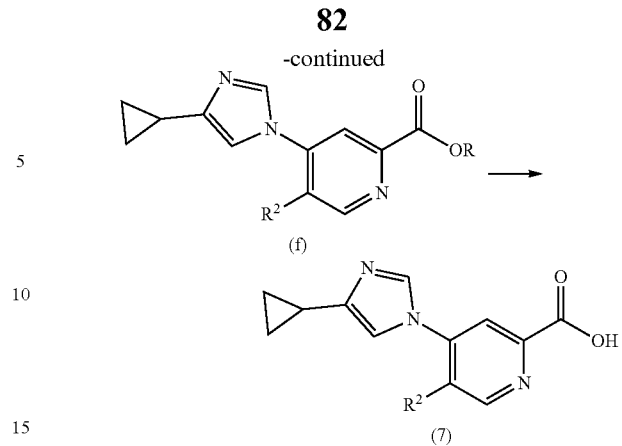

(f)

(7)

wherein R is a suitable protecting group, and $R^2$ is defined herein for any embodiment or variation of the compound of formula (IA).

Scheme VIIA shows a synthesis of compounds of general formula (7). 2-chloro-5-fluoro-4-iodopyridine reacts with 4-cyclopropyl-1H-imidazole under cross coupling conditions, for example with $Cu_2O$, $Cs_2CO_3$, and 8-hydroxyquinoline in PEG-3350 and butyronitrile under elevated temperature, to afford 19b. Compound 19b can be converted to esters of general formula (s) using, for example, $Pd(dppf)Cl_2$ and CO under elevated temperature. Compounds of general formula (s) react with $R^2H$, for example amines or alcohols, under elevated temperature to afford (f). Ester (f) can be transformed to acid (7) by reagents such as LiOH in the presence of $H_2O$.

Reaction Scheme VIII

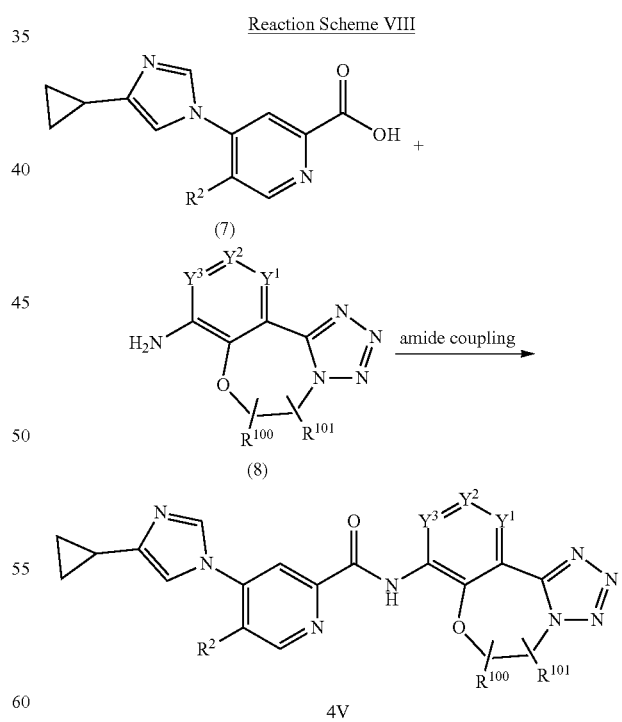

(7)

(8)

4V wherein $Y^1$, $Y^2$, $Y^3$, $R^2$, $R^{100}$, and $R^{101}$ are as defined herein for any embodiment or variation of the compound of formula (IA).

Reaction Scheme VIII shows a synthesis of compounds of general formula 4V. Compounds of formula 4V can be assembled from acid (7) and amine (8) through amide coupling, for example with HATU, NMM in DMF.

Reaction Scheme IX

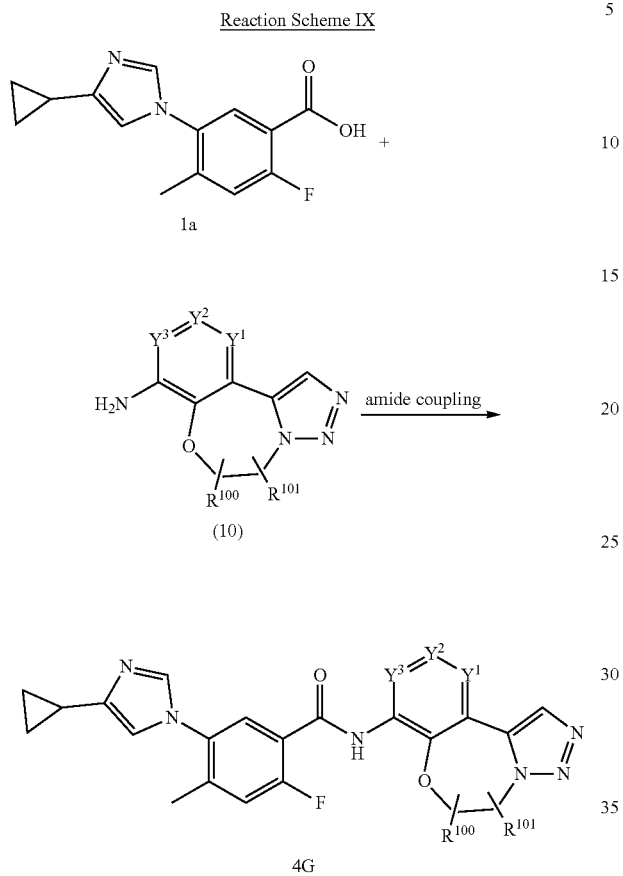

(10)

4G wherein $Y^1$, $Y^2$, $Y^3$, $R^{100}$, and $R^{101}$ are as defined herein for any embodiment or variation of the compound of formula (IA).

Reaction Scheme IX shows a synthesis of compounds of general formula 4G. Compounds of formula 4G can be assembled from 1a and amine (10) through amide coupling, for example with HATU, NMM in DMF.

Scheme IXA

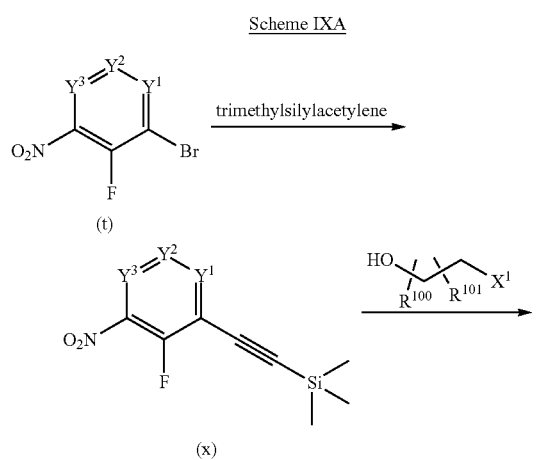

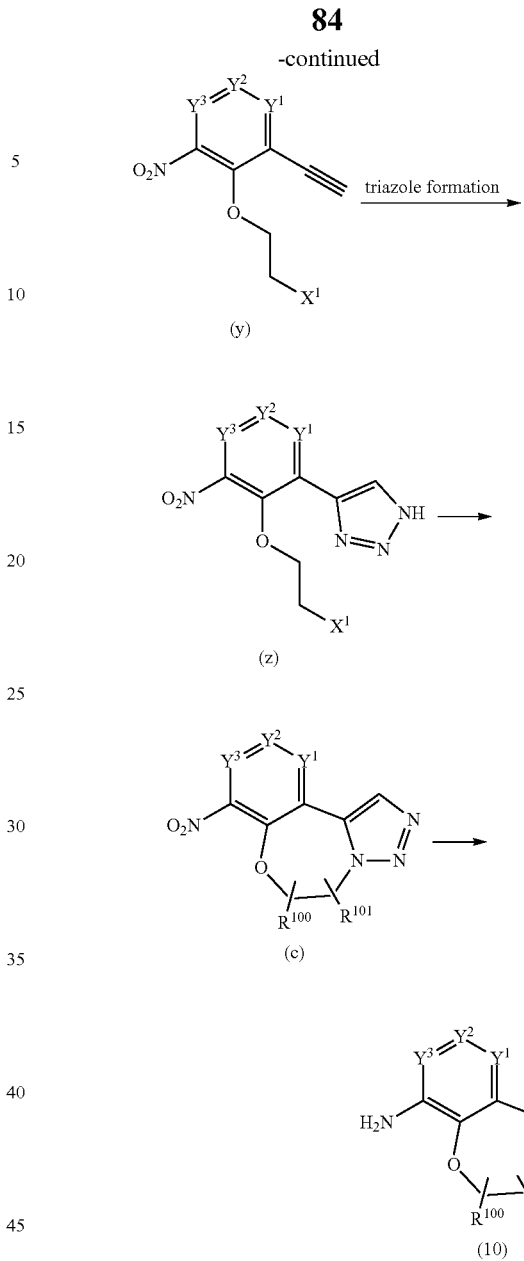

(10)

wherein $Y^1$, $Y^2$, $Y^3$, $R^{100}$, and $R^{100}$ are as defined herein for any embodiment or variation of the compound of formula (IA), and $X^1$ is a suitable leaving group.

Scheme IXA shows a synthesis of compounds of general formula (10). Compounds of general formula (t) can undergo a coupling reaction with trimethylsilylacetylene using reagents such as $Pd(PPh_3)_2Cl_2$, CuI and TEA to afford (x). Compounds of formula (x) can react with an optionally substituted alcohol to afford compounds of general formula (y), followed by triazole formation using reagents such as CuI, $TMSN_3$ in solvents such as MeOH and DMF under elevated temperature to make trizoles of general formula (z), where $X^1$ is a suitable leaving group such as Cl. Intramolecular cyclization of (z) in the presence of a base, for example $K_2CO_3$ in a solvent such as DMF under elevated temperature, affords compounds of general formula (c), which can be reduced to compounds of general formula (10) in a similar manner as outlined above for (o) to (8).

Reaction Scheme X

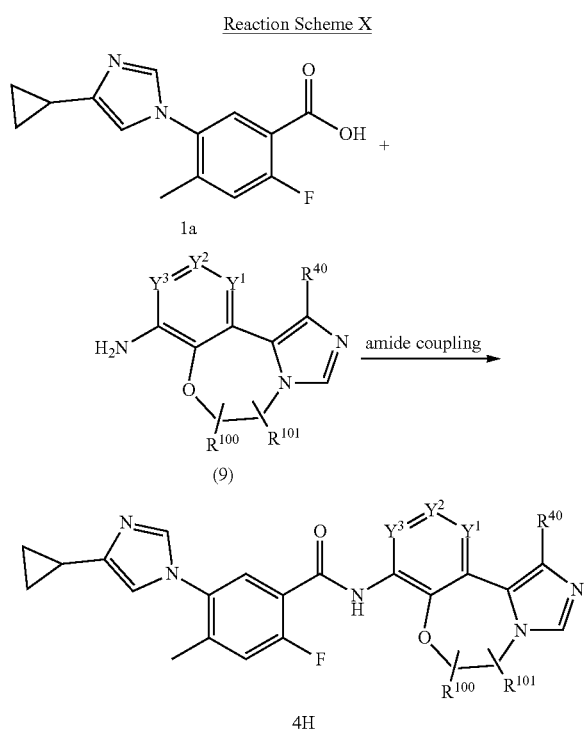

4H wherein $Y^1$, $Y^2$, $Y^3$, $R^{100}$, $R^{101}$, and $R^{40}$ are as defined herein for any embodiment or variation of the compound of formula (IA).

Reaction Scheme X shows a synthesis of compounds of general formula 4H. Compounds of formula 4H can be assembled from acid 1a and amine (9) through amide coupling, for example with HATU, NMM in DMF.

Scheme XA

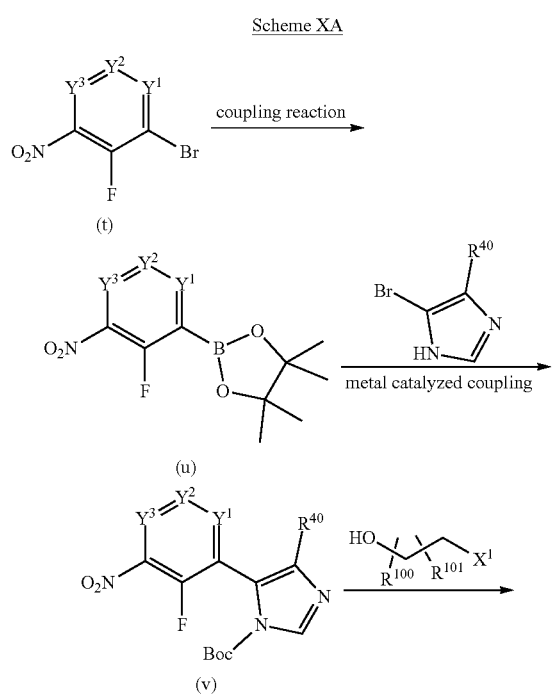

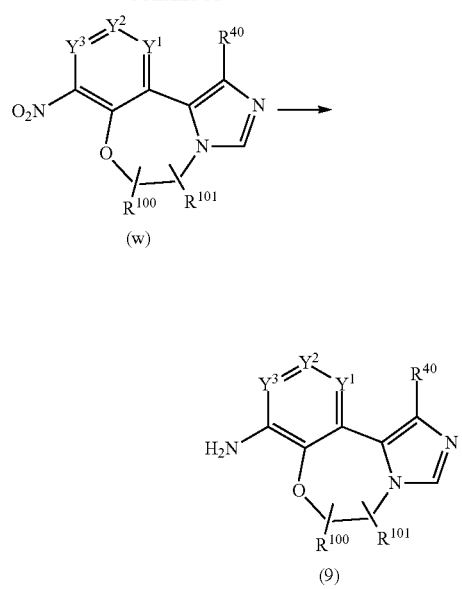

wherein $Y^1$, $Y^2$, $Y^3$, $R^{40}$, $R^{100}$, and $R^{101}$ are as defined herein for any embodiment or variation of the compound of formula (IA).

Scheme XA shows a synthesis of compounds of general formula (9). Compounds of general formula (t) can be coupled with 4,4,5,5-tetramethyl-2-(4,4,5,5-tetramethyl-1,3,2-dioxaborolan-2-yl)-1,3,2-dioxaborolane using reagents such as Pd(dppf)Cl$_2$ and KOAc under elevated temperature to afford compounds of general formula (u), which can then be coupled with optionally substituted imidazoles in the presence of Boc$_2$O and reagents such as Pd(dppf)Cl$_2$CH$_2$Cl$_2$ and KOAc to afford compounds of general formula (v). Compounds of general formula (v) can react with an optionally substituted alcohol in the presence of a base such as NaH to afford compounds of general formula (w). Compounds of formula (w) can be reduced to compounds of general formula (9) in a similar manner as outlined above for (o) to (8).

Reaction Scheme XI

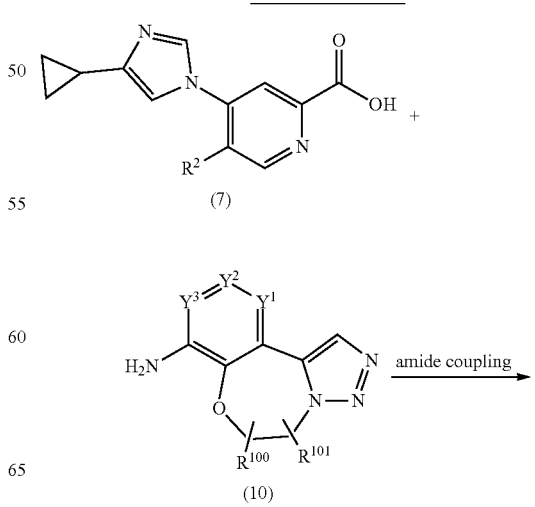

-continued

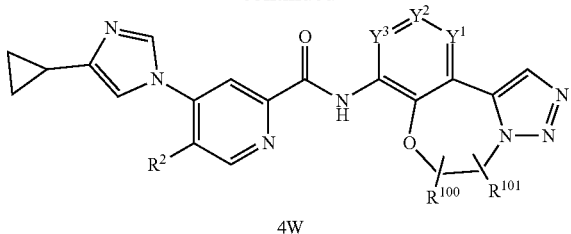

4W wherein $Y^1$, $Y^2$, $Y^3$, $R^2$, $R^{100}$, and $R^{101}$ are as defined herein for any embodiment or variation of the compound of formula (IA).

Reaction Scheme XI shows a synthesis of compounds of general formula 4W. Compounds of formula 4W can be assembled from acid (7) and amine (10) through amide coupling, for example with HATU, NMM in DMF.

Reaction Scheme XII

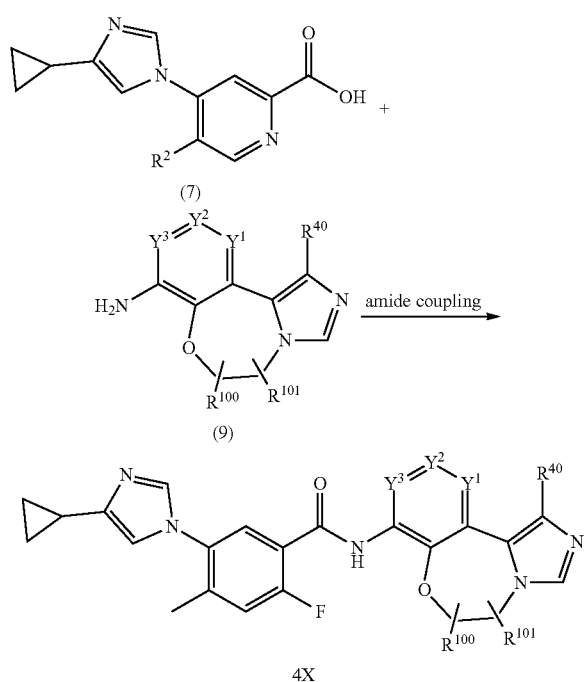

4X wherein $Y^1$, $Y^2$, $Y^3$, $R^2$, $R^{40}$, $R^{100}$, and $R^{101}$ are as defined herein for any embodiment or variation of the compound of formula (IA).

Reaction Scheme XII shows a synthesis of compounds of general formula 4X. Compounds of formula 4X can be assembled from acid (7) and amine (9) through amide coupling, for example with HATU, NMM in DMF.

Synthesis of certain compounds provided herein are schematically illustrated above, and provided in the Examples section below. Synthesis of other compounds provided herein will be apparent to the skilled artisan based on the guidance provided herein and based on synthetic methods well known to the skilled artisan.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization, and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein or a pharmaceutically acceptable salt thereof are also contemplated. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

It is understood that the synthetic process disclosed here may be modified to arrive at various compounds of the invention by selection of appropriate reagents and starting materials. It is also understood that where protection of certain active or incompatible groups (e.g., an amine or a carboxylic acid) is required, the formulae in e.g., the scheme(s) provided here intend and include compounds where such active or incompatible groups are in appropriate protected forms. For a general description of protecting groups and their use, see P. G. M. Wuts and T. W. Greene, Greene's Protective Groups in Organic Synthesis $4^{th}$ edition, Wiley-Interscience, New York, 2006.

This disclosure also includes all salts, such as pharmaceutically acceptable salts, of compounds referred to herein. This disclosure also includes any or all of the stereochemical forms, including any enantiomeric or diastereomeric forms, and any tautomers or other forms, such as N-oxides, solvates, prodrugs, or isotopomers, of the compounds described. Unless stereochemistry is explicitly indicated in a chemical structure or name, the structure or name is intended to embrace all possible stereoisomers of a compound depicted. In addition, where a specific stereochemical form is depicted, it is understood that other stereochemical forms are also embraced by the invention. All forms of the compounds are also embraced by the invention, such as crystalline or non-crystalline forms of the compounds. Compositions comprising a compound of the invention are also intended, such as a composition of substantially pure compound, including a specific stereochemical form thereof. Compositions comprising a mixture of compounds of the invention in any ratio are also embraced by the invention, including mixtures of two or more stereochemical forms of a compound of the invention in any ratio, such that racemic, non-racemic, enantioenriched and scalemic mixtures of a compound are embraced.

In the descriptions herein, it is understood that every description, variation, embodiment, or aspect of a moiety can be combined with every description, variation, embodiment, or aspect of other moieties the same as if each and every combination of descriptions is specifically and individually listed. For example, every description, variation, embodiment, or aspect provided herein with respect to $R^1$ of formula (IA) may be combined with every description, variation, embodiment, or aspect of ring A, ring B, $L^1$, $L^2$, $R^2$, $R^3$, $R^4$, $R^{11}$, $R^{12}$, $R^{40}$, $R^{100}$, $R^{101}$, $R^{200}$, $R^{201}$, $R^{202}$, $X^1$, $X^2$, and/or $X^3$ the same as if each and every combination were specifically and individually listed. It is also understood that all descriptions, variations, embodiments or aspects of formula (IA), where applicable, apply equally to other formulae detailed herein, and are equally described, the same as if each and every description, variation, embodiment or aspect were separately and individually listed for all formulae. For example, all descriptions, variations, embodiments, or aspects of formula (IA), where applicable, apply equally to any of formulae (IB), (IC), (ID), (IE), (IF), (IG), (IH), (2A), (2B), (2C), (2D), (2E), (2F), (2G), (2H), (3A), (3B), (3C), (3D), (3E), (3F), (3G), (3H), (3I), (3J), (3K), (3L), (3M), (3N), (3O), (3P), (3Q), (3R), (4A), (4B), (4C), (4D), (4E), (4F), (4G), (4H), (4I), (4J), (4K), (4L), (4M), (4N), (4O), (4P), (4Q), (4R), (4S), (4T), (4U), (5A), (5B), (5C), (5D), (5E), (5F), (5G), (5H), (5I), (5J), (5K), (5L), (5M), (5N), (5O), (5P), (5Q), (5R), (5S), and (5T) detailed herein, and are equally described, the same as if each and every description, variation, embodiment or aspect were separately and individually listed for all formulae.

Pharmaceutical Compositions and Formulations

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. For example, a composition of a substantially pure compound selected from a compound of Table 1 (A, B, etc.) intends a composition that contains no more than 35% impurity, wherein the impurity denotes a compound other than the compound or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, and without limitation, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual such as a human. In another variation, compositions are provided containing a compound in substantially pure form. In another variation, the invention embraces pharmaceutical compositions comprising a compound detailed herein and a pharmaceutically acceptable carrier or excipient. In another variation, methods of administering a compound are provided. The purified forms, pharmaceutical compositions and methods of administering the compounds are suitable for any compound or form thereof detailed herein.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington: The Science and Practice of Pharmacy*, Lippincott Williams & Wilkins, 21$^{st}$ ed. (2005), which is incorporated herein by reference.

Compounds as described herein may be administered to individuals (e.g., a human) in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid polyols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described.

Compositions comprising a compound provided herein are also described. In one variation, the composition comprises a compound and a pharmaceutically acceptable carrier or excipient. In another variation, a composition of substantially pure compound is provided.

Methods of Use/Treatment

Methods of treating a disorder, which is mediated by ASK1, such as, without limitation, NASH, diabetic kidney disease, PAH, and the like are well known to the skilled artisan and can be adapted to treating such a disorder with a compound provided herein.

Compounds and compositions detailed herein, such as a pharmaceutical composition containing a compound of any formula provided herein, or a pharmaceutically acceptable salt thereof, and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease or disorder in an individual in need thereof comprising administering a compound described herein or any embodiment, variation, or aspect thereof, or a pharmaceutically acceptable salt thereof. In some embodiments, the compound, pharmaceutically acceptable salt thereof, or composition is administered to the individual according to a dosage and/or method of administration described herein.

Compounds and compositions detailed herein can inhibit the activity of ASK1. For example, the compounds of the disclosure can be used to inhibit activity of ASK1 in a cell or in an individual or patient in need thereof by administering an effective amount of a compound of the disclosure to the cell, individual, or patient.

In some embodiments, provided herein is a method for treating a condition mediated by ASK1 activity comprising administering to a mammal in need of treatment an effective amount of a compound of formula (IA) or any variation thereof, or a pharmaceutically acceptable salt thereof. In some embodiments, the condition mediated by ASK1 activity is a neurodegenerative, cardiovascular, inflammatory, autoimmune, or metabolic disease or disorder. In some embodiments, the condition mediated by ASK1 activity is a cardio-renal disease such as a kidney disease, diabetic kidney disease, chronic kidney disease, fibrotic disease, lung fibrosis, kidney fibrosis, respiratory disease, chronic obstructive pulmonary disease (COPD), acute lung injury, acute liver disease, or chronic liver disease.

In some embodiments, provided herein is a method for treating liver disease, comprising administering to a mammal in need thereof an effective amount of a compound of formula (IA) or any variation thereof, or a pharmaceutically acceptable salt thereof. In some embodiments, the liver disease is a chronic liver disease. In some embodiments, the liver disease is nonalcoholic steatohepatitis (NASH). In some embodiments, provided herein is a method for treating nonalcoholic steatohepatitis (NASH), comprising administering to a mammal in need thereof an effective amount of a compound of formula (IA) or any variation thereof, or a pharmaceutically acceptable salt thereof.

In one aspect, provided herein is a method of treating a disease, wherein modulation of ASK1 activity prevents, inhibits, or ameliorates the pathology and/or symptomology of the disease, in a patient, comprising administering to the patient a therapeutically effective amount of a compound or composition provided herein. In one embodiment, provided herein is a method of treating a disease, wherein modulation of ASK1 activity prevents the pathology and/or symptomology of the disease, in a patient, comprising administering to the patient a therapeutically effective amount of a compound or composition provided herein. In one embodiment, provided herein is a method of treating a disease, wherein modulation of ASK1 activity inhibits the pathology and/or symptomology of the disease, in a patient, comprising administering to the patient a therapeutically effective amount of a compound or composition provided herein. In one embodiment, provided herein is a method of treating a disease, wherein modulation of ASK1 activity ameliorates the pathology and/or symptomology of the disease, in a patient, comprising administering to the patient a therapeutically effective amount of a compound or composition provided herein.

In another aspect, provided herein is a method of delaying the onset and/or development of a disease or disorder that is mediated by ASK1 activity in a patient (such as a human) who is at risk for developing the disease or disorder. It is appreciated that delayed development may encompass prevention in the event the individual or patient does not develop the disease or disorder. In one aspect, an individual or patient at risk of developing a disease or disorder that is mediated by ASK1 activity has one or more risk factors for developing the disease or disorder, such as diet, body weight, a family history of an individual or patient having the disease or disorder, or having an underlying condition, such as obesity, diabetes, or metabolic syndrome, that is associated with an increased likelihood of developing the disease or disorder.

In one aspect, provided herein is a method of delaying the onset and/or development of liver disease in a patient in need thereof, comprising administering to the patient a therapeutically effective amount of a compound or composition provided herein. In one variation, provided herein is a method of delaying the onset and/or development of chronic liver disease in a patient in need thereof, comprising administering to the patient a therapeutically effective amount of a compound or composition provided herein. In one variation, provided herein is a method of delaying the onset and/or development of NASH in a patient in need thereof, comprising administering to the patient a therapeutically effective amount of a compound or composition provided herein.

In one aspect, provided herein is a compound of formula (IA) or any variation thereof, or a pharmaceutically acceptable salt thereof, for use in therapy. In some embodiments, provided herein is a compound of formula (IA) or any variation thereof, or a pharmaceutically acceptable salt thereof or pharmaceutical composition comprising such compound or a pharmaceutically acceptable salt thereof, for use in the treatment of liver disease. In some embodiments, provided is a compound of formula (IA) or any variation thereof, or a pharmaceutically acceptable salt thereof, or a pharmaceutical composition comprising such compound or a pharmaceutically acceptable salt thereof, for use in the treatment of NASH.

In another embodiment, provided herein is a compound of formula (IA) or any variation thereof, or a pharmaceutically acceptable salt thereof, for use in the manufacture of a medicament for the treatment of liver disease. In some embodiments, the medicament is for the treatment of NASH.

In some embodiments, the individual or patient is a mammal. In some embodiments, the patient is a primate, dog, cat, rabbit, or rodent. In some embodiments, the patient is a primate. In some embodiments, the patient is a human. In some embodiments, the human is at least about or is about any of 18, 21, 30, 50, 60, 65, 70, 75, 80, or 85 years old. In some embodiments, the human is a child. In some embodiments, the human is less than about or about any of 21, 18, 15, 10, 5, 4, 3, 2, or 1 years old. In some embodiments, the patient has an underlying condition, such as obesity, diabetes, or metabolic syndrome, that is associated with an increased likelihood of developing the disease, such as NASH.

a. Dosing and Method of Administration

The dose of a compound described herein, or a pharmaceutically acceptable salt thereof, administered to an individual (such as a human) may vary with the particular compound or pharmaceutically acceptable salt thereof, the method of administration, and the particular disease, such as type and stage of NASH, being treated. In some embodiments, the amount of the compound, or a pharmaceutically acceptable salt thereof, is a therapeutically effective amount.

The compounds provided herein, or a pharmaceutically acceptable salt thereof, may be administered to a patient via various routes, including, e.g., intravenous, intramuscular, subcutaneous, oral and transdermal.

The effective amount of the compound may in one aspect be a dose of between about 0.01 and about 100 mg/kg. Effective amounts or doses of the compounds of the present disclosure may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein, or a pharmaceutically acceptable salt thereof, and a pharmaceutically acceptable excipient.

A compound or composition provided herein may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

b. Articles of Manufacture and Kits

The present disclosure further provides articles of manufacture comprising a compound described herein, or a pharmaceutically acceptable salt thereof, a composition described herein, or one or more unit dosages described herein in suitable packaging. In certain embodiments, the article of manufacture is for use in any of the methods described herein. Suitable packaging is known in the art and includes, for example, vials, vessels, ampules, bottles, jars, flexible packaging and the like. An article of manufacture may further be sterilized and/or sealed.

The present disclosure further provides kits for carrying out the methods of the present disclosure, which comprises one or more compounds described herein or a composition comprising a compound described herein. The kits may employ any of the compounds disclosed herein. In one variation, the kit employs a compound described herein or pharmaceutically acceptable salt thereof. The kits may be used for any one or more of the uses described herein, and, accordingly, may contain instructions for the treatment of any disease or described herein, for example for the treatment of NASH.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present disclosure. The instructions included with the kit generally include information as to the components and their administration to an individual.

EXEMPLARY EMBODIMENTS

The present disclosure is further described by the following embodiments. The features of each of the embodiments are combinable with any of the other embodiments where appropriate and practical.

Embodiment 1

A compound of formula (IA):

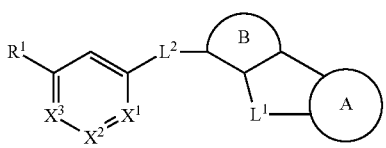

(IA)

or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding, wherein:
ring A is an optionally substituted 5-membered heteroaryl ring, preferably containing heteroatoms selected from N, O, and S, more preferably, containing one or more, such as 1-4 ring N atoms;
ring B is aryl, preferably $C_6$-$C_{10}$ aryl, more preferably phenyl, or is heteroaryl, preferably 5-10 membered heteroaryl, more preferably, 6 membered heteroaryl containing 1-2 ring nitrogen atoms;
$L^1$ is optionally substituted $C_2$-$C_6$ alkylene or optionally substituted $C_2$-$C_6$ heteroalkylene;
$L^2$ is —CO—NH—, —NH—CO—, —SO$_2$—NH—, or —NH—SO$_2$—;
$R^1$ is optionally substituted cycloalkyl, optionally substituted aryl, optionally substituted heteroaryl, optionally substituted heterocyclyl, —CONR$^{11}$R$^{12}$ or —SO$_2$NR$^{11}$R$^{12}$, preferably, when substituted, the cycloalkyl, aryl, heteroaryl, or heterocyclyl is substituted with a $C_3$-$C_6$ cycloalkyl optionally substituted with one or more, preferably 1-2 substituents selected from $C_1$-$C_6$ alkyl, $C_2$-$C_6$ alkenyl, and $C_2$-$C_6$ alkynyl or, the cycloalkyl, aryl, heteroaryl, or heterocyclyl is substituted with 1-2 $C_1$-$C_6$ alkyl;
each of $R^{11}$ and $R^{12}$ is independently selected from hydrogen, optionally substituted $C_1$-$C_6$ alkyl, and optionally substituted $C_3$-$C_8$ cycloalkyl, preferably optionally substituted $C_3$-$C_5$ cycloalkyl;
or $R^{11}$ and $R^{12}$, together with the nitrogen atom they are attached to form a 4-7 membered heterocycle;
$X^1$, $X^2$, and $X^3$ are independently optionally substituted CH, preferably, —CR$^2$; or N;
$R^2$ is independently hydrogen, optionally substituted alkyl preferably optionally substituted $C_1$-$C_6$ alkyl, optionally substituted alkoxy preferably optionally substituted $C_1$-$C_6$ alkoxy, optionally substituted cycloalkyl preferably optionally substituted $C_3$-$C_8$ cycloalkyl, optionally substituted aryl preferably optionally substituted 6 membered aryl, optionally substituted heteroaryl preferably optionally substituted 5-10 membered heteroaryl, optionally substituted heterocyclyl preferably optionally substituted 5-10 membered heterocyclyl, halo, —NO$_2$, haloalkyl, haloalkoxy, —CN, —O—R$^3$, —S—R$^3$, —N(R$^3$)(R$^4$), —S(═O)—R$^3$, —S(═O)$_2$R$^3$, —S(═O)$_2$—N(R$^3$)(R$^4$), —S(═O)$_2$—O—R$^3$, —N(R$^3$)—C(O)—R$^4$, —N(R$^3$)—C(O)—O—R$^4$, —N(R$^3$)—C(O)—N(R$^3$)(R$^4$), —C(O)—R$^3$, —C(O)—O—R$^3$, —C(O)—N(R$^3$)(R$^4$), or —N(R$^3$)—S(═O)$_2$—R$^4$; and
$R^3$ and $R^4$ are independently selected from the group consisting of hydrogen, optionally substituted alkyl preferably optionally substituted $C_1$-$C_6$ alkyl, optionally substituted alkoxy preferably optionally substituted $C_1$-$C_6$ alkoxy, optionally substituted cycloalkyl preferably optionally substituted $C_3$-$C_8$ cycloalkyl, optionally substituted aryl preferably optionally substituted 6 membered aryl, optionally substituted heteroaryl preferably optionally substituted 5-10 membered heteroaryl, optionally substituted heterocyclyl preferably optionally substituted 5-10 membered heterocyclyl; or $R^3$ and $R^4$ when taken together with the nitrogen, or with the intervening atoms to which they are attached form an optionally substituted heterocycle preferably an optionally substituted 4-10 membered heterocycle.

Embodiment 2

The compound of embodiment 1 of formula (IB):

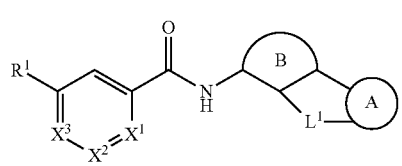

(IB)

wherein the remaining variables are defined as in embodiment 1.

Embodiment 3

The compound of embodiment 1 of formula (IC):

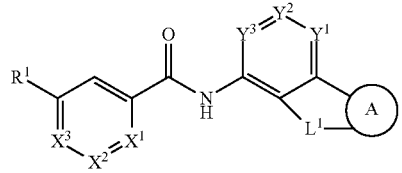

(IC)

wherein $Y^1$, $Y^2$, and $Y^3$ independently are CH or N; and the remaining variables are defined as in embodiment 1.

Embodiment 4

The compound of embodiment 1 of formula (ID):

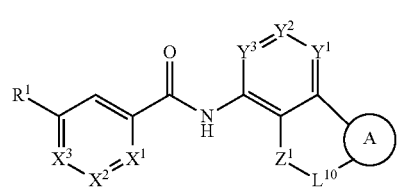

(ID)

wherein $Y^1$, $Y^2$, and $Y^3$ independently are CH or N;
$Z^1$ is O, S(O)$_n$, or NR$^{15}$;
n is 0, 1, or 2;
$R^{15}$ is H or $C_1$-$C_3$ alkyl;

$L^{10}$ is optionally substituted $C_1$-$C_5$ alkylene or optionally substituted $C_1$-$C_5$ heteroalkylene; and
the remaining variables are defined as in embodiment 1.

Embodiment 5

The compound of embodiment 1 of formula (IE) or (IF):

(IE)
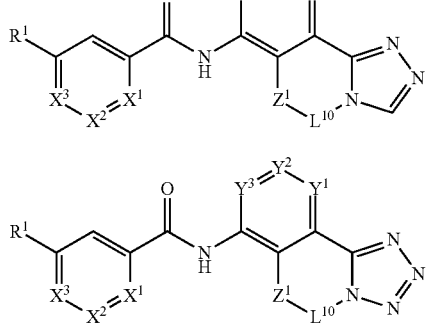

(IF)
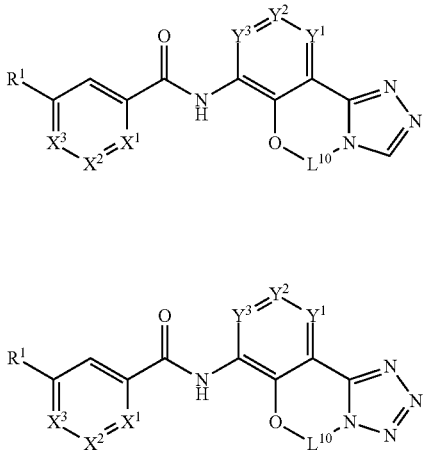

wherein $Y^1$, $Y^2$, and $Y^3$ independently are CH or N;
$Z^1$ is O, $S(O)_n$, or $NR^{15}$;
n is 0, 1, or 2;
$R^{15}$ is H or $C_1$-$C_3$ alkyl;
$L^{10}$ is optionally substituted $C_1$-$C_5$ alkylene or optionally substituted $C_1$-$C_5$ heteroalkylene; and
the remaining variables are defined as in embodiment 1.

Embodiment 6

The compound of embodiment 1 of formula (2A) or (2B):

(2A)

(2B)

wherein $Y^1$, $Y^2$, and $Y^3$ independently are CH or N;
$L^{10}$ is optionally substituted $C_1$-$C_5$ alkylene or optionally substituted $C_1$-$C_5$ heteroalkylene; and
the remaining variables are defined as in embodiment 1.

Embodiment 7

The compound of embodiment 1 of formula (2C) or (2D):

(2C)

(2D)

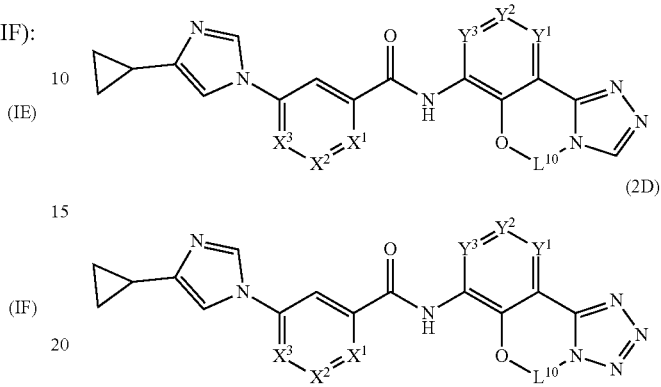

wherein $Y^1$, $Y^2$, and $Y^3$ independently are CH or N;
$L^{10}$ is optionally substituted $C_1$-$C_5$ alkylene or optionally substituted $C_1$-$C_5$ heteroalkylene; and
the remaining variables are defined as in embodiment 1.

Embodiment 8

The compound of embodiment 1 of formula (3A), (3B), (3C), (3D), (3E), or (3F):

(3A)

(3B)

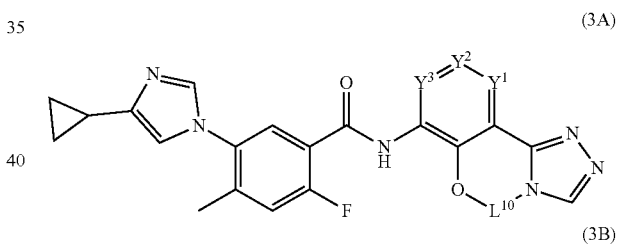

(3C)

(3D)

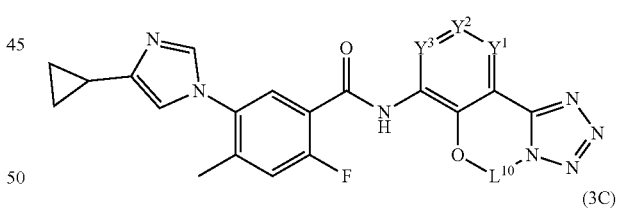

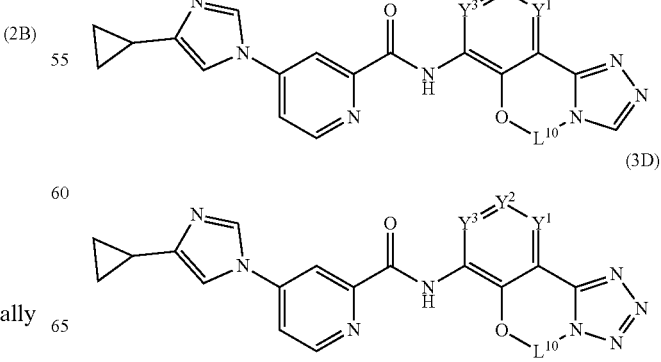

(3E)

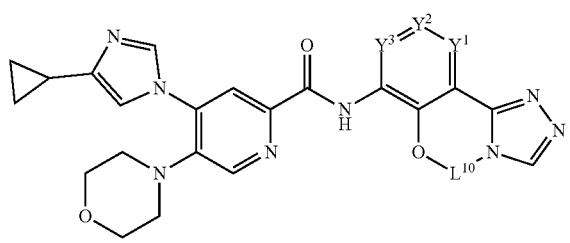

(3F)

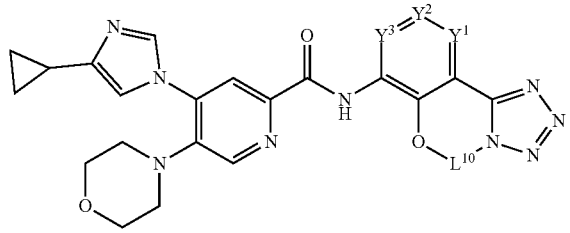

wherein Y¹, Y², and Y³ independently are CH or N;
L¹⁰ is optionally substituted $C_1$-$C_5$ alkylene or optionally substituted $C_1$-$C_5$ heteroalkylene.

Embodiment 9

The compound of embodiment 1 of formula (4A), (4B), (4C), (4D), (4E), or (4F):

(4A)

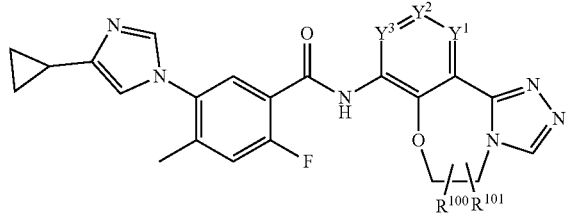

(4B)

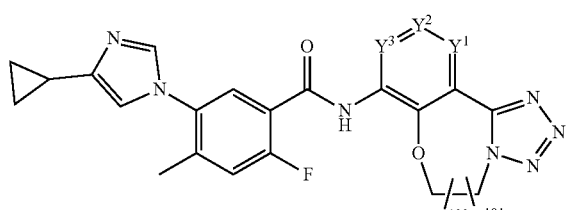

(4C)

(4D)

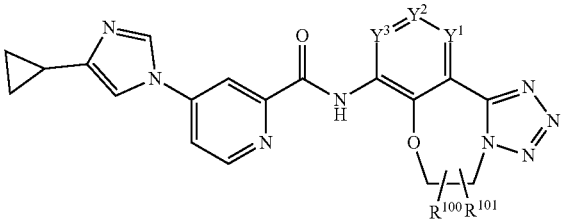

(4E)

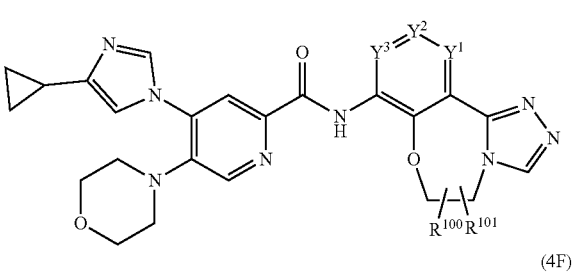

(4F)

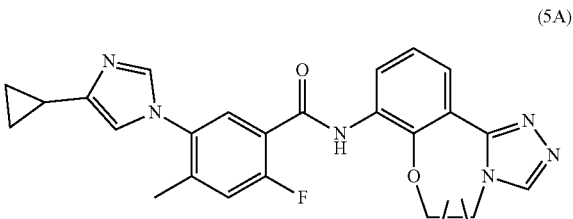

wherein Y¹, Y², and Y³ independently are CH or N; and $R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, and optionally substituted 5 membered heteroaryl; or $R^{100}$ and $R^{101}$ together with the carbon atom or carbon atoms they are attached to form a $C_3$-$C_5$ cycloalkyl.

Embodiment 10

The compound of embodiment 1 of formula (5A), (5B), (5C), (5D), (5E), or (5F):

(5A)

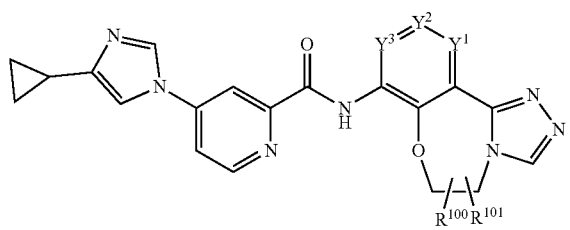

(5B)

-continued (5C)
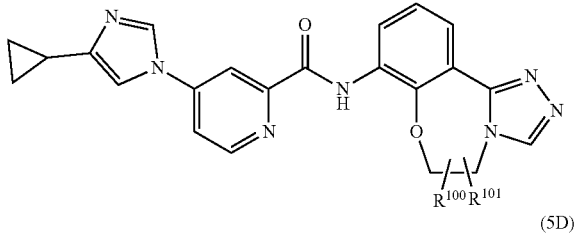

(5D)
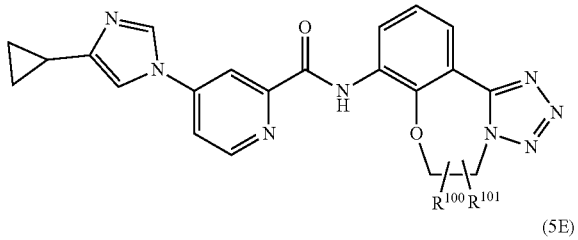

(5E)
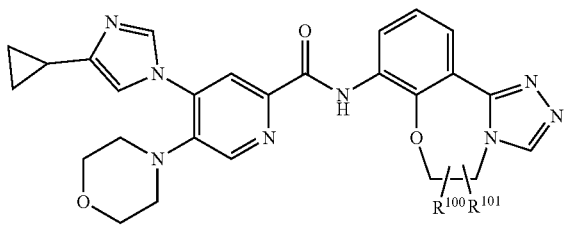

(5F)
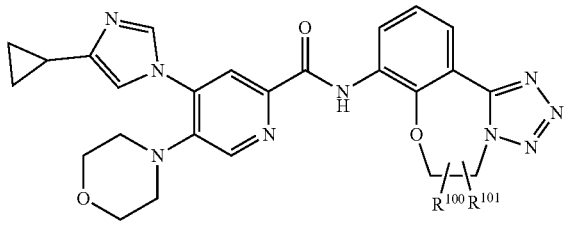

wherein, $R^{100}$ and $R^{101}$ are independently H, optionally substituted $C_1$-$C_6$ alkyl, halo, optionally substituted $C_3$-$C_5$ cycloalkyl, optionally substituted 4-5 membered heterocyclyl, and optionally substituted 5 membered heteroaryl; or $R^{100}$ and $R^{101}$ together with the carbon atom or carbon atoms they are attached to form a $C_3$-$C_5$ cycloalkyl.

Embodiment 11

The compound of embodiment 9 or 10, wherein, $R^{100}$ is H; and $R^{101}$ is $C_1$-$C_3$ alkyl optionally substituted with 1-3 hydroxy or halo, such as fluoro, or is $C_3$-$C_5$ cyclopropyl group; or
each $R^{100}$ and $R^{101}$ are independently $C_1$-$C_3$ alkyl; or
$R^{100}$ and $R^{101}$ together with the carbon atom they are attached to form a $C_3$-$C_5$ cycloalkyl group.

Embodiment 12

The compound of embodiment 9 or 10, wherein, $R^{100}$ is H, and $R^{101}$ is methyl, hydroxymethyl, fluoromethyl, or cyclopropyl; or each $R^{100}$ and $R^{101}$ are independently methyl or ethyl; or
$R^{100}$ and $R^{101}$ together with the carbon atom they are attached to form a cyclopropyl group.

Embodiment 13

The compound of any one of embodiments 1-12 wherein -$L^1$-, —$Z^1$-$L^{10}$-, —O-$L^{10}$-, or

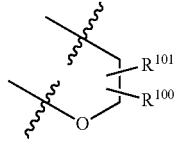

is: —O—$CH_2$—$CH_2$—, —O—$CH_2$—CH(Me)-, —O—$CH_2$—C(Me)$_2$-, —O—CH(Me)-$CH_2$—, —O—$CH_2$—CH($CH_2$OH)—, —O—$CH_2$—CH($CH_2$F)—,

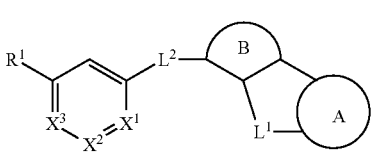

Embodiment 14

A compound selected from Table 1 or a tautomer or an N-oxide thereof, or an isotopomer of each thereof, or a prodrug of each of the above, or a stereoisomer of the aforesaid, or a pharmaceutically acceptable salt of each of the foregoing, or a solvate of each of the preceding.

Embodiment 15

A pharmaceutical composition comprising a compound of any one of embodiments 1-14, and at least one pharmaceutically acceptable excipient.

Embodiment 16

A method of inhibiting ASK1, comprising contacting ASK1 with an effective amount of a compound of any one of embodiments 1-14, or the composition of embodiment 15.

Embodiment 17

A method of treating a disorder, which is mediated by ASK1, comprising administering to a patient in need thereof a therapeutically effective amount of a compound of any one of embodiments 1-14, or the composition of embodiment 15.

Embodiment 18

A compound of formula (IA):

(IA)

or a pharmaceutically acceptable salt thereof, wherein:
ring A is an optionally substituted 5-membered heteroaryl ring;
ring B is $C_6$-$C_{10}$ aryl or 5- to 10-membered heteroaryl;
$L^1$ is optionally substituted $C_2$-$C_6$ alkylene or optionally substituted $C_2$-$C_6$ heteroalkylene;
$L^2$ is —CO—NH—, —NH—CO—, —SO$_2$—NH—, or —NH—SO$_2$—;
$R^1$ is optionally substituted $C_3$-$C_8$ cycloalkyl, optionally substituted 6-membered aryl, optionally substituted 5- to 6-membered heteroaryl, optionally substituted 4- to 6-membered heterocyclyl, —CONR$^{11}$R$^{12}$ or —SO$_2$NR$^{11}$R$^{12}$;
$R^{11}$ and $R^{12}$ are independently selected from the group consisting of hydrogen, optionally substituted $C_1$-$C_6$ alkyl, and optionally substituted $C_3$-$C_8$ cycloalkyl;
or $R^{11}$ and $R^{12}$ are taken together with the nitrogen atom to which they are attached to form a 4- to 7-membered heterocyclyl;
$X^1$, $X^2$, and $X^3$ are independently $CR^2$ or N;
each $R^2$ is independently hydrogen, optionally substituted $C_1$-$C_6$ alkyl, optionally substituted $C_1$-$C_6$ alkoxy, optionally substituted $C_3$-$C_8$ cycloalkyl, optionally substituted 6-membered aryl, optionally substituted 5- to 10-membered heteroaryl, optionally substituted 4- to 10-membered heterocyclyl, halo, —NO$_2$, haloalkyl, haloalkoxy, —CN, —O—R$^3$, —S—R$^3$, —N(R$^3$)(R$^4$), —S(=O)—R$^3$, —S(=O)$_2$R$^3$, —S(=O)$_2$—N(R$^3$)(R$^4$), —S(=O)$_2$—O—R$^3$, —N(R$^3$)—C(O)—R$^4$, —N(R$^3$)—C(O)—O—R$^4$, —N(R$^3$)—C(O)—N(R$^3$)(R$^4$), —C(O)—R$^3$, —C(O)—O—R$^3$, —C(O)—N(R$^3$)(R), or —N(R$^3$)—S(=O)$_2$—R$^4$; and
$R^3$ and $R^4$ are independently selected from the group consisting of hydrogen, optionally substituted $C_1$-$C_6$ alkyl, optionally substituted $C_1$-$C_6$ alkoxy, optionally substituted $C_3$-$C_8$ cycloalkyl, optionally substituted 6-membered aryl, optionally substituted 5- to 10-membered heteroaryl, and optionally substituted 5- to 10-membered heterocyclyl;
or $R^3$ and $R^4$ are taken together with the nitrogen atom or with the intervening atoms to which they are attached to form an optionally substituted 4- to 10-membered heterocyclyl.

Embodiment 19

The compound of embodiment 18, or a pharmaceutically acceptable salt thereof, wherein:
ring B is phenyl.

Embodiment 20

The compound of embodiment 18 or 19, or a pharmaceutically acceptable salt thereof, wherein:
ring A is

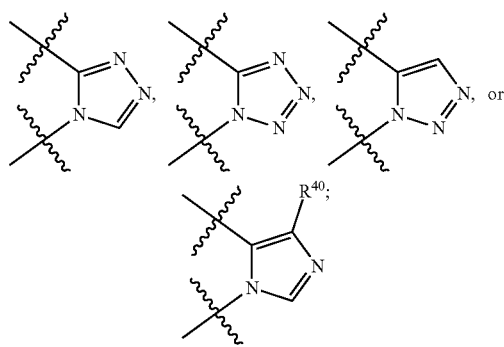

and
$R^{40}$ is H, $C_1$-$C_6$ alkyl, or halo.

Embodiment 21

The compound of any one of embodiments 18-20, or a pharmaceutically acceptable salt thereof, wherein:
$L^1$ is —O-$L^{10}$-; and
$L^{10}$ is optionally substituted $C_1$-$C_5$ alkylene or optionally substituted $C_1$-$C_5$ heteroalkylene.

Embodiment 22

The compound of any one of embodiments 18-21, or a pharmaceutically acceptable salt thereof, wherein:
$L^1$ is

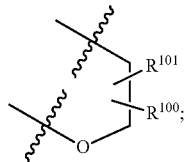

and
$R^{100}$ and $R^{101}$ are independently H, optionally substituted $C_1$-$C_6$ alkyl, halo, optionally substituted $C_3$-$C_5$ cycloalkyl, optionally substituted 4- to 5-membered heterocyclyl, or optionally substituted 5-membered heteroaryl;
or $R^{100}$ and $R^{101}$ are taken together with the carbon atom or carbon atoms to which they are attached to form a $C_3$-$C_5$ cycloalkyl.

Embodiment 23

The compound of embodiment 22, or a pharmaceutically acceptable salt thereof, wherein:
$R^{100}$ and $R^{101}$ are independently H; $C_1$-$C_6$ alkyl optionally substituted with 1-3 hydroxyl or halo; halo; $C_3$-$C_5$ cycloalkyl optionally substituted with 1-3 $C_1$-$C_6$ alkyl, hydroxyl, or halo; 4- to 5-membered heterocyclyl optionally substituted with 1-3 $C_1$-$C_6$ alkyl, hydroxyl, or halo; or 5-membered heteroaryl optionally substituted with 1-3 $C_1$-$C_6$ alkyl, hydroxyl, or halo;
or $R^{100}$ and $R^{101}$ are taken together with the carbon atom or carbon atoms to which they are attached to form a $C_3$-$C_5$ cycloalkyl.

Embodiment 24

The compound of any one of embodiments 18-23, or a pharmaceutically acceptable salt thereof, wherein:
$L^1$ is —O—CH$_2$—CH$_2$—, —O—CH$_2$—CH(Me)-, —O—CH$_2$—C(Me)$_2$-, —O—CH(Me)-CH$_2$—, —O—CH$_2$—CH(CH$_2$OH)—, —O—CH$_2$—CH(CH$_2$F)—,

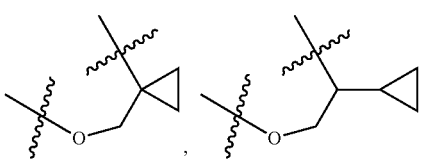

,

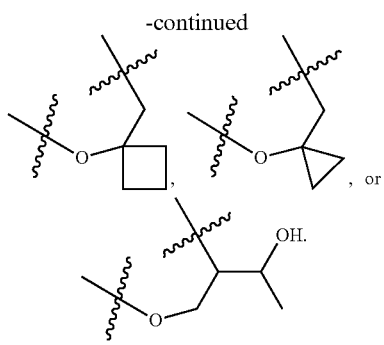

Embodiment 25

The compound of any one of embodiments 18-24, or a pharmaceutically acceptable salt thereof, wherein:
$L^2$ is —CO—NH—.

Embodiment 26

The compound of any one of embodiments 18-25, or a pharmaceutically acceptable salt thereof, wherein:
$R^1$ is $C_3$-$C_8$ cycloalkyl, 6-membered aryl, 5- to 6-membered heteroaryl, or 4- to 6-membered heterocyclyl, each of which is optionally substituted with 1-2 $C_1$-$C_6$ alkyl or with one $C_3$-$C_6$ cycloalkyl which is optionally substituted with 1-2 substituents selected from the group consisting of $C_1$-$C_6$ alkyl, $C_2$-$C_6$ alkenyl, and $C_2$-$C_6$ alkynyl; —CONR$^{11}$R$^{12}$; or —SO$_2$NR$^{11}$R$^{12}$ Embodiment 27

The compound of any one of embodiments 18-26, or a pharmaceutically acceptable salt thereof, wherein:
$R^1$ is

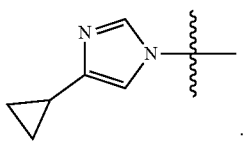

Embodiment 28

The compound of any one of embodiments 18-27, or a pharmaceutically acceptable salt thereof, wherein:
$R^2$ is hydrogen; $C_1$-$C_6$ alkyl optionally substituted with 1-3 halo, —CF$_3$, —OCF$_3$, hydroxyl, —CN or —N(R$^3$)(R$^4$); $C_1$-$C_6$ alkoxy optionally substituted with 1-3 halo, —CF$_3$, —OCF$_3$, hydroxyl, —CN or —N(R$^3$)(R$^4$); $C_3$-$C_8$ cycloalkyl optionally substituted with 1-3 halo, $C_1$-$C_6$ alkyl, —CF$_3$, —OCF$_3$, hydroxyl, —CN or —N(R$^3$)(R$^4$); 6-membered aryl optionally substituted with 1-3 halo, $C_1$-$C_6$ alkyl, —CF$_3$, —OCF$_3$, hydroxy, —CN or —N(R$^3$)(R$^4$); 5- to 10-membered heteroaryl optionally substituted with 1-3 halo, $C_1$-$C_6$ alkyl, —CF$_3$, —OCF$_3$, hydroxyl, —CN or —N(R$^3$)(R$^4$); 5- to 10-membered heterocyclyl optionally substituted with 1-3 halo, $C_1$-$C_6$ alkyl, —CF$_3$, —OCF$_3$, hydroxyl, —CN or —N(R$^3$)(R$^4$); or halo; and
$R^3$ and $R^4$ are independently selected from the group consisting of hydrogen; $C_1$-$C_6$ alkyl optionally substituted with 1-3 halo, —CF$_3$, —OCF$_3$, hydroxyl, or —CN; $C_3$-$C_8$ cycloalkyl optionally substituted with 1-3 halo, $C_1$-$C_6$ alkyl, —CF$_3$, —OCF$_3$, hydroxyl, or —CN; 6-membered aryl optionally substituted with 1-3 halo, $C_1$-$C_6$ alkyl, —CF$_3$, —OCF$_3$, hydroxyl, or —CN; 5- to 10-membered heteroaryl optionally substituted with 1-3 halo, $C_1$-$C_6$ alkyl, —CF$_3$, —OCF$_3$, hydroxyl, or —CN; or 5- to 10-membered heterocyclyl optionally substituted with 1-3 halo, $C_1$-$C_6$ alkyl, —CF$_3$, —OCF$_3$, hydroxyl, or —CN;
or $R^3$ and $R^4$ are taken together with the nitrogen atom or with the intervening atoms to which they are attached to form a 4- to 10-membered heterocyclyl optionally substituted with 1-3 halo, $C_1$-$C_6$ alkyl, —CF$_3$, —OCF$_3$, hydroxyl, or —CN.

Embodiment 29

The compound of any one of embodiments 18-28, or a pharmaceutically acceptable salt thereof, wherein:
$X^1$ is N or CR$^2$; and
$R^2$ is halo.

Embodiment 30

The compound of any one of embodiments 18-29, or a pharmaceutically acceptable salt thereof, wherein:
$X^2$ is CH.

Embodiment 31

The compound of any one of embodiments 18-30, or a pharmaceutically acceptable salt thereof, wherein:
$X^3$ is CR$^2$; and
$R^2$ is hydrogen; $C_1$-$C_6$ alkyl optionally substituted with 1-2 halo or hydroxyl; $C_1$-$C_6$ alkoxy optionally substituted with 1-2 halo or hydroxyl; 4-10 membered heterocyclyl optionally substituted with 1-2 $C_1$-$C_6$ alkyl or hydroxyl; —O—R$^3$; or —N(R$^3$)(R$^4$); and
$R^3$ and $R^4$ are independently hydrogen or $C_1$-$C_6$ alkyl;
or $R^3$ and $R^4$ are taken together with the nitrogen atom or with the intervening atoms to which they are attached to form a 4- to 7-membered heterocyclyl optionally substituted with 1-2 $C_1$-$C_6$ alkyl or hydroxyl.

Embodiment 32

The compound of embodiment 31, or a pharmaceutically acceptable salt thereof, wherein:
$X^3$ is CR$^2$; and
$R^2$ is H, —CH$_3$, —OCH(CH$_3$)$_2$, —N(CH$_3$)$_2$,

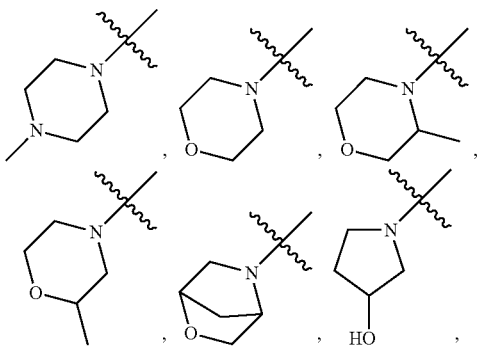

-continued

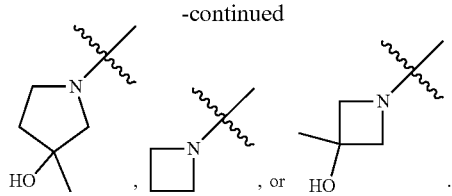

Embodiment 33

The compound of embodiment 18, or a pharmaceutically acceptable salt thereof, which is of formula (5A) or (5B):

(5A)
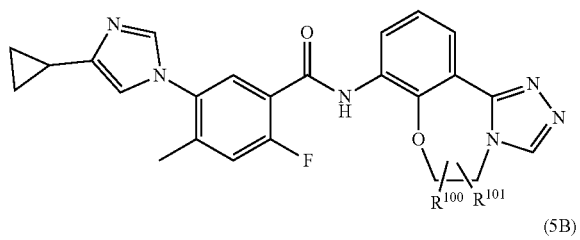

(5B)

wherein:
$R^{100}$ and $R^{101}$ are independently H; $C_1$-$C_6$ alkyl optionally substituted with 1-3 hydroxyl or halo; halo; $C_3$-$C_5$ cycloalkyl optionally substituted with 1-3 $C_1$-$C_6$ alkyl, hydroxyl, or halo; 4- to 5-membered heterocyclyl optionally substituted with 1-3 $C_1$-$C_6$ alkyl, hydroxyl, or halo; or 5-membered heteroaryl optionally substituted with 1-3 $C_1$-$C_6$ alkyl, hydroxyl, or halo;
or $R^{100}$ and $R^{101}$ are taken together with the carbon atom or carbon atoms to which they are attached to form a $C_3$-$C_5$ cycloalkyl.

Embodiment 34

A compound selected from Table 1 or a pharmaceutically acceptable salt thereof.

Embodiment 35

A pharmaceutical composition comprising the compound of any one of embodiments 18-34, or a pharmaceutically acceptable salt thereof, and at least one pharmaceutically acceptable excipient.

Embodiment 36

A method of inhibiting ASK1, comprising contacting ASK1 with an effective amount of the compound of any one of embodiments 18-34, or a pharmaceutically acceptable salt thereof, or the pharmaceutical composition of embodiment 35.

Embodiment 37

A method of treating a disorder which is mediated by ASK1, comprising administering to a patient in need thereof a therapeutically effective amount of the compound of any one of embodiments 18-34, or a pharmaceutically acceptable salt thereof, or the pharmaceutical composition of embodiment 35.

Embodiment 38

The method of embodiment 37, wherein the disorder which is mediated by ASK1 is pulmonary arterial hypertension (PAH), diabetic kidney disease, heart failure, a vascular disease, a neurodegenerative disorder, an inflammatory disease, or liver disease.

Embodiment 39

The method of embodiment 38, wherein the disorder is liver disease.

Embodiment 40

The method of embodiment 39, wherein the liver disease is a chronic liver disease.

Embodiment 41

The method of embodiment 39 or 40, wherein the liver disease is nonalcoholic steatohepatitis (NASH).

EXAMPLES

Example S1

(R)-5-(4-cyclopropyl-1H-imidazol-1-yl)-2-fluoro-4-methyl-N-(5-methyl-5,6-dihydrobenzo[f][1,2,4]triazolo[4,3-d][1,4]oxazepin-8-yl)benzamide (Example 1), (S)-5-(4-cyclopropyl-1H-imidazol-1-yl)-2-fluoro-4-methyl-N-(5-methyl-5,6-dihydrobenzo[f][1,2,4]triazolo[4,3-d][1,4]oxazepin-8-yl)benzamide (Example 2), 5-(4-cyclopropyl-1H-imidazol-1-yl)-N-(5,6-dihydrobenzo[f][1,2,4]triazolo[4,3-d][1,4]oxazepin-8-yl)-2-fluoro-4-methylbenzamide (Example 7), (R)-5-(4-cyclopropyl-1H-imidazol-1-yl)-N-(5-cyclopropyl-5,6-dihydrobenzo[f][1,2,4]triazolo[4,3-d][1,4]oxazepin-8-yl)-2-fluoro-4-methylbenzamide (Example 8), 5-(4-cyclopropyl-1H-imidazol-1-yl)-N-(5,5-dimethyl-5,6-dihydrobenzo[f][1,2,4]triazolo[4,3-d][1,4]oxazepin-8-yl)-2-fluoro-4-methylbenzamide (Example 9), and 5-(4-cyclopropyl-1H-imidazol-1-yl)-2-fluoro-4-methyl-N-(6H-spiro[benzo[f][1,2,4]triazolo[4,3-d][1,4]oxazepine-5,1'-cyclopropan]-8-yl)benzamide (Example 10) were synthesized according the schemes provided below.

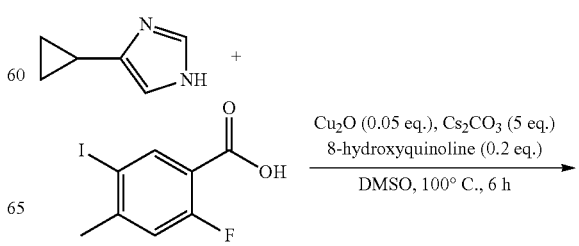

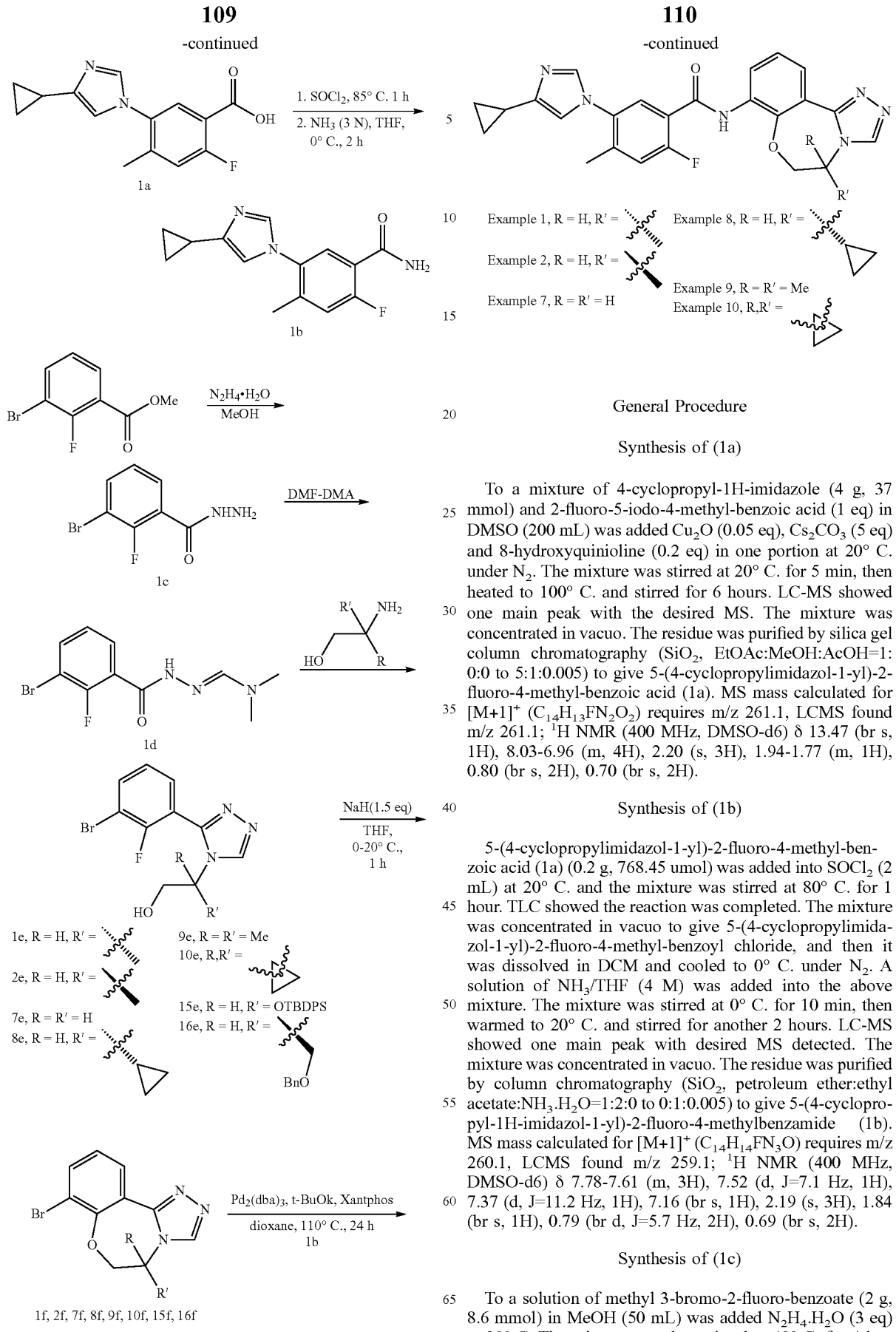

General Procedure

Synthesis of (1a)

To a mixture of 4-cyclopropyl-1H-imidazole (4 g, 37 mmol) and 2-fluoro-5-iodo-4-methyl-benzoic acid (1 eq) in DMSO (200 mL) was added $Cu_2O$ (0.05 eq), $Cs_2CO_3$ (5 eq) and 8-hydroxyquinioline (0.2 eq) in one portion at 20° C. under $N_2$. The mixture was stirred at 20° C. for 5 min, then heated to 100° C. and stirred for 6 hours. LC-MS showed one main peak with the desired MS. The mixture was concentrated in vacuo. The residue was purified by silica gel column chromatography ($SiO_2$, EtOAc:MeOH:AcOH=1:0:0 to 5:1:0.005) to give 5-(4-cyclopropylimidazol-1-yl)-2-fluoro-4-methyl-benzoic acid (1a). MS mass calculated for $[M+1]^+$ ($C_{14}H_{13}FN_2O_2$) requires m/z 261.1, LCMS found m/z 261.1; $^1H$ NMR (400 MHz, DMSO-d6) δ 13.47 (br s, 1H), 8.03-6.96 (m, 4H), 2.20 (s, 3H), 1.94-1.77 (m, 1H), 0.80 (br s, 2H), 0.70 (br s, 2H).

Synthesis of (1b)

5-(4-cyclopropylimidazol-1-yl)-2-fluoro-4-methyl-benzoic acid (1a) (0.2 g, 768.45 umol) was added into $SOCl_2$ (2 mL) at 20° C. and the mixture was stirred at 80° C. for 1 hour. TLC showed the reaction was completed. The mixture was concentrated in vacuo to give 5-(4-cyclopropylimidazol-1-yl)-2-fluoro-4-methyl-benzoyl chloride, and then it was dissolved in DCM and cooled to 0° C. under $N_2$. A solution of $NH_3$/THF (4 M) was added into the above mixture. The mixture was stirred at 0° C. for 10 min, then warmed to 20° C. and stirred for another 2 hours. LC-MS showed one main peak with desired MS detected. The mixture was concentrated in vacuo. The residue was purified by column chromatography ($SiO_2$, petroleum ether:ethyl acetate:$NH_3.H_2O$=1:2:0 to 0:1:0.005) to give 5-(4-cyclopropyl-1H-imidazol-1-yl)-2-fluoro-4-methylbenzamide (1b). MS mass calculated for $[M+1]^+$ ($C_{14}H_{14}FN_3O$) requires m/z 260.1, LCMS found m/z 259.1; $^1H$ NMR (400 MHz, DMSO-d6) δ 7.78-7.61 (m, 3H), 7.52 (d, J=7.1 Hz, 1H), 7.37 (d, J=11.2 Hz, 1H), 7.16 (br s, 1H), 2.19 (s, 3H), 1.84 (br s, 1H), 0.79 (br d, J=5.7 Hz, 2H), 0.69 (br s, 2H).

Synthesis of (1c)

To a solution of methyl 3-bromo-2-fluoro-benzoate (2 g, 8.6 mmol) in MeOH (50 mL) was added $N_2H_4.H_2O$ (3 eq) at 20° C. The mixture was then stirred at 40° C. for 4 hrs, white solid precipitated from the reaction mixture. TLC (petroleum ether:ethyl acetate=1:1, $R_f$=0.07) showed the starting material was consumed completely and one new spot with higher polarity was formed. The reaction mixture was concentrated to give a solid. The solid was triturated with EtOH (20 mL) and filtered; the filter cake was concentrated to give 3-bromo-2-fluorobenzohydrazide (1c) which was used directly in the next step.

Synthesis of (1d)

To a solution of 3-bromo-2-fluorobenzohydrazide (1c) (0.5 g, 2.15 mmol) in $CH_3CN$ (10 mL) was added DMF-DMA (4 eq) at 15° C. The reaction mixture was heated to 90° C. for 4 hrs. LCMS showed one main peak with desired MS. The reaction mixture was concentrated and the residue was diluted with EtOH (20 mL) and filtered. The filter cake was collected to give (E)-N'-(3-bromo-2-fluorobenzoyl)-N,N-dimethylformohydrazonamide (1d).

Synthesis of (e)

A solution of (E)-N'-(3-bromo-2-fluorobenzoyl)-N, N-dimethylformohydrazonamide (1d) (0.2 g, 0.69 mmol) and $RNH_2$ (5 eq) in $CH_3CN$ (5 mL) was added AcOH (2 eq) at 15° C. The mixture was heated to 100° C. for 3 hrs. LCMS showed one peak with desired MS detected. The reaction mixture was concentrated. The residue was purified by prep-TLC (Dichloromethane:Methanol=0.5) to give e.

Synthesis of (f)

A solution of e (0.28 mmol) in THF (20 mL) was cooled to 0° C., then NaH (1.2 eq) was added to the mixture at 0° C. The mixture was then stirred at 20° C. for 1 hr. LCMS showed one main peak with desired MS detected. The reaction mixture was quenched with sat. ammonium chloride solution (5 mL) and water (20 mL) and concentrated to remove most of the THF, then extracted with ethyl acetate (30 mL*3). The combined organic layer was washed with brine (20 mL), dried over sodium sulfate, filtered and concentrated. The residue was purified by prep-TLC (Dichloromethane:Methanol=0.5) to give f.

Synthesis of (R)-5-(4-cyclopropyl-1H-imidazol-1-yl)-2-fluoro-4-methyl-N-(5-methyl-5,6-dihydrobenzo[f][1,2,4]triazolo[4,3-d][1,4]oxazepin-8-yl)benzamide (Example 1)

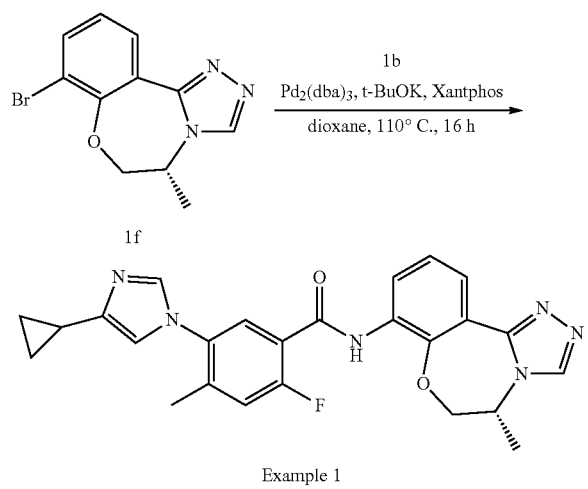

Example 1

To a mixture of (R)-8-bromo-5-methyl-5,6-dihydrobenzo[f][1,2,4]triazolo[4,3-d][1,4]oxazepine (1f) (70 mg, 249.89 umol) and 5-(4-cyclopropyl-1H-imidazol-1-yl)-2-fluoro-4-methylbenzamide (1b) (84.23 mg, 324.86 umol) in dioxane (20 mL) was added $Pd_2(dba)_3$ (45.77 mg, 49.98 umol), Xantphos (43.38 mg, 74.97 umol) and t-BuOK (56.08 mg, 499.79 umol) under $N_2$. The mixture was degassed and purged with $N_2$ for 3 times and was stirred at 110° C. for 16 hrs. LCMS showed 1f was consumed completely and desired mass was detected. The mixture was filtered and the filtrate was concentrated to give a residue. The residue was purified by prep-HPLC (neutral condition) to give Example 1. MS mass calculated for $[M+1]^+$ ($C_{25}H_{23}FN_6O_2$) requires m/z 459.2, LCMS found m/z 459.1; $^1$H NMR (400 MHz, CHLOROFORM-d) δ 9.40 (br d, J=15.5 Hz, 1H), 8.64 (br d, J=8.4 Hz, 1H), 8.45 (d, J=7.0 Hz, 1H), 8.32 (s, 1H), 8.11 (d, J=7.5 Hz, 1H), 7.48 (s, 1H), 7.19 (d, J=12.3 Hz, 1H), 6.82 (s, 1H), 4.79 (br d, J=4.4 Hz, 1H), 4.66-4.58 (m, 1H), 4.46 (br d, J=12.2 Hz, 1H), 2.31 (s, 3H), 1.99-1.89 (m, 1H), 1.70 (d, J=6.7 Hz, 3H), 0.98-0.89 (m, 2H), 0.86 (br d, J=2.9 Hz, 2H).

Synthesis of (S)-5-(4-cyclopropyl-1H-imidazol-1-yl)-2-fluoro-4-methyl-N-(5-methyl-5,6-dihydrobenzo[f][1,2,4]triazolo[4,3-d][1,4]oxazepin-8-yl)benzamide (Example 2)

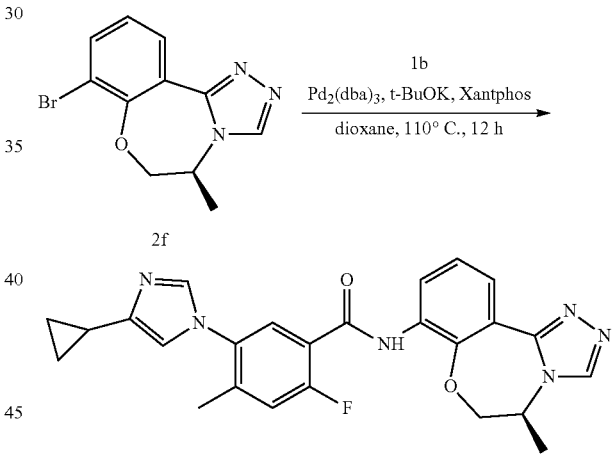

Example 2

To a solution of (S)-8-bromo-5-methyl-5,6-dihydrobenzo[f][1,2,4]triazolo[4,3-d][1,4]oxazepine (2f) (60 mg, 214.19 umol) and 5-(4-cyclopropyl-1H-imidazol-1-yl)-2-fluoro-4-methylbenzamide (1b) (66.64 mg, 257.03 umol, 1.2 eq) in dioxane (20 mL) was added $Pd_2(dba)_3$ (39.23 mg, 42.84 umol), Xantphos (37.18 mg, 64.26 umol) and t-BuOK (48.07 mg, 428.39 umol) under nitrogen. The reaction mixture was then stirred at 110° C. for 12 hrs. LCMS showed one peak with desired MS detected. The reaction mixture was diluted with methanol (30 mL) and filtered, the filtrate was concentrated. The residue was purified by prep-HPLC (column: Agela Durashell C18 150*25 5u; mobile phase: [water (10 mM $NH_4HCO_3$)-ACN]; B %: 25%-55%, 10 min) to give Example 2. MS mass calculated for $[M+1]^+$ ($C_{25}H_{23}FN_6O_2$) requires m/z 459.2, LCMS found m/z 459.1; $^1$H NMR (400 MHz, CHLOROFORM-d) δ=9.39 (br d, J=15.9 Hz, 1H), 8.63 (d, J=8.2 Hz, 1H), 8.44 (dd, J=1.2, 8.3 Hz, 1H), 8.30 (s, 1H), 8.09 (d, J=7.3 Hz, 1H), 7.46 (s, 1H), 7.26-7.23 (m, 1H), 7.18 (d, J=12.3 Hz, 1H), 6.81 (s, 1H), 4.85-4.72 (m, 1H), 4.67-4.55 (m, 1H), 4.44 (d, J=12.6 Hz, 1H), 2.30 (s, 3H), 1.97-1.86 (m, 1H), 1.69 (d, J=6.8 Hz, 3H), 0.95-0.88 (m, 2H), 0.87-0.80 (m, 2H).

Synthesis of 5-(4-cyclopropyl-1H-imidazol-1-yl)-N-(5,6-dihydrobenzo[f][1,2,4]triazolo[4,3-d][1,4]oxazepin-8-yl)-2-fluoro-4-methylbenzamide (Example 7)

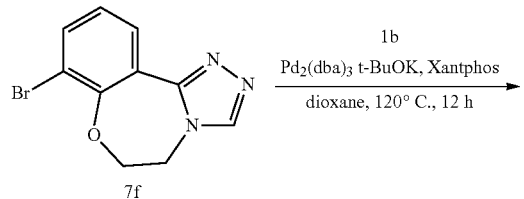

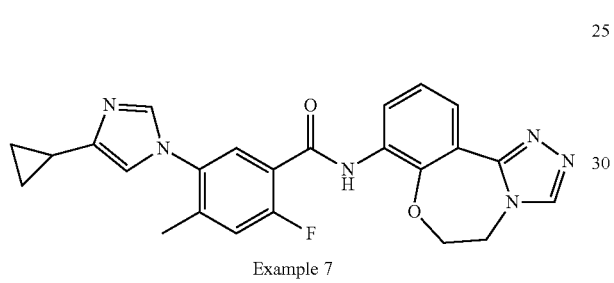

Example 7

Synthesis of (R)-5-(4-cyclopropyl-1H-imidazol-1-yl)-N-(5-cyclopropyl-5,6-dihydrobenzo[f][1,2,4]triazolo[4,3-d][1,4]oxazepin-8-yl)-2-fluoro-4-methylbenzamide (Example 8)

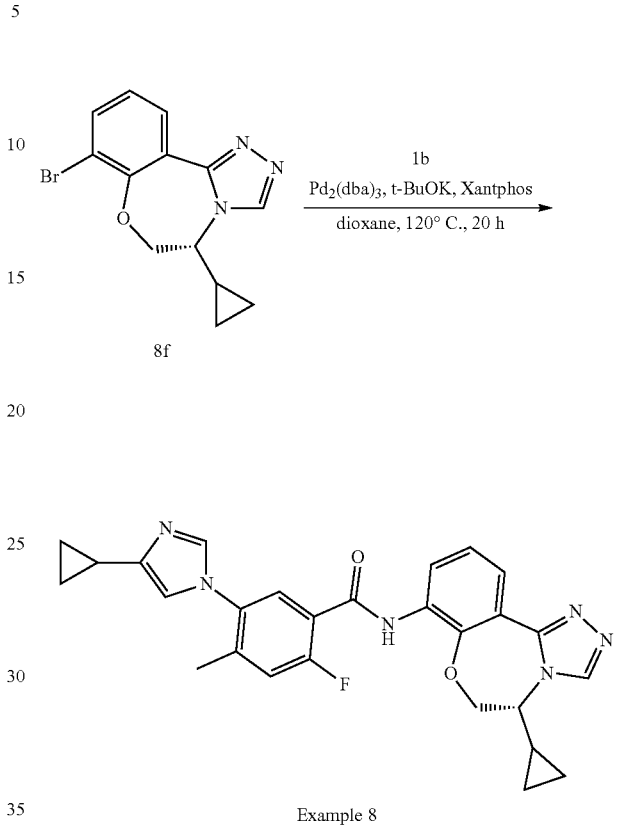

Example 8

To a solution of 5-(4-cyclopropyl-1H-imidazol-1-yl)-2-fluoro-4-methylbenzamide (1b) (9.74 mg, 37.58 umol) and 8-bromo-5,6-dihydrobenzo[f][1,2,4]triazolo[4,3-d][1,4]oxazepine (7f) (10 mg, 37.58 umol) in dioxane (10 mL) was added Xantphos (4.35 mg, 7.52 umol), t-BuOK (8.43 mg, 75.16 umol) and Pd$_2$(dba)$_3$ (3.44 mg, 3.76 umol) under nitrogen, the mixture was stirred at 120° C. for 12 hrs. LCMS showed one peak with desired MS detected. The reaction mixture was quenched with water (10 mL) and extracted with DCM (10 mL*3). The combined organic layers were combined and washed with brine (5 mL), dried over Na$_2$SO$_4$ and concentrated. The residue was purified by prep-HPLC (column: YMC-Actus Triart C18 100*30 mm*5 um; mobile phase: [water (10 mM NH$_4$HCO$_3$)-ACN]; B %: 20%-55%, 12 min) to give Example 7. MS mass calculated for [M+1]$^+$ (C$_{24}$H$_{21}$FN$_6$O$_2$) requires m/z 445.2, LCMS found m/z 445.1; $^1$H NMR (CHLOROFORM-d, 400 MHz): δ (ppm) 9.37 (br d, J=16.1 Hz, 1H), 8.62 (d, J=8.2 Hz, 1H), 8.39-8.47 (m, 1H), 8.25 (s, 1H), 8.08 (d, J=7.5 Hz, 1H), 7.44 (s, 1H), 7.22-7.25 (m, 1H), 7.17 (d, J=12.6 Hz, 1H), 6.79 (s, 1H), 4.61-4.71 (m, 2H), 4.55 (br d, J=3.7 Hz, 2H), 2.28 (s, 3H), 1.82-2.03 (m, 1H), 0.87-0.93 (m, 2H), 0.80-0.86 (m, 2H).

(R)-8-bromo-5-cyclopropyl-5,6-dihydrobenzo[f][1,2,4]triazolo[4,3-d][1,4]oxazepine (8f) (0.015 g, 48.99 umol), 5-(4-cyclopropyl-1H-imidazol-1-yl)-2-fluoro-4-methylbenzamide (1b) (12.70 mg, 48.99 umol), Pd$_2$(dba)$_3$ (4.49 mg, 4.90 umol), Xantphos (4.25 mg, 7.35 umol) and t-BuOK (11.00 mg, 97.99 umol) in 1,4-dioxane (10 mL) was degassed 3 times at 20° C. and heated to 120° C. and stirred for 20 hrs under N$_2$. LCMS showed a new peak with desired MS. The reaction mixture was filtered through a Celite pad and the Celite pad was washed with MeOH (20 mL). The filtrate was collected and concentrated to give a residue, which was purified by prep-HPLC (column: Nano-Micro UniSil 5-100 C18 ULTRA 100*250 mm 5 um; mobile phase: [water (0.1% TFA)-ACN]; B %: 15%-45%, 11 min) and lyophilized to afford Example 8. MS mass calculated for [M+H]$^+$ (C$_{27}$H$_{25}$FN$_6$O$_2$) requires m/z 485.2, LCMS found m/z 485.1; $^1$H NMR (400 MHz, MeOD) δ=9.11 (d, J=1.1 Hz, 1H), 9.01-8.86 (m, 1H), 8.42 (br d, J=7.5 Hz, 1H), 8.29-8.20 (m, 1H), 8.09 (br d, J=6.6 Hz, 1H), 7.59 (s, 1H), 7.51 (br d, J=11.7 Hz, 1H), 7.26 (t, J=8.2 Hz, 1H), 4.81 (dd, J=4.9, 13.2 Hz, 1H), 4.54 (br d, J=12.8 Hz, 1H), 4.07-3.98 (m, 1H), 2.33 (s, 3H), 2.13-2.00 (m, 1H), 1.44-1.30 (m, 1H), 1.20-1.10 (m, 2H), 0.95-0.88 (m, 2H), 0.85-0.77 (m, 3H), 0.66 (br s, 1H).

Synthesis of 5-(4-cyclopropyl-1H-imidazol-1-yl)-N-(5,5-dimethyl-5,6-dihydrobenzo[f][1,2,4]triazolo[4,3-d][1,4]oxazepin-8-yl)-2-fluoro-4-methylbenzamide (Example 9)

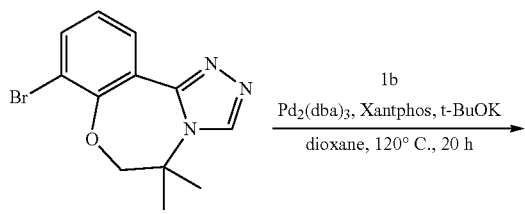

9f

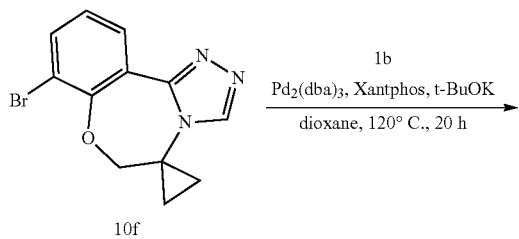

Example 9

8-bromo-5,5-dimethyl-5,6-dihydrobenzo[f][1,2,4]triazolo[4,3-d][1,4]oxazepine (9f) (0.02 g, 67.99 umol), 5-(4-cyclopropyl-1H-imidazol-1-yl)-2-fluoro-4-methylbenzamide (1b) (17.63 mg, 67.99 umol), Pd$_2$(dba)$_3$ (6.23 mg, 6.80 umol), Xantphos (5.90 mg, 10.20 umol) and t-BuOK (15.26 mg, 135.99 umol) in 1,4-dioxane (10 mL) was de-gassed 3 times at 20° C. and heated to 120° C. for 20 hrs under N$_2$. The reaction mixture was filtered through a Celite pad and the Celite pad was washed with MeOH (20 mL), the filtrate was collected and concentrated. The residue was purified by prep-HPLC (column: YMC-Actus Triart C18 100*30 mm*5 um; mobile phase: [water (10 mM NH$_4$HCO$_3$)-ACN]; B %: 35%-55%, 12 min) and lyophilized to give Example 9. MS mass calculated for [M+H]$^+$ (C$_{26}$H$_{25}$FN$_6$O$_2$) requires m/z 473.2, LCMS found m/z 473.2; $^1$H NMR (400 MHz, MeOD) δ=8.91 (s, 1H), 8.36 (d, J=7.9 Hz, 1H), 8.24 (d, J=8.3 Hz, 1H), 7.87 (d, J=6.6 Hz, 1H), 7.69 (s, 1H), 7.38 (d, J=11.8 Hz, 1H), 7.25 (t, J=8.1 Hz, 1H), 7.05 (s, 1H), 4.43 (s, 2H), 2.27 (s, 3H), 1.98-1.85 (m, 1H), 1.73 (s, 6H), 0.93-0.86 (m, 2H), 0.80-0.71 (m, 2H).

Synthesis of 5-(4-cyclopropyl-1H-imidazol-1-yl)-2-fluoro-4-methyl-N-(6H-spiro[benzo[f][1,2,4]triazolo[4,3-d][1,4]oxazepine-5,1'-cyclopropan]-8-yl)benzamide (Example 10)

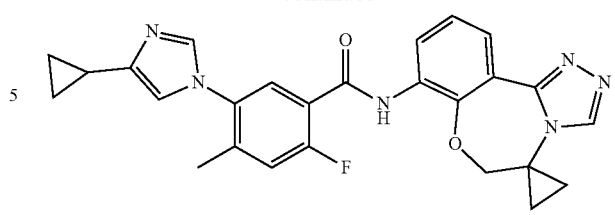

10f

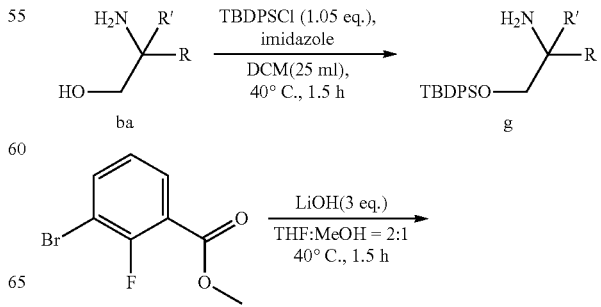

Example 10

8-bromo-6H-spiro[benzo[f][1,2,4]triazolo[4,3-d][1,4]oxazepine-5,1'-cyclopropane] (10f) (0.01 g, 34.23 umol), 5-(4-cyclopropyl-1H-imidazol-1-yl)-2-fluoro-4-methylbenzamide (1b) (8.88 mg, 34.23 umol), Pd$_2$(dba)$_3$ (3.13 mg, 3.42 umol), Xantphos (2.97 mg, 5.13 umol) and t-BuOK (7.68 mg, 68.46 umol) in 1,4-dioxane (5 mL) was de-gassed 3 times at 20° C. and then heated to 120° C. and stirred for 20 hrs under N$_2$. LCMS indicated a main peak with desired MS detected. The reaction mixture was filtered through a Celite pad and the Celite pad was washed with MeOH (10 mL). The filtrate was concentrated in vacuo. The residue was purified by prep-HPLC (column: Waters Xbridge 150*25 5 u; mobile phase: [water (0.04% NH$_3$H$_2$O+10 mM NH$_4$HCO$_3$)-ACN]; B %: 25%-45%, 10 min) and lyophilized to give Example 10. MS mass calculated for [M+H]$^+$ (C$_{26}$H$_{23}$FN$_6$O$_2$) requires m/z 471.2, LCMS found m/z 471.2; $^1$H NMR (400 MHz, CDCl$_3$) δ=9.34 (br d, J=14.9 Hz, 1H), 8.66 (d, J=6.6 Hz, 1H), 8.28 (d, J=6.6 Hz, 1H), 8.09 (d, J=7.5 Hz, 1H), 8.06 (s, 1H), 7.45 (s, 1H), 7.27-7.12 (m, 2H), 6.80 (s, 1H), 4.45 (s, 2H), 2.29 (s, 3H), 1.92 (s, 1H), 1.50-1.44 (m, 2H), 1.39-1.34 (m, 2H), 0.94-0.87 (m, 2H), 0.87-0.82 (m, 2H).

Example S2

(S)-5-(4-cyclopropyl-1H-imidazol-1-yl)-2-fluoro-4-methyl-N-(5-methyl-5,6-dihydrobenzo[f]tetrazolo[1,5-d][1,4]oxazepin-8-yl)benzamide (Example 3), (R)-5-(4-cyclopropyl-1H-imidazol-1-yl)-2-fluoro-4-methyl-N-(5-methyl-5,6-dihydrobenzo[f]tetrazolo[1,5-d][1,4]oxazepin-8-yl)benzamide (Example 5), and (R)-5-(4-cyclopropyl-1H-imidazol-1-yl)-N-(5-cyclopropyl-5,6-dihydrobenzo[f]tetrazolo[1,5-d][1,4]oxazepin-8-yl)-2-fluoro-4-methylbenzamide (Example 12) and 5-(4-cyclopropyl-1H-imidazol-1-yl)-N-(5,6-dihydrobenzo[f]tetrazolo[1,5-d][1,4]oxazepin-8-yl)-2-fluoro-4-methylbenzamide (Example 79) were synthesized according to the schemes provided below.

-continued

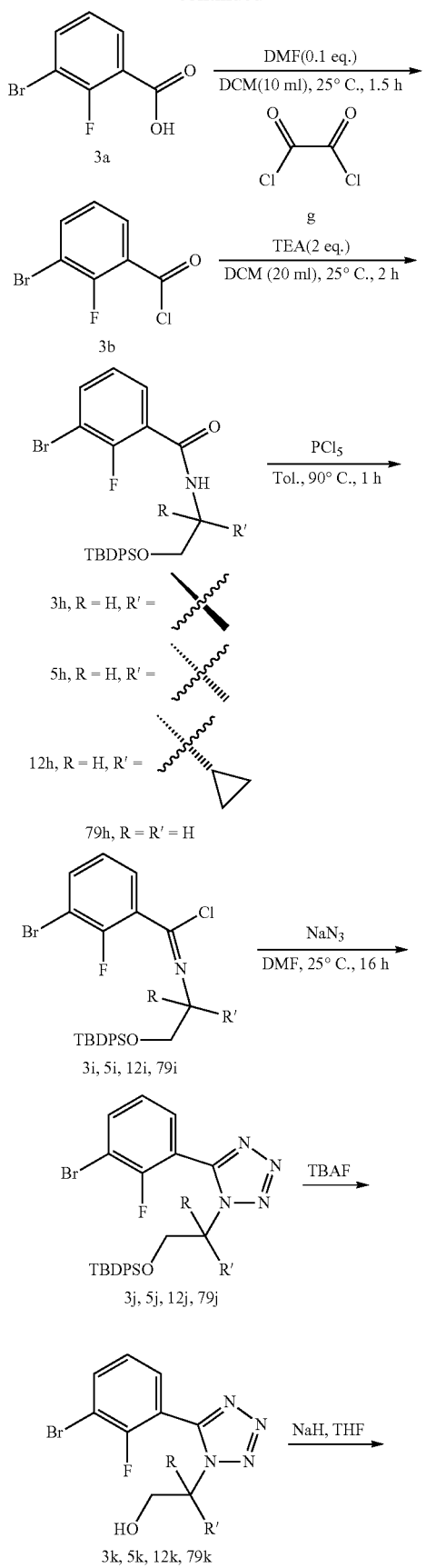

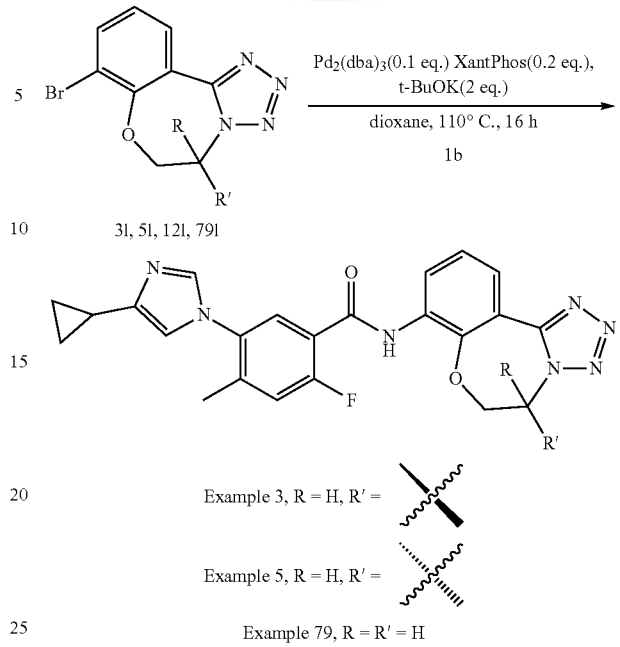

Example 3, R = H, R' =

Example 5, R = H, R' =

Example 79, R = R' = H

Synthesis of (g)

To a solution of alcohol ba (13.3 mmol) in DCM (20 mL) was added imidazole (2 eq) and TBDPSCl (1.05 eq) at 25° C. under $N_2$. The mixture was stirred at 40° C. for 1.5 h. LC-MS showed one main peak with desired MS. The reaction mixture was diluted with DCM (50 mL), and washed with $H_2O$ (15 mL*3). The combined organic layers were combined and washed with brine (15 mL*1), dried over $Na_2SO_4$, filtered and concentrated under reduced pressure to give g which was used directly in the next step without purification.

Synthesis of (3a)

To a solution of methyl 3-bromo-2-fluorobenzoate (4.78 g, 20.51 mmol) in THF (20 mL) and MeOH (10 mL) was added LiOH (1.47 g, 61.54 mmol) at 25° C. under $N_2$. The mixture was stirred at 40° C. for 1.5 hrs. TLC indicated 3-bromo-2-fluorobenzoate was consumed completely and one new spot formed. The reaction was poured into water (30 mL), then the pH of the mixture was adjusted to 5-6 with 1 M HCl solution. The reaction mixture was then extracted with ethyl acetate (20 mL*4). the combined organic layers were combined and washed with brine (10 mL), dried over $Na_2SO_4$, filtered and concentrated under reduced pressure to give 3-bromo-2-fluorobenzoic acid (3a) which was used directly in the next step without further purification. $^1$H NMR (400 MHz, MeOD) δ 7.90 (ddd, J=1.7, 6.5, 7.9 Hz, 1H), 7.83 (ddd, J=1.7, 6.3, 8.0 Hz, 1H), 7.19 (dt, J=0.9, 7.9 Hz, 1H), 3.31 (td, J=1.6, 3.3 Hz, 2H).

Synthesis of (3b)

To a solution of 3-bromo-2-fluorobenzoic acid (3a) (2.5 g, 11.42 mmol) in DCM (10 mL) were added DMF (83.44 mg, 1.14 mmol, 87.83 uL) and oxalyl dichloride (2.90 g, 22.83 mmol, 2.00 mL) at 0° C. under $N_2$. After addition, the mixture was stirred at 25° C. under $N_2$ for 2 hrs. The reaction

119 mixture was concentrated under reduced pressure to give 3-bromo-2-fluorobenzoyl chloride (3b) which was used directly in the next step.

Synthesis of (h)

To a solution of g (10.7 mmol) and TEA (2 eq) in DCM (10 mL) was added 3-bromo-2-fluorobenzoyl chloride (3b) (1 eq) at 25° C. under $N_2$. The mixture was stirred at 25° C. for 2 hrs. LC-MS showed one main peak with desired MS. The reaction mixture was diluted with DCM (30 mL), washed with $H_2O$ (12 mL*3) and brine (10 mL*1). The organic layer was dried over $Na_2SO_4$, filtered and concentrated under reduced pressure to give a residue. The residue was purified by column chromatography ($SiO_2$, Petroleum ether:Ethyl acetate=5:1) to give h.

Synthesis of (i)

To a solution of h (0.97 mmol) in toluene (10 mL) was added $PCl_5$ (1.1 eq) at 25° C. under $N_2$. The mixture was stirred at 90° C. for 1 h. The reaction was concentrated under reduced pressure to give i, which was used directly in the next step without further purification.

Synthesis of (j)

To a solution of i (0.98 mmol) in DMF (10 mL) was added $NaN_3$ (2 eq) at 0° C. under $N_2$. The mixture was stirred at 25° C. for 16 hrs. LC-MS showed one main peak with desired MS. The residue was diluted with ethyl acetate (30 mL) and washed with $H_2O$ (8 mL*3). The organic layers were combined and dried over $Na_2SO_4$, filtered and concentrated under reduced pressure to give a residue. The residue was purified by column chromatography ($SiO_2$, Petroleum ether: Ethyl acetate=5:1) to give j.

Synthesis of (k)

To a solution of j (0.7 mmol) in THF (5 mL) was added TBAF (1 M, 1 eq) at 25° C. under $N_2$. The mixture was stirred at 25° C. for 2 hrs. LC-MS showed j was consumed completely and desired MS was detected. The reaction mixture was added ethyl acetate (30 mL), and then washed with $H_2O$ (8 mL*3). The combined organic layers were washed with brine (5 mL*1), dried over $Na_2SO_4$, filtered and concentrated under reduced pressure to give a residue. The residue was purified by prep-TLC ($SiO_2$, Petroleum ether:Ethyl acetate=3:1) to give k.

Synthesis of (l)

To a solution of k (0.5 mmol) in THF (20 mL) was added NaH (60% purity, 1.1 eq) at 0° C. under $N_2$. The mixture was stirred at 25° C. under $N_2$ for 12 h. LC-MS showed starting material was consumed completely and one new peak with desired MS was detected. The reaction mixture was quenched with sat. ammonium chloride solution (10 mL) and water (10 mL), then extracted with EtOAc (20 mL*3). The combined organic layers were washed with brine (10 mL), dried over $Na_2SO_4$, filtered and concentrated under reduced pressure to give a residue. The residue was purified by prep-TLC ($SiO_2$, Petroleum ether:Ethyl acetate=1:1) to give l.

120

Synthesis of (S)-5-(4-cyclopropyl-1H-imidazol-1-yl)-2-fluoro-4-methyl-N-(5-methyl-5,6-dihydrobenzo[f]tetrazolo[1,5-d][1,4]oxazepin-8-yl)benzamide (Example 3)

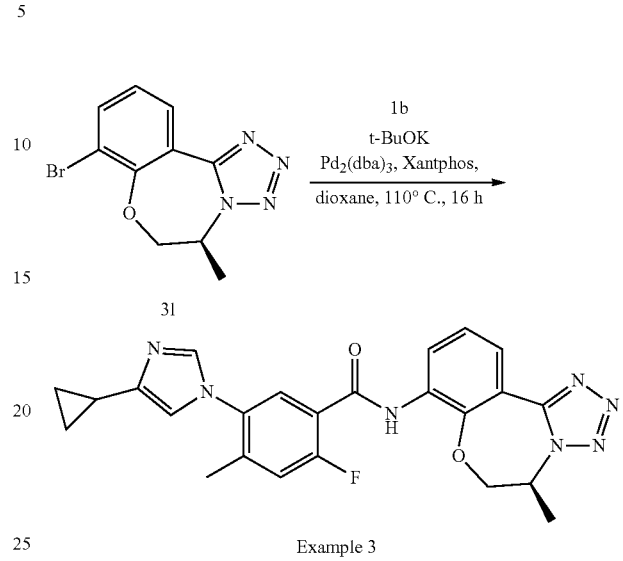

Example 3

To a solution of (S)-8-bromo-5-methyl-5,6-dihydrobenzo[f]tetrazolo[1,5-d][1,4]oxazepine (31) (25 mg, 96.42 umol) and 5-(4-cyclopropyl-1H-imidazol-1-yl)-2-fluoro-4-methylbenzamide (1b) (27.10 mg, 96.42 umol) in dioxane (3 mL) were added Xantphos (11.16 mg, 19.28 umol), t-BuOK (21.64 mg, 192.84 umol) and $Pd_2(dba)_3$ (8.83 mg, 9.64 umol) at 25° C. under $N_2$. The mixture was stirred at 110° C. for 16 hrs. LC-MS showed one new peak with desired MS. The reaction mixture was diluted with MeOH (20 ml) and the resulting mixture was filtered, the filtrate was concentrated under reduced pressure to give a residue. The residue was purified by prep-HPLC (basic condition) to give Example 3. MS mass calculated for $[M+1]^+$ ($C_{24}H_{22}FN_7O_2$) requires m/z 460.2, LCMS found m/z 460.2; $^1$H NMR (400 MHz, $CDCl_3$) δ 9.39 (br d, J=16.3 Hz, 1H), 8.74 (dd, J=1.4, 8.1 Hz, 1H), 8.37 (dd, J=1.5, 8.1 Hz, 1H), 8.09 (d, J=7.3 Hz, 1H), 7.46 (d, J=1.3 Hz, 1H), 7.32 (t, J=8.1 Hz, 1H), 7.20 (d, J=12.2 Hz, 1H), 6.81 (d, J=1.2 Hz, 1H), 5.24 (ddd, J=1.8, 4.7, 6.8 Hz, 1H), 4.66 (dd, J=4.6, 13.1 Hz, 1H), 4.49 (dd, J=1.8, 13.1 Hz, 1H), 2.31 (s, 3H), 1.97-1.88 (m, 1H), 1.81 (d, J=6.8 Hz, 3H), 0.94-0.89 (m, 2H), 0.87-0.82 (m, 2H).

Synthesis of (R)-5-(4-cyclopropyl-1H-imidazol-1-yl)-2-fluoro-4-methyl-N-(5-methyl-5,6-dihydrobenzo[f]tetrazolo[1,5-d][1,4]oxazepin-8-yl)benzamide (Example 5)

51

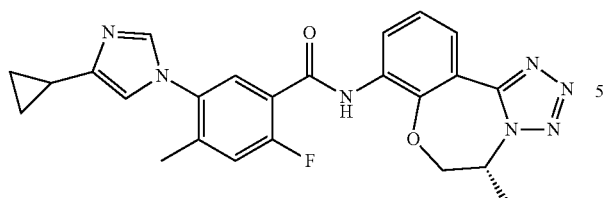

Example 5

To a solution of 5-(4-cyclopropyl-1H-imidazol-1-yl)-2-fluoro-4-methylbenzamide (1b) (10.15 mg, 39.13 umol) and (R)-8-bromo-5-methyl-5,6-dihydrobenzo[f]tetrazolo[1,5-d][1,4]oxazepine (5I) (10 mg, 35.57 umol) in dioxane (5 mL) was added t-BuOK (7.98 mg, 71.15 umol), Xantphos (4.12 mg, 7.11 umol) and Pd$_2$(dba)$_3$ (3.26 mg, 3.56 umol) under nitrogen. The mixture was stirred for 12 hrs at 110° C. LCMS showed one peak with desired MS. The reaction mixture was diluted with MeOH (5 mL) and filtered, the filtrate was concentrated to a residue. The residue was purified by prep-HPLC (column: Phenomenex Synergi C18 100*21.2 mm*4 um; mobile phase: [water (0.1% TFA)-ACN]; B %: 15%-40%, 10 min) to give Example 5. MS mass calculated for [M+1]$^+$ (C$_{24}$H$_{22}$FN$_7$O$_2$) requires m/z 460.2, LCMS found m/z 460.1; $^1$H NMR (CHLOROFORM-d, 400 MHz): δ (ppm) 9.31 (br d, J=16.3 Hz, 1H), 8.66 (dd, J=8.2, 1.3 Hz, 1H), 8.29 (dd, J=8.2, 1.5 Hz, 1H), 8.01 (d, J=7.5 Hz, 1H), 7.39 (s, 1H), 7.24 (t, J=8.2 Hz, 1H), 7.12 (d, J=12.3 Hz, 1H), 6.73 (s, 1H), 5.16 (ddd, J=6.8, 4.8, 1.9 Hz, 1H), 4.58 (dd, J=13.0, 4.6 Hz, 1H), 4.41 (dd, J=13.1, 1.7 Hz, 1H), 2.23 (s, 3H), 1.80-1.91 (m, 1H), 1.74 (d, J=6.8 Hz, 3H), 0.80-0.88 (m, 2H), 0.72-0.79 (m, 2H).

Synthesis of Example 79

Example 79 was made in a similar manner as Example 3 and Example 5. MS mass calculated for [M+1]$^+$ (C$_{23}$H$_{20}$FN$_7$O$_2$) requires m/z 446.2, LCMS found m/z 446.1; $^1$H NMR (400 MHz, METHANOL-d$_4$) δ=8.47 (br d, J=7.5 Hz, 1H), 8.27 (dd, J=1.3, 8.2 Hz, 1H), 7.86 (d, J=6.8 Hz, 1H), 7.69 (s, 1H), 7.38 (d, J=12.1 Hz, 1H), 7.29 (t, J=8.2 Hz, 1H), 7.05 (s, 1H), 5.04-4.97 (m, 2H), 4.74-4.68 (m, 2H), 2.27 (s, 3H), 1.96-1.86 (m, 1H), 0.93-0.85 (m, 2H), 0.79-0.72 (m, 2H).

Example 12 was synthesized according to the schemes and procedures outlined below.

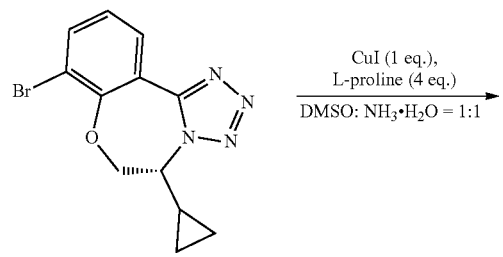

121

CuI (1 eq.),
L-proline (4 eq.)
⟶
DMSO: NH$_3$·H$_2$O = 1:1

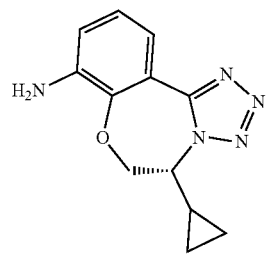

12m

Synthesis of (12q)

A solution of (R)-8-bromo-5-cyclopropyl-5,6-dihydrobenzo[f]tetrazolo[1,5-d][1,4]oxazepine (121) (0.03 g, 97.67 umol), CuI (18.60 mg, 97.67 umol) and L-proline (44.98 mg, 390.69 umol) in DMSO (3 mL) and NH$_3$.H$_2$O (3 mL) was stirred in a 30 mL of sealed tube at 100° C. for 18 hrs. The reaction mixture was concentrated to remove NH$_3$.H$_2$O, then it was extracted with DCM (5 mL), the organic phase was washed with brine (3 mL*3), dried over Na$_2$SO$_4$, filtered and concentrated. The residue was purified by prep-TLC to afford (R)-5-cyclopropyl-5,6-dihydrobenzo[f]tetrazolo[1,5-d][1,4]oxazepin-8-amine (12q). $^1$H NMR (400 MHz, METHANOL-d4) δ=7.75 (dd, J=2.0, 7.7 Hz, 1H), 7.07-6.91 (m, 2H), 4.93 (d, J=3.5 Hz, 1H), 4.37 (br d, J=9.6 Hz, 1H), 4.29 (d, J=12.7 Hz, 1H), 1.46-1.38 (m, 1H), 0.92-0.83 (m, 1H), 0.91-0.64 (m, 3H).

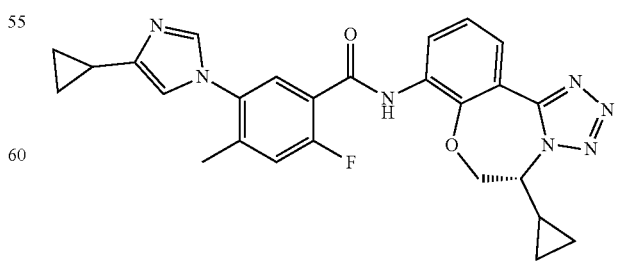

Example 12

Synthesis of (R)-5-(4-cyclopropyl-1H-imidazol-1-yl)-N-(5-cyclopropyl-5,6-dihydrobenzo[f]tetrazolo[1,5-d][1,4]oxazepin-8-yl)-2-fluoro-4-methylbenzamide (Example 12)

To a solution of 5-(4-cyclopropyl-1H-imidazol-1-yl)-2-fluoro-4-methylbenzoic acid (6 mg, 18.44 umol) in DMF (1 mL) was added HATU (10.52 mg, 27.66 umol) and NMM (3.73 mg, 36.88 umol, 4.06 uL) at 15° C. and stirred for 10 min, then (R)-5-cyclopropyl-5,6-dihydrobenzo[f]tetrazolo[1,5-d][1,4]oxazepin-8-amine (12q) (4.49 mg, 18.44 umol) dissolved in DMF (1 mL) was added and the mixture was stirred for another 2 hours at 30° C. The reaction mixture was diluted with water (5 mL) and extracted with EtOAc (10 mL). The organic phase was washed with brine (5 mL*2), dried over $Na_2SO_4$, filtered and concentrated. The residue was purified by prep-HPLC (TFA condition, column: Luna C18 100*30 5u; mobile phase: [water (0.1% TFA)-ACN]; B %: 15%-45%, 10 min) to afford Example 12. MS mass calculated for $[M+1]^+$ ($C_{26}H_{24}FN_7O_2$) requires m/z 486.2, LCMS found m/z 486.2; $^1$H NMR (400 MHz, METHANOL-d4) δ=9.05 (s, 1H), 8.48 (br d, J=8.3 Hz, 1H), 8.33 (d, J=7.9 Hz, 1H), 8.09 (d, J=6.6 Hz, 1H), 7.57 (s, 1H), 7.52 (d, J=11.8 Hz, 1H), 7.32 (t, J=8.1 Hz, 1H), 4.89 (m, 1H) 4.48-4.40 (m, 2H), 2.34 (s, 3H), 2.06 (s, 1H), 1.42 (s, 1H), 1.17-1.09 (m, 2H), 0.94-0.86 (m, 3H), 0.81-0.69 (m, 3H)

Example S3

(R)-4-(4-cyclopropyl-1H-imidazol-1-yl)-N-(5-methyl-5,6-dihydrobenzo[f]tetrazolo[1,5-d][1,4]oxazepin-8-yl)picolinamide (Example 4) and (S)-4-(4-cyclopropyl-1H-imidazol-1-yl)-N-(5-methyl-5,6-dihydrobenzo[f]tetrazolo[1,5-d][1,4]oxazepin-8-yl)picolinamide (Example 6) were synthesized according to the schemes provided below.

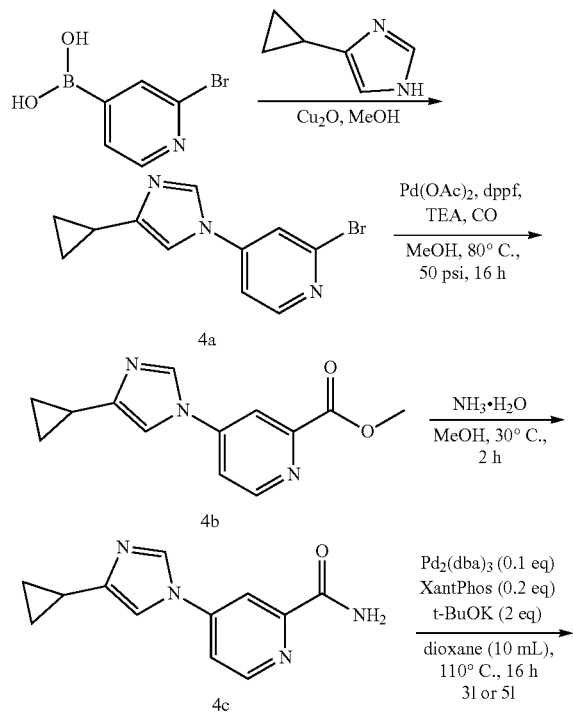

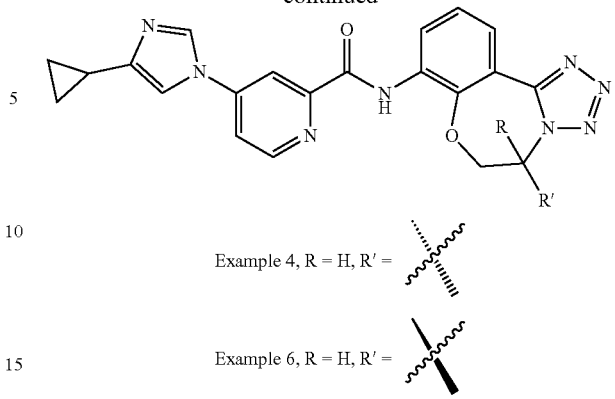

2-bromo-4-(4-cyclopropyl-1H-imidazol-1-yl)pyridine (4a)

To a mixture of 4-cyclopropyl-1H-imidazole (3.5 g, 32.37 mmol) and (2-bromopyridin-4-yl)boronic acid (7.18 g, 35.60 mmol) in MeOH (50 mL) was added $Cu_2O$ (463.12 mg, 3.24 mmol) in one portion at 20° C. under $O_2$. The mixture was stirred at 20° C. for 10 min, then heated to 50° C. and stirred for 16 hours. LCMS showed one new peak with desired MS. The mixture was filtered and the filtrate was concentrated in vacuo. The residue was purified by flash silica gel chromatography (ISCO®; 10 g SepaFlash® Silica Flash Column, Eluent of 100% Ethyl acetate gradient @ 200 mL/min) to give 2-bromo-4-(4-cyclopropyl-1H-imidazol-1-yl)pyridine (4a). MS mass calculated for $[M+1]^+$ ($C_{11}H_{10}BrN_3$) requires m/z 264.0, LCMS found m/z 264.0; $^1$H NMR (400 MHz, MeOD) δ 8.39 (d, J=5.6 Hz, 1H), 8.32 (s, 1H), 7.94 (d, J=1.8 Hz, 1H), 7.66 (dd, J=2.0, 5.6 Hz, 1H), 7.53 (s, 1H), 1.93-1.85 (m, 1H), 0.93-0.84 (m, 2H), 0.82-0.71 (m, 2H).

Methyl 4-(4-cyclopropyl-1H-imidazol-1-yl)picolinate (4b)

To a solution of 2-bromo-4-(4-cyclopropylimidazol-1-yl)pyridine (4a) (0.6 g, 2.27 mmol) in MeOH (30 mL) was added TEA (1.15 g, 11.36 mmol), $Pd(OAc)_2$ (204.00 mg, 908.68 umol) and DPPF (251.88 mg, 454.34 umol) under $N_2$. The solution was degassed under vacuum and purged with CO several times. The mixture was stirred under CO (50 psi) at 80° C. for 16 hours. LC-MS showed one main peak with desired MSdetected. The mixture was concentrated in vacuo. The residue was purified by prep-TLC ($SiO_2$, Ethyl acetate:Methanol=10:1) to give methyl 4-(4-cyclopropyl-1H-imidazol-1-yl)picolinate (4b). MS mass calculated for $[M+1]^+$ ($C_{13}H_{13}N_3O_2$) requires m/z 244.1, LCMS found m/z 244.2; $^1$H NMR (400 MHz, MeOD) δ 8.72 (d, J=5.5 Hz, 1H), 8.39 (d, J=1.1 Hz, 1H), 8.34 (d, J=1.8 Hz, 1H), 7.87 (dd, J=2.4, 5.5 Hz, 1H), 7.59 (d, J=1.1 Hz, 1H), 4.02 (s, 3H), 1.97-1.86 (m, 1H), 0.96-0.86 (m, 2H), 0.81-0.73 (m, 2H).

4-(4-cyclopropyl-1H-imidazol-1-yl)picolinamide (4c)

To a mixture of methyl 4-(4-cyclopropylimidazol-1-yl)pyridine-2-carboxylate (4b) (474 mg, 1.95 mmol) in MeOH (4 mL) was added $NH_3.H_2O$ (4 mL) in one portion at 20° C.

The mixture was stirred at 20° C. for 5 min, then heated to 30° C. and stirred for 2 hours. LC-MS showed one main peak with desired MS. The mixture was concentrated in vacuo. The residue was purified by column chromatography (SiO$_2$, ethyl acetate:methanol=50:1 to 1:1) to give 4-(4-cyclopropyl-1H-imidazol-1-yl)picolinamide (4c). MS mass calculated for [M+1]$^+$ (C$_{12}$H$_{12}$N$_4$O) requires m/z 229.1, LCMS found m/z 229.1; $^1$H NMR (400 MHz, MeOD) δ 8.69 (d, J=5.4 Hz, 1H), 8.34 (s, 1H), 8.27 (d, J=2.1 Hz, 1H), 7.78 (dd, J=2.1, 5.4 Hz, 1H), 7.55 (s, 1H), 1.97-1.85 (m, 1H), 0.96-0.87 (m, 2H), 0.83-0.74 (m, 2H).

Synthesis of (R)-4-(4-cyclopropyl-1H-imidazol-1-yl)-N-(5-methyl-5,6-dihydrobenzo[f]tetrazolo[1,5-d][1,4]oxazepin-8-yl)picolinamide (Example 4)

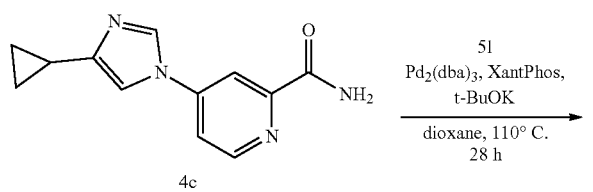

To a solution of (R)-8-bromo-5-methyl-5,6-dihydrobenzo[f]tetrazolo[1,5-d][1,4]oxazepine (51) (20 mg, 71.15 umol) and 4-(4-cyclopropyl-1H-imidazol-1-yl)picolinamide (4c) (17.86 mg, 78.26 umol) in dioxane (5 mL) was added Xantphos (8.23 mg, 14.23 umol), t-BuOK (15.97 mg, 142.29 umol) and Pd$_2$(dba)$_3$ (6.52 mg, 7.11 umol) under nitrogen. The mixture was stirred at 110° C. for 16 hrs. The starting material remained and the desired MS was detected by LCMS. The reaction mixture was stirred for another 12 hrs. The reaction mixture was diluted with ethyl acetate (30 mL) and filtered, and the filtrate was concentrated to a residue. The residue was diluted with MeOH (0.5 mL), solid precipitated. The mixture was filtered. The filter cake was collected and purified by prep-TLC (Dichloromethane:Methanol=10:1, R$_f$=0.49) to give Example 4. MS mass calculated for [M+1]$^+$ (C$_{22}$H$_{20}$N$_8$O$_2$) requires m/z 429.2, LCMS found m/z 429.1; $^1$H NMR (METHANOL-d4, 400 MHz): δ (ppm) 9.03 (s, 1H), 8.49 (br d, J=7.1 Hz, 1H), 8.32 (d, J=8.2 Hz, 1H), 8.11 (br d, J=7.2 Hz, 1H), 7.57 (s, 1H), 7.53 (d, J=11.4 Hz, 1H), 7.34 (t, J=8.1 Hz, 1H), 5.31 (br s, 1H), 4.75 (dd, J=13.4, 4.5 Hz, 1H), 4.55 (d, J=12.2 Hz, 1H), 2.03-2.14 (m, 1H), 1.76 (d, J=6.8 Hz, 3H), 1.09-1.21 (m, 2H), 0.84-0.96 (m, 2H).

Synthesis of (S)-4-(4-cyclopropyl-1H-imidazol-1-yl)-N-(5-methyl-5,6-dihydrobenzo[f]tetrazolo[1,5-d][1,4]oxazepin-8-yl)picolinamide (Example 6)

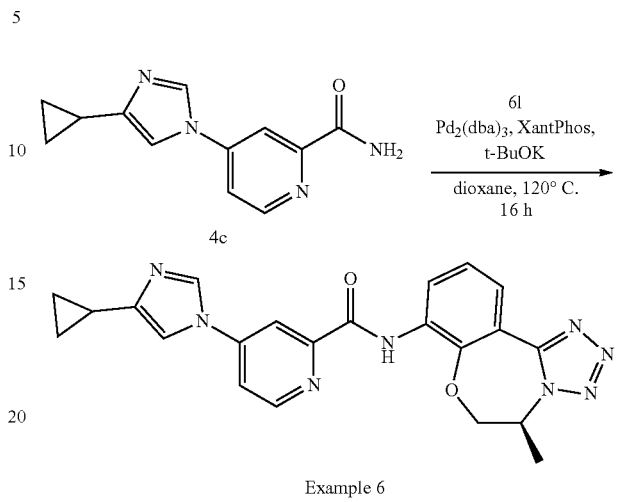

To a solution of (S)-8-bromo-5-methyl-5,6-dihydrobenzo[f]tetrazolo[1,5-d][1,4]oxazepine (61) (10 mg, 35.57 umol, 1 eq), 4-(4-cyclopropyl-1H-imidazol-1-yl)picolinamide (4c) (8.12 mg, 35.57 umol) in dioxane (5 mL) were added Xantphos (4.12 mg, 7.11 umol), Pd$_2$(dba)$_3$ (3.26 mg, 3.56 umol) and t-BuOK (7.98 mg, 71.15 umol) at 25° C. under N$_2$. The mixture was stirred at 120° C. for 16 hrs. LCMS showed one new peak with desired MS. The reaction mixture was diluted with MeOH (20 ml), filtered and the filtrate was concentrated under reduced pressure to give a residue. The residue was purified by prep-TLC (DCM:MeOH=10:1) to give Example 6. MS mass calculated for [M+1]$^+$ (C$_{22}$H$_{20}$N$_8$O$_2$) requires m/z 429.2, LCMS found m/z 429.2; $^1$H NMR (400 MHz, CDCl$_3$) δ 10.73 (s, 1H), 8.82 (dd, J=1.5, 8.1 Hz, 1H), 8.72 (d, J=5.7 Hz, 1H), 8.38 (dd, J=1.3, 8.3 Hz, 1H), 8.31 (d, J=2.2 Hz, 1H), 8.03 (s, 1H), 7.50 (dd, J=2.4, 5.5 Hz, 1H), 7.34 (t, J=8.1 Hz, 1H), 7.27 (s, 2H), 7.25 (d, J=0.9 Hz, 1H), 7.25-7.23 (m, 1H), 5.29-5.21 (m, 1H), 4.73 (dd, J=4.8, 13.2 Hz, 1H), 4.53 (dd, J=1.8, 13.2 Hz, 1H), 1.97-1.90 (m, 1H), 1.83 (d, J=7.0 Hz, 3H), 0.94 (td, J=2.9, 8.3 Hz, 2H), 0.89-0.83 (m, 3H).

Example S4

(R)-4-(4-cyclopropyl-1H-imidazol-1-yl)-N-(5-methyl-5,6-dihydrobenzo[f][1,2,4]triazolo[4,3-d][1,4]oxazepin-8-yl)picolinamide (Example 11) was synthesized according to the schemes provided below.

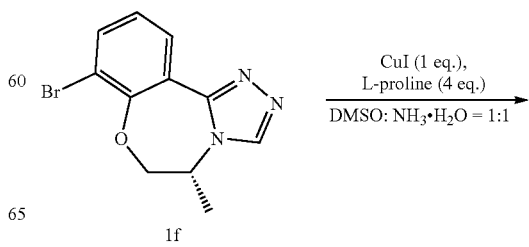

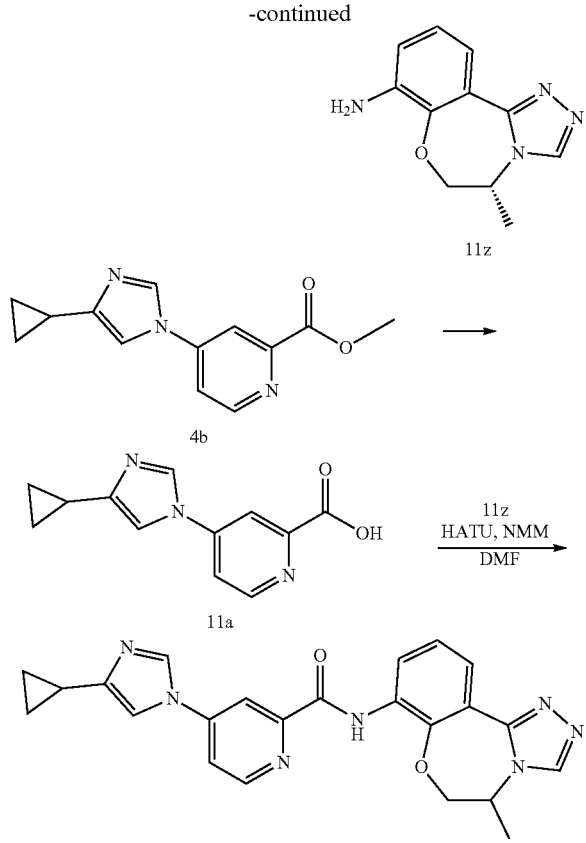

Example 11

(R)-5-methyl-5,6-dihydrobenzo[f][1,2,4]triazolo[4,3-d][1,4]oxazepin-8-amine (11z)

To a solution of (R)-8-bromo-5-methyl-5,6-dihydrobenzo[f][1,2,4]triazolo[4,3-d][1,4]oxazepine (1f) (15 mg, 53.55 umol) in DMSO (1 mL) and NH$_3$·H$_2$O (1 mL) was added L-proline (24.66 mg, 214.19 umol) and CuI (10.20 mg, 53.55 umol) at 25° C. The mixture was stirred at 100° C. for 36 h. LCMS showed 1f was consumed completely. The reaction mixture was concentrated under reduced pressure, and diluted with H$_2$O (8 mL) and extracted with (DCM:isopropyl alcohol=9:1) (10 mL*10). The combined organic layers were washed with brine (8 mL*1), dried over Na$_2$SO$_4$, filtered and concentrated under reduced pressure to give a residue. The residue was purified by prep-TLC (DCM:MeOH=10:1) to give (R)-5-methyl-5,6-dihydrobenzo[f][1,2,4]triazolo[4,3-d][1,4]oxazepin-8-amine (11z). MS mass calculated for [M+1]$^+$ (C$_{11}$H$_{12}$N$_4$O) requires m/z 217.1, LCMS found m/z 217.1; $^1$H NMR (400 MHz, CDCl$_3$) δ 8.26 (s, 1H), 8.02 (dd, J=1.6, 8.1 Hz, 1H), 7.27 (s, 3H), 7.02-6.97 (m, 1H), 6.82 (dd, J=1.6, 7.7 Hz, 1H), 4.74-4.65 (m, 1H), 4.54-4.48 (m, 1H), 4.33 (dd, J=1.5, 12.9 Hz, 1H), 3.98 (br s, 2H), 1.64 (d, J=6.8 Hz, 3H).

(4-(4-cyclopropyl-1H-imidazol-1-yl)picolinic acid (11a)

To a solution of methyl 4-(4-cyclopropyl-1H-imidazol-1-yl)picolinate (4b) (500 mg, 2.06 mmol) in THF (2 mL) and MeOH (2 mL) and H$_2$O (0.4 mL) was added LiOH·H$_2$O (86.52 mg) at 25° C. and the mixture was stirred for 2 hrs. The pH of the mixture was adjusted to 5 with 0.5 M HCl solution. The mixture was concentrated under reduced pressure to give 4-(4-cyclopropyl-1H-imidazol-1-yl)picolinic acid (11a), which was used directly without further purification.

Synthesis of (R)-4-(4-cyclopropyl-1H-imidazol-1-yl)-N-(5-methyl-5,6-dihydrobenzo[f][1,2,4]triazolo[4,3-d][1,4]oxazepin-8-yl)picolinamide (Example 11)

To a solution of 4-(4-cyclopropyl-1H-imidazol-1-yl)picolinic acid (11a) (21.20 mg, 92.49 umol), HATU (26.38 mg, 69.37 umol) and NMM (9.36 mg, 92.49 umol, 10.17 uL) in DMF (1 mL) at 25° C. under N$_2$. The mixture was stirred for 10 min, and then 11z (10 mg, 46.25 umol) was added at 25° C. under N$_2$. The mixture was stirred at 25° C. for 1 h. LCMS showed desired MS was detected. The reaction mixture was poured into H$_2$O (10 mL) at 25° C., the mixture was filtered. The filter cake was washed with MeOH (0.5 mL*2), the filter cake was collected to give Example 11. MS mass calculated for [M+1]$^+$ (C$_{23}$H$_{21}$N$_7$O$_2$) requires m/z 428.2, LCMS found m/z 428.2; $^1$H NMR (400 MHz, DMSO) δ 10.69 (s, 1H), 9.33 (br s, 1H), 8.93 (d, J=5.5 Hz, 1H), 8.85 (s, 1H), 8.56-8.51 (m, 2H), 8.27 (dd, J=1.6, 8.2 Hz, 1H), 8.16 (s, 1H), 8.09 (dd, J=2.3, 5.5 Hz, 1H), 7.28 (t, J=8.1 Hz, 1H), 4.99-4.89 (m, 1H), 4.70 (dd, J=4.5, 13.1 Hz, 1H), 4.51 (d, J=11.5 Hz, 1H), 2.03-1.91 (m, 1H), 1.55 (d, J=6.8 Hz, 3H), 1.02-0.94 (m, 2H), 0.86-0.78 (m, 2H).

Example S5

(S)-4-(4-cyclopropyl-1H-imidazol-1-yl)-N-(5-methyl-5,6-dihydrobenzo[f][1,2,4]triazolo[4,3-d][1,4]oxazepin-8-yl)picolinamide (Example 80) was made in a similar manner as Example 11 by using 2f. MS mass calculated for [M+1]$^+$ (C$_{23}$H$_{21}$N$_7$O$_2$) requires m/z 428.2, LCMS found m/z 428.2; $^1$H NMR (400 MHz, DMSO-d6) δ=10.68 (s, 1H), 9.04 (br s, 1H), 8.87 (d, J=5.5 Hz, 1H), 8.81 (s, 1H), 8.52 (dd, J=1.6, 7.9 Hz, 1H), 8.49 (d, J=2.0 Hz, 1H), 8.26 (dd, J=1.6, 8.2 Hz, 1H), 8.07-8.03 (m, 2H), 7.26 (t, J=8.1 Hz, 1H), 4.95-4.88 (m, 1H), 4.68 (dd, J=4.5, 13.0 Hz, 1H), 4.49 (d, J=12.3 Hz, 1H), 2.54-2.45 (m, 1H), 1.98-1.86 (m, 1H), 1.54 (d, J=6.8 Hz, 3H), 0.95-0.88 (m, 2H), 0.82-0.75 (m, 2H).

Example S6

5-(4-cyclopropyl-1H-imidazol-1-yl)-N-(5,5-dimethyl-5,6-dihydrobenzo[f]tetrazolo[1,5-d][1,4]oxazepin-8-yl)-2-fluoro-4-methylbenzamide (Example 13) and 5-(4-cyclopropyl-1H-imidazol-1-yl)-2-fluoro-4-methyl-N-(6H-spiro[benzo[f]tetrazolo[1,5-d][1,4]oxazepine-5,1'-cyclopropan]-8-yl)benzamide (Example 14) were synthesized according to the schemes provided below.

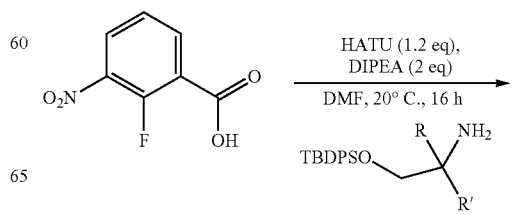

-continued

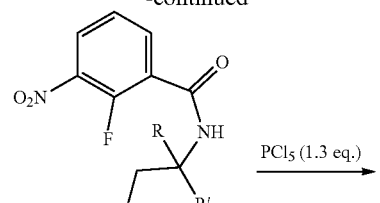

13m, R = R' = Me

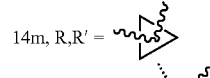

14m, R,R' =

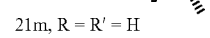

19m, R = H., R' =

21m, R = R' = H

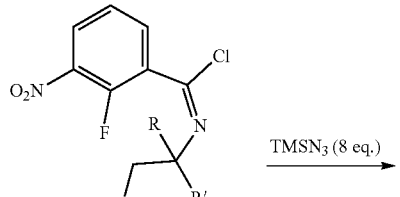

13n, R = R' = Me

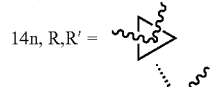

14n, R,R' =

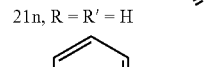

19n, R = H., R' =

21n, R = R' = H

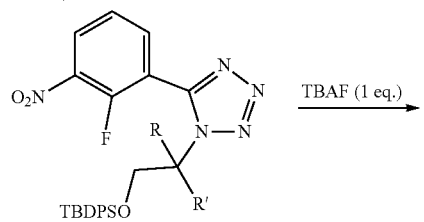

13o, 14o, 19o, 21o

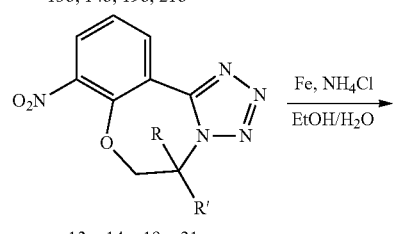

13p, 14p, 19p, 21p

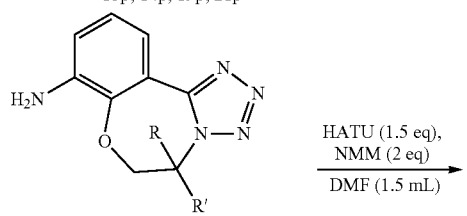

13q, R = R' = Me

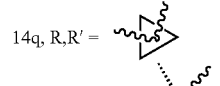

14q, R,R' =

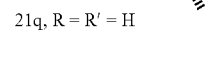

19q, R = H., R' =

21q, R = R' = H

-continued

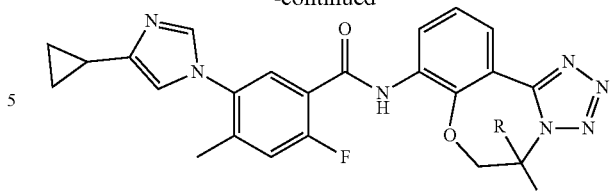

Example 13, R = R' = Me

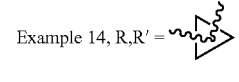

Example 14, R,R' =

Synthesis of (m)

A solution of 2-fluoro-3-nitrobenzoic acid (3.3 mmol), HATU (1.2 eq) and DIPEA (2 eq) in DMF (5 mL) at 25° C. under $N_2$ was stirred for 10 min at 25° C., then $RNH_2$ (1 eq) was added to the mixture at 25° C. under $N_2$. The mixture was stirred at 25° C. for 16 h. LCMS showed desired MS was detected. The reaction mixture was added ethyl acetate (80 mL), and washed with $H_2O$ (20 mL*3). The combined organic layers were washed with sat. $NH_4Cl$ (5 ml*3) and NaCl (5 mL), dried over $Na_2SO_4$, filtered and concentrated under reduced pressure to give a residue. The residue was purified by column chromatography ($SiO_2$, Petroleum ether/ Ethyl acetate=7:1 to 2:1) to give (m).

Synthesis of (n)

To a solution of (m) (0.81 mmol) in DCM (5 mL) was added $PCl_5$ (1.5 eq) at 25° C. under $N_2$. The mixture was stirred at 25° C. under $N_2$ for 2 h. (n) in DCM was used directly in the next step.

Synthesis of (o)

To a solution of (n) (0.81 mmol) in DCM (2 mL) was added $TMSN_3$ (8 eq) at 25° C. under $N_2$. The mixture was stirred at 25° C. under $N_2$ for 16 h. TLC indicated the reaction was completed. The reaction mixture was quenched by addition of sat. $NaHCO_3$ (2 mL) at 25° C., the mixture was diluted with $H_2O$ (10 mL) and extracted with ethyl acetate 75 mL (25 mL*3). The combined organic layers were washed with brine (8 mL*1), dried over $Na_2SO_4$, filtered and concentrated under reduced pressure to give a residue. The residue was purified by prep-TLC ($SiO_2$, Petroleum ether:Ethyl acetate=3:1) to give (o).

Synthesis of (p)

To a solution of (o) (0.68 mmol) in THF (10 mL) was added TBAF (1 eq) at 25° C. under N2. The mixture was stirred at 25° C. for 16 h. LCMS showed desired MS was detected. The reaction mixture was diluted with ethyl acetate (50 mL) and washed with $H_2O$ (5 mL*3). The combined organic layers were washed with brine (8 mL), dried over $Na_2SO_4$, filtered and concentrated under reduced pressure to give a solid. The solid was washed with DCM (0.5 mL*3) and collected to give (p).

Synthesis of (q)

To a solution of (p) (0.19 mmol) in EtOH (5 mL) and $H_2O$ (1 mL) were added Fe (5 eq) and $NH_4Cl$ (10 eq) at 25° C.

under N₂. The mixture was stirred at 70° C. for 2 h. TLC indicated the reaction was completed. The reaction mixture was filtered and concentrated under reduced pressure to give a residue, and then diluted with H₂O (10 mL) and extracted with Ethyl acetate (25 mL*3). The combined organic layers were washed with brine (8 mL), dried over Na₂SO₄, filtered and the filtrate was concentrated under reduced pressure to give (q).

Synthesis of 5-(4-cyclopropyl-1H-imidazol-1-yl)-N-(5,5-dimethyl-5,6-dihydrobenzo[f]tetrazolo[1,5-d][1,4]oxazepin-8-yl)-2-fluoro-4-methylbenzamide (Example 13)

To a solution of 1a (40 mg, 153.69 umol) in DMF (1 mL) was added HATU (70.13 mg, 184.43 umol) and NMM (31.09 mg, 307.38 umol, 33.79 uL) at 15° C. and stirred for 10 min, then 5,5-dimethyl-5,6-dihydrobenzo[f]tetrazolo[1,5-d][1,4]oxazepin-8-amine (13q) (42.65 mg, 184.43 umol) in DMF (1 mL) was added and stirred for another 18 hours at 40° C. The reaction solution was diluted with water (5 mL) and extracted with EtOAc (10 mL*2), the combined organic layers were washed with NaHCO₃ (5 mL), brine (10 mL), dried over Na₂SO₄, filtered and concentrated. The residue was dissolved with DCM (3 mL), then MTBE (10 mL) was added, solid precipitated and the mixture was filtered, the filter cake was washed with MBTE (5 mL), water (5 mL) and collected and was dried in vacuo to afford Example 13. MS mass calculated for [M+1]⁺ ($C_{25}H_{24}FN_7O_2$) requires m/z 474.2, LCMS found m/z 474.2; ¹H NMR (400 MHz, CHLOROFORM-d) δ=9.37 (br d, J=16.7 Hz, 1H), 8.71 (d, J=7.9 Hz, 1H), 8.35 (d, J=8.3 Hz, 1H), 8.09 (d, J=7.5 Hz, 1H), 7.46 (s, 1H), 7.32 (t, J=7.9 Hz, 1H), 7.19 (d, J=12.3 Hz, 1H), 6.81 (s, 1H), 4.40 (s, 2H), 2.31 (s, 3H), 1.92 (s, 1H), 1.85 (s, 6H), 0.96-0.88 (m, 2H), 0.84 (br d, J=3.1 Hz, 2H).

Synthesis of 5-(4-cyclopropyl-1H-imidazol-1-yl)-2-fluoro-4-methyl-N-(6H-spiro[benzo[f]tetrazolo[1,5-d][1,4]oxazepine-5,1'-cyclopropan]-8-yl)benzamide (Example 14)

To a solution (1a) (22.71 mg, 87.25 umol), HATU (49.76 mg, 130.87 umol) and NMM (17.65 mg, 174.49 umol, 19.18 uL) in DMF (1.5 mL) was added 6H-spiro[benzo[f]tetrazolo[1,5-d][1,4]oxazepine-5,1'-cyclopropan]-8-amine (20 mg, 87.25 umol) at 25° C. under N₂, The mixture was stirred at 25° C. for 16 h. LCMS showed desired MS was detected. The reaction mixture was diluted with ethyl acetate (50 mL), and then washed with H₂O (8 mL*3) and brine (5 mL*1), dried over Na₂SO₄, filtered and concentrated under reduced pressure to give a residue. The residue was purified by prep-TLC (SiO₂, DCM:MeOH=10:1) to give Example 14. MS mass calculated for [M+1]⁺ ($C_{25}H_{22}FN_7O_2$) requires m/z 472.2, LCMS found m/z 472.2; ¹H NMR (400 MHz, MeOD) δ 8.47 (br d, J=7.7 Hz, 1H), 8.28 (dd, J=1.6, 8.2 Hz, 1H), 7.87 (d, J=7.0 Hz, 1H), 7.68 (d, J=1.3 Hz, 1H), 7.37 (d, J=12.0 Hz, 1H), 7.30 (t, J=8.1 Hz, 1H), 7.04 (d, J=1.0 Hz, 1H), 4.59 (s, 2H), 3.31 (td, J=1.6, 3.2 Hz, 23H), 2.27 (s, 3H), 1.96-1.90 (m, 3H), 1.56-1.49 (m, 2H), 0.93-0.84 (m, 2H), 0.79-0.71 (m, 2H).

Example S7

4-(4-cyclopropyl-1H-imidazol-1-yl)-N-(5-(hydroxymethyl)-5,6-dihydrobenzo[f][1,2,4]triazolo[4,3-d][1,4]oxazepin-8-yl)picolinamide (Example 15) was synthesized according to the schemes provided below.

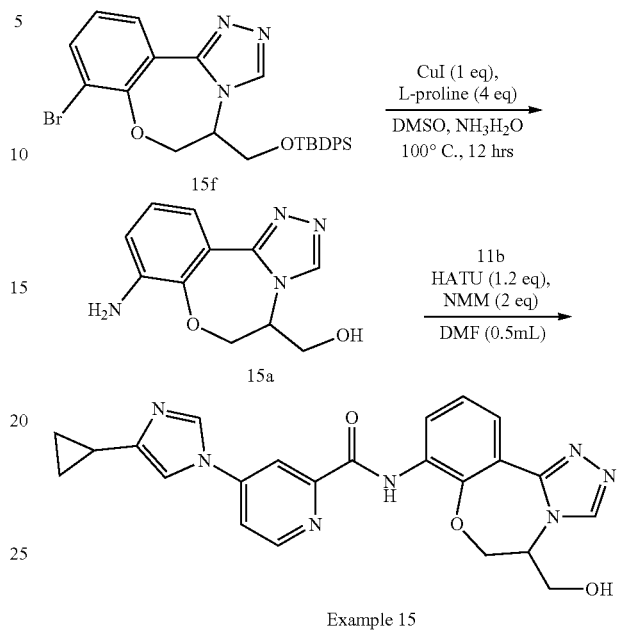

(8-amino-5,6-dihydrobenzo[f][2,4]triazolo[4,3-d][1,4]oxazepin-5-yl)methanol (15a)

To a mixture of 8-bromo-5-(((tert-butyldiphenylsilyl)oxy)methyl)-5,6-dihydrobenzo[f][1,2,4]triazolo[4,3-d][1,4]oxazepine (15f) (100 mg, 187.08 umol) in DMSO (2 mL) and NH₃·H₂O (4 mL) was added L-proline (86.16 mg, 748.34 umol) and CuI (35.63 mg, 187.08 umol) in one portion at 20° C. The mixture was stirred at 20° C. for 5 min, then heated to 100° C. and stirred for 16 hours. TLC indicated the reaction was completed. The mixture was cooled to 20° C. and concentrated in reduced pressure at 80° C. to remove most of DMSO. The residue was dissolved in DCM (10 mL) and water (3 mL) was added, the mixture was stirred for 5 min and the phases were separated. The aqueous phase was extracted with DCM (10 mL*10). The combined organic layers were washed with brine (3 mL), dried with anhydrous Na₂SO₄, filtered and the filtrate was concentrated in vacuo. The residue was purified by prep-TLC (SiO2, DCM:MeOH=5:1) to give (8-amino-5,6-dihydrobenzo[f][1,2,4]triazolo[4,3-d][1,4]oxazepin-5-yl)methanol (15a). ¹H NMR (400 MHz, DMSO-d6) δ 8.57 (s, 1H), 7.62 (dd, J=1.6, 7.9 Hz, 1H), 6.86 (t, J=7.8 Hz, 1H), 6.73 (dd, J=1.7, 7.8 Hz, 1H), 5.30 (t, J=5.3 Hz, 1H), 5.04 (s, 2H), 4.72 (dd, J=3.7, 13.0 Hz, 1H), 4.66-4.57 (m, 1H), 4.15 (dd, J=1.7, 13.0 Hz, 1H), 3.81 (td, J=5.6, 10.7 Hz, 1H), 3.60 (ddd, J=5.7, 7.3, 11.0 Hz, 1H).

Synthesis of 4-(4-cyclopropyl-1H-imidazol-1-yl)-N-(5-(hydroxymethyl)-5,6-dihydrobenzo[f][1,2,4]triazolo[4,3-d][1,4]oxazepin-8-yl)picolinamide (Example 15)

To a mixture of 4-(4-cyclopropyl-1H-imidazol-1-yl)picolinic acid (11b) (10 mg, 43.62 umol) in DMF (0.5 mL) was added HATU (11.61 mg, 30.54 umol) and DIEA (5.64 mg, 43.62 umol, 7.60 uL) in one portion at 20° C. under N₂.

The mixture was stirred at 20° C. for 10 min, then (8-amino-5,6-dihydrobenzo[f][1,2,4]triazolo[4,3-d][1,4]oxazepin-5-yl)methanol (15a) (5.07 mg, 21.81 umol) was added. The mixture was stirred at 20° C. for 16 hours. LCMS showed one main peak with desired MS. Ethyl acetate (50 mL) was added into the mixture and the mixture was stirred for 5 mins and was washed with sat. NaHCO₃ (3 mL*3). The organic phase was washed with brine (3 mL*2), dried with anhydrous Na₂SO₄, filtered and the filtrate was concentrated in vacuo to a residue. The residue was purified by prep-HPLC (neutral condition) to give Example 15. MS mass calculated for [M+H]⁺ ($C_{23}H_{21}N_7O_3$) requires m/z 444.2, LCMS found m/z 444.1; ¹H NMR (400 MHz, DMSO-d6) δ 10.66 (s, 1H), 8.81 (d, J=5.5 Hz, 1H), 8.66 (s, 1H), 8.61-8.48 (m, 2H), 8.41 (d, J=2.2 Hz, 1H), 8.29 (dd, J=1.6, 8.2 Hz, 1H), 8.01 (dd, J=2.3, 5.6 Hz, 1H), 7.87 (d, J=1.1 Hz, 1H), 7.26 (t, J=8.1 Hz, 1H), 5.39 (t, J=5.1 Hz, 1H), 4.93 (dd, J=3.5, 13.2 Hz, 1H), 4.74 (br s, 1H), 4.42 (d, J=12.1 Hz, 1H), 3.89 (td, J=5.5, 10.9 Hz, 1H), 3.73-3.62 (m, 1H), 1.93-1.81 (m, 1H), 0.91-0.80 (m, 2H), 0.77-0.69 (m, 2H).

Example S8

5-(4-cyclopropyl-1H-imidazol-1-yl)-2-fluoro-N-(5-(hydroxymethyl)-5,6-dihydrobenzo[f][1,2,4]triazolo[4,3-d][1,4]oxazepin-8-yl)-4-methylbenzamide (Example 81) was made in a similar manner as Example 15 by using 1a for the amide coupling reaction: MS mass calculated for [M+H]⁺ ($C_{25}H_{23}FN_6O_3$) requires m/z 475.2, LCMS found m/z 475.1; ¹H NMR (400 MHz, METHANOL-d4) δ=8.66 (s, 1H), 8.37 (br d, J=8.4 Hz, 1H), 8.29 (d, J=8.2 Hz, 1H), 8.05 (s, 1H), 7.92 (d, J=6.6 Hz, 1H), 7.41 (d, J=11.7 Hz, 1H), 7.27-7.16 (m, 2H), 4.97 (dd, J=3.4, 13.3 Hz, 1H), 4.78 (br s, 1H), 4.38 (d, J=12.8 Hz, 1H), 4.03 (dd, J=5.4, 11.4 Hz, 1H), 3.82 (dd, J=7.9, 11.2 Hz, 1H), 2.29 (s, 3H), 2.00-1.91 (m, 1H), 0.99-0.92 (m, 2H), 0.81-0.77 (m, 2H).

Example S9

(S)-5-(4-cyclopropyl-1H-imidazol-1-yl)-2-fluoro-N-(5-(hydroxymethyl)-5,6-dihydrobenzo[f][1,2,4]triazolo[4,3-d][1,4]oxazepin-8-yl)-4-methylbenzamide (Example 16) was synthesized according to the schemes provided below.

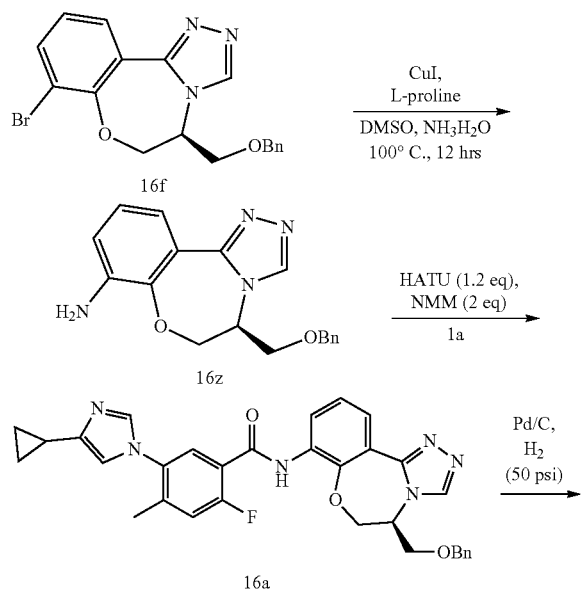

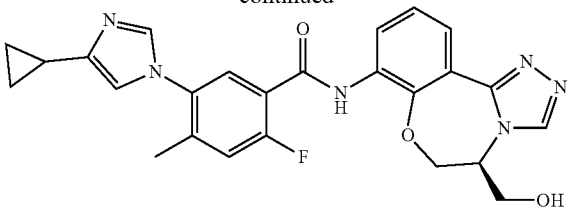

Example 16

((S)-5-((benzyloxy)methyl)-5,6-dihydrobenzo[f][1,2,4]triazolo[4,3-d][1,4]oxazepin-8-amine (16z)

To a solution of (S)-5-((benzyloxy)methyl)-8-bromo-5,6-dihydrobenzo[f][1,2,4]triazolo[4,3-d][1,4]oxazepine (16f) (100 mg, 258.91 umol) in DMSO (2 mL) and NH₃·H₂O (4 mL) was added L-proline (119.23 mg, 1.04 mmol) and CuI (49.31 mg, 258.91 umol) at 20° C., the mixture was heated to 100° C. in a sealed tube for 16 hrs. TLC indicated the reaction was completed. The reaction mixture was concentrated to remove most of the ammonium hydroxide, and was poured into water (10 mL) and extracted with a solution of DCM:i-PrOH(9:1)(20 mL*4), the combined organic layers were washed with brine(5 mL), dried over sodium sulfate and filtered, the filtrate was concentrated to a residue. The residue was purified by prep-TLC to give ((S)-5-((benzyloxy)methyl)-5,6-dihydrobenzo[f][1,2,4]triazolo[4,3-d][1,4]oxazepin-8-amine 16z was obtained. ¹H NMR (CHLOROFORM-d, 400 MHz): δ (ppm) 8.35 (s, 1H), 8.08 (dd, J=8.2, 1.3 Hz, 1H), 7.29-7.41 (m, 5H), 7.01 (t, J=7.9 Hz, 1H), 6.82 (dd, J=7.7, 1.3 Hz, 1H), 4.84 (dd, J=13.0, 3.2 Hz, 1H), 4.62-4.71 (m, 1H), 4.49-4.61 (m, 2H), 4.24 (dd, J=13.0, 1.2 Hz, 1H), 3.90-3.99 (m, 3H), 3.72 (dd, J=9.7, 8.3 Hz, 1H).

(S)—N-(5-((benzyloxy)methyl)-5,6-dihydrobenzo[f][1,2,4]triazolo[4,3-d][1,4]oxazepin-8-yl)-5-(4-cyclopropyl-1H-imidazol-1-yl)-2-fluoro-4-methylbenzamide (16a)

To a solution of 1a (24.22 mg, 93.06 umol) in DMF (2 mL) was added HATU (35.39 mg, 93.06 umol) and NMM (9.41 mg, 93.06 umol, 10.23 uL) at 20° C. After stirring for 10 min, ((S)-5-((benzyloxy)methyl)-5,6-dihydrobenzo[f][1,2,4]triazolo[4,3-d][1,4]oxazepin-8-amine (16z) (15 mg, 46.53 umol) was added to the mixture. The reaction mixture was stirred at 20° C. for 2 hrs. LCMS showed the reaction was completed. The reaction mixture was diluted with ethyl acetate (10 mL) and washed with water (5 mL) and brine (5 mL). The organic layer was dried over sodium sulfate and filtered, and the filtrate was concentrated. The residue was purified by prep-TLC to give 16a. MS mass calculated for [M+1]⁺ ($C_{32}H_{29}FN_6O_3$) requires m/z 565.2, LCMS found m/z 565.0.

Synthesis of (S)-5-(4-cyclopropyl-1H-imidazol-1-yl)-2-fluoro-N-(5-(hydroxymethyl)5,6dihydrobenzo[f][1,2,4]triazolo[4,3-d][1,4]oxazepin-8-yl)-4-methylbenzamide (Example 16)

To a solution of compound (S)—N-(5-((benzyloxy)methyl)-5,6-dihydrobenzo[f][1,2,4]triazolo[4,3-d][1,4]oxazepin-8-yl)-5-(4-cyclopropyl-1H-imidazol-1-yl)-2-fluoro-4-methylbenzamide (16a) (15 mg, 26.57 umol) in MeOH (10 mL) and HCl (0.1 mL) was added Pd/C (10 mg, 26.57 umol, 10% purity) under argon. The mixture was then stirred at 25° C. for 3 hrs under hydrogen atmosphere at 50 psi. LCMS showed the reaction was completed. The reaction mixture was filtered, the filtrate was concentrated to a solid. The solid was triturate with ethyl acetate (1 mL) and filtered; the filter cake was washed with ethyl acetate (0.5 mL) and dried in vacuo to give Example 16. MS mass calculated for [M+1]$^+$ (C$_{25}$H$_{23}$FN$_6$O$_3$) requires m/z 475.2, LCMS found m/z 475.2; $^1$H NMR (METHANOL-d4, 400 MHz): δ (ppm) 9.12 (s, 1H), 9.04 (br s, 1H), 8.42 (br d, J=7.7 Hz, 1H), 8.26 (d, J=7.1 Hz, 1H), 8.09 (d, J=6.8 Hz, 1H), 7.59 (s, 1H), 7.50 (d, J=11.2 Hz, 1H), 7.28 (t, J=8.2 Hz, 1H), 5.00 (br d, J=10.1 Hz, 1H), 4.64-4.77 (m, 1H), 4.44 (br d, J=13.5 Hz, 1H), 4.06 (br dd, J=11.8, 4.5 Hz, 1H), 3.84 (dd, J=11.6, 7.6 Hz, 1H), 2.33 (s, 3H), 1.99-2.13 (m, 1H), 1.07-1.20 (m, 2H), 0.83-0.98 (m, 2H).

Example S10

(R)-5-(4-cyclopropyl-1H-imidazol-1-yl)-2-fluoro-N-(5-(hydroxymethyl)-5,6-dihydrobenzo[f]tetrazolo[1,5-d][1,4]oxazepin-8-yl)-4-methylbenzamide (Example 17) was synthesized according to the schemes provided below.

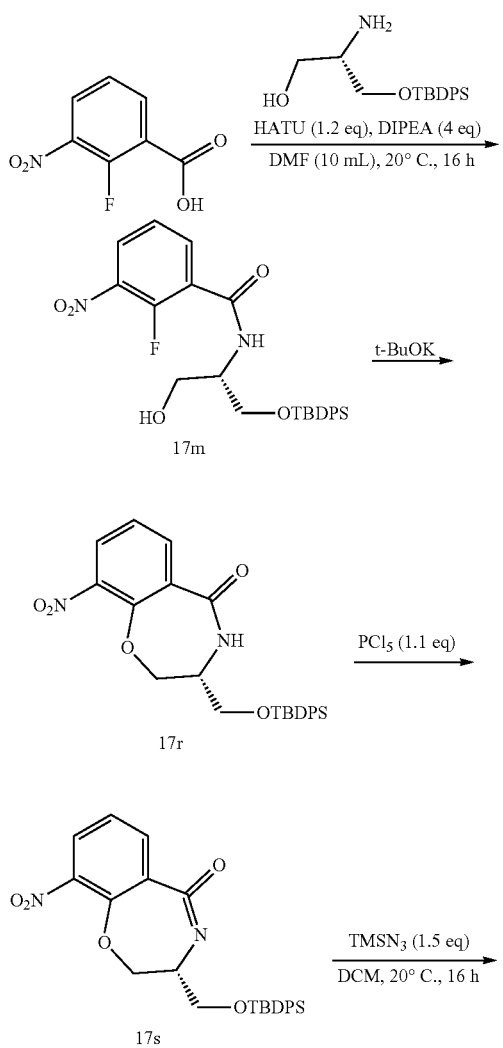

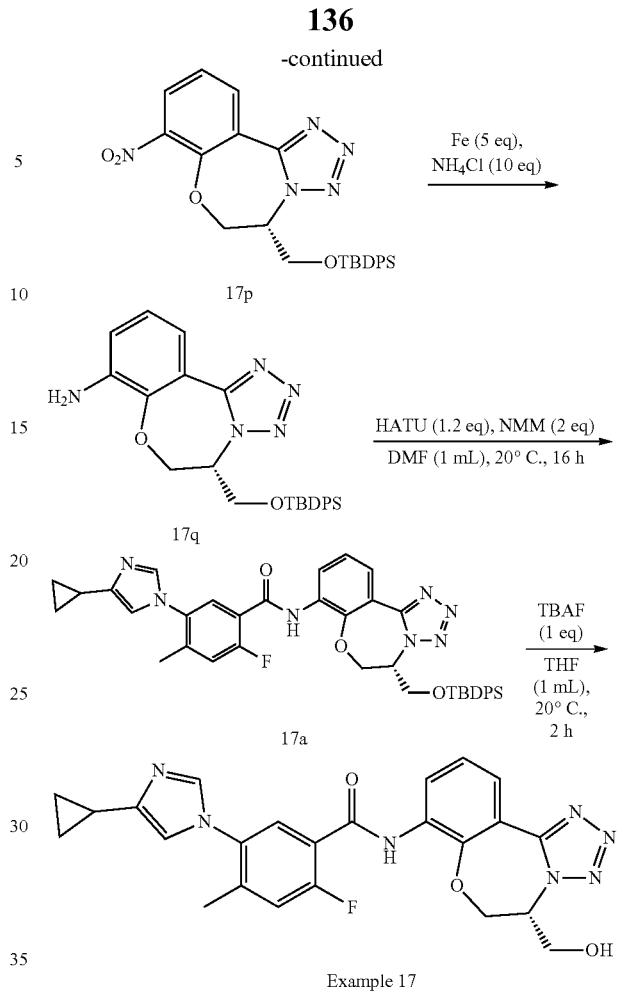

(S)—N-(1-((tert-butyldiphenylsilyl)oxy)-3-hydroxypropan-2-yl)-2-fluoro-3-nitrobenzamide (17m)

To a mixture of 2-fluoro-3-nitrobenzoic acid (617.95 mg, 3.34 mmol) and (S)-2-amino-3-((tert-butyldiphenylsilyl)oxy)propan-1-ol (1.1 g, 3.34 mmol) in DMF (10 mL), HATU (1.52 g, 4.01 mmol) and DIEA (1.73 g, 13.35 mmol, 2.33 mL) were added at 20° C. under N$_2$. The mixture was stirred at 20° C. for 16 hours. LCMS showed one main peak with desired MS. Ethyl acetate (100 mL) was added to the mixture and the mixture was stirred for 5 min. The mixture was washed by H$_2$O (10 mL*5). The organic phase was washed with brine (10 mL*2), dried with anhydrous Na$_2$SO$_4$, filtered and the filtrate was concentrated in vacuo. The residue was purified by column chromatography (SiO$_2$, Petroleum ether:Ethyl acetate=10:1 to 2:1) to give (S)—N-(1-((tert-butyldiphenylsilyl)oxy)-3-hydroxypropan-2-yl)-2-fluoro-3-nitrobenzamide (17m). MS mass calculated for [M+H]$^+$ (C$_{26}$H$_{29}$FN$_2$O$_5$Si) requires m/z 496.1, LCMS found m/z 496.1; $^1$H NMR (400 MHz, CHLOROFORM-d) δ 8.38-8.29 (m, 1H), 8.21-8.14 (m, 1H), 7.65 (dd, J=1.5, 6.2 Hz, 4H), 7.46-7.33 (m, 7H), 4.27 (br s, 1H), 4.03-3.94 (m, 2H), 3.94-3.88 (m, 1H), 3.84-3.75 (m, 1H), 1.10 (s, 9H).

(S)-3-(((tert-butyldiphenylsilyl)oxy)methyl)-9-nitro-3,4-dihydrobenzo[f][1,4]oxazepin-5(2H)-one (17r)

To a mixture of (S)—N-(1-((tert-butyldiphenyl silyl)oxy)-3-hydroxypropan-2-yl)-2-fluoro-3-nitrobenzamide (17m)

(617.95 mg, 3.34 mmol) in DCM (300 mL) was added t-BuOK (1 M in THF, 664.52 uL) in one portion at 45° C. and stirred for 16 hour. TLC indicated the reaction was completed. The mixture was concentrated in vacuo. The residue was purified by prep-TLC (SiO$_2$, Petroleum ether: Ethyl acetate=2:1) to give (S)-3-(((tert-butyldiphenylsilyl)oxy)methyl)-9-nitro-3,4-dihydrobenzo[f][1,4]oxazepin-5 (2H)-one (17r). $^1$H NMR (400 MHz, METHANOL-d4) δ 8.12 (dd, J=1.7, 7.9 Hz, 1H), 7.93 (dd, J=1.7, 7.9 Hz, 1H), 7.64 (dd, J=1.5, 7.9 Hz, 4H), 7.47-7.36 (m, 6H), 7.31 (t, J=8.0 Hz, 1H), 4.58 (dd, J=8.4, 11.3 Hz, 1H), 4.43 (dd, J=2.9, 11.4 Hz, 1H), 3.83-3.77 (m, 2H), 3.75-3.67 (m, 1H), 1.04 (s, 9H).

(S)-3-(((tert-butyldiphenylsilyl)oxy)methyl)-5-chloro-9-nitro-2,3-dihydrobenzo[f][1,4]oxazepine (17s)

To a mixture of (S)-3-(((tert-butyldiphenylsilyl)oxy)methyl)-9-nitro-3,4-dihydrobenzo[f][1,4]oxazepin-5(2H)-one (17r) (55 mg, 115.40 umol) in DCM (1 mL) was added PCl$_5$ (26.43 mg, 126.94 umol) in one portion at 20° C. under N$_2$. The mixture was stirred at 20° C. for 3 hours. to afford (S)-3-(((tert-butyldiphenylsilyl)oxy)methyl)-5-chloro-9-nitro-2,3-dihydrobenzo[f][1,4]oxazepine (17s) in DCM solution which was used directly in the next step.

(S)-5-(((tert-butyldiphenylsilyl)oxy)methyl)-8-nitro-5,6-dihydrobenzo[f]tetrazolo[1,5-d][1,4]oxazepine (17p)

To a mixture of (S)-3-(((tert-butyldiphenyl silyl)oxy)methyl)-5-chloro-9-nitro-2,3-dihydrobenzo[f][1,4] oxazepine (17s) (57 mg, 115.14 umol) in DCM (1 mL) was added TMSN$_3$ (26.53 mg, 230.28 umol, 30.29 uL) in one portion at 20° C. under N$_2$. The mixture was stirred at 20° C. for 16 hours. LCMS indicated the reaction mixture was H$_2$O (5 mL) and DCM (10 mL) were added to the mixture and the phases were separated. The aqueous phase was extracted with DCM (10 mL*3). The combined organic layers were washed with brine (3 mL*2), dried with anhydrous Na$_2$SO$_4$, filtered and concentrated in vacuo. The residue was purified by prep-TLC (SiO$_2$, Petroleum ether: Ethyl acetate=2:1) to give (S)-5-(((tert-butyldiphenylsilyl)oxy)methyl)-8-nitro-5,6-dihydrobenzo[f]tetrazolo[1,5-d][1,4]oxazepine (17p). MS mass calculated for [M+H]$^+$ (C$_{26}$H$_{27}$N$_5$O$_4$Si) requires m/z 501.1, LCMS found m/z 501.1; $^1$H NMR (400 MHz, METHANOL-d4) δ 8.26 (d, J=7.7 Hz, 1H), 8.07 (t, J=7.9 Hz, 1H), 7.68 (d, J=8.2 Hz, 1H), 6.17-6.03 (m, 1H), 4.99-4.93 (m, 1H), 4.89 (d, J=4.2 Hz, 1H), 4.85-4.81 (m, 1H), 4.79-4.73 (m, 1H), 1.70 (dd, J=1.4, 6.9 Hz, 3H).

(S)-5-(((tert-butyldiphenylsilyl)oxy)methyl)-5,6-dihydrobenzo[f]tetrazolo[1,5-d][1,4]oxazepin-8-amine (17q)

To a mixture of (S)-5-(((tert-butyldiphenylsilyl)oxy)methyl)-8-nitro-5,6-dihydrobenzo[f]tetrazolo[1,5-d][1,4] oxazepine (17p) (19 mg, 37.88 umol) in EtOH (4 mL) and H$_2$O (0.8 mL) was added Fe (10.58 mg, 189.39 umol) and NH$_4$Cl (20.26 mg, 378.78 umol, 13.24 uL) in one portion at 20° C. under N$_2$. The mixture was heated to 70° C. for 16 hours. LCMS indicated the reaction was completed. The mixture was extracted with ethyl acetate (10 mL*3). The combined organic phase was washed with brine (5 mL*2), dried with anhydrous Na$_2$SO$_4$, filtered and the filtrate was concentrated in vacuo. The residue was purified by prep-TLC (SiO$_2$, Petroleum ether:Ethyl acetate=1:1) to give (S)-5-(((tert-butyldiphenylsilyl)oxy)methyl)-5,6-dihydrobenzo[f]tetrazolo[1,5-d][1,4]oxazepin-8-amine (17q). MS mass calculated for [M+H]$^+$ (C$_{26}$H$_{29}$N$_5$O$_2$Si) requires m/z 471.2, LCMS found m/z 471.2; 1H NMR (400 MHz, CHLOROFORM-d) δ 7.92 (dd, J=1.6, 8.1 Hz, 1H), 7.64 (ddd, J=1.5, 7.9, 9.3 Hz, 4H), 7.48-7.36 (m, 6H), 7.07-7.00 (m, 1H), 6.89 (dd, J=1.5, 7.8 Hz, 1H), 5.15-5.08 (m, 1H), 5.03 (dd, J=4.0, 13.0 Hz, 1H), 4.30 (dd, J=1.6, 13.0 Hz, 1H), 4.23-4.12 (m, 2H), 4.01 (s, 2H), 1.07 (s, 9H).

(S)—N-(5-(((tert-butyldiphenylsilyl)oxy)methyl)-5,6-dihydrobenzo[f]tetrazolo[1,5-d][1,4]oxazepin-8-yl)-5-(4-cyclopropyl-1H-imidazol-1-yl)-2-fluoro-4-methylbenzamide (17a)

To a mixture of 5-(4-cyclopropyl-1H-imidazol-1-yl)-2-fluoro-4-methylbenzoic acid (1a) (15 mg, 57.63 umol) in DMF (1 mL) was added HATU (24.11 mg, 63.40 umol) and NMM (11.66 mg, 115.27 umol, 12.67 uL) in one portion at 20° C. under N$_2$. The mixture was stirred at 20° C. for 30 min, then (S)-5-(((tert-butyldiphenylsilyl)oxy)methyl)-5,6-dihydrobenzo[f]tetrazolo[1,5-d][1,4]oxazepin-8-amine (17q) (13.59 mg, 28.82 umol) was added into the mixture. Once LCMS indicated the reaction was completed ethyl acetate (30 mL) and sat. NaHCO$_3$ (3 mL) were added into the mixture, the mixture was stirred for 5 min and was washed with the saturated NaHCO$_3$ solution (3 mL*3). The organic phase was washed with brine (3 mL*2), dried with anhydrous Na$_2$SO$_4$, filtered and the filtrate was concentrated in vacuo to give (S)—N-(5-(((tert-butyldiphenylsilyl)oxy)methyl)-5,6-dihydrobenzo[f]tetrazolo[1,5-d][1,4]oxazepin-8-yl)-5-(4-cyclopropyl-1H-imidazol-1-yl)-2-fluoro-4-methylbenzamide (17a). MS mass calculated for [M+H]$^+$ (C$_{40}$H$_{40}$FN$_7$O$_3$Si) requires m/z 714.2, LCMS found m/z 714.2.

Synthesis of (R)-5-(4-cyclopropyl-1H-imidazol-1-yl)-2-fluoro-N-(5-(hydroxymethyl)-5,6dihydrobenzo [f]tetrazolo [1,5-d][1,4]oxazepin-8-yl)-4-methylbenzamide (Example 17)

To a mixture of (S)—N-(5-(((tert-butyldiphenylsilyl)oxy)methyl)-5,6-dihydrobenzo[f]tetrazolo[1,5-d][1,4]oxazepin-8-yl)-5-(4-cyclopropyl-1H-imidazol-1-yl)-2-fluoro-4-methylbenzamide (17a) (42 mg, 58.83 umol) in THF (2 mL) was added TBAF (1 M in THF, 58.83 uL) in one portion at 20° C. under N$_2$. The mixture was stirred at 20° C. for 2 hours. LCMS indicated the reaction was completed. Ethyl acetate (50 mL) and H$_2$O (5 mL) was added into the mixture, the mixture was stirred at 20° C. for 5 min and the phases were separated. The organic phase was washed with H$_2$O (5 mL*5) and brine (5 mL*2), dried with anhydrous Na$_2$SO$_4$, filtered and the filtrate was concentrated in vacuo. The residue was purified by prep-TLC (SiO$_2$, DCM:MeOH=10:1) to give Example 17. MS mass calculated for [M+H]$^+$ (C$_{24}$H$_{22}$FN$_7$O$_3$) requires m/z 476.1, LCMS found m/z 476.1; $^1$H NMR (400 MHz, DMSO-d6) δ 9.92 (br d, J=4.9 Hz, 1H), 8.29-8.17 (m, 2H), 7.80-7.64 (m, 2H), 7.50 (br d, J=11.2 Hz, 1H), 7.32 (t, J=8.0 Hz, 1H), 7.19 (br s, 1H), 5.34 (t, J=5.7 Hz, 1H), 5.12 (br d, J=4.4 Hz, 1H), 4.83 (br dd, J=4.3, 13.4 Hz, 1H), 4.50 (br d, J=13.2 Hz, 1H), 4.00-3.85 (m, 2H), 2.24 (s, 3H), 1.85 (br s, 1H), 0.85-0.77 (m, 2H), 0.74-0.68 (m, 2H).

Example S11

(R)-4-(4-cyclopropyl-1H-imidazol-1-yl)-N-(5-(hydroxymethyl)-5,6-dihydrobenzo[f]tetrazolo[1,5-d][1,4]

oxazepin-8-yl)picolinamide (Example 18) was synthesized according to the schemes provided below.

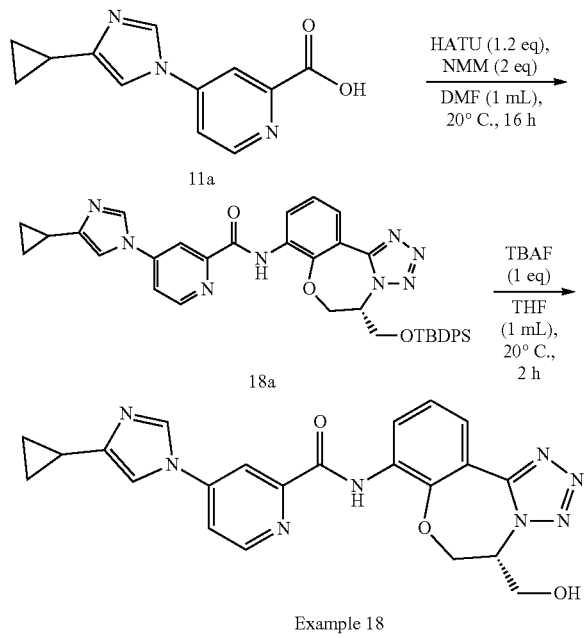

Example 18

(S)—N-(5-(((tert-butyldiphenylsilyl)oxy)methyl)-5,6-dihydrobenzo[f]tetrazolo[1,5-d][1,4]oxazepin-8-yl)-4-(4-cyclopropyl-1H-imidazol-1-yl)picolinamide (18a)

To a mixture of 4-(4-cyclopropyl-1H-imidazol-1-yl)picolinic acid (11a) (12 mg, 52.35 umol) in DMF (1 mL) was added HATU (21.89 mg, 57.58 umol) and NMM (5.29 mg, 52.35 umol, 5.76 uL) at 20° C. under $N_2$. The mixture was stirred at 20° C. for 30 min, then (S)-5-(((tert-butyldiphenylsilyl)oxy)methyl)-5,6-dihydrobenzo[f]tetrazolo[1,5-d][1,4]oxazepin-8-amine (17q) (12.34 mg, 26.17 umol) was added into the mixture. The mixture was stirred at 20° C. for 3 hours. LCMS showed one main peak with desired MS. Ethyl acetate (50 mL) was added into the mixture and stirred for 5 mins. The mixture was washed with saturated $NaHCO_3$ solution (3 mL*3), brine (3 mL*2), dried with anhydrous $Na_2SO_4$, filtered and the filtrate was concentrated in vacuo to give (S)—N-(5-(((tert-butyldiphenylsilyl)oxy)methyl)-5,6-dihydrobenzo[f]tetrazolo[1,5-d][1,4]oxazepin-8-yl)-4-(4-cyclopropyl-1H-imidazol-1-yl)picolinamide (18a) and it was used directly. MS mass calculated for [M+H]$^+$ ($C_{38}H_{38}N_8O_3Si$) requires m/z 683.3, LCMS found m/z 683.2.

Synthesis of (R)-4-(4-cyclopropyl-1H-imidazol-1-yl)-N-(5-(hydroxymethyl)-5,6-dihydrobenzo[f]tetrazolo[1,5-d][1,4]oxazepin-8-yl)picolinamide (Example 18)

To a mixture of (S)—N-(5-(((tert-butyldiphenylsilyl)oxy)methyl)-5,6-dihydrobenzo[f]tetrazolo[1,5-d][1,4]oxazepin-8-yl)-4-(4-cyclopropyl-1H-imidazol-1-yl)picolinamide (18a) (61 mg, 89.33 umol) in THF (1 mL) was added TBAF (1 M in THF, 89.33 uL) at 20° C. under $N_2$. The mixture was stirred at 20° C. for 2 hours. LCMS showed one main peak with desired MS. Ethyl acetate (50 mL) and $H_2O$ (5 mL) was added into the mixture, the mixture was stirred at 20° C. for 5 min and the phases were separated. The organic phase was washed with $H_2O$ (5 mL*5), brine (5 mL*2), dried with anhydrous $Na_2SO_4$, filtered and the filtrate was concentrated in vacuo. The residue was purified by prep-TLC ($SiO_2$, DCM:MeOH=10:1) to give Example 18. MS mass calculated for [M+H]$^+$ ($C_{22}H_{20}N_8O_3$) requires m/z 445.1, LCMS found m/z 445.1; $^1$H NMR (400 MHz, DMSO-d6) δ 10.70 (s, 1H), 8.83 (d, J=5.5 Hz, 1H), 8.62 (br d, J=7.9 Hz, 1H), 8.56 (s, 1H), 8.41 (d, J=2.0 Hz, 1H), 8.27-8.21 (m, 1H), 8.01 (dd, J=2.2, 5.5 Hz, 1H), 7.87 (s, 1H), 7.37 (t, J=8.1 Hz, 1H), 5.42 (t, J=5.7 Hz, 1H), 5.18 (br s, 1H), 4.97 (dd, J=4.1, 13.4 Hz, 1H), 4.61 (br d, J=13.0 Hz, 1H), 4.06-3.90 (m, 2H), 1.93-1.83 (m, 1H), 0.87-0.81 (m, 2H), 0.76-0.71 (m, 2H).

Example S12

(R)-4-(4-cyclopropyl-1H-imidazol-1-yl)-N-(5-methyl-5,6-dihydrobenzo[f]tetrazolo[1,5-d][1,4]oxazepin-8-yl)-5-morpholinopicolinamide (Example 19), 4-(4-cyclopropyl-1H-imidazol-1-yl)-5-morpholino-N-(6H-spiro[benzo[f]tetrazolo[1,5-d][1,4]oxazepine-5,1'-cyclopropan]-8-yl)picolinamide (Example 20), and 4-(4-cyclopropyl-1H-imidazol-1-yl)-N-(5,6-dihydrobenzo[f]tetrazolo[1,5-d][1,4]oxazepin-8-yl)-5-morpholinopicolinamide (Example 21) were synthesized according to the scheme provided below.

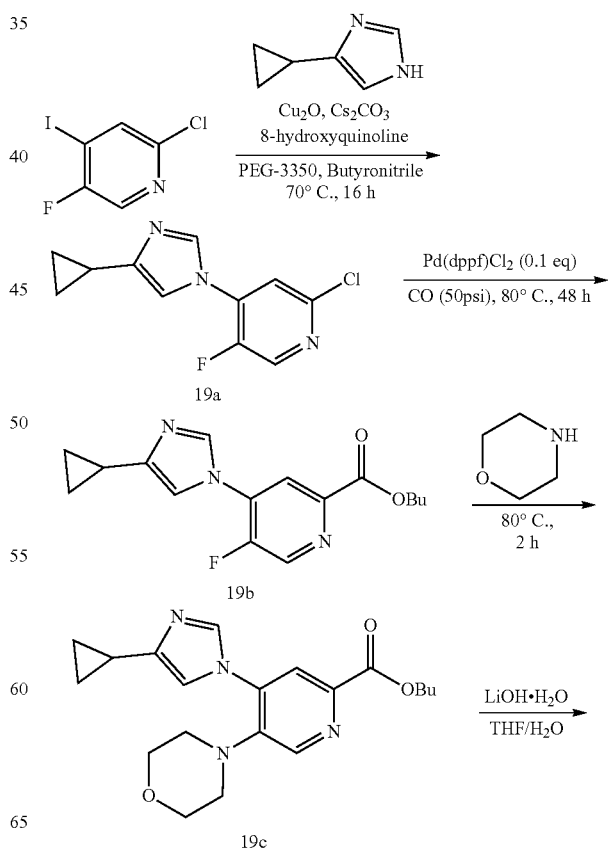

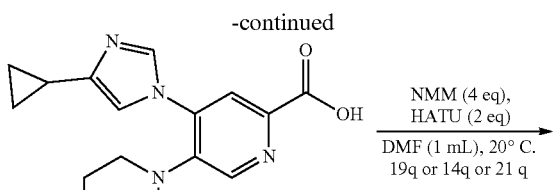

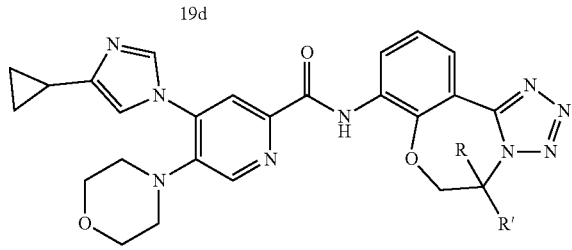

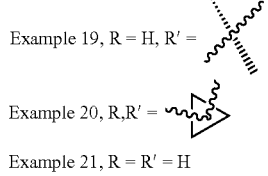

Example 19, R = H, R' =

Example 20, R,R' =

Example 21, R = R' = H

2-chloro-4-(4-cyclopropyl-1H-imidazol-1-yl)-5-fluoropyridine (19a)

To a mixture of 4-cyclopropyl-1H-imidazole (1.4 g, 12.95 mmol) and 2-chloro-5-fluoro-4-iodopyridine (3.50 g, 13.59 mmol) in butyronitrile (210 mL) was added $Cu_2O$ (185.25 mg, 1.29 mmol), 8-hydroxyquinoline (281.88 mg, 1.94 mmol), $Cs_2CO_3$ (8.44 g, 25.89 mmol) and PEG-3350 (1.09 g, 12.95 mmol) at 20° C. under $N_2$. The mixture was stirred at 20° C. for 10 min, then heated to 70° C. and stirred for 16 hours. LCMS showed one new peak with desired MS. The mixture was cooled to 25° C. and filtered and concentrated in vacuo. The residue was dissolved in DCM (50 mL) and $H_2O$ (40 mL) was added, the mixture was extracted with DCM (30 mL*3). The combined organic layers were washed with brine (20 mL*2), dried with anhydrous $Na_2SO_4$, filtered and concentrated in vacuo. The residue was purified by column chromatography ($SiO_2$, Petroleum ether:Ethyl acetate=100:1 to 30:1) to give 2-chloro-4-(4-cyclopropyl-1H-imidazol-1-yl)-5-fluoropyridine (19a). $^1$H NMR (400 MHz, CHLOROFORM-d) δ 8.41 (d, J=2.7 Hz, 1H), 7.90 (s, 1H), 7.37 (d, J=5.4 Hz, 1H), 7.10 (s, 1H), 1.95-1.86 (m, 1H), 0.95-0.89 (m, 2H), 0.87-0.81 (m, 2H).

Butyl 4-(4-cyclopropyl-1H-imidazol-1-yl)-5-fluoropicolinate (19b)

To a solution of 2-chloro-4-(4-cyclopropyl-1H-imidazol-1-yl)-5-fluoropyridine (19a) (1 g, 4.21 mmol) in n-BuOH (50 mL) was added $Pd(dppf)Cl_2$ (615.76 mg, 841.54 umol) and TEA (2.13 g, 21.04 mmol, 2.93 mL) under $N_2$. The suspension was degassed under vacuum and purged with CO several times. The mixture was stirred under carbon monoxide balloon at 80° C. for 3 hours. TLC indicated the reaction was completed. The reaction mixture was filtered and the filtrate was concentrated. The residue was purified by column chromatography ($SiO_2$, Petroleum ether:Ethyl acetate=50:1 to 4:1) to give butyl 4-(4-cyclopropyl-1H-imidazol-1-yl)-5-fluoropicolinate (19b). $^1$H NMR (400 MHz, CHLOROFORM-d) δ 8.73 (d, J=2.8 Hz, 1H), 8.19 (d, J=6.2 Hz, 1H), 7.97 (s, 1H), 7.19 (s, 1H), 4.46 (t, J=6.8 Hz, 2H), 2.00-1.89 (m, 1H), 1.83 (quin, J=7.2 Hz, 2H), 1.54-1.41 (m, 2H), 0.99 (t, J=7.4 Hz, 3H), 0.96-0.90 (m, 2H), 0.89-0.83 (m, 2H).

Butyl 4-(4-cyclopropyl-1H-imidazol-1-yl)-5-morpholinopicolinate (19c)

A solution of butyl 4-(4-cyclopropyl-1H-imidazol-1-yl)-5-fluoropicolinate (19b) (0.65 g, 2.14 mmol) in dry morpholine (30 mL) was heated to 80° C. for 8 hrs. TLC indicated the reaction was competed. The mixture was concentrated in vacuo. The residue was purified by column chromatography ($SiO_2$, Petroleum ether:Ethyl acetate=5:1 to 1:1) to give butyl 4-(4-cyclopropyl-1H-imidazol-1-yl)-5-morpholinopicolinate (19c). $^1$H NMR (400 MHz, CHLOROFORM-d) δ 8.47 (s, 1H), 7.95-7.89 (m, 2H), 7.14-7.10 (m, 1H), 7.13 (d, J=1.1 Hz, 1H), 4.42 (t, J=6.8 Hz, 2H), 3.82-3.71 (m, 4H), 2.94-2.83 (m, 4H), 1.99-1.88 (m, 1H), 1.86-1.76 (m, 2H), 1.47 (qd, J=7.5, 15.0 Hz, 2H), 0.98 (t, J=7.3 Hz, 3H), 0.92 (td, J=2.9, 8.3 Hz, 2H), 0.85-0.79 (m, 2H).

4-(4-cyclopropyl-1H-imidazol-1-yl)-5-morpholinopicolinic acid (19d)

To a mixture of butyl 4-(4-cyclopropyl-1H-imidazol-1-yl)-5-morpholinopicolinate (19c) (0.776 g, 2.09 mmol) in MeOH (5 mL), THF (5 mL) and $H_2O$ (0.5 mL) was added $LiOH.H_2O$ (87.90 mg, 2.09 mmol) at 25° C. under $N_2$. The mixture was stirred at 25° C. for 1 hour. LCMS indicated the reaction was completed. The pH of the mixture was adjusted to 5 with 1 M HCl solution. The mixture was concentrated in vacuo to give 4-(4-cyclopropyl-1H-imidazol-1-yl)-5-morpholinopicolinic acid (19d). $^1$H NMR (400 MHz, METHANOL-d4) δ 8.44 (s, 1H), 8.14 (d, J=1.2 Hz, 1H), 7.98 (s, 1H), 8.03-7.91 (m, 1H), 7.38 (d, J=1.0 Hz, 1H), 3.77-3.69 (m, 4H), 2.92-2.84 (m, 4H), 1.97-1.87 (m, 1H), 0.95-0.87 (m, 2H), 0.81-0.72 (m, 2H).

Synthesis of (R)-4-(4-cyclopropyl-1H-imidazol-1-yl)-N-(5-methyl-5,6-dihydrobenzo[f]tetrazolo[1,5-d][1,4]oxazepin-8-yl)-5-morpholinopicolinamide (Example 19)

To a mixture of 4-(4-cyclopropyl-1H-imidazol-1-yl)-5-morpholinopicolinic acid (19d) (10 mg, 31.81 umol) in DMF (1 mL) was added HATU (24.19 mg, 63.63 umol) and NMM (12.87 mg, 127.25 umol, 13.99 uL) in one portion at 20° C. under $N_2$. The mixture was stirred at 20° C. for 30 min, then 19q (6.91 mg, 31.81 umol) was added into the mixture. The mixture was stirred at 20° C. for 16 hours. LCMS showed one main peak with desired MS. Ethyl acetate (50 mL) was added into the mixture and the mixture was stirred for 5 mins and washed with saturated $NaHCO_3$ solution (10 mL*3). The organic phase was washed with brine (10 mL*2), dried with anhydrous $Na_2SO_4$, filtered and concentrated in vacuo. The residue was purified by prep-TLC ($SiO_2$, DCM:MeOH=10:1) to give Example 19. MS mass calculated for $[M+H]^+$ ($C_{26}H_{27}N_9O_3$) requires m/z 514.2, LCMS found m/z 514.2; $^1$H NMR (400 MHz, CHLOROFORM-d) δ 10.54 (s, 1H), 8.79 (d, J=7.9 Hz, 1H), 8.42 (s, 1H), 8.36 (d, J=8.2 Hz, 1H), 8.17-7.96 (m, 2H), 7.32 (t, J=8.2 Hz, 1H), 7.21 (br s, 1H), 5.29-5.19 (m, 1H), 4.71 (dd, J=4.3, 13.1 Hz, 1H), 4.51 (br d, J=12.1 Hz, 1H), 3.81 (br s, 4H), 2.94 (br s, 4H), 1.95 (br s, 1H), 1.83 (d, J=6.8 Hz, 3H), 0.95 (br s, 2H), 0.84 (br s, 2H).

Synthesis of 4-(4-cyclopropyl-1H-imidazol-1-yl)-5-morpholino-N-(6H-spiro[benzo[f]tetrazolo[1,5-d][1,4]oxazepine-5,1'-cyclopropan]-8-yl)picolinamide (Example 20)

To a mixture of 4-(4-cyclopropyl-1H-imidazol-1-yl)-5-morpholinopicolinic acid (20d) (10 mg, 31.81 umol) in DMF (1 mL) was added HATU (24.19 mg, 63.63 umol) and NMM (12.87 mg, 127.25 umol, 13.99 uL) at 20° C. under $N_2$. The mixture was stirred at 20° C. for 30 min, then 6H-spiro[benzo[f]tetrazolo[1,5-d][1,4]oxazepine-5,1'-cyclopropan]-8-amine (14q) (7.29 mg, 31.81 umol) was added. The mixture was stirred at 20° C. for 16 hours. LCMS showed one main peak with desired MS. Ethyl acetate (50 mL) was added into the mixture and the mixture was stirred for 5 mins, the mixture was washed with saturated $NaHCO_3$ solution (10 mL*3). The organic phase was washed with brine (10 mL*2), dried with anhydrous $Na_2SO_4$, filtered and the filtrate was concentrated in vacuo. The residue was purified by prep-TLC ($SiO_2$, DCM:MeOH=10:1) to give Example 20. MS mass calculated for $[M+H]^+$ ($C_{27}H_{27}N_9O_3$) requires m/z 526.2, LCMS found m/z 526.3; $^1$H NMR (400 MHz, CHLOROFORM-d) δ 10.53 (s, 1H), 8.80 (d, J=7.1 Hz, 1H), 8.47-8.32 (m, 2H), 8.11 (s, 1H), 8.02 (br s, 1H), 7.32 (t, J=8.2 Hz, 1H), 7.19 (br s, 1H), 4.53 (s, 2H), 3.80 (br s, 4H), 2.92 (br s, 4H), 2.11-2.02 (m, 2H), 1.94 (br s, 1H), 1.51-1.45 (m, 2H), 0.94 (br d, J=5.5 Hz, 2H), 0.84 (br s, 2H).

Synthesis of 4-(4-cyclopropyl-1H-imidazol-1-yl)-N-(5,6-dihydrobenzo[f]tetrazolo[1,5-d][1,4]oxazepin-8-yl)-5-morpholinopicolinamide (Example 21)

To a solution of 19d (10 mg, 31.81 umol) in DMF (1 mL) was added HATU (24.19 mg, 63.63 umol) and NMM (12.87 mg, 127.25 umol, 13.99 uL) at 30° C., after 10 min, 21q (7.11 mg, 34.99 umol, 1.1 eq) was added to the mixture. The mixture was then stirred at 30° C. for 12 hrs. TLC indicated the reaction was completed. The reaction mixture was quenched with water (10 mL) and extracted with ethyl acetate (10 mL*3), the combined organic layers were washed with brine, dried over $Na_2SO_4$ and filtered, and the filtrate was concentrated to a residue. The residue was purified by prep-TLC to give Example 21. MS mass calculated for $[M+H]^+$ ($C_{25}H_{25}N_9O_3$) requires m/z 500.2, LCMS found m/z 500.3; $^1$H NMR (CHLOROFORM-d, 400 MHz): δ (ppm) 10.53 (s, 1H), 8.79 (d, J=8.4 Hz, 1H), 8.38 (s, 1H), 8.35 (d, J=8.2 Hz, 1H), 8.10 (s, 1H), 8.00 (s, 1H), 7.31 (t, J=8.0 Hz, 1H), 7.17 (s, 1H), 4.98 (br d, J=4.6 Hz, 2H), 4.63-4.79 (m, 2H), 3.79 (br d, J=4.2 Hz, 4H), 2.92 (br s, 4H), 1.85-2.01 (m, 1H), 0.93 (br d, J=8.6 Hz, 2H), 0.83 (br s, 2H).

Example S13

(S)-4-(4-cyclopropyl-1H-imidazol-1-yl)-N-(5-methyl-5,6-dihydrobenzo[f]tetrazolo[1,5-d][1,4]oxazepin-8-yl)-5-morpholinopicolinamide (Example 22), (R)-5-(4-cyclopropyl-1H-imidazol-1-yl)-2-fluoro-N-(5-(fluoromethyl)-5,6-dihydrobenzo[f]tetrazolo[1,5-d][1,4]oxazepin-8-yl)-4-methylbenzamide (Example 26), and 4-(4-cyclopropyl-1H-imidazol-1-yl)-N-(5,5-dimethyl-5,6-dihydrobenzo[f]tetrazolo[1,5-d][1,4]oxazepin-8-yl)-5-morpholinopicolinamide (Example 37) were synthesized according to the schemes provided below.

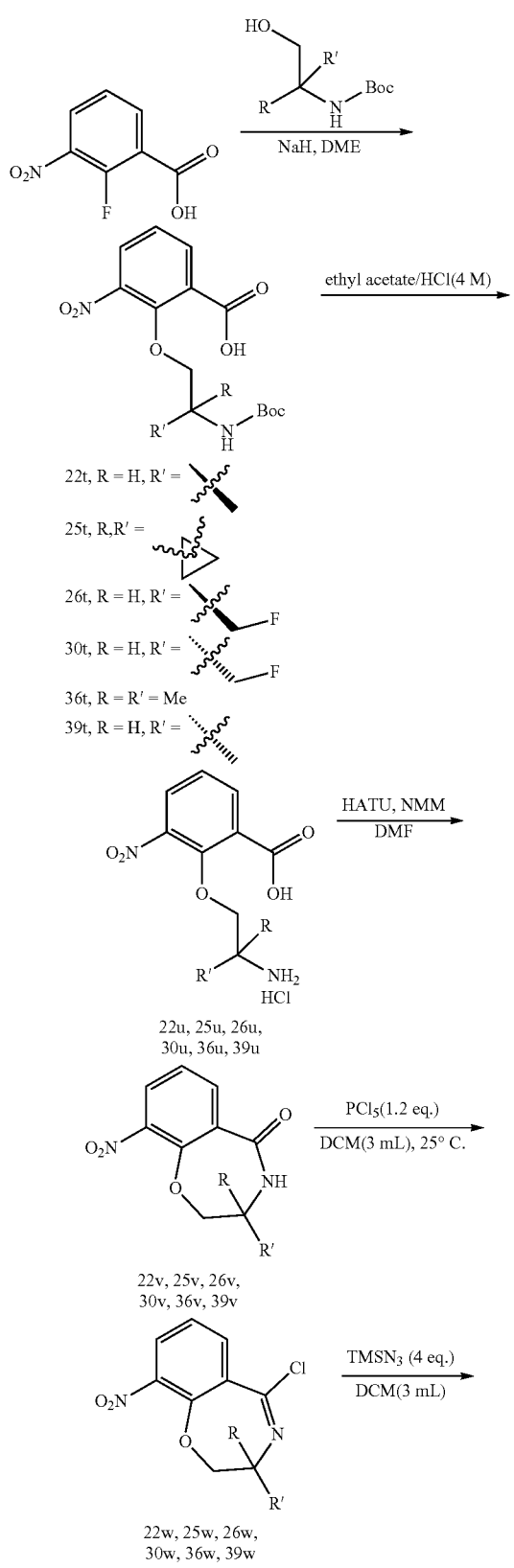

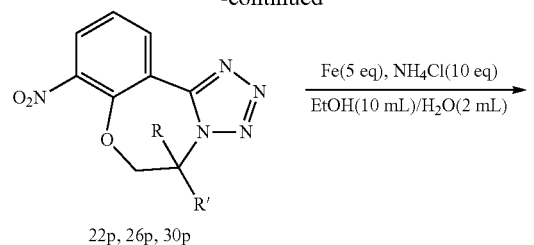

22p, 26p, 30p

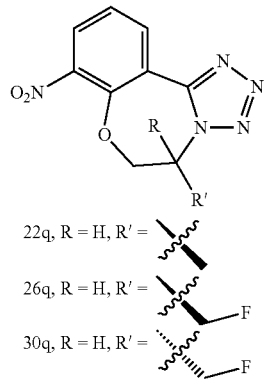

22q, R = H, R' = [wedge bond]

26q, R = H, R' = [wedge bond]-F

30q, R = H, R' = [dashed wedge bond]-F

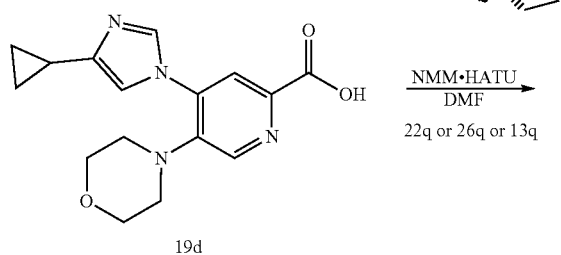

19d

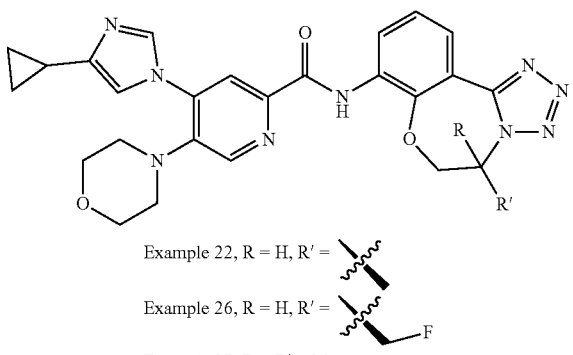

Example 22, R = H, R' = [wedge bond]

Example 26, R = H, R' = [wedge bond]-F

Example 37, R = R' = Me

Synthesis of (t)

To a solution of 2-fluoro-3-nitrobenzoic acid (28 mmol) in DME (90 mL) was added NaH (2.5 eq) at 0° C. and stirred for 10 min, then alcohol (1 eq) dissolved in DME (10 mL) was added at this temperature and stirred for 2 hours. The reaction mixture was cooled to 0° C. and acidified to pH 5 with 0.5M HCl solution. The reaction mixture was diluted with water (20 mL) and extracted with EtOAc (20 mL*3), the organic phase layers were combined and dried over $Na_2SO_4$, filtered and concentrated to give crude t which was used directly in the next step.

Synthesis of (u)

A solution of t (3.3 mmol) in HCl/EtOAc (20 mL, 4M) was stirred at 10° C. for 2 hours while solid precipitated. The reaction mixture was filtered; the filter cake was rinsed with EtOAc (10 mL) and dried in vacuo to give u.

Synthesis of (v)

To a solution of u (6.7 mmol, HCl salt) in DMF (120 mL) was added HATU (1.5 eq) and NMM (4 eq) at 25° C. and stirred for 18 hours. The reaction mixture was concentrated in vacuo, then diluted with water (10 mL) and extracted with EtOAc (15 mL*3), the organic layers were combined and washed with brine (10 mL), dried over $Na_2SO_4$, filtered and concentrated. The residue was purified by column chromatography ($SiO_2$, Petroleum ether/Ethyl acetate=10/1 to 1:1) to give v.

Synthesis of (w)

To a solution of v (0.33 mmol) in DCM (3 mL) was added $PCl_5$ (1.2 eq) at 25° C. and stirred for 4 hours. TLC indicated the reaction was completed. w in DCM was used directly in the the next step.

Synthesis of (p)

To a solution of w (0.33 mmol) in DCM (3 mL) was added $TMSN_3$ (3 eq) at 25° C. and stirred for 20 hours. The reaction mixture was diluted with DCM (10 mL) and washed with water (5 mL), brine (5 mL), dried over $Na_2SO_4$, filtered and concentrated. The residue was purified by prep-TLC to afford p.

Synthesis of (q)

To a solution of p (0.16 mmol) in EtOH (5 mL) and $H_2O$ (1 mL) was added Fe (5 eq.) and $NH_4Cl$ (10 eq) at 25° C., then heated to 70° C. and stirred for 2 hours. The reaction mixture was filtered through a Celite pad, the Celite pad was rinsed with EtOH (10 mL) and EtOAc (10 mL), and the filtrate was concentrated. The residue was diluted with water (8 mL) and extracted with DCM (10 mL*2), the combined organic layers were washed with brine (5 mL) and dried with $Na_2SO_4$ and concentrated in vacuo to give q.

Synthesis of (S)-4-(4-cyclopropyl-1H-imidazol-1-yl)-N-(5-methyl-5,6-dihydrobenzo[f]tetrazolo[1,5-d][1,4]oxazepin-8-yl)-5-morpholinopicolinamide (Example 22)

To a solution of 4-(4-cyclopropyl-1H-imidazol-1-yl)-5-morpholinopicolinic acid (19d) (7.96 mg, 25.32 umol) in DMF (1 mL) was added NMM (9.31 mg, 92.07 umol, 10.12 uL) and HATU (17.50 mg, 46.03 umol) at 25° C., after stirring for 10 min, (S)-5-methyl-5,6 dihydrobenzo [f]tetrazolo [1,5-d][1,4]oxazepin-8-amine (22q) (5 mg, 23.02 umol) was added to the mixture at 25° C. and stirred for another 2 hrs. LCMS showed one main peak with desired MS. The reaction mixture was diluted with ethyl acetate (20 mL), washed with sat. sodium bicarbonate solution (5 mL), and brine(5 mL). The organic layer was dried over sodium sulfate, filtered and concentrated. The residue was purified by prep-TLC to give Example 22. MS mass calculated for $[M+1]^+$ ($C_{26}H_{27}N_9O_3$) requires m/z 514.2, LCMS found m/z 514.3; $^1H$ NMR (CHLOROFORM-d, 400 MHz): δ (ppm) 10.47 (s, 1H), 8.72 (dd, J=8.0, 1.7 Hz, 1H), 8.34 (s, 1H), 8.28 (dd, J=8.0, 1.7 Hz, 1H), 8.04 (s, 1H), 7.94 (d, J=1.1 Hz, 1H), 7.25 (t, J=8.0 Hz, 1H), 7.11 (d, J=1.1 Hz, 1H), 5.07-5.22 (m, 1H), 4.63 (dd, J=13.0, 4.6 Hz, 1H), 4.43

(dd, J=13.1, 1.7 Hz, 1H), 3.66-3.78 (m, 4H), 2.73-2.93 (m, 4H), 1.82-1.91 (m, 1H), 1.75 (d, J=6.8 Hz, 3H), 0.82-0.93 (m, 2H), 0.70-0.80 (m, 2H).

Synthesis of (R)-5-(4-cyclopropyl-1H-imidazol-1-yl)-2-fluoro-N-(5-(fluoromethyl)-5,6-dihydrobenzo[f]tetrazolo[1,5-d][1,4]oxazepin-8-yl)-4-methylbenzamide (Example 26)

To a mixture of 5-(4-cyclopropyl-1H-imidazol-1-yl)-2-fluoro-4-methylbenzoic acid (19d) (4.65 mg, 17.86 umol) in DMF (1 mL) was added HATU (8.73 mg, 22.96 umol) and NMM (3.87 mg, 38.26 umol, 4.21 uL) at 20° C. under $N_2$. The mixture was stirred at 20° C. for 10 min, then (R)-5-(fluoromethyl)-5,6-dihydrobenzo[f]tetrazolo[1,5-d][1,4]oxazepin-8-amine (26q) (3 mg, 12.75 umol) was added into the mixture. The mixture was stirred at 20° C. for 16 hours. LCMS showed the reaction was completed. The mixture was concentrated in vacuo. The residue was diluted with Ethyl acetate (40 mL), then washed with the saturated $NaHCO_3$ solution (5 mL*5), brine (5 mL*2), dried with anhydrous $Na_2SO_4$, filtered and the filtrate was concentrated in vacuo. The residue was purified by prep-TLC ($SiO_2$, ethyl acetate: methanol=10:1) to give a product, which was repurified by re-crystallization from MTBE (1 mL) at 25° C. to give Example 26. MS mass calculated for $[M+1]^+$ ($C_{24}H_{21}F_2N_7O_2$) requires m/z 477.2, LCMS found m/z 478.2; $^1$H NMR (400 MHz, METHANOL-$d_4$) δ 8.45 (br d, J=8.2 Hz, 1H), 8.31 (br d, J=8.2 Hz, 1H), 7.92-7.67 (m, 2H), 7.45-7.27 (m, 2H), 7.08 (s, 1H), 5.47 (br dd, J=4.7, 11.6 Hz, 1H), 5.17 (br dd, J=5.6, 9.8 Hz, 1H), 5.08-4.96 (m, 2H), 4.91 (br d, J=4.9 Hz, 1H), 4.61 (br d, J=13.7 Hz, 1H), 2.28 (s, 3H), 1.98-1.89 (m, 1H), 0.93-0.88 (m, 2H), 0.79-0.73 (m, 2H).

Synthesis of 4-(4-cyclopropyl-1H-imidazol-1-yl)-N-(5,5-dimethyl-5,6-dihydrobenzo[f]tetrazolo[1,5-d][1,4]oxazepin-8-yl)-5-morpholinopicolinamide (Example 37)

To a solution of 4-(4-cyclopropyl-1H-imidazol-1-yl)-5-morpholinopicolinic acid (19d) (30 mg, 95.44 umol) in DMF (1 mL) was added HATU (72.58 mg, 190.88 umol) and NMM (38.61 mg, 381.75 umol, 41.97 uL) at 25° C., then 5,5-dimethyl-5,6-dihydrobenzo[f]tetrazolo[1,5-d][1,4]oxazepin-8-amine (13q) (22.07 mg, 95.44 umol) was added and stirred for 4 hours under 40° C. while solid precipitated out. The reaction mixture was filtered. The filter cake was washed with MTBE (10 mL), $H_2O$ (10 mL), then dried in vacuo to afford Example 37. MS mass calculated for $[M+1]^+$ ($C_{27}H_{29}N_9O_3$) requires m/z 528.2, LCMS found m/z 528.2; $^1$H NMR (400 MHz, CHLOROFORM-d) δ=10.52 (s, 1H), 8.77 (dd, J=1.5, 8.3 Hz, 1H), 8.42 (s, 1H), 8.34 (dd, J=1.7, 8.1 Hz, 1H), 8.11 (s, 1H), 8.01 (d, J=1.5 Hz, 1H), 7.32 (t, J=8.1 Hz, 1H), 7.18 (d, J=1.0 Hz, 1H), 4.44 (s, 2H), 3.86-3.75 (m, 4H), 3.00-2.86 (m, 4H), 1.99-1.90 (m, 1H), 1.86 (s, 6H), 0.99-0.91 (m, 2H), 0.87-0.79 (m, 2H).

Example S14

(S)-5-(4-cyclopropyl-1H-imidazol-1-yl)-2-fluoro-N-(5-(hydroxymethyl)-5,6-dihydrobenzo[f]tetrazolo[1,5-d][1,4]oxazepin-8-yl)-4-methylbenzamide (Example 23) was synthesized according to the schemes provided below.

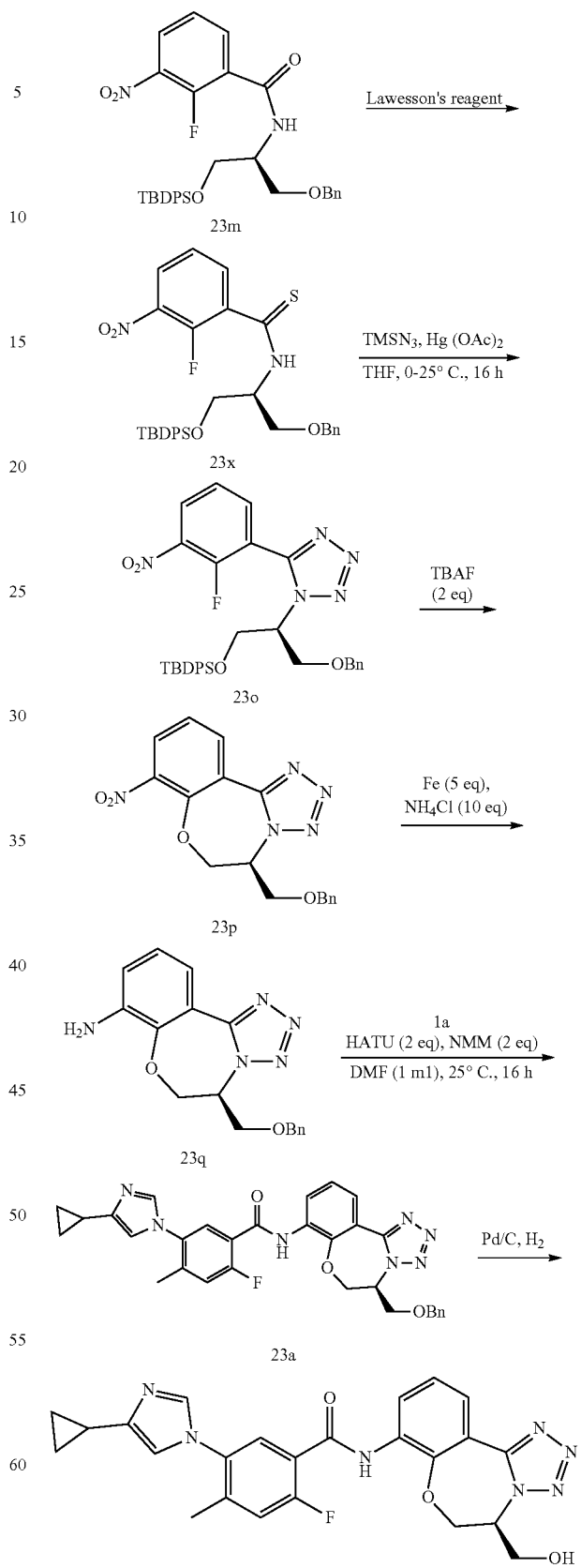

Example 23

(S)—N-(1-(benzyloxy)-3-((tert-butyldiphenylsilyl)oxy)propan-2-yl)-2-fluoro-3-nitrobenzothioamide (23x)

To a mixture of (S)—N-(1-(benzyloxy)-3-((tert-butyldiphenyl silyl)oxy)propan-2-yl)-2-fluoro-3-nitrobenzamide (23m) (320 mg, 545.40 umol) in toluene (10 mL) was added 2,4-bis(4-methoxyphenyl)-2,4-dithioxo-1,3,2,4dithiadiphosphetane (154.42 mg, 381.78 umol) under $N_2$. The mixture was stirred at 110° C. for 16 hours. LCMS showed the desired MS was detected. The mixture was poured into water (5 mL) and the phases were separated. The aqueous phase was extracted with ethyl acetate (10 mL*3), the combined organic layers were washed with brine (10 mL), dried with anhydrous $Na_2SO_4$, filtered and the filtrate was concentrated in vacuo. The residue was purified by prep-TLC ($SiO_2$, Petroleum ether:Ethyl acetate=10:1) to give (S)—N-(1-(benzyloxy)-3-((tert-butyldiphenylsilyl)oxy)propan-2-yl)-2-fluoro-3-nitrobenzothioamide 23x. MS mass calculated for $[M+1]^+$ ($C_{33}H_{35}FN_2O_4SSi$) requires m/z 603.2, LCMS found m/z 603.2; $^1$H NMR (400 MHz, CDCl$_3$) δ 8.19 (br t, J=7.5 Hz, 1H), 8.12-8.02 (m, 2H), 7.66 (br t, J=6.2 Hz, 4H), 7.42-7.30 (m, 11H), 5.02 (br s, 1H), 4.59 (s, 2H), 4.11 (dd, J=3.9, 10.1 Hz, 1H), 4.01-3.89 (m, 2H), 3.78 (dd, J=5.8, 9.2 Hz, 1H), 1.08 (s, 9H).

(S)-1-(1-(benzyloxy)-3-((tert-butyldiphenylsilyl)oxy)propan-2-yl)-5-(2-fluoro-3-nitrophenyl)-1H-tetrazole (23o)

To a mixture of (S)—N-(1-(benzyloxy)-3-((tert-butyldiphenylsilyl)oxy)propan-2-yl)-2-fluoro-3-nitrobenzothioamide (23x) (250 mg, 414.74 umol) in THF (2 mL) was added Hg(OAc)$_2$ (264.34 mg, 829.48 umol) and TMSN$_3$ (334.47 mg, 2.90 mmol, 381.82 uL) at 0° C. The mixture was stirred at 0° C. for 30 min, then heated to 30° C. and stirred for 16 hours. LCMS showed desired MS was detected. The residue was poured into ice-water (5 mL) and the phases were separated. The aqueous phase was extracted with ethyl acetate (10 mL*3). The combined organic layers were washed with brine (5 mL*2), dried with anhydrous $Na_2SO_4$, filtered and the filtrate was concentrated in vacuo. The residue was purified by prep-TLC ($SiO_2$, Petroleum ether:Ethyl acetate=3:1) to give (S)-1-(1-(benzyloxy)-3-((tert-butyldiphenylsilyl)oxy)propan-2-yl)-5-(2-fluoro-3-nitrophenyl)-1H-tetrazole (23o). MS mass calculated for $[M+1]^+$ ($C_{33}H_{34}FN_5O_4Si$) requires m/z 612.2, LCMS found m/z 612.1; $^1$H NMR (400 MHz, CDCl$_3$) δ 8.29-8.22 (m, 1H), 7.71 (br t, J=6.0 Hz, 1H), 7.52-7.41 (m, 6H), 7.40-7.34 (m, 4H), 7.34-7.28 (m, 4H), 7.12-7.05 (m, 2H), 4.66-4.54 (m, 1H), 4.43-4.32 (m, 2H), 4.25-4.15 (m, 2H), 4.13-4.04 (m, 1H), 3.95-3.80 (m, 2H), 0.94 (s, 9H).

(S)-5-((benzyloxy)methyl)-8-nitro-5,6-dihydrobenzo[f]tetrazolo[1,5-d][1,4]oxazepine (23p)

To a mixture of (S)-1-(1-(benzyloxy)-3-((tert-butyldiphenylsilyl)oxy)propan-2-yl)-5-(2-fluoro-3-nitrophenyl)-1H-tetrazole (23o) (145 mg, 237.03 umol) in THF (10 mL) was added TBAF (1 M in THF, 237.03 uL) at 40° C. under $N_2$. The mixture was stirred at 40° C. for 16h. LCMS showed desired MS was detected. The mixture was poured into water (10 mL) and stirred for 10 min and the phases were separated. The aqueous phase was extracted with ethyl acetate (10 mL*3). The combined organic layers were washed with brine (10 mL*2), dried with anhydrous $Na_2SO_4$, filtered and the filtrate was concentrated in vacuo. The residue was purified by prep-TLC ($SiO_2$, petroleum ether:ethyl acetate=3:1) to give (S)-5-((benzyloxy)methyl)-8-nitro-5,6-dihydrobenzo[f]tetrazolo[1,5-d][1,4]oxazepine (23p). MS mass calculated for $[M+1]^+$ ($C_{17}H_{15}N_5O_4$) requires m/z 354.1, LCMS found m/z 354.1; 1H NMR (400 MHz, CDCl3) δ 8.82 (dd, J=1.6, 8.1 Hz, 1H), 7.90 (dd, J=1.6, 7.9 Hz, 1H), 7.42-7.27 (m, 6H), 5.22 (dtd, J=2.1, 4.9, 7.1 Hz, 1H), 4.96 (dd, J=4.9, 13.3 Hz, 1H), 4.59 (s, 2H), 4.51 (dd, J=2.0, 13.3 Hz, 1H), 4.15-4.06 (m, 2H).

(S)-5-((benzyloxy)methyl)-5,6-dihydrobenzo[f]tetrazolo[1,5-d][1,4]oxazepin-8-amine (23q)

To a mixture of (S)-5-((benzyloxy)methyl)-8-nitro-5,6-dihydrobenzo[f]tetrazolo[1,5-d][1,4]oxazepine (23p) (45 mg, 127.36 umol) in EtOH (5 mL) and $H_2O$ (1 mL) was added Fe (35.56 mg, 636.80 umol) and NH$_4$Cl (68.13 mg, 1.27 mmol) in one portion at 25° C. under $N_2$. The mixture was stirred at 70° C. for 3 hours. LCMS indicated the reaction was completed. The reaction mixture was filtered and the filtrate was concentrated under reduced pressure to remove most of the EtOH and $H_2O$. The residue was poured into ice-water (5 mL) and was extracted with ethyl acetate (10 mL*3). The organic phase was washed with brine (5 mL), dried with anhydrous $Na_2SO_4$, filtered and concentrated in vacuo to afford (S)-5-((benzyloxy)methyl)-5,6-dihydrobenzo[f]tetrazolo[1,5-d][1,4]oxazepin-8-amine (23q). MS mass calculated for $[M+1]^+$ ($C_{17}H_{17}N_5O_2$) requires m/z 324.1, LCMS found m/z 324.1; $^1$H NMR (400 MHz, CDCl$_3$) δ 7.94 (dd, J=1.2, 8.0 Hz, 1H), 7.42-7.30 (m, 5H), 7.04 (t, J=7.9 Hz, 1H), 6.89 (dd, J=1.2, 7.7 Hz, 1H), 5.21-5.13 (m, 1H), 4.94 (dd, J=4.2, 13.1 Hz, 1H), 4.62 (s, 2H), 4.31 (dd, J=1.6, 13.1 Hz, 1H), 4.06-4.02 (m, 2H).

(S)—N-(5-((benzyloxy)methyl)-5,6-dihydrobenzo[f]tetrazolo[1,5-d][1,4]oxazepin-8-yl)-5-(4-cyclopropyl-1H-imidazol-1-yl)-2-fluoro-4-methylbenzamide (23a)

To a mixture of 1a (12.07 mg, 46.39 umol) and HATU (23.52 mg, 61.85 umol) in DMF (1 mL) was added NMM (6.26 mg, 61.85 umol, 6.80 uL) and (S)-5-((benzyloxy)methyl)-5,6-dihydrobenzo[f]tetrazolo[1,5-d][1,4]oxazepin-8-amine (23q) (10 mg, 30.93 umol) under $N_2$. The mixture was stirred at 25° C. for 16 hours. LCMS showed desired mass was detected. The reaction mixture was concentrated under reduced pressure. The residue was purified by prep-TLC ($SiO_2$, DCM:MeOH=10:1) to give (S)—N-(5-((benzyloxy)methyl)-5,6-dihydrobenzo[f]tetrazolo[1,5-d][1,4]oxazepin-8-yl)-5-(4-cyclopropyl-1H-imidazol-1-yl)-2-fluoro-4-methylbenzamide (23a). MS mass calculated for $[M+1]^+$ ($C_{31}H_{28}FN_7O_3$) requires m/z 566.2, LCMS found m/z 566.2; $^1$H NMR (400 MHz, CDCl$_3$) δ 9.41 (br d, J=17.2 Hz, 1H), 8.75 (dd, J=1.6, 8.1 Hz, 1H), 8.37 (dd, J=1.5, 8.1 Hz, 1H), 8.11 (d, J=7.3 Hz, 1H), 7.48 (d, J=1.3 Hz, 1H), 7.38-7.34 (m, 5H), 7.22 (d, J=12.0 Hz, 1H), 6.82 (d, J=1.3 Hz, 1H), 5.25 (br s, 1H), 5.05 (dd, J=4.6, 13.1 Hz, 1H), 4.68-4.61 (m, 2H), 4.48 (br d, J=13.2 Hz, 1H), 4.12-4.04 (m, 2H), 2.33 (s, 3H), 1.99-1.90 (m, 1H), 0.93 (td, J=2.8, 8.3 Hz, 2H), 0.88-0.82 (m, 2H).

Synthesis of (S)-5-(4-cyclopropyl-1H-imidazol-1-yl)-2-fluoro-N-(5-(hydroxymethyl)-5,6dihydrobenzo[f]tetrazolo [1,5-d][1,4]oxazepin-8-yl)-4-methylbenzamide (Example 23)

To a solution of (S)—N-(5-((benzyloxy)methyl)-5,6-dihydrobenzo[f]tetrazolo[1,5-d][1,4]oxazepin-8-yl)-5-(4-cyclopropyl-1H-imidazol-1-yl)-2-fluoro-4-methylbenzamide (23a) (10 mg, 17.68 umol) in MeOH (1 mL) was added Pd/C (6 mg, 17.68 umol, 10% purity) and HCl (0.05 mL) under $N_2$. The suspension was degassed under vacuum and purged with $H_2$ several times. The mixture was stirred under hydrogen balloon at 25° C. for 12 hr. LCMS showed desired MS was detected. The reaction mixture was filtered and the filtrate was concentrated under reduced pressure. The residue was purified by prep-TLC (SiO2, DCM:MeOH=10:1) to give Example 23. MS mass calculated for $[M+H]^+$ ($C_{24}H_{22}FN_7O_3$) requires m/z 476.2, LCMS found m/z 476.2; $^1$H NMR (400 MHz, DMSO) δ 9.94 (br s, 1H), 8.24 (br d, J=8.2 Hz, 2H), 7.81-7.64 (m, 2H), 7.50 (br d, J=11.2 Hz, 1H), 7.32 (t, J=7.9 Hz, 1H), 7.19 (s, 1H), 5.38 (br s, 1H), 5.12 (br s, 1H), 4.83 (br dd, J=4.4, 13.5 Hz, 1H), 4.49 (br d, J=13.2 Hz, 1H), 3.92 (br s, 2H), 2.24 (s, 3H), 1.89-1.81 (m, 1H), 0.84-0.78 (m, 2H), 0.73-0.66 (m, 2H).

Example S15

(S)-4-(4-cyclopropyl-1H-imidazol-1-yl)-N-(5-(hydroxymethyl)-5,6-dihydrobenzo[f]tetrazolo[1,5-d][1,4]oxazepin-8-yl)picolinamide (Example 24) was synthesized according to the schemes provided below.

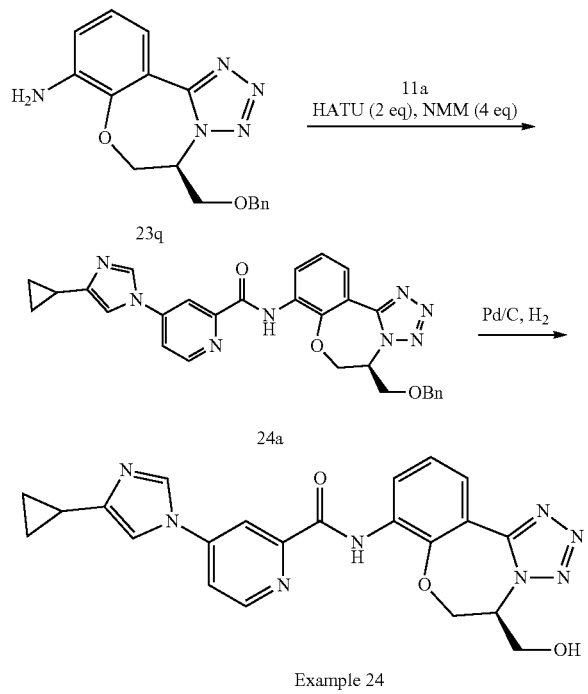

(S)—N-(5-((benzyloxy)methyl)-5,6-dihydrobenzo[f]tetrazolo[1,5-d][1,4]oxazepin-8-yl)-4-(4-cyclopropyl-1H-imidazol-1-yl)picolinamide (24a)

To a mixture of (S)-5-((benzyloxy)methyl)-5,6-dihydrobenzo[f]tetrazolo[1,5-d][1,4]oxazepin-8-amine (23q) (10 mg, 30.93 umol) and NMM (6.26 mg, 61.85 umol, 6.80 uL) in DMF (1.5 mL) was added HATU (29.40 mg, 77.32 umol) and 11a (14.18 mg, 61.85 umol) under $N_2$. The mixture was stirred at 25° C. for 16 hr. LCMS showed one main peak with desired MS. The residue was poured into water (5 mL) and the phases were separated, the aqueous phase was extracted with ethyl acetate (10 mL*3). The combined organic layers were washed with brine (5 mL), dried with anhydrous $Na_2SO_4$, filtered and concentrated in vacuo. The residue was used directly in the next step without further purification. (S)—N-(5-((benzyloxy)methyl)-5,6-dihydrobenzo[f]tetrazolo[1,5-d][1,4]oxazepin-8-yl)-4-(4-cyclopropyl-1Himidazol-1-yl)picolinamide (24a). MS mass calculated for $[M+H]^+$ ($C_{29}H_{26}N_8O_3$) requires m/z 535.2, LCMS found m/z 535.2; $^1$H NMR (400 MHz, CDCl$_3$) δ 10.74 (s, 1H), 8.85-8.78 (m, 1H), 8.75 (d, J=5.4 Hz, 1H), 8.37 (dd, J=1.4, 8.1 Hz, 1H), 8.32 (d, J=2.1 Hz, 1H), 8.20 (s, 1H), 7.54 (dd, J=2.3, 5.4 Hz, 1H), 7.41 (dd, J=4.6, 8.4 Hz, 1H), 7.36-7.31 (m, 5H), 7.24 (s, 1H), 5.29-5.22 (m, 1H), 5.08 (dd, J=4.6, 13.2 Hz, 1H), 4.70-4.60 (m, 2H), 4.53 (br d, J=11.5 Hz, 1H), 4.10 (d, J=6.5 Hz, 2H), 1.98-1.90 (m, 1H), 0.99-0.92 (m, 2H), 0.88-0.80 (m, 2H).

Synthesis of (S)-4-(4-cyclopropyl-1H-imidazol-1-yl)-N-(5-(hydroxymethyl)-5,6-dihydrobenzo[f]tetrazolo[1,5-d][1,4]oxazepin-8-yl)picolinamide (Example 24)

To a mixture of (S)—N-(5-((benzyloxy)methyl)-5,6-dihydrobenzo[f]tetrazolo[1,5-d][1,4]oxazepin-8-yl)-4-(4-cyclopropyl-1H-imidazol-1-yl)picolinamide (24a) (10 mg, 18.71 umol) in MeOH (1 mL) was added Pd/C (10 mg, 18.71 umol, 10% purity) and HCl (0.05 mL). The suspension was degassed under vacuum and purged with $H_2$ several times. The mixture was stirred under hydrogen balloon at 25° C. for 12 hr. LCMS showed desired mass was detected. The reaction mixture was filtered and the filtrate was concentrated under reduced pressure. The residue was purified by prep-HPLC (TFA condition) to give Example 24. MS mass calculated for $[M+H]^+$ ($C_{22}H_{20}N_8O_3$) requires m/z 445.2, LCMS found m/z 445.2; $^1$H NMR (400 MHz, MeOD) δ 9.22 (br s, 1H), 8.90 (d, J=5.4 Hz, 1H), 8.73 (dd, J=1.5, 7.9 Hz, 1H), 8.53 (d, J=2.1 Hz, 1H), 8.29 (d, J=8.1 Hz, 1H), 7.97 (dd, J=2.2, 5.4 Hz, 1H), 7.93 (s, 1H), 7.34 (t, J=8.1 Hz, 1H), 5.23-5.18 (m, 1H), 5.12 (dd, J=4.2, 13.3 Hz, 1H), 4.61-4.55 (m, 1H), 4.22-4.08 (m, 2H), 2.06-1.97 (m, 1H), 1.11-1.05 (m, 2H), 0.93-0.85 (m, 2H).

Example S16

4-(4-cyclopropyl-1H-imidazol-1-yl)-5-morpholino-N-(6H-spiro[benzo[f][1,2,4]triazolo[4,3-d][1,4]oxazepine-5,1'-cyclopropan]-8-yl)picolinamide (Example 25), 4-(4-cyclopropyl-1H-imidazol-1-yl)-N-(5,5-dimethyl-5,6-dihydrobenzo[f][1,2,4]triazolo[4,3-d][1,4]oxazepin-8-yl)-5-morpholinopicolinamide (Example 36), (S)-4-(4-cyclopropyl-1H-imidazol-1-yl)-N-(5-methyl-5,6-dihydrobenzo[f][1,2,4]triazolo[4,3-d][1,4]oxazepin-8-yl)-5-morpholinopicolinamide (Example 38), and (R)-4-(4-cyclopropyl-1H-imidazol-1-yl)-N-(5-methyl-5,6-dihydrobenzo[f][1,2,4]triazolo[4,3-d][1,4]oxazepin-8-yl)-5-morpholinopicolinamide (Example 39) were synthesized according to the schemes provided below.

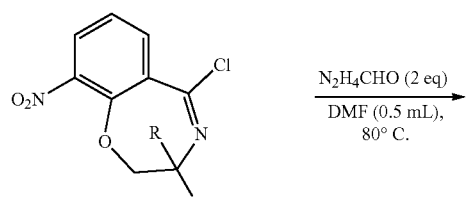

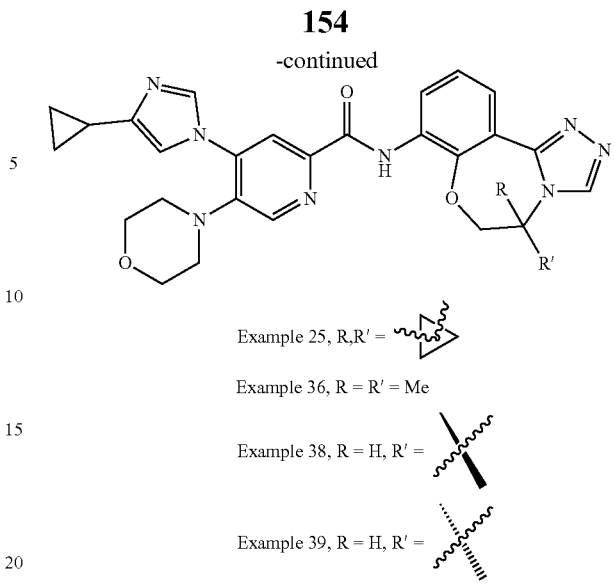

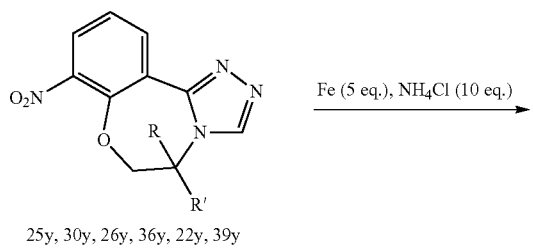

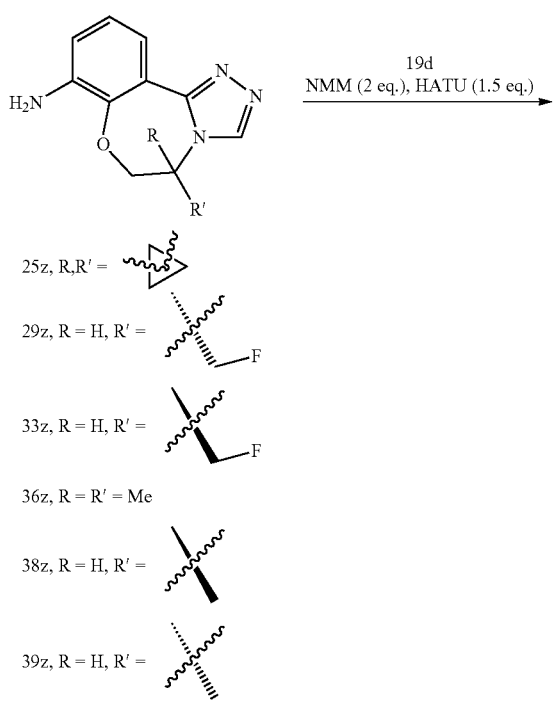

(y). The mixture of w (0.2 mmol) in DCM (3 mL) was concentrated in vacuo, and then formohydrazide (3 eq) in DMF (3 mL) was added at 25° C. The mixture was then heated to 70° C. and stirred for 20 hours under $N_2$. The reaction mixture was concentrated in vacuo to remove DMF, then diluted with water (8 mL) and extracted with DCM (10 mL*2), the organic layers were combined and washed with brine (10 mL) and dried over $Na_2SO_4$, filtered and the filtrate was concentrated. The residue was purified by prep-TLC to give y.

(z). To a solution of y (0.24 mmol) in EtOH (5 mL) and $H_2O$ (1 mL) was added Fe (5 eq) and $NH_4Cl$ (10 eq) at 25° C., then heated to 70° C. and stirred for 2 hours. The reaction mixture was filtered through a Celite pad, the Celite pad was rinsed with EtOH (10 mL) and EtOAc (10 mL), and the filtrate was concentrated. The residue was diluted with water (8 mL) and extracted with DCM (10 mL*2), the combined organic layers were washed with brine (5 mL) and dried in vacuo to give crude z.

Synthesis of 4-(4-cyclopropyl-1H-imidazol-1-yl)-5-morpholino-N-(6H-spiro[benzo[f][1,2,4]triazolo[4,3-d][1,4]oxazepine-5,1'-cyclopropan]-8-yl)picolinamide (Example 25)

A solution of (19d) (0.03 mmol), HATU (1.5 eq) and NMM (2 eq) in DMF (2 mL) was stirred at 25° C. for 10 min, then 6H-spiro[benzo[f][1,2,4]triazolo[4,3-d][1,4]oxazepine-5,1'-cyclopropan]-8-amine (25z) (1 eq) was added and the mixture was stirred at 25° C. for 1 h. LCMS indicated the reaction was completed. Ethyl acetate (50 mL) was added to the reaction mixture, and the mixture was washed with $H_2O$ (8 mL*3), $NaHCO_3$ (8 ml*3) and brine (5 mL*1), dried over $Na_2SO_4$, filtered and the filtrate concentrated under reduced pressure to give a residue. The residue was purified by prep-TLC ($SiO_2$, Ethyl acetate:Methanol=10:1) to give Example 25. MS mass calculated for $[M+H]^+$ ($C_{28}H_{28}N_8O_3$) requires m/z 525.2, LCMS found m/z 525.2; $^1H$ NMR (400 MHz, $CDCl_3$) δ 10.41 (s, 1H), 8.64 (dd, J=1.7, 8.0 Hz, 1H), 8.30 (s, 1H), 8.20 (dd, J=1.5, 8.2 Hz, 1H), 8.03 (s, 1H), 7.99-7.92 (m, 2H), 7.18-7.15 (m, 1H), 7.10 (d, J=1.1 Hz, 1H), 4.41 (s, 2H), 3.75-3.68 (m, 4H), 2.87-2.81 (m, 4H), 1.91-1.82 (m, 1H), 1.44-1.36 (m, 2H), 1.34-1.27 (m, 2H), 0.90-0.82 (m, 2H), 0.79-0.73 (m, 2H).

Synthesis of 4-(4-cyclopropyl-1H-imidazol-1-yl)-N-(5,5-dimethyl-5,6-dihydrobenzo[f][1,2,4]triazolo[4,3-d][1,4]oxazepin-8-yl)-5-morpholinopicolinamide (Example 36)

To a solution of 4-(4-cyclopropyl-1H-imidazol-1-yl)-5-morpholinopicolinic acid (19d) (36.56 mg, 104.23 umol, HCl) in DMF (1 mL) was added HATU (49.54 mg, 130.28 umol) and NMM (35.14 mg, 347.43 umol, 38.20 uL) at 25° C., then 5,5-dimethyl-5,6-dihydrobenzo[f][1,2,4]triazolo[4,3-d][1,4]oxazepin-8-amine (36z) (0.02 g, 86.86 umol) dissolved in DMF (1 mL) was added at this temperature and stirred for 18 hours. The mixture was purified by prep-HPLC (basic condition) to give Example 36. MS mass calculated for [M+1]$^+$ (C$_{28}$H$_{30}$N$_8$O$_3$) requires m/z 527.2, LCMS found m/z 527.2; $^1$H NMR (400 MHz, CHLOROFORM-d) δ=10.49 (s, 1H), 8.67 (dd, J=1.5, 8.1 Hz, 1H), 8.42-8.41 (m, 1H), 8.40 (s, 1H), 8.37 (s, 1H), 8.11 (s, 1H), 8.02 (d, J=0.9 Hz, 1H), 7.26-7.16 (m, 2H), 4.39 (s, 2H), 3.83-3.77 (m, 4H), 2.95-2.89 (m, 4H), 1.99-1.87 (m, 1H), 1.73 (s, 6H), 0.94 (dd, J=2.2, 8.3 Hz, 2H), 0.83 (dd, J=2.0, 5.0 Hz, 2H).

Synthesis of (S)-4-(4-cyclopropyl-1H-imidazol-1-yl)-N-(5-methyl-5,6-dihydrobenzo[f][1,2,4]triazolo[4,3-d][1,4]oxazepin-8-yl)-5-morpholinopicolinamide (Example 38)

To a solution of (S)-5-methyl-5,6-dihydrobenzo[f][1,2,4]triazolo[4,3-d][1,4]oxazepin-8-amine (38z) (10 mg, 40.61 umol) and 4-(4-cyclopropyl-1H-imidazol-1l-yl)-5-morpholinopicolinic acid (19d) (12.77 mg, 40.61 umol, 1 eq) in DMF (0.5 mL) was added HATU (30.89 mg, 81.23 umol) and NMM (16.43 mg, 162.46 umol) at 20° C. The mixture was then stirred at 20° C. for 2h. LCMS showed the reaction was completed. The reaction mixture was concentrated, the residue was purified by prep-HPLC (column: Phenomenex Synergi C18 100*30 mm*4 um; mobile phase: [water (0.1% TFA)-ACN]; B %: 10%-35%, 12 min) to give Example 38. MS mass calculated for [M+1]$^+$ (C$_{27}$H$_{28}$N$_8$O$_3$) requires m/z 512.2, LCMS found m/z 513.2; $^1$H NMR (DMSO-d6, 400 MHz): δ (ppm) 10.53 (s, 1H), 8.93 (br s, 1H), 8.82 (s, 1H), 8.63 (s, 1H), 8.51 (dd, J=7.9, 1.5 Hz, 1H), 8.24 (dd, J=8.2, 1.6 Hz, 1H), 8.16 (s, 1H), 7.80 (s, 1H), 7.25 (t, J=8.1 Hz, 1H), 4.87-4.98 (m, 1H), 4.68 (dd, J=13.1, 4.3 Hz, 1H), 4.49 (br d, J=12.0 Hz, 1H), 3.61-3.74 (m, 4H), 2.91 (br d, J=4.0 Hz, 4H), 1.92-2.06 (m, 1H), 1.55 (d, J=6.7 Hz, 3H), 0.92-1.02 (m, 2H), 0.76-0.85 (m, 2H).

Synthesis of (R)-4-(4-cyclopropyl-1H-imidazol-1-yl)-N-(5-methyl-5,6-dihydrobenzo[f][1,2,4]triazolo[4,3-d][1,4]oxazepin-8-yl)-5-morpholinopicolinamide (Example 39)

To a solution of 4-(4-cyclopropyl-1H-imidazol-1-yl)-5-morpholinopicolinic acid (19d) (24.33 mg, 69.37 umol, HCl) in DMF (1 mL) was added HATU (39.56 mg, 104.05 umol) and NMM (21.05 mg, 208.10 umol, 22.88 uL) at 25° C., then (R)-5-methyl-5,6-dihydrobenzo[f][1,2,4]triazolo[4,3-d][1,4]oxazepin-8-amine (39z) (0.015 g, 69.37 umol) was added in and stirred for 4 hours at 40° C. The reaction mixture was poured into water (2 mL) and filtered. The filter cake was washed with water (5 mL), dried in vacuo to give Example 39. MS mass calculated for [M+1]$^+$ (C$_{27}$H$_{28}$N$_8$O$_3$) requires m/z 513.2, LCMS found m/z 513.2; $^1$H NMR (400 MHz, CHLOROFORM-d) δ=10.51 (s, 1H), 8.69 (dd, J=1.5, 8.3 Hz, 1H), 8.46-8.38 (m, 2H), 8.29 (s, 1H), 8.11 (s, 1H), 8.01 (s, 1H), 7.27-7.22 (m, 1H), 7.18 (d, J=1.0 Hz, 1H), 4.83-4.71 (m, 1H), 4.69-4.59 (m, 1H), 4.47 (d, J=11.7 Hz, 1H), 3.88-3.72 (m, 4H), 2.99-2.86 (m, 4H), 1.98-1.88 (m, 1H), 1.70 (d, J=6.8 Hz, 3H), 0.97-0.90 (m, 2H), 0.87-0.81 (m, 2H).

Example S17

(R)-4-(4-cyclopropyl-1H-imidazol-1-yl)-N-(5-(fluoromethyl)-5,6-dihydrobenzo[f]tetrazolo[1,5-d][1,4]oxazepin-8-yl)picolinamide (Example 27) was synthesized according to the scheme provided below.

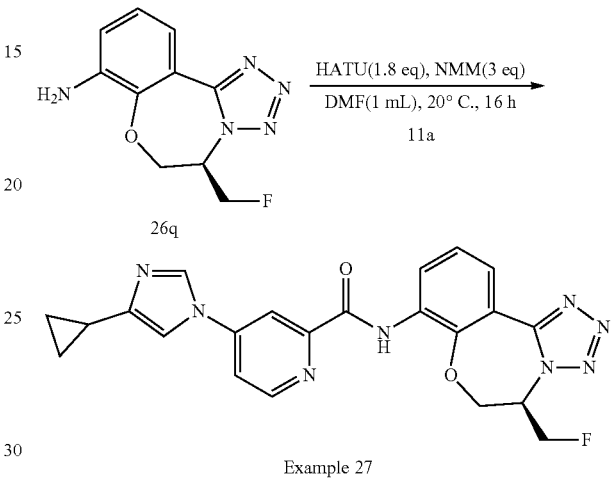

Synthesis of (R)-4-(4-cyclopropyl-1H-imidazol-1-yl)-N-(5-(fluoromethyl)-5,6-dihydrobenzo[f]tetrazolo[1,5-d][1,4]oxazepin-8-yl)picolinamide (Example 27)

To a mixture of 4-(4-cyclopropyl-1H-imidazol-1-yl)picolinic acid (11a) (4.09 mg, 17.86 umol) in DMF (1 mL) was added HATU (8.73 mg, 22.96 umol) and NMM (3.87 mg, 38.26 umol, 4.21 uL) at 20° C. under N$_2$. The mixture was stirred at 20° C. for 10 min, then (R)-5-(fluoromethyl)-5,6-dihydrobenzo[f]tetrazolo[1,5-d][1,4]oxazepin-8-amine (26q) (3 mg, 12.75 umol) was added into the mixture. The mixture was stirred at 20° C. for 16 hours. LCMS showed the reaction was completed. The mixture was concentrated in vacuo. The residue was diluted with Ethyl acetate (40 mL), then was washed with the saturated NaHCO$_3$ solution (5 mL*5), brine (5 mL*2), dried with anhydrous Na$_2$SO$_4$, filtered and the filtrate was concentrated in vacuo. MeOH (1 mL) was added into the residue and the mixture was stirred for 10 mins. The solid was collected by filtration to give Example 27. MS mass calculated for [M+1]$^+$ (C$_{22}$H$_{19}$FN$_8$O$_2$) requires m/z 447.2, LCMS found m/z 447.2; $^1$H NMR (400 MHz, DMSO-d6) δ 10.68 (s, 1H), 8.81 (d, J=5.5 Hz, 1H), 8.67-8.54 (m, 2H), 8.41 (d, J=2.0 Hz, 1H), 8.27 (dd, J=1.3, 8.2 Hz, 1H), 8.02 (dd, J=2.3, 5.5 Hz, 1H), 7.88 (s, 1H), 7.39 (t, J=8.1 Hz, 1H), 5.58 (br d, J=16.1 Hz, 1H), 5.21 (dd, J=4.5, 10.0 Hz, 1H), 5.12-4.99 (m, 2H), 4.93 (dd, J=5.3, 10.1 Hz, 1H), 4.73 (br d, J=13.8 Hz, 1H), 1.93-1.80 (m, 1H), 0.91-0.80 (m, 2H), 0.79-0.67 (m, 2H).

Example S18

(S)-5-(4-cyclopropyl-1H-imidazol-1-yl)-2-fluoro-N-(5-(fluoromethyl)-5,6-dihydrobenzo[f][1,2,4]triazolo[4,3-d][1, 4]oxazepin-8-yl)-4-methylbenzamide (Example 28) was synthesized according to the scheme provided below.

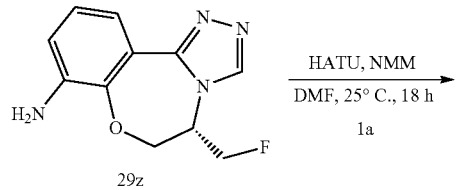

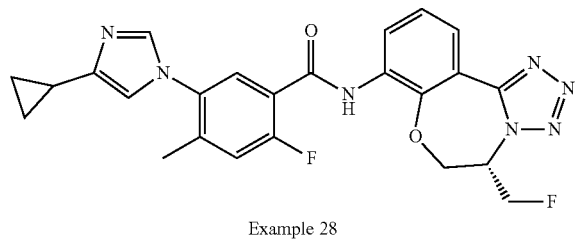

Example 28

Synthesis of (S)-5-(4-cyclopropyl-1H-imidazol-1-yl)-2-fluoro-N-(5-(fluoromethyl)-5,6-dihydrobenzo[f][1,2,4]triazolo[4,3-d][1,4]oxazepin-8-yl)-4-methylbenzamide (Example 28)

To a solution of 1a (10.00 mg, 38.42 umol) in DMF (1.5 mL) was added HATU (21.91 mg, 57.64 umol) and NMM (15.55 mg, 153.70 umol, 16.90 uL) and stirred for 5 min Then (S)-5-(fluoromethyl)-5,6-dihydrobenzo[f][1,2,4]triazolo[4,3-d][1,4]oxazepin-8-amine (29z) (0.009 g, 38.42 umol) was added at 25° C. and the mixture was stirred for 18 hours. The reaction mixture was diluted with water (5 mL) and extracted with EtOAc (10 mL*2), the combined organic layers were washed with brine (5 mL*2), dried over Na$_2$SO$_4$, filtered and concentrated. The residue was purified by prep-TLC to give Example 28. MS mass calculated for [M+1]$^+$ (C$_{25}$H$_{22}$F$_2$N$_6$O$_2$) requires m/z 477.2, LCMS found m/z 477.2; $^1$H NMR (400 MHz, DMSO-d6) δ=9.84 (d, J=4.8 Hz, 1H), 8.73 (s, 1H), 8.36-8.27 (m, 1H), 8.13 (br d, J=7.0 Hz, 1H), 7.75-7.65 (m, 2H), 7.50 (d, J=11.8 Hz, 1H), 7.23 (t, J=7.9 Hz, 1H), 7.19 (s, 1H), 5.17-4.80 (m, 3H), 4.78-4.60 (m, 1H), 4.38 (br d, J=12.3 Hz, 1H), 2.24 (s, 3H), 1.89-1.81 (m, 1H), 0.83-0.77 (m, 2H), 0.75-0.66 (m, 2H).

Example S19

(S)-4-(4-cyclopropyl-1H-imidazol-1-yl)-N-(5-(fluoromethyl)-5,6-dihydrobenzo[f][1,2,4]triazolo[4,3-d][1,4]oxazepin-8-yl)picolinamide (Example 29) was synthesized according to the scheme provided below.

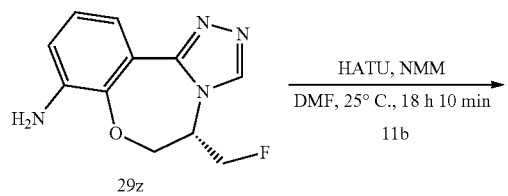

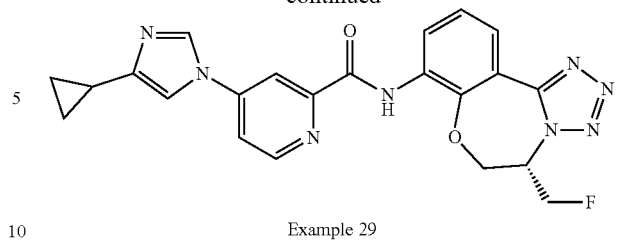

Example 29

Synthesis of (S)-4-(4-cyclopropyl-1H-imidazol-1-yl)-N-(5-(fluoromethyl)-5,6-dihydrobenzo[f][1,2,4]triazolo[4,3-d][1,4]oxazepin-8-yl)picolinamide (Example 29)

To a solution of 11b (13.70 mg, 59.77 umol) in DMF (1 mL) was added HATU (25.97 mg, 68.31 umol) and NMM (12.95 mg, 128.08 umol, 14.08 uL) and the mixture was stirred for 5 min, then (S)-5-(fluoromethyl)-5,6-dihydrobenzo[f][1,2,4]triazolo[4,3-d][1,4]oxazepin-8-amine (29z) (10 mg, 42.69 umol) was added at 25° C. and stirred for 18 hours. The reaction mixture was diluted with water (5 mL) and extracted with EtOAc (10 mL*2), the combined organic layers were washed with brine (5 mL*2), dried over Na$_2$SO$_4$, filtered and concentrated. The residue was purified by prep-TLC to give Example 29. MS mass calculated for [M+1]$^+$ (C$_{23}$H$_{20}$FN$_7$O$_2$) requires m/z 446.1, LCMS found m/z 446.1; $^1$H NMR (400 MHz, DMSO-d6) δ=10.65 (s, 1H), 8.81 (d, J=5.7 Hz, 1H), 8.75 (s, 1H), 8.58 (d, J=1.3 Hz, 1H), 8.53 (dd, J=1.8, 7.9 Hz, 1H), 8.41 (d, J=2.2 Hz, 1H), 8.32 (dd, J=1.8, 8.3 Hz, 1H), 8.01 (dd, J=2.4, 5.5 Hz, 1H), 7.88 (s, 1H), 7.29 (t, J=7.9 Hz, 1H), 5.17 (br s, 1H), 5.10-4.92 (m, 2H), 4.87-4.65 (m, 1H), 4.52 (br d, J=13.2 Hz, 1H), 1.92-1.82 (m, 1H), 0.88-0.82 (m, 2H), 0.79-0.71 (m, 2H).

Example S20

(S)-5-(4-cyclopropyl-1H-imidazol-1-yl)-2-fluoro-N-(5-(fluoromethyl)-5,6-dihydrobenzo[f]tetrazolo[1,5-d][1,4]oxazepin-8-yl)-4-methylbenzamide (Example 30) was synthesized according to the scheme provided below.

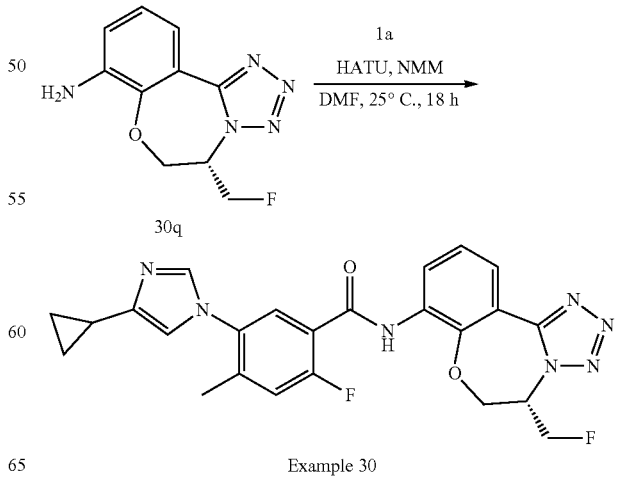

Example 30

Synthesis of (S)-5-(4-cyclopropyl-1H-imidazol-1-yl)-2-fluoro-N-(5-(fluoromethyl)-5,6-dihydrobenzo[f]tetrazolo[1,5-d][1,4]oxazepin-8-yl)-4-methylbenzamide (Example 30)

To a solution of 1a (15.49 mg, 59.52 umol) in DMF (2 mL) was added HATU (25.86 mg, 68.02 umol) and NMM (12.90 mg, 127.54 umol, 14.02 uL) and the mixture was stirred for 5 min, then (S)-5-(fluoromethyl)-5,6-dihydrobenzo[f]tetrazolo[1,5-d][1,4]oxazepin-8-amine (30q) (10 mg, 42.51 umol) was added at 25° C. and the mixture was stirred for 18 hours. The reaction mixture was diluted with water (5 mL) and extracted with EtOAc (10 mL*2), the combined organic layers were washed with brine (5 mL*2), dried over $Na_2SO_4$, filtered and concentrated. The residue was purified by prep-TLC, then resulting product was diluted with water (3 mL) and stirred for 10 min and filtered, the solid was collected and dried in vacuo to afford Example 30. MS mass calculated for $[M+1]^+$ ($C_{24}H_{21}F_2N_7O_2$) requires m/z 478.2, LCMS found m/z 478.1; $^1$H NMR (400 MHz, CHLOROFORM-d) δ=9.37 (br d, J=16.1 Hz, 1H), 8.80-8.72 (m, 1H), 8.37 (dd, J=1.5, 8.3 Hz, 1H), 8.09 (d, J=7.3 Hz, 1H), 7.46 (s, 1H), 7.35 (t, J=8.3 Hz, 1H), 7.21 (d, J=12.2 Hz, 1H), 6.81 (s, 1H), 5.44-5.29 (m, 1H), 5.13-4.95 (m, 3H), 4.54 (br d, J=13.7 Hz, 1H), 2.31 (s, 3H), 1.98-1.86 (m, 1H), 0.94-0.88 (m, 2H), 0.88-0.81 (m, 2H).

Example S21

(S)-4-(4-cyclopropyl-1H-imidazol-1-yl)-N-(5-(fluoromethyl)-5,6-dihydrobenzo[f]tetrazolo[1,5-d][1,4]oxazepin-8-yl)picolinamide (Example 31) was synthesized according to the scheme provided below.

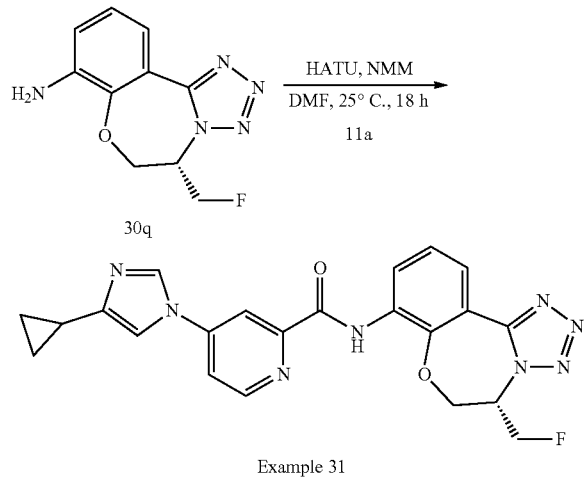

Synthesis of (S)-4-(4-cyclopropyl-1H-imidazol-1-yl)-N-(5-(fluoromethyl)-5,6-dihydrobenzo[f]tetrazolo[1,5-d][1,4]oxazepin-8-yl)picolinamide (Example 31)

To a solution of 11a (13.64 mg, 59.52 umol) in DMF (1 mL) was added HATU (25.86 mg, 68.02 umol) and NMM (12.90 mg, 127.54 umol, 14.02 uL) and the mixture was stirred for 5 min, then (S)-5-(fluoromethyl)-5,6-dihydrobenzo[f]tetrazolo[1,5-d][1,4]oxazepin-8-amine (30 q) (10 mg, 42.51 umol) was added at 25° C. and the mixture was stirred for 18 hours The reaction mixture was diluted with water (5 mL) and extracted with EtOAc (10 mL*2), the combined organic layers were washed with brine (5 mL*2), dried over $Na_2SO_4$, filtered and concentrated. The residue was purified by prep-TLC to give Example 31. MS mass calculated for $[M+1]^+$ ($C_{22}H_{19}FN_8O_2$) requires m/z 447.1, LCMS found m/z 447.1; $^1$H NMR (400 MHz, DMSO-d6) δ=10.69 (s, 1H), 8.82 (d, J=5.7 Hz, 1H), 8.62 (d, J=9.2 Hz, 1H), 8.57 (s, 1H), 8.41 (s, 1H), 8.27 (d, J=6.6 Hz, 1H), 8.04-8.00 (m, 1H), 7.88 (s, 1H), 7.39 (t, J=8.3 Hz, 1H), 5.63-5.53 (m, 1H), 5.26-4.87 (m, 3H), 4.72 (br d, J=12.7 Hz, 1H), 1.86 (br d, J=4.8 Hz, 1H), 0.87-0.81 (m, 2H), 0.74 (br d, J=4.8 Hz, 2H).

Example S22

(R)-5-(4-cyclopropyl-1H-imidazol-1-yl)-2-fluoro-N-(5-(fluoromethyl)-5,6-dihydrobenzo[f][1,2,4]triazolo[4,3-d][1,4]oxazepin-8-yl)-4-methylbenzamide (Example 32) was synthesized according to the scheme provided below.

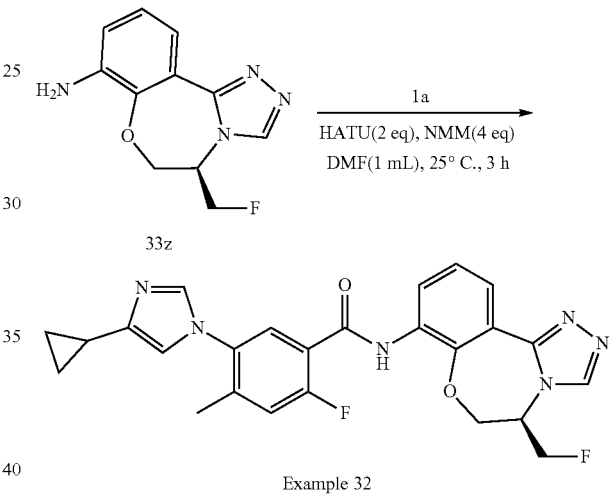

Synthesis of (R)-5-(4-cyclopropyl-1H-imidazol-1-yl)-2-fluoro-N-(5-(fluoromethyl)-5,6-dihydrobenzo[f][1,2,4]triazolo[4,3-d][1,4]oxazepin-8-yl)-4-methylbenzamide (Example 32)

To a mixture of 5-(4-cyclopropyl-1H-imidazol-1-yl)-2-fluoro-4-methylbenzoic acid (1a) (14.00 mg, 53.79 umol) in DMF (1 mL) was added HATU (29.22 mg, 76.85 umol) and NMM (15.55 mg, 153.70 umol, 16.90 uL) at 25° C. under $N_2$. The mixture was stirred at 25° C. for 10 min, then (R)-5-(fluoromethyl)-5,6-dihydrobenzo[f][1,2,4]triazolo[4,3-d][1,4]oxazepin-8-amine (33z) (9 mg, 38.42 umol) was added into the mixture. The mixture was stirred at 25° C. for 16 hours. LCMS showed the reaction was completed. Ethyl acetate (40 mL) was added and the mixture was washed with the saturated solution of $NaHCO_3$ (5 mL*3), brine (5 mL*2), dried with anhydrous $Na_2SO_4$, filtered and concentrated in vacuo. The residue was purified by prep-TLC ($SiO_2$, DCM:MeOH=10:1) to give Example 32. MS mass calculated for $[M+1]^+$ ($C_{25}H_{22}F_2N_6O_2$) requires m/z 447.2, LCMS found m/z 447.1; $^1$H NMR (400 MHz, ACETONITRILE-d3) δ 9.28 (br d, J=10.1 Hz, 1H), 8.50 (d, J=7.9 Hz, 1H), 8.43-8.35 (m, 2H), 7.87 (d, J=7.3 Hz, 1H), 7.46 (s, 1H), 7.32 (d, J=12.3 Hz, 1H), 7.23 (t, J=8.2 Hz, 1H), 6.95 (d, J=1.1 Hz, 1H), 5.02-4.93 (m, 2H), 4.92-4.82 (m, 1H), 4.79-4.70 (m, 1H), 4.67-4.59 (m, 1H), 4.35 (dd, J=3.2, 12.7 Hz, 1H), 2.23 (s, 3H), 1.91-1.83 (m, 1H), 0.89-0.80 (m, 2H), 0.77-0.69 (m, 2H).

Example S23

(R)-4-(4-cyclopropyl-1H-imidazol-1-yl)-N-(5-(fluoromethyl)-5,6-dihydrobenzo[f][1,2,4]triazolo[4,3-d][1,4]oxazepin-8-yl)picolinamide (Example 33) was synthesized according to the scheme provided below.

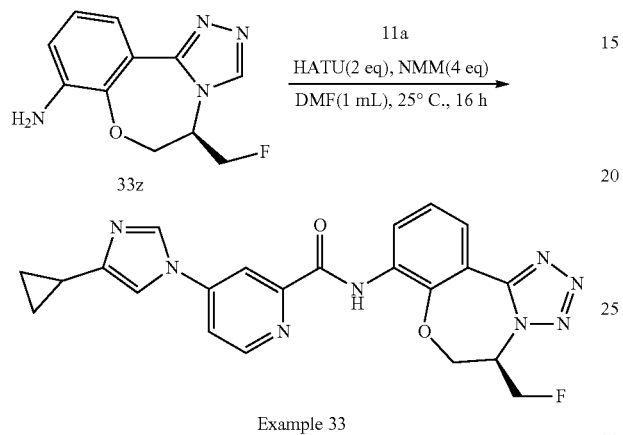

Synthesis of (R)-4-(4-cyclopropyl-1H-imidazol-1-yl)-N-(5-(fluoromethyl)-5,6-dihydrobenzo[f][1,2,4]triazolo[4,3-d][1,4]oxazepin-8-yl)picolinamide (Example 33)

To a mixture of 4-(4-cyclopropyl-1H-imidazol-1-yl)picolinic acid (1b) (12.33 mg, 53.79 umol) in DMF (1 mL) was added HATU (29.22 mg, 76.85 umol) and NMM (15.55 mg, 153.70 umol, 16.90 uL) at 25° C. under $N_2$. After stirring at 25° C. for 10 min, then (R)-5-(fluoromethyl)-5,6-dihydrobenzo[f][1,2,4]triazolo[4,3-d][1,4]oxazepin-8-amine (33z) (9 mg, 38.42 umol) was added into the mixture. The mixture was stirred at 25° C. for 16 hours. LCMS showed the reaction was completed. The mixture was diluted with ethyl acetate (40 mL), then was washed with the saturated solution of $NaHCO_3$ (5 mL*3), $NH_4Cl$ (5 mL*3), brine (5 mL*2), dried with anhydrous $Na_2SO_4$, filtered and the filtrate was concentrated in vacuo. The residue was purified by prep-TLC ($SiO_2$, DCM:MeOH=10:1) to give Example 33. MS mass calculated for $[M+1]^+$ ($C_{23}H_{20}FN_7O_2$) requires m/z 446.2, LCMS found m/z 446.1; $^1$H NMR (400 MHz, ACETONITRILE-d3) δ 10.68 (s, 1H), 8.72 (d, J=5.5 Hz, 1H), 8.68-8.62 (m, 1H), 8.43-8.36 (m, 2H), 8.32 (d, J=2.0 Hz, 1H), 8.14 (s, 1H), 7.69 (dd, J=2.2, 5.5 Hz, 1H), 7.47 (s, 1H), 7.25 (t, J=8.2 Hz, 1H), 5.05-4.95 (m, 2H), 4.90 (dd, J=4.6, 9.7 Hz, 1H), 4.83-4.76 (m, 1H), 4.71-4.64 (m, 1H), 4.42 (dd, J=3.4, 12.0 Hz, 1H), 1.92-1.87 (m, 1H), 0.90-0.84 (m, 2H), 0.80-0.74 (m, 2H).

Example S24

(R)-5-(4-cyclopropyl-1H-imidazol-1-yl)-2-fluoro-4-methyl-N-(6-methyl-5,6-dihydrobenzo[f][1,2,4]triazolo[4,3-d][1,4]oxazepin-8-yl)benzamide (Example 34) and (S)-5-(4-cyclopropyl-1H-imidazol-1-yl)-2-fluoro-4-methyl-N-(6-methyl-5,6-dihydrobenzo[f][1,2,4]triazolo[4,3-d][1,4]oxazepin-8-yl)benzamide (Example 35) were synthesized according to the schemes provided below.

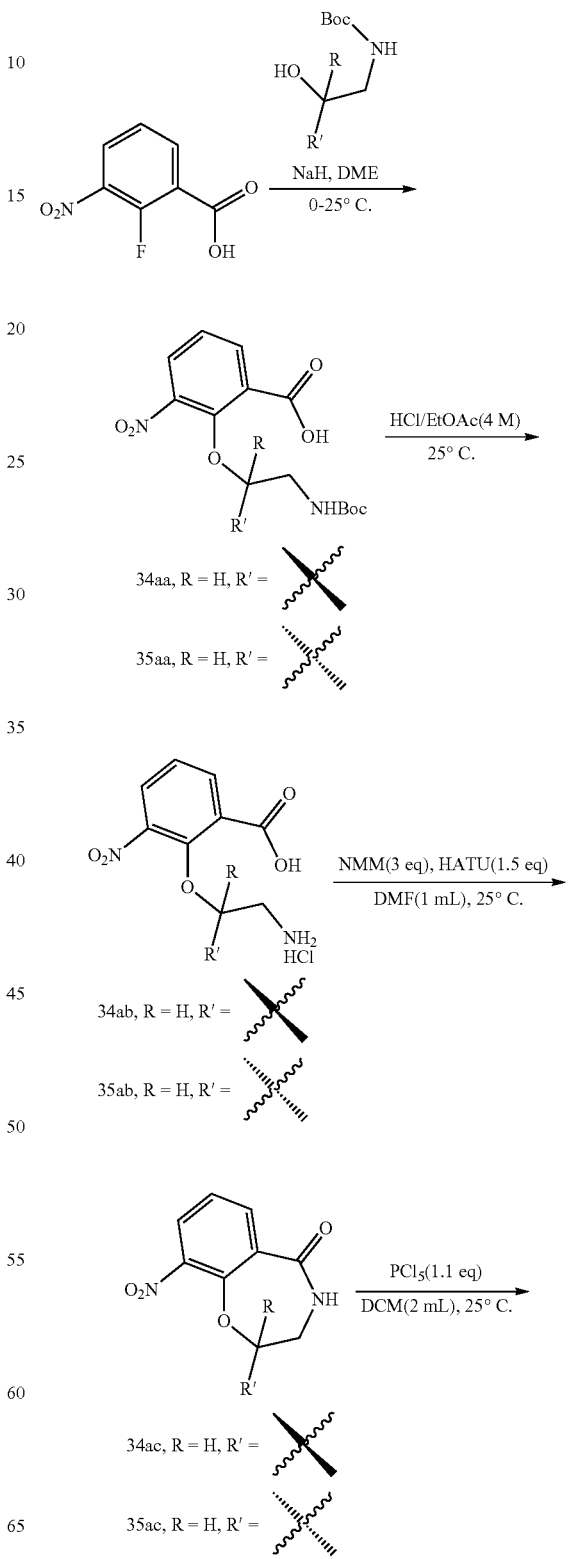

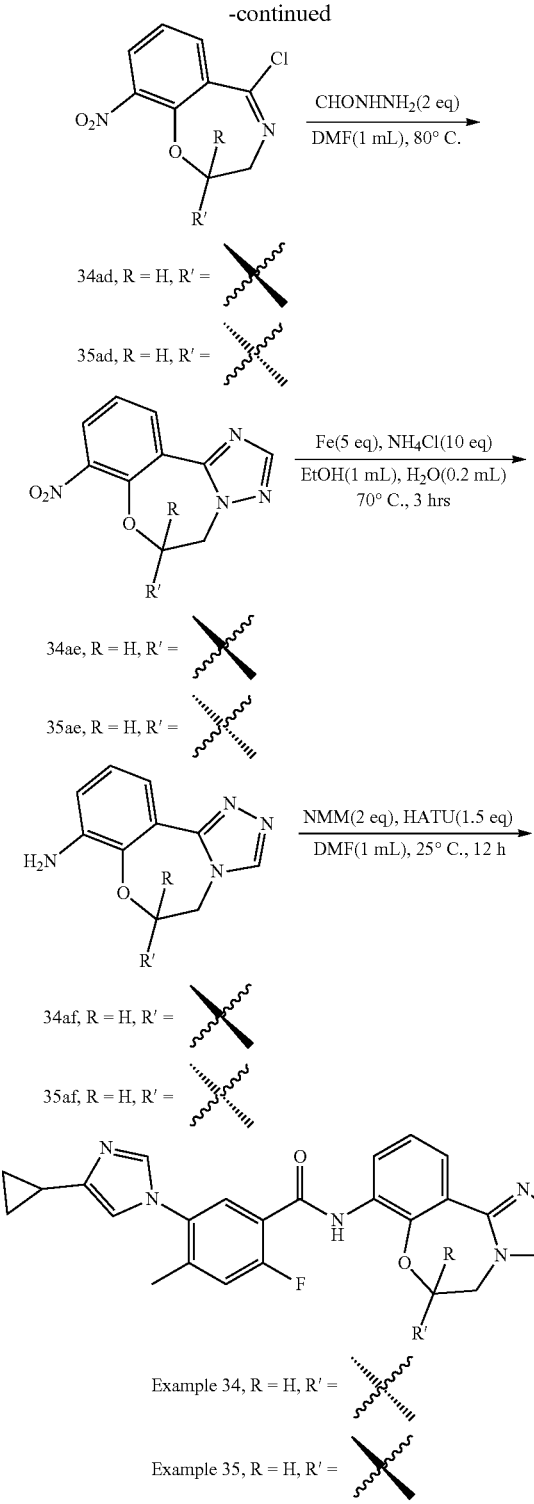

General Procedure

Synthesis of (aa)

To a solution of alcohol (1 mmol) in DME (5 mL) was added NaH (2.5 eq) at 0° C. under $N_2$, the mixture was stirred at 0° C. for 10 min, then 2-fluoro-3-nitrobenzoic acid (1 eq) dissolved in DME (2 mL) was added in drop-wise at 0° C. under $N_2$, the mixture was stirred at 25° C. for 2 hours. LCMS showed the reaction was completed. The reaction mixture was cooled to 0° C. and quenched with water (10 mL), washed with EtOAc (20 mL), the aqueous phase was acidified with 0.5N HCl to pH=5, then extracted with EtOAc (10 mL*3), the combined organic layers were washed with brine (5 mL), dried over $Na_2SO_4$, filtered and concentrated to give aa.

Synthesis of (ab)

A solution of aa (1.2 mmol) in HCl/EtOAc (10 mL, 4 M) was stirred at 25° C. for 2 hours. LCMS showed the reaction was completed. The reaction mixture was filtered, the filter cake was washed with EtOAc (5 mL), and then dried in vacuo to give ab.

Synthesis of (ac)

To a solution of ab (HCl salt, 0.36 mmol) in DMF (30 mL) was added NMM (3 eq) and HATU (1.2 eq). The mixture was stirred at 25° C. for 2 h. LCMS show the reaction was completed. The mixture was poured into water (100 mL) and was extracted with ethyl acetate (10 mL*2). The combined organic layers were washed with brine (20 mL*3), dried with anhydrous $Na_2SO_4$, filtered and concentrated in vacuo. The crude product was purified by prep-TLC to give ac.

Synthesis of (ad)

To a solution of ac (0.18 mmol) in DCM (2 mL) was added $PCl_5$ (1.1 eq). The mixture was stirred at 25° C. for 2 h. TLC show the reaction was completed. The mixture was concentrated to give ad.

Synthesis of (ae)

To a solution of ad (0.17 mmol) in DMF (1 mL) was added formohydrazide (2 eq). The mixture was stirred at 70° C. for 12 h. LCMS showed the reaction was completed. The residue was poured into water (5 mL) and extracted with ethyl acetate (2 mL*2). The combined organic layers were washed with brine (1 mL), dried with anhydrous $Na_2SO_4$, filtered and concentrated in vacuo. The crude product was purified by prep-TLC to give ae.

Synthesis of (af)

To a solution of ae (0.16 mmol) in EtOH (2 mL) and $H_2O$ (0.4 mL) was added Fe (5 eq) and $NH_4Cl$ (10 eq). The mixture was stirred at 70° C. for 3 h. LCMS show the reaction was completed. The residue was poured into water (2 mL) and was extracted with ethyl acetate (2 mL*2). The combined organic layers were washed with brine (1 mL*2), dried with anhydrous $Na_2SO_4$, filtered and concentrated in vacuo to give af.

Synthesis of (R)-5-(4-cyclopropyl-1H-imidazol-1-yl)-2-fluoro-4-methyl-N-(6-methyl-5,6-dihydrobenzo[f][1,2,4]triazolo[4,3-d][1,4]oxazepin-8-yl)benzamide (Example 34)

To a solution of 5-(4-cyclopropyl-1H-imidazol-1-yl)-2-fluoro-4-methylbenzoic acid (15 mg, 69.37 umol) in DMF (1 mL) was added HATU (39.56 mg, 104.05 umol), NMM (21.05 mg, 208.10 umol) and (R)-6-methyl-5,6-dihydrobenzo[f][1,2,4]triazolo[4,3-d][1,4]oxazepin-8-amine (34af) (19.86 mg, 76.30 umol). The mixture was stirred at 25° C. for 12 h. LCMS show the reaction was completed. The residue was poured into water (2 mL) and was extracted with ethyl acetate (2 mL*2). The combined organic layers were washed with brine (2 mL*2), dried with anhydrous Na$_2$SO$_4$, filtered and concentrated in vacuo. The residue was purified by prep-TLC (DCM:Methanol=10/1, R$_f$=0.4) followed by prep-HPLC (column: Nano-micro Kromasil C18 100*30 mm 5 um; mobile phase: [water (0.1% TFA)-ACN]; B %: 15%-45%, 10 min) to give Example 34. MS mass calculated for [M+1]$^+$ (C$_{25}$H$_{23}$FN$_6$O$_2$) requires m/z 458.4, LCMS found m/z 459.1; $^1$H NMR (400 MHz, CHLOROFORM-d) δ ppm 9.47 (d, J=16.1 Hz, 1H) 8.65 (d, J=8.2 Hz, 1H) 8.49 (s, 1H) 8.37 (d, J=9.5 Hz, 1H) 8.26 (s, 1H) 8.19 (d, J=7.1 Hz, 1H) 7.30 (s, 1H) 7.22-7.26 (m, 1H) 6.89 (s, 1H) 4.45-4.60 (m, 2H) 4.32-4.40 (m, 1H) 2.32 (s, 3H) 2.01-2.09 (m, 2H) 1.73 (d, J=6.6 Hz, 3H) 1.14 (q, J=6.5 Hz, 2H) 0.92-0.99 (m, 2H).

Synthesis of (S)-5-(4-cyclopropyl-1H-imidazol-1-yl)-2-fluoro-4-methyl-N-(6-methyl-5,6-dihydrobenzo[f][1,2,4]triazolo[4,3-d][1,4]oxazepin-8-yl)benzamide (Example 35)

To a mixture of (S)-6-methyl-5,6-dihydrobenzo[f][1,2,4]triazolo[4,3-d][1,4]oxazepin-8-amine (35af) (30 mg, 138.74 umol) and (1a) (50.55 mg, 194.23 umol) in DMF (2 mL) was added HATU (105.50 mg, 277.47 umol) and NMM (28.07 mg, 277.47 umol, 30.51 uL) under N$_2$. The mixture was stirred at 25° C. for 16 hours. LCMS showed desired MS was detected. The mixture was poured into saturated aqueous NaHCO$_3$ (5 mL) and was extracted with ethyl acetate (10 mL*2). The combined organic layers were washed with brine (10 mL), dried with anhydrous Na$_2$SO$_4$, filtered and the filtrate was concentrated in vacuo. The residue was purified by prep-TLC (SiO$_2$, Ethyl acetate:Methanol=10:1) to give Example 35. MS mass calculated for [M+H]$^+$ (C$_{25}$H$_{23}$FN$_6$O$_2$) requires m/z 459.2, LCMS found m/z 459.2; $^1$H NMR (400 MHz, CDCl$_3$) δ 9.48 (br d, J=16.7 Hz, 1H), 8.66 (d, J=6.6 Hz, 1H), 8.44-8.30 (m, 1H), 8.22 (s, 1H), 8.10 (d, J=7.0 Hz, 1H), 7.50 (br s, 1H), 7.25-7.21 (m, 1H), 7.19 (d, J=12.7 Hz, 1H), 6.79 (br s, 1H), 4.54 (br t, J=6.8 Hz, 1H), 4.50-4.42 (m, 1H), 4.39-4.29 (m, 1H), 2.28 (s, 3H), 1.91 (br s, 1H), 1.71 (d, J=6.6 Hz, 3H), 0.94-0.86 (m, 2H), 0.82 (br d, J=4.4 Hz, 2H).

Example S25

5-(4-cyclopropyl-1H-imidazol-1-yl)-N-(5,6-dihydrobenzo[f][1,2,3]triazolo[1,5-d][1,4]oxazepin-8-yl)-2-fluoro-4-methylbenzamide (Example 40) was synthesized according to the schemes provided below.

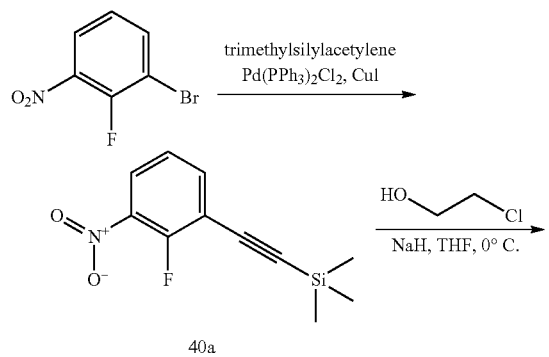

40a

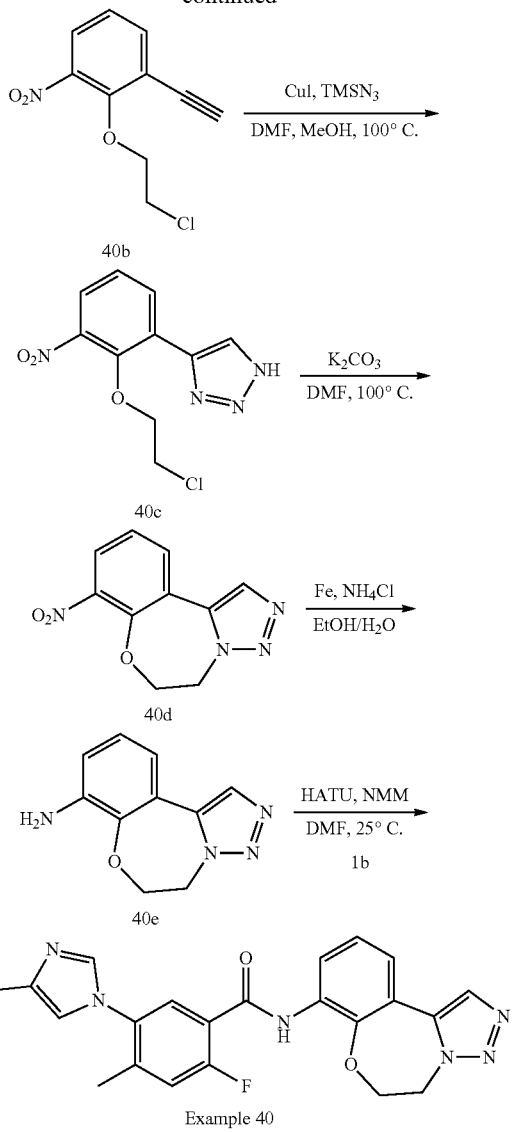

Example 40

((2-fluoro-3-nitrophenyl)ethynyl)trimethylsilane (40a)

To a solution of 1-bromo-2-fluoro-3-nitrobenzene (200 mg, 909.11 umol) in TEA (2 mL) was added trimethylsilylacetylene (357.16 mg, 3.64 mmol, 503.76 uL), Pd(PPh$_3$)$_2$Cl$_2$ (63.81 mg, 90.91 umol) and CuI (17.31 mg, 90.91 umol) at 20° C. under N$_2$, then the mixture was degassed and purged with N$_2$ three times, the resulting mixture was heated to 60° C. and stirred for 18 hours. TLC (Petroleum ether:Ethyl acetate=10:1) showed starting material was consumed. The reaction mixture was filtered through a Celite pad and the filter cake was rinsed with EtOAc (20 mL). The filtrate was concentrated in vacuo, then diluted with water (10 mL) and extracted with EtOAc (20 mL*2), the combined organic layers were washed with brine (10 mL), dried over anhydrous Na$_2$SO$_4$, filtered and concentrated. The residue was purified by prep-TLC (SiO$_2$, Petroleum ether:Ethyl acetate=10:1, product R$_f$=0.47) to afford 40a. $^1$H NMR (400 MHz, CHLOROFORM-d) δ=7.98

(ddd, J=1.8, 6.7, 8.3 Hz, 1H), 7.72 (ddd, J=1.8, 6.0, 7.7 Hz, 1H), 7.23 (dt, J=1.1, 8.0 Hz, 1H), 0.31-0.27 (m, 9H).

2-(2-chloroethoxy)-1-ethynyl-3-nitrobenzene (40b)

To a solution of ((2-fluoro-3-nitrophenyl)ethynyl)-trimethylsilane (40a) (100.00 mg, 421.40 umol) in THF (2 mL), NaH (33.71 mg, 842.81 umol, 60% purity) was added at 0° C. and the mixture was stirred for 10 min. 2-chloroethanol (50.89 mg, 632.11 umol, 42.41 uL) was added at this temperature and the mixture was stirred for another 20 min. TLC (Petroleum ether:Ethyl acetate=10:1) showed starting material was consumed. The reaction mixture was quenched with saturated NH$_4$Cl solution (5 mL), and then extracted with EtOAc (10 mL*2). The combined organic layers were washed with brine (10 mL), dried over anhydrous Na$_2$SO$_4$, filtered and concentrated. The residue was purified by prep-TLC (SiO$_2$, Petroleum ether:Ethyl acetate=10:1, Product R$_f$=0.33) to afford 40b. $^1$H NMR (400 MHz, CHLOROFORM-d) δ=7.80 (dd, J=1.8, 8.2 Hz, 1H), 7.70 (dd, J=1.5, 7.7 Hz, 1H), 7.21 (t, J=7.9 Hz, 1H), 4.54 (t, J=6.2 Hz, 2H), 3.88 (t, J=6.2 Hz, 2H), 3.46 (s, 1H).

4-(2-(2-chloroethoxy)-3-nitrophenyl)-1H-1,2,3-triazole (40c) and 8-nitro-5,6-dihydrobenzo[f][1,2,3]triazolo[1,5-d][1,4]oxazepine (40d)

To a solution of 2-(2-chloroethoxy)-1-ethynyl-3-nitrobenzene (40b) (80 mg, 354.57 umol) and TMSN$_3$ (61.27 mg, 531.85 umol, 69.95 uL) in DMF (1.8 mL) and MeOH (0.2 mL) was added CuI (6.75 mg, 35.46 umol) at 25° C. under N$_2$. The mixture was degassed and purged with N$_2$ three times, and stirred at 100° C. for 16 hours. K$_2$CO$_3$ (49.00 mg, 354.57 umol) was added to the above solution and stirred for another 5 hours. The reaction mixture was filtered through a Celite pad and the filter cake was rinsed with EtOAc (20 mL). The filtrate was concentrated in vacuo. The residue was diluted with water (8 mL) and extracted with EtOAc (10 mL*3). The combined organic layers were washed with brine (5 mL*2), dried over anhydrous Na$_2$SO$_4$, filtered and concentrated. The residue was purified by prep-TLC (SiO$_2$, Petroleum ether:Ethyl acetate=1:1, product R$_f$=0.43) to afford 40d. MS mass calculated for [M+1]$^+$ (C$_{10}$H$_8$N$_4$O$_3$) requires m/z 233.1, LCMS found m/z 233.0; $^1$H NMR (400 MHz, CHLOROFORM-d) δ=8.09 (s, 1H), 7.97-7.90 (m, 1H), 7.76-7.69 (m, 1H), 7.27 (t, 1H), 5.03-4.97 (m, 2H), 4.71-4.64 (m, 2H).

5,6-dihydrobenzo[f][1,2,3]triazolo[1,5-d][1,4]oxazepin-8-amine (40e)

To a solution of 8-nitro-5,6-dihydrobenzo[f][1,2,3]triazolo[1,5-d][1,4]oxazepine (40d) (0.045 g, 193.80 umol) in EtOH (5 mL) and H$_2$O (1 mL) was added Fe (54.11 mg, 969.01 umol) and NH$_4$Cl (103.67 mg, 1.94 mmol) at 25° C. and the mixture was stirred for 3 hours at 70° C. TLC (Petroleum ether:Ethyl acetate=1:1) showed the reaction was completed and a product was detected. The reaction mixture was filtered through a Celite pad, the filter cake was rinsed with EtOH (30 mL) and the filtrate was concentrated. The residue was diluted with water (10 mL) and extracted with DCM (15 mL*3). The combined organic layers were collected and washed with water (10 mL), brine (10 mL), dried over anhydrous Na$_2$SO$_4$, filtered and concentrated to give 40e. MS mass calculated for [M+1]$^+$ (C$_{10}$H$_{10}$N$_4$O) requires m/z 203.1, LCMS found m/z 203.0; $^1$H NMR (400 MHz, CHLOROFORM-d) δ=8.02 (s, 1H), 7.11 (dd, J=1.7, 8.1 Hz, 1H), 6.94 (t, J=8.1 Hz, 1H), 6.76 (dd, J=1.7, 7.6 Hz, 1H), 5.04-4.79 (m, 2H), 4.62-4.48 (m, 2H), 4.12-3.92 (m, 2H).

Synthesis of 5-(4-cyclopropyl-1H-imidazol-1-yl)-N-(5,6-dihydrobenzo[f][1,2,3]triazolo[1,5-d][1,4]oxazepin-8-yl)-2-fluoro-4-methylbenzamide (Example 40)

To a solution of 5-(4-cyclopropyl-1H-imidazol-1-yl)-2-fluoro-4-methylbenzoic acid (1b) (58.56 mg, 225.01 umol) in DMF (2 mL) was added HATU (98.72 mg, 259.63 umol) and NMM (52.52 mg, 519.26 umol, 57.09 uL) at 25° C., then 5,6-dihydrobenzo[f][1,2,3]triazolo[1,5-d][1,4]oxazepin-8-amine (40e) (0.035 g, 173.09 umol) was added and the mixture was stirred for 18 hours. LCMS showed a main peak with desired MS. The mixture was concentrated in vacuo and purified by prep-HPLC (basic condition) to afford Example 40. MS mass calculated for [M+1]$^+$ (C$_{24}$H$_{21}$FN$_6$O$_2$) requires m/z 445.2 LCMS found m/z 445.1; $^1$H NMR (400 MHz, CHLOROFORM-d) δ=9.43 (br d, J=16.1 Hz, 1H), 8.61 (d, J=8.2 Hz, 1H), 8.08 (t, J=3.5 Hz, 2H), 7.52 (d, J=8.2 Hz, 1H), 7.47-7.39 (m, 1H), 7.24-7.14 (m, 2H), 6.80 (br s, 1H), 5.11-4.92 (m, 2H), 4.77-4.59 (m, 2H), 2.29 (s, 3H), 1.99-1.85 (m, 1H), 0.96-0.80 (m, 4H).

Example S26

5-(4-cyclopropyl-1H-imidazol-1-yl)-N-(5,6-dihydrobenzo[f]imidazo[1,5-d][1,4]oxazepin-8-yl)-2-fluoro-4-methylbenzamide (Example 41), (S)-5-(4-cyclopropyl-1H-imidazol-1-yl)-2-fluoro-4-methyl-N-(5-methyl-5,6-dihydrobenzo[f]imidazo[1,5-d][1,4]oxazepin-8-yl) benzamide (Example 46), and (R)-5-(4-cyclopropyl-1H-imidazol-1-yl)-2-fluoro-4-methyl-N-(5-methyl-5,6-dihydrobenzo[f]imidazo[1,5-d][1,4]oxazepin-8-yl) benzamide (Example 47) were synthesized according to the schemes provided below.

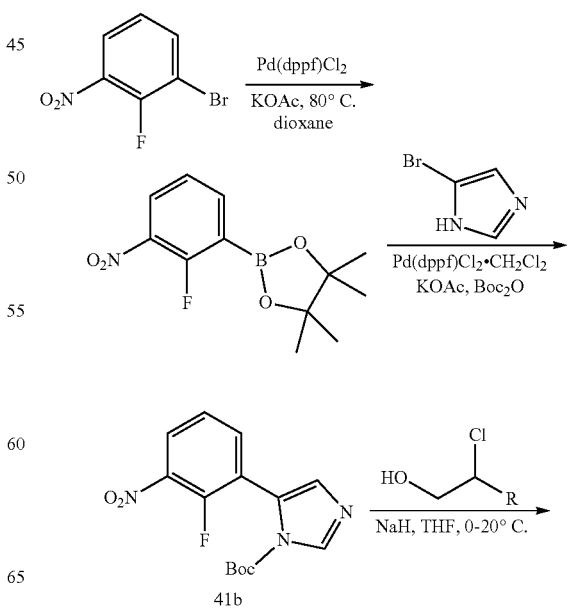

-continued

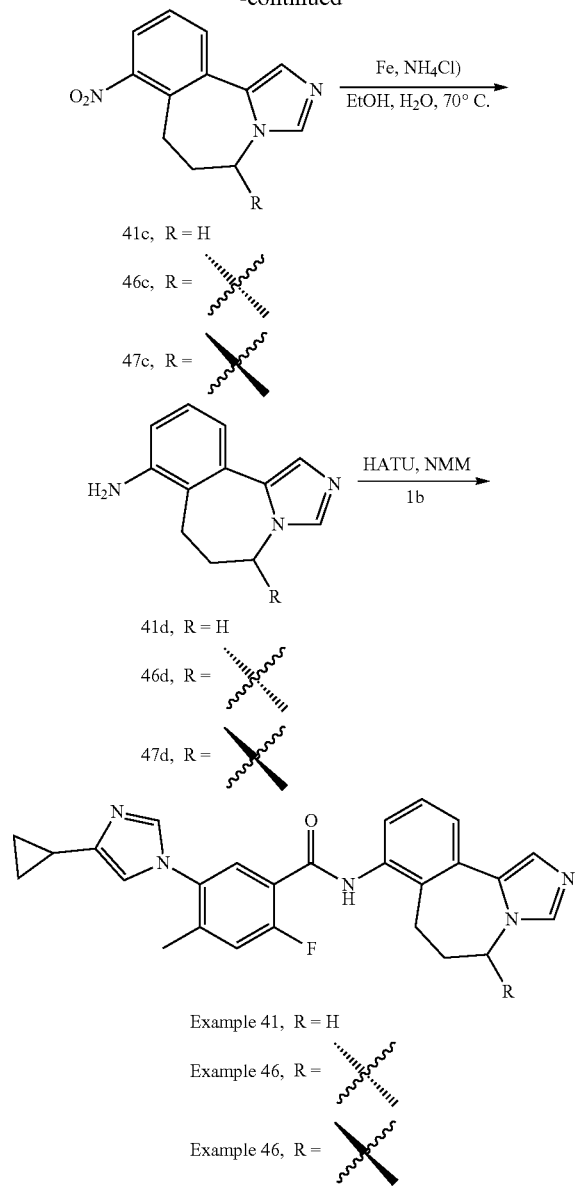

General Procedure

Synthesis of (41a)

To a mixture of 1-bromo-2-fluoro-3-nitrobenzene (1.4 mmol) in dioxane (10 mL) was added 4,4,5,5-tetramethyl-2-(4,4,5,5-tetramethyl-1,3,2-dioxaborolan-2-yl)-1,3,2-dioxaborolane (1.5 eq) and KOAc (2 eq), and Pd(dppf)Cl$_2$ (0.1 eq). The mixture was degassed and purged with N$_2$ for 3 times. The mixture was stirred at 80° C. for 16 hours and was poured into water and extracted with ethyl acetate 3 times. The combined organic layers were washed with brine, dried with anhydrous Na$_2$SO$_4$, filtered and concentrated in vacuo. The residue was purified by column chromatography (SiO$_2$, Petroleum ether/Ethyl acetate=15:1 to 10:1) to give 2-(2-fluoro-3-nitrophenyl)-4,4,5,5-tetramethyl-1,3,2-dioxaborolane (41a). $^1$H NMR (400 MHz, DMSO) δ 13.47 (br s, 1H), 8.03-6.96 (m, 4H), 2.20 (s, 3H), 1.94-1.77 (m, 1H), 0.80 (br s, 2H), 0.70 (br s, 2H).

Synthesis of (41b)

To a mixture of 2-(2-fluoro-3-nitrophenyl)-4,4,5,5-tetramethyl-1,3,2-dioxaborolane (41a) (0.86 mmol) and 5-bromo-1H-imidazole (1.5 eq) in dioxane (10 mL) was added Pd(dppf)Cl$_2$.CH$_2$Cl$_2$ (0.1 eq), (Boc)$_2$O (2 eq) and KOAc (3 eq) at 25° C. under N$_2$. The mixture was stirred at 80° C. for 16 hours. LC-MS showed desired MS was detected. The residue was poured into water and the mixture was extracted with ethyl acetate. The organic phase was washed with brine, dried with anhydrous Na$_2$SO$_4$, filtered and concentrated in vacuo. The residue was purified by prep-TLC (SiO$_2$, Petroleum ether:Ethyl acetate=3:1) to give tert-butyl 5-(2-fluoro-3-nitrophenyl)-1H-imidazole-1-carboxylate (41b). MS mass calculated for [M+1]$^+$ (C$_{14}$H$_{14}$FN$_3$O$_4$) requires m/z 306.1, LCMS found m/z 207.9.

Synthesis of (c)

To a mixture of tert-butyl 5-(2-fluoro-3-nitrophenyl)-1H-imidazole-1-carboxylate (41b) (0.11 mmol) and alcohol (2 eq) in THF (3 mL) was added NaH (2 eq) at 0° C. under N$_2$. The mixture was stirred at 25° C. for 2 hours. LCMS showed desired MS was detected. The residue was poured into ice-water and extracted with ethyl acetate. The organic phase was washed with brine (10 mL), dried with anhydrous Na$_2$SO$_4$, filtered and concentrated in vacuo to give compound c.

Synthesis of (d)

To a mixture of c (0.11 mmol) in EtOH/H$_2$O (5 mL/1 mL) was added Fe (5 eq) and NH$_4$Cl (10 eq) at 25° C. under N$_2$. The mixture was stirred at 70° C. for 2 hours. TLC (Dichloromethane:Methanol=10:1) indicated reactant was consumed completely and one new spot formed. The reaction mixture was filtered and the filtrate was concentrated under reduced pressure. The residue was poured into water and was extracted with ethyl acetate 3 times. The combined organic layers were washed with brine, dried with anhydrous Na$_2$SO$_4$, filtered and concentrated in vacuo. The residue was purified by prep-TLC (SiO$_2$, DCM:MeOH=10:1) to give compound d.

Synthesis of 5-(4-cyclopropyl-1H-imidazol-1-yl)-N-(5,6-dihydrobenzo[f]imidazo[1,5-d][1,4]oxazepin-8-yl)-2-fluoro-4-methylbenzamide (Example 41)

To a mixture of 5,6-dihydrobenzo[f]imidazo[1,5-d][1,4]oxazepin-8-amine (41d) (12 mg, 59.64 umol, 1 eq) and 5-(4-cyclopropyl-1H-imidazol-1-yl)-2-fluoro-4-methylbenzoic acid (1b) (23.28 mg, 89.45 umol, 1.5 eq) in DMF (1 mL) was added HATU (34.01 mg, 89.45 umol, 1.5 eq) and NMM (24.13 mg, 238.54 umol, 26.23 uL, 4 eq) under N$_2$. The mixture was stirred at 25° C. for 12 hours. LCMS showed one main peak with desired MS. The reaction mixture was poured into water (10 mL) and was extracted with ethyl acetate (10 mL*3). The combined organic layers were washed with brine (10 mL*2), dried with anhydrous Na$_2$SO$_4$, filtered and concentrated in vacuo. The residue was purified by prep-TLC (SiO$_2$, DCM:MeOH=10:1) to give Example 41. MS mass calculated for [M+1]$^+$ (C$_{25}$H$_{22}$FN$_5$O$_2$) requires m/z 444.2, LCMS found m/z 444.1; $^1$H NMR (400 MHz, CHLOROFORM-d) δ 9.40 (br d, J=15.5 Hz, 1H), 8.47 (dd, J=1.2, 8.1 Hz, 1H), 8.08 (d, J=7.3 Hz, 1H), 7.60 (s, 1H), 7.52 (br s, 1H), 7.49 (dd, J=1.5, 8.1 Hz, 1H), 7.45 (d, J=1.2 Hz, 1H), 7.20-7.15 (m, 1H), 7.14-7.11 (m, 1H), 6.79 (d, J=1.2 Hz, 1H), 4.64-4.58 (m, 2H), 4.53-4.47 (m, 2H), 2.28 (s, 3H), 1.92 (tt, J=5.2, 8.3 Hz, 1H), 0.94-0.87 (m, 2H), 0.86-0.80 (m, 2H).

Synthesis of (S)-5-(4-cyclopropyl-1H-imidazol-1-yl)-2-fluoro-4-methyl-N-(5-methyl-5,6-dihydrobenzo[f]imidazo[1,5-d][1,4]oxazepin-8-yl)benzamide (Example 46)

To a mixture of (S)-5-methyl-5,6-dihydrobenzo[f]imidazo[1,5-d][1,4]oxazepin-8-amine (46d) (3 mg, 13.94 umol, 1 eq) and 5-(4-cyclopropyl-1H-imidazol-1-yl)-2-fluoro-4-methylbenzoic acid (1b) (3.99 mg, 15.33 umol, 1.1 eq) in DMF (1 mL) was added HATU (6.36 mg, 16.72 umol, 1.2 eq) and NMM (5.64 mg, 55.75 umol, 6.13 uL, 4 eq) under $N_2$. The mixture was stirred at 25° C. for 12 hours. LCMS showed one main peak with desired MS. The reaction mixture was concentrated under reduced pressure. The residue was purified by prep-HPLC (basic condition) to give Example 46. MS mass calculated for $[M+1]^+$ ($C_{26}H_{24}FN_5O_2$) requires m/z 458.1, LCMS found m/z 458.1; $^1$H NMR (400 MHz, CHLOROFORM-d) δ 9.43 (br d, J=15.5 Hz, 1H), 8.48 (dd, J=1.3, 8.0 Hz, 1H), 8.10 (d, J=7.3 Hz, 1H), 7.66 (s, 1H), 7.53 (d, J=1.5 Hz, 1H), 7.51 (s, 1H), 7.47 (d, J=1.2 Hz, 1H), 7.19 (d, J=13.4 Hz, 1H), 7.16-7.11 (m, 1H), 6.81 (d, J=1.2 Hz, 1H), 4.75-4.68 (m, 1H), 4.58-4.52 (m, 1H), 4.51-4.43 (m, 1H), 2.30 (s, 3H), 1.97-1.90 (m, 1H), 1.67 (d, J=6.8 Hz, 3H), 0.94-0.90 (m, 2H), 0.87-0.83 (m, 2H).

Synthesis of (R)-5-(4-cyclopropyl-1H-imidazol-1-yl)-2-fluoro-4-methyl-N-(5-methyl-5,6-dihydrobenzo[f]imidazo[1,5-d][1,4]oxazepin-8-yl)benzamide (Example 47)

To a mixture of (S)-5-methyl-5,6-dihydrobenzo[f]imidazo[1,5-d][1,4]oxazepin-8-amine (47d) (8 mg, 37.17 umol, 1 eq) and 5-(4-cyclopropyl-1H-imidazol-1-yl)-2-fluoro-4-methylbenzoic acid (1b) (13.23 mg, 44.60 umol, 1.2 eq, HCl) in DMF (1 mL) was added HATU (16.96 mg, 44.60 umol, 1.2 eq) and NMM (15.04 mg, 148.66 umol, 16.34 uL, 4 eq) under $N_2$. The mixture was stirred at 25° C. for 12 hours. LCMS showed one main peak with desired MS was detected. The reaction mixture was concentrated under reduced pressure. The residue was purified by prep-HPLC (basic condition) to give Example 47. MS mass calculated for $[M+1]^+$ ($C_{26}H_{24}FN_5O_2$) requires m/z 458.1, LCMS found m/z 458.1; $^1$H NMR (400 MHz, CHLOROFORM-d) δ 9.41 (br d, J=15.7 Hz, 1H), 8.46 (d, J=7.9 Hz, 1H), 8.08 (d, J=7.3 Hz, 1H), 7.64 (s, 1H), 7.52-7.48 (m, 2H), 7.45 (d, J=1.2 Hz, 1H), 7.17 (d, J=13.3 Hz, 1H), 7.14-7.09 (m, 1H), 6.80 (d, J=1.1 Hz, 1H), 4.75-4.66 (m, 1H), 4.57-4.51 (m, 1H), 4.49-4.42 (m, 1H), 2.29 (s, 3H), 1.96-1.88 (m, 1H), 1.66 (d, J=6.8 Hz, 3H), 0.94-0.87 (m, 2H), 0.86-0.81 (m, 2H).

8-nitro-5,6-dihydrobenzo[f]imidazo[1,5-d][1,4]oxazepine (41c)

MS mass calculated for $[M+1]^+$ ($C_{11}H_9N_3O_3$) requires m/z 232.1, LCMS found m/z 232.3; $^1$H NMR (400 MHz, CHLOROFORM-d) δ 7.85 (d, J=8.2 Hz, 1H), 7.70 (br s, 1H), 7.64 (d, J=7.7 Hz, 1H), 7.52 (s, 1H), 7.21 (t, J=8.0 Hz, 1H), 4.67-4.62 (m, 2H), 4.49-4.44 (m, 2H).

(R)-5-methyl-8-nitro-5,6-dihydrobenzo[f]imidazo[1,5-d][1,4]oxazepine (46c)

MS mass calculated for $[M+1]^+$ ($C_{12}H_{11}N_3O_3$) requires m/z 246.1, LCMS found m/z 246.2.

(S)-5-methyl-8-nitro-5,6-dihydrobenzo[f]imidazo[1,5-d][1,4]oxazepine (47c)

MS mass calculated for $[M+1]^+$ ($C_{12}H_{11}N_3O_3$) requires m/z 246.1, LCMS found m/z 246.2.

5,6-dihydrobenzo[f]imidazo[1,5-d][1,4]oxazepin-8-amine (41d)

$^1$H NMR (400 MHz, CHLOROFORM-d) δ 7.56 (br s, 1H), 7.44 (br s, 1H), 7.15-7.02 (m, 1H), 6.89 (dt, J=5.0, 7.8 Hz, 1H), 6.74-6.60 (m, 1H), 4.51 (br d, J=2.6 Hz, 2H), 4.42 (br d, J=3.7 Hz, 2H).

(R)-5-methyl-5,6-dihydrobenzo[f]imidazo[1,5-d][1,4]oxazepin-8-amine (46d)

MS mass calculated for $[M+1]^+$ ($C_{12}H_{13}N_3O$) requires m/z 216.1, LCMS found m/z 216.1.

(S)-5-methyl-5,6-dihydrobenzo[f]imidazo[1,5-d][1,4]oxazepin-8-amine (47d)

MS mass calculated for $[M+1]^+$ ($C_{12}H_{13}N_3O$) requires m/z 216.1, LCMS found m/z 216.1.

Example S27

(S)-5-(4-cyclopropyl-1H-imidazol-1-yl)-2-fluoro-4-methyl-N-(6-methyl-5,6-dihydrobenzo[f]tetrazolo[1,5-d][1,4]oxazepin-8-yl)benzamide (Example 42), (R)-5-(4-cyclopropyl-1H-imidazol-1-yl)-2-fluoro-4-methyl-N-(6-methyl-5,6-dihydrobenzo[f]tetrazolo[1,5-d][1,4]oxazepin-8-yl)benzamide (Example 43), and 5-(4-cyclopropyl-1H-imidazol-1-yl)-2-fluoro-4-methyl-N-(5H-spiro[benzo[f]tetrazolo[1,5-d][1,4]oxazepine-6,1'-cyclopropan]-8-yl)benzamide (Example 59) were synthesized according to the schemes provided below.

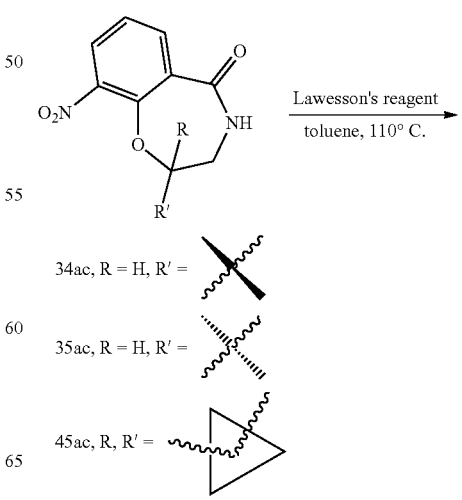

173
-continued

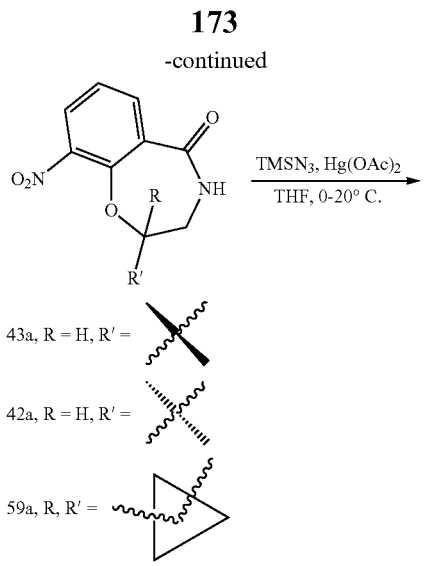

174
-continued

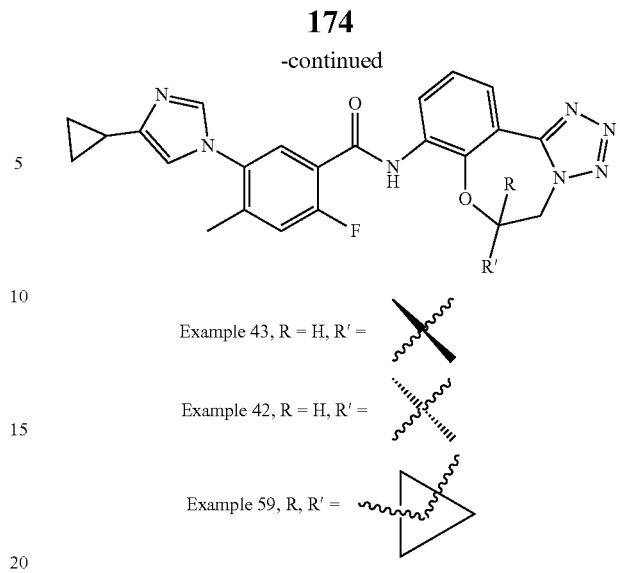

General Procedure

Synthesis of (a)

To a solution of ac (0.73 mmol) in toluene (2 mL) was added Lawesson's reagent (0.6 eq) at 25° C., then heated to 110° C. and stirred for 2 hours. TLC (Petroleum ether:Ethyl acetate=1:1) showed starting material was consumed and a main spot with lower polarity was detected. The reaction mixture was concentrated, then diluted with water and extracted with EtOAc. The organic phase was washed with brine, dried over $Na_2SO_4$, filtered and concentrated under reduced pressure to give a residue which was purified by prep-TLC ($SiO_2$, Petroleum ether:Ethyl acetate=1:1) to give compound a.

Synthesis of (b)

To a solution of a (0.52 mmol) in THF (2 mL) was added $Hg(OAc)_2$ (2 eq) and $TMSN_3$ (7 eq) at 0° C. Then the mixture was warmed to 25° C. and stirred for 2 hours. TLC (Petroleum ether:Ethyl acetate=3:1) showed starting material was consumed and a main spot with lower polarity was detected. LCMS showed a main peak with desired MS. The reaction mixture was concentrated in vacuo, and then diluted with water, extracted with EtOAc, the organic phase was collected and washed with brine, dried over $Na_2SO_4$, filtered and concentrated to give b (crude) that was used in the next step without further purification.

Synthesis of (c)

To a solution of b (0.46 mmol) in EtOH/$H_2O$ (10 mL/2 mL) was added Fe (5 eq) and $NH_4Cl$ (10 eq) at 25° C., then heated to 70° C. and the mixture was stirred for 2 hours. TLC (Petroleum ether:Ethyl acetate=1:1) showed starting material was consumed and a main spot was detected. The reaction mixture was filtered through a Celite pad and rinsed with EtOH, the filtrate was concentrated. The residue was diluted with DCM and filtered, the filtrate was concentrated and purified by prep-TLC ($SiO_2$, Dichloromethane:Methanol=10:1) to give c.

Synthesis of (S)-5-(4-cyclopropyl-1H-imidazol-1-yl)-2-fluoro-4-methyl-N-(6-methyl-5,6-dihydrobenzo[f]tetrazolo-[1,5-d][1,4]oxazepin-8-yl)benzamide (Example 42)

To a mixture of 5-(4-cyclopropyl-1H-imidazol-1-yl)-2-fluoro-4-methylbenzoic acid (1b) (35.94 mg, 138.10 umol, 1.2 eq) and HATU (65.64 mg, 172.63 umol, 1.5 eq) and NMM (46.56 mg, 460.35 umol, 50.61 uL, 4 eq) in DMF (5 mL) was added (6S)-6-methyl-5,6-dihydrotetrazolo[1,5-d][1,4]benzoxazepin-8-amine (42c) (25 mg, 115.09 umol, 1 eq) at 25° C. under $N_2$. The mixture was stirred at 25° C. for 16 hours. LCMS showed desired MS was detected. The reaction mixture was poured into water (5 mL) and was extracted with ethyl acetate (10 mL*2). The combined organic layers were washed with brine (10 mL), dried with anhydrous $Na_2SO_4$, filtered and concentrated in vacuo. The residue was purified by prep-TLC ($SiO_2$, DCM:MeOH=10:1) to give Example 42. MS mass calculated for $[M+1]^+$ ($C_{24}H_{22}FN_7O_2$) requires m/z 460.2, LCMS found m/z 460.2; $^1$H NMR (400 MHz, CHLOROFORM-d) δ 9.49 (br d, J=16.8 Hz, 1H), 8.78 (dd, J=1.5, 8.1 Hz, 1H), 8.32 (dd, J=1.6, 8.2 Hz, 1H), 8.12 (d, J=7.5 Hz, 1H), 7.46 (s, 1H), 7.31 (t, J=8.1 Hz, 1H), 7.21 (d, J=12.5 Hz, 1H), 6.81 (s, 1H), 5.03 (dd, J=1.2, 14.5 Hz, 1H), 4.72-4.64 (m, 1H), 4.57-4.49 (m, 1H), 2.30 (s, 3H), 1.97-1.88 (m, 1H), 1.79 (d, J=6.4 Hz, 3H), 0.94-0.89 (m, 2H), 0.86-0.81 (m, 2H).

Synthesis of (R)-5-(4-cyclopropyl-1H-imidazol-1-yl)-2-fluoro-4-methyl-N-(6-methyl-5,6-dihydrobenzo[f]tetrazolo[1,5-d][1,4]oxazepin-8-yl)benzamide (Example 43)

To a solution of 5-(4-cyclopropyl-1H-imidazol-1-yl)-2-fluoro-4-methylbenzoic acid (1b) (26.96 mg, 103.58 umol) in DMF (1 mL) was added HATU (52.51 mg, 138.10 umol) and NMM (34.92 mg, 345.26 umol, 37.96 uL) at 25° C. Then (R)-6-methyl-5,6-dihydrobenzo[f]tetrazolo[1,5-d][1,4]oxazepin-8-amine (43c) (0.015 g, 69.05 umol) was added and the mixture was stirred for 24 hours. The reaction mixture was concentrated in vacuo, then diluted with water (5 mL), extracted with EtOAc (10 mL*3). The combined organic layers were washed with brine (10 mL), dried over $Na_2SO_4$, filtered and concentrated. The residue was purified by prep-TLC ($SiO_2$, DCM:MeOH=10:1, product $R_f$=0.50) to afford Example 43. MS mass calculated for $[M+1]^+$ ($C_{24}H_{22}FN_7O_2$) requires m/z 460.2 LCMS found m/z 460.2; $^1$H NMR (400 MHz, CHLOROFORM-d) δ=9.48 (br d, J=16.6 Hz, 1H), 8.78 (dd, J=1.7, 8.1 Hz, 1H), 8.33 (dd, J=1.7, 8.1 Hz, 1H), 8.12 (d, J=7.3 Hz, 1H), 7.46 (s, 1H), 7.31 (t, J=8.1 Hz, 1H), 7.21 (d, J=12.7 Hz, 1H), 6.80 (s, 1H), 5.03 (dd, J=1.2, 14.4 Hz, 1H), 4.68 (dd, J=9.5, 14.4 Hz, 1H), 4.59-4.48 (m, 1H), 2.30 (s, 3H), 1.99-1.86 (m, 1H), 1.79 (d, J=6.4 Hz, 3H), 0.95-0.87 (m, 2H), 0.87-0.82 (m, 2H).

Synthesis of 5-(4-cyclopropyl-1H-imidazol-1-yl)-2-fluoro-4-methyl-N-(5H-spiro[benzo[f]tetrazolo[1,5-d][1,4]oxazepine-6,1'-cyclopropan]-8-yl)benzamide (Example 59)

To a solution of 5-(4-cyclopropyl-1H-imidazol-1-yl)-2-fluoro-4-methylbenzoic acid (1b) (13.80 mg, 53.01 umol) in DMF (2 mL) was added HATU (27.49 mg, 72.29 umol) and NMM (19.50 mg, 192.77 umol, 21.19 uL) at 25° C., then 5H-spiro[benzo[f]tetrazolo[1,5-d][1,4]oxazepine-6,1'-cyclopropan]-amine (59c) (11 mg, 48.19 umol) was added and the mixture was stirred for 18 hours. The reaction mixture was concentrated. The residue was purified by prep-HPLC (basic condition, column: Kromasil 150*25 mm*10 um; mobile phase: [water(0.04% $NH_3H_2O$+10 mM $NH_4HCO_3$)-ACN]; B %: 25%-45%, 10 min) and lyophilized to afford Example 59. MS mass calculated for $[M+1]^+$ ($C_{25}H_{22}FN_7O_2$) requires m/z 472.2, LCMS found m/z 472.1; $^1$H NMR (400 MHz, CHLOROFORM-d) δ=9.16 (br d, J=16.6 Hz, 1H), 8.74 (dd, J=1.5, 8.3 Hz, 1H), 8.40 (dd, J=1.5, 8.3 Hz, 1H), 8.09 (d, J=7.3 Hz, 1H), 7.45 (d, J=1.5 Hz, 1H), 7.32 (t, J=8.1 Hz, 1H), 7.20 (d, J=12.7 Hz, 1H), 6.80 (d, J=1.5 Hz, 1H), 4.92 (s, 2H), 2.30 (s, 3H), 1.98-1.85 (m, 1H), 1.33-1.25 (m, 2H), 1.10-1.01 (m, 2H), 0.94-0.87 (m, 2H), 0.87-0.80 (m, 2H).

(S)-2-methyl-9-nitro-3,4-dihydrobenzo[f][1,4]oxazepine-5(2H)-thione (42a)

MS mass calculated for $[M+1]^+$ ($C_{10}H_{10}N_2O_3S$) requires m/z 239.0, LCMS found m/z 239.2.

(R)-2-methyl-9-nitro-3,4-dihydrobenzo[f][1,4]oxazepine-5(2H)-thione (43a)

MS mass calculated for $[M+1]^+$ ($C_{10}H_{10}N_2O_3S$) requires m/z 239.0 LCMS found m/z 238.9; $^1$H NMR (400 MHz, CHLOROFORM-d) δ=8.83 (br s, 1H), 8.23 (dd, J=1.8, 7.9 Hz, 1H), 7.89 (dd, J=1.8, 7.9 Hz, 1H), 7.30 (t, J=7.9 Hz, 1H), 5.10-4.77 (m, 1H), 3.82-3.59 (m, 1H), 3.30 (ddd, J=3.7, 6.6, 15.1 Hz, 1H), 1.48 (d, J=6.6 Hz, 3H).

9-nitro-3H-spiro[benzo[f][1,4]oxazepine-2,1'-cyclopropane]-5(4H)-thione (59a)

MS mass calculated for $[M+1]^+$ ($C_{11}H_{10}N_2O_3S$) requires m/z 251.0, LCMS found m/z 251.0; $^1$H NMR (400 MHz, CHLOROFORM-d) δ=8.72 (br s, 1H), 8.28 (dd, J=2.0, 7.8 Hz, 1H), 7.86 (dd, J=1.7, 8.1 Hz, 1H), 7.32-7.28 (m, 1H), 3.58 (d, J=6.4 Hz, 2H), 1.42-1.31 (m, 2H), 0.76-0.69 (m, 2H).

(S)-6-methyl-8-nitro-5,6-dihydrobenzo[f]tetrazolo[1,5-d][1,4]oxazepine (42b)

MS mass calculated for $[M+1]^+$ ($C_{10}H_9N_5O_3$) requires m/z 248.1, LCMS found m/z 248.3.

(R)-6-methyl-8-nitro-5,6-dihydrobenzo[f]tetrazolo[1,5-d][1,4]oxazepine (43b)

MS mass calculated for $[M+1]^+$ ($C_{10}H_9N_5O_3$) requires m/z 248.1 LCMS found m/z 247.9; $^1$H NMR (400 MHz, CHLOROFORM-d) δ=8.85-8.74 (m, 1H), 7.89 (dd, J=1.7, 8.1 Hz, 1H), 7.37 (t, J=8.1 Hz, 1H), 5.00 (dd, J=1.5, 14.7 Hz, 1H), 4.72 (dd, J=9.5, 14.4 Hz, 1H), 4.63-4.53 (m, 1H), 1.71 (d, J=6.4 Hz, 3H).

8-nitro-5H-spiro[benzo[f]tetrazolo[1,5-d][1,4]oxazepine-6,1'-cyclopropane] (59b)

MS mass calculated for $[M+1]^+$ ($C_{11}H_9N_5O_3$) requires m/z 260.1, LCMS found m/z 260.0; $^1$H NMR (400 MHz, CHLOROFORM-d) δ=9.02-8.66 (m, 1H), 7.89-7.80 (m, 1H), 7.39 (dt, J=1.0, 8.1 Hz, 1H), 4.93 (s, 2H), 1.50-1.33 (m, 2H), 1.11-0.93 (m, 2H).

(S)-6-methyl-5,6-dihydrobenzo[f]tetrazolo[1,5-d][1,4]oxazepin-8-amine (42c)

MS mass calculated for $[M+1]^+$ ($C_{10}H_{11}N_5O_3$) requires m/z 218.1, LCMS found m/z 218.3; $^1$H NMR (400 MHz, CHLOROFORM-d) δ=7.89 (dd, J=1.3, 7.9 Hz, 1H), 7.02 (t, J=7.8 Hz, 1H), 6.89 (dd, J=1.4, 7.8 Hz, 1H), 4.93 (dd, J=1.1, 14.3 Hz, 1H), 4.64-4.55 (m, 1H), 4.47-4.38 (m, 1H), 4.00 (br s, 2H), 1.67 (d, J=6.4 Hz, 3H).

(R)-6-methyl-5,6-dihydrobenzo[f]tetrazolo[1,5-d][1,4]oxazepin-8-amine (43c)

MS mass calculated for [M+1]$^+$ (C$_{10}$H$_{11}$N$_5$O) requires m/z 218.1 LCMS found m/z 218.0; 1H NMR (400 MHz, CHLOROFORM-d) δ=7.95-7.85 (m, 1H), 7.04 (t, J=7.8 Hz, 1H), 6.94-6.85 (m, 1H), 4.94 (dd, J=1.5, 14.2 Hz, 1H), 4.61 (dd, J=9.3, 14.7 Hz, 1H), 4.51-4.37 (m, 1H), 4.01 (br s, 2H), 1.68 (d, J=6.4 Hz, 3H).

5H-spiro[benzo[f]tetrazolo[1,5-d][1,4]oxazepine-6,1'-cyclopropan]-8-amine (59c)

MS mass calculated for [M+1]$^+$ (C$_{11}$H$_{11}$N$_5$O) requires m/z 230.1, LCMS found m/z 230.0; $^1$H NMR (400 MHz, CHLOROFORM-d) δ=7.96 (dd, J=1.4, 8.0 Hz, 1H), 7.03 (t, J=7.9 Hz, 1H), 6.85 (dd, J=1.4, 7.8 Hz, 1H), 4.83 (s, 2H), 3.81 (br s, 2H), 1.22-1.15 (m, 2H), 0.98-0.92 (m, 2H).

Example S28

4-(4-cyclopropyl-1H-imidazol-1-yl)-N-(5,6-dihydrobenzo[f][1,2,4]triazolo[4,3-d][1,4]oxazepin-8-yl)-5-morpholinopicolinamide (Example 44) was synthesized according to the schemes provided below.

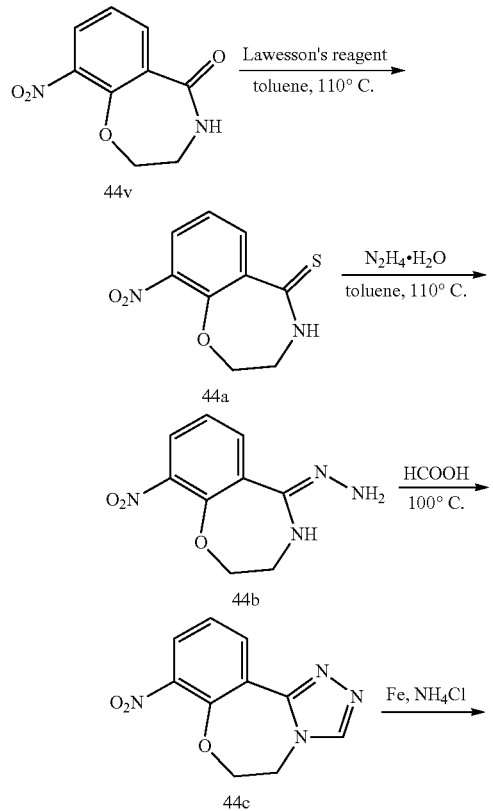

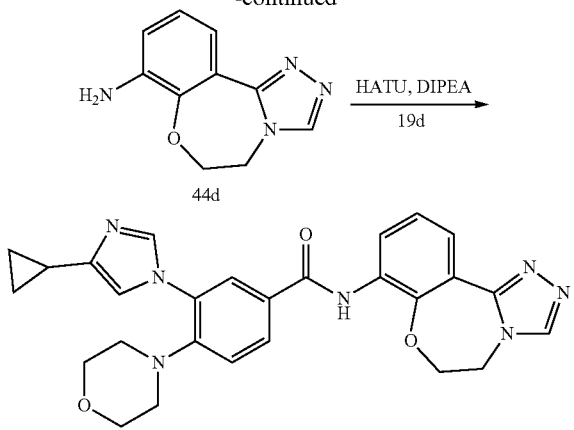

Example 44

9-nitro-3,4-dihydrobenzo[f][1,4]oxazepine-5(2H)-thione (44a)

To a solution of 9-nitro-3,4-dihydro-benzo[f][1,4]oxazepin-5(2H)-one (44v) (65 mg, 312.24 umol) in toluene (2 mL) was added Lawesson's reagent (88.40 mg, 218.57 umol). The mixture was stirred at 110° C. for 2h. TLC (Petroleum ether/Ethyl acetate=1:1, R$_f$=0.75) showed the reaction was completed. The mixture was concentrated in vacuo. The residue was purified by prep-TLC (Petroleum ether/Ethyl acetate=1:1, R$_f$=0.75) to give 44a. MS mass calculated for [M+1]$^+$ (C$_9$H$_8$N$_2$O$_3$S) requires m/z 225.2, LCMS found m/z 224.9.

(Z)-5-hydrazono-9-nitro-2,3,4,5-tetrahydrobenzo[f][1,4]oxazepine (44b)

To a solution of 9-nitro-3,4-dihydro-2H-1,4-benzoxazepine-5-thione (44a) (50 mg, 222.98 umol) in toluene (2 mL) was added N$_2$H$_4$.H$_2$O (111.62 mg, 2.23 mmol). The mixture was stirred at 100° C. for 12 h. LCMS show the reaction was completed. The mixture was concentrated in vacuo to give 44b (crude) without any purification. MS mass calculated for [M+1]$^+$ (C$_9$H$_{10}$N$_4$O$_3$) requires m/z 223.2, LCMS found m/z 223.0.

8-nitro-5,6-dihydrobenzo[f][1,2,4]triazolo[4,3-d][1,4]oxazepine (44c)

The solution of (Z)-5-hydrazono-9-nitro-2,3,4,5-tetrahydrobenzo[f][1,4]oxazepine (44b) (50 mg, 225.02 umol) in formic acid (2 mL) was stirred at 100° C. for 12 h. LCMS showed the reaction was completed. The mixture was concentrated in vacuo. The crude product was purified by prep-TLC (Dichloromethane:Methanol=10:1: Rt=0.8) to give 44c. MS mass calculated for [M+1](C$_{10}$H$_8$N$_4$O$_3$) requires m/z 233.2, LCMS found m/z 233.0.

5,6-dihydrobenzo[f][1,2,4]triazolo[4,3-d][1,4]oxazepin-8-amine (44d)

To a solution of 8-nitro-5,6-dihydrobenzo[f][1,2,4]triazolo[4,3-d][1,4]oxazepine (44c) (40 mg, 172.27 umol) in EtOH (2 mL) was added Fe (48.10 mg, 861.34 umol), NH$_4$Cl (92.15 mg, 1.72 mmol) and H$_2$O (0.5 mL). The mixture was stirred at 70° C. for 2 h. LCMS showed the reaction was completed. The residue was poured into water (1 mL) and the mixture was extracted with ethyl acetate (2 mL*3). The combined organic layers were washed with brine (1 mL*1), dried with anhydrous Na$_2$SO$_4$, filtered and concentrated in vacuo. The residue was purified by prep-TLC (Dichloromethane:Methanol=10:1, R$_f$=0.25) to give 44d. MS mass calculated for [M+1]$^+$ (C$_{10}$H$_{10}$N$_4$O) requires m/z 203.2, LCMS found m/z 203.0. $^1$H NMR (400 MHz, CHLOROFORM-d) δ ppm 8.22 (s, 1H) 8.00 (d, J=8.3 Hz, 1H) 6.97-7.04 (m, 1H) 6.80-6.85 (m, 1H) 4.53 (s, 2H) 4.48 (s, 2H).

Synthesis of 4-(4-cyclopropyl-1H-imidazol-1-yl)-N-(5,6-dihydrobenzo[f][1,2,4]triazolo[4,3-d][1,4]oxazepin-8-yl)-5-morpholinopicolinamide (Example 44)

To a solution of 19d (15.54 mg, 49.45 umol) in DMF (1 mL) was added DIEA (12.78 mg, 98.91 umol), HATU (22.56 mg, 59.34 umol) and 5,6-dihydrobenzo[f][1,2,4]triazolo[4,3-d][1,4]oxazepin-8-amine (44d) (10 mg, 49.45 umol). The mixture was stirred at 25° C. for 12 h. LCMS showed the reaction was completed. The residue was poured into water (2 mL). The mixture was extracted with ethyl acetate (1 mL*2). The combined organic layers were washed with brine (1 mL*1), dried with anhydrous Na$_2$SO$_4$, filtered and concentrated in vacuo. The crude product was purified by prep-TLC (Methanol:Dichloromethane=10:1, R$_f$=0.5) to give Example 44. MS mass calculated for [M+1] (C$_{26}$H$_{26}$N$_8$O$_3$) requires m/z 499.5, LCMS found m/z 499.2. $^1$H NMR (400 MHz, DMSO-d6) δ ppm 9.97 (s, 1H) 8.13 (s, 1H) 8.03 (d, J=9.2 Hz, 1H) 7.92 (d, J=7.8 Hz, 1H) 7.66 (d, J=7.6 Hz, 1H) 7.58 (dd, J=9.0, 2.8 Hz, 1H) 7.09 (t, J=8.4 Hz, 1H) 5.19 (s, 2H) 3.98-4.03 (m, 2H) 3.89 (s, 6H) 2.97 (d, J=6.2 Hz, 3H) 1.96 (s, 2H).

Example S29

5-(4-cyclopropyl-1H-imidazol-1-yl)-2-fluoro-4-methyl-N-(5H-spiro[benzo[f][1,2,4]triazolo[4,3-d][1,4]oxazepine-6,1'-cyclopropan]-8-yl)benzamide (Example 45) was synthesized according to the schemes provided below.

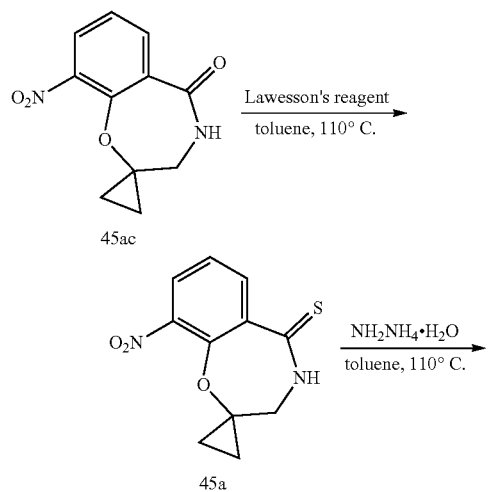

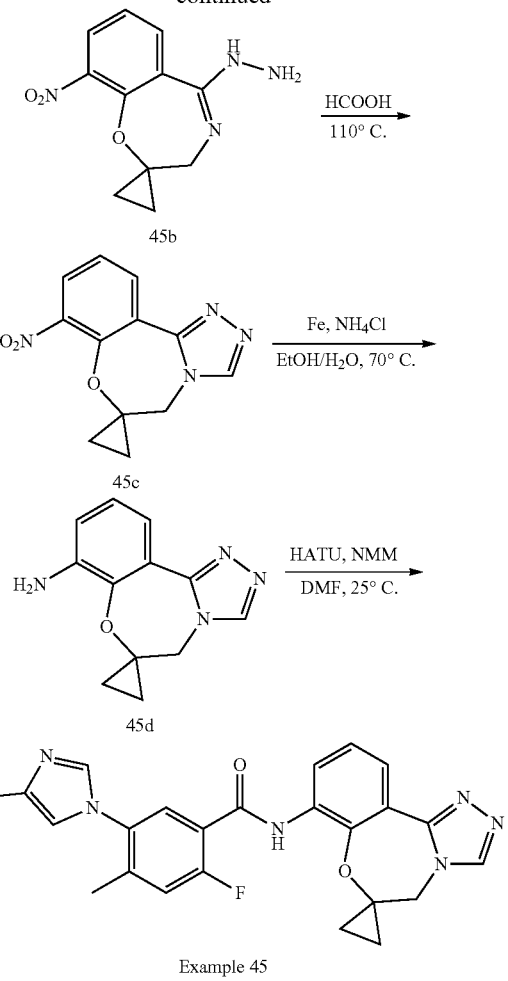

Example 45

9-nitro-3H-spiro[benzo[f][1,4]oxazepine-2,1'-cyclopropane]-5(4H)-thione (45a)

To a solution of 9-nitro-3H-spiro[benzo[f][1,4]oxazepine-2,1'-cyclopropan]-5(4H)-one (45ac) (130 mg, 555.06 umol) in toluene (6 mL) was added Lawesson's reagent (157.15 mg, 388.54 umol) at 25° C. under N$_2$. The mixture was heated to 110° C. and stirred for 20 hours. TLC (petroleum ether:ethyl acetate=1:1) showed starting material was consumed and a main spot with lower polarity (R$_f$=0.56) was detected. The reaction mixture was concentrated in vacuo, then diluted with water (5 mL) and extracted with DCM (10 mL). The organic phase was washed with brine (5 mL), dried over anhydrous Na$_2$SO$_4$, filtered and concentrated. The residue was purified by prep-TLC (SiO$_2$, Petroleum ether:Ethyl acetate=1:1, R$_f$=0.56) to afford 45a. MS mass calculated for [M+1]$^+$ (C$_{11}$H$_{10}$N$_2$O$_3$S) requires m/z 251.0 LCMS found m/z 251.1; $^1$H NMR (400 MHz, CHLOROFORM-d) δ=8.69 (br s, 1H), 8.28 (dd, J=1.7, 7.8 Hz, 1H), 7.86 (dd, J=1.7, 8.0 Hz, 1H), 7.30 (t, J=7.9 Hz, 1H), 3.58 (d, J=6.4 Hz, 2H), 1.41-1.31 (m, 2H), 0.80-0.65 (m, 2H).

5-hydrazinyl-9-nitro-3H-spiro[benzo[f][1,4]oxazepine-2,1'-cyclopropane] (45b)

To a solution of 9-nitro-3H-spiro[benzo[f][1,4]oxazepine-2,1'-cyclopropane]-5(4H)-thione (45a) (83 mg, 331.64 umol) in toluene (5 mL) was added NH$_2$NH$_2$H$_2$O (332.04 mg, 6.63 mmol) at 25° C. The mixture was heated to 110° C. and stirred for 2 hours. TLC (petroleum ether:ethyl acetate=1:1) showed starting material was consumed and one main spot (R$_f$=0.02) was detected. The reaction mixture was concentrated to give 45b (crude), which was used in the next step without further purification. MS mass calculated for [M+1]$^+$ (C$_{11}$H$_{12}$N$_4$O$_3$) requires m/z 249.1 LCMS found m/z 248.9.

8-nitro-5H-spiro [benzo[f][1,2,4]triazolo[4,3-d][1,4] oxazepine-6,1'-cyclopropane](45c)

A solution of 5-hydrazinyl-9-nitro-3H-spiro[benzo[f][1,4]oxazepine-2,1'-cyclopropane](45b) (82 mg, 330.33 umol) in HCOOH (2 mL) was heated to 110° C. and stirred for 18 hours. TLC (dichloromethane:methanol=10:1) showed two main spots formed. The reaction mixture was dried in vacuo. The residue was purified by prep-TLC (SiO$_2$, DCM:MeOH=10:1, product R$_f$=0.68) to afford 45c. MS mass calculated for [M+1]$^+$ (C$_{12}$H$_{10}$N$_4$O$_3$) requires m/z 259.1, LCMS found m/z 259.0; $^1$H NMR (400 MHz, CHLOROFORM-d) δ=8.94 (dd, J=1.5, 8.2 Hz, 1H), 8.26 (s, 1H), 7.73 (dd, J=1.8, 7.9 Hz, 1H), 7.31 (t, J=8.0 Hz, 1H), 4.51 (s, 2H), 1.44-1.31 (m, 2H), 1.03-0.88 (m, 2H).

5H-spiro[benzo[f][1,2,4]triazolo[4,3-d][1,4] oxazepine-6,1'-cyclopropan]-8-amine (45d)

To a solution of 8-nitro-5H-spiro[benzo[f][1,2,4]triazolo[4,3-d][1,4]oxazepine-6,1'-cyclopropane] (45c) (26 mg, 100.68 umol) in EtOH (5 mL) and H$_2$O (1 mL) was added Fe (28.11 mg, 503.42 umol) and NH$_4$Cl (53.86 mg, 1.01 mmol) at 25° C., then the mixture was heated to 70° C. and stirred for 3 hours. TLC (dichloromethane:methanol=10:1) showed the starting material was consumed and a main spot was detected. The reaction mixture was filtered with Celite pad, the Celite pad was rinsed with EtOH (10 mL) and EtOAc (10 mL) and the filtrate was concentrated. The residue was purified by prep-TLC (SiO$_2$, DCM:MeOH=10:1, product R$_f$=0.51) to afford 45d. $^1$H NMR (400 MHz, CHLOROFORM-d) δ=8.18 (s, 1H), 8.04 (dd, J=1.5, 7.9 Hz, 1H), 6.99 (t, J=7.9 Hz, 1H), 6.78 (dd, J=1.5, 7.7 Hz, 1H), 4.44 (s, 2H), 1.23-1.14 (m, 2H), 0.94-0.88 (m, 2H).

Synthesis of 5-(4-cyclopropyl-1H-imidazol-1-yl)-2-fluoro-4-methyl-N-(5H-spiro[benzo[f][1,2,4]triazolo [4,3-d][1,4]oxazepine-6,1'-cyclopropan]-8-yl)benzamide (Example 45)

To a solution of 5-(4-cyclopropyl-1H-imidazol-1-yl)-2-fluoro-4-methylbenzoic acid (1b) (13.80 mg, 53.01 umol) in DMF (2 mL) was added HATU (27.49 mg, 72.29 umol) and NMM (19.50 mg, 192.77 umol, 21.19 uL) at 25° C., then 5H-spiro[benzo[f][1,2,4]triazolo[4,3-d][1,4]oxazepine-6,1'-cyclopropan]-8-amine (45d) (11 mg, 48.19 umol) was added and the mixture was stirred for 18 hours. The reaction mixture was concentrated. The residue was purified by prep-HPLC (basic condition, column: Kromasil 150*25 mm*10 um; mobile phase: [water (0.04% NH$_3$H$_2$O+10 mM NH$_4$HCO$_3$)-ACN]; B %: 25%-45%, 10 min) and lyophilized to afford Example 45. MS mass calculated for [M+1]$^+$ (C$_{26}$H$_{23}$FN$_6$O$_2$) requires m/z 471.2, LCMS found m/z 471.2; $^1$H NMR (400 MHz, CHLOROFORM-d) δ=9.17 (br d, J=17.0 Hz, 1H), 8.63 (d, J=7.9 Hz, 1H), 8.47 (dd, J=1.5, 8.2 Hz, 1H), 8.21 (s, 1H), 8.09 (d, J=7.5 Hz, 1H), 7.45 (s, 1H), 7.26-7.15 (m, 2H), 6.85-6.75 (m, 1H), 4.51 (s, 2H), 2.29 (s, 3H), 1.97-1.88 (m, 1H), 1.29-1.23 (m, 2H), 1.03-0.95 (m, 2H), 0.95-0.88 (m, 2H), 0.87-0.80 (m, 2H).

Example S30

5-(4-cyclopropyl-1H-imidazol-1-yl)-2-fluoro-N—((S)-5-((S)-1-hydroxyethyl)-5,6-dihydrobenzo[f]tetrazolo[1,5-d][1,4]oxazepin-8-yl)-4-methylbenzamide (Example 48) and 5-(4-cyclopropyl-1H-imidazol-1-yl)-2-fluoro-N—((S)-5-((R)-1-hydroxyethyl)-5,6-dihydrobenzo[f]tetrazolo[1,5-d][1,4]oxazepin-8-yl)-4-methylbenzamide (Example 53) were synthesized according to the schemes provided below.

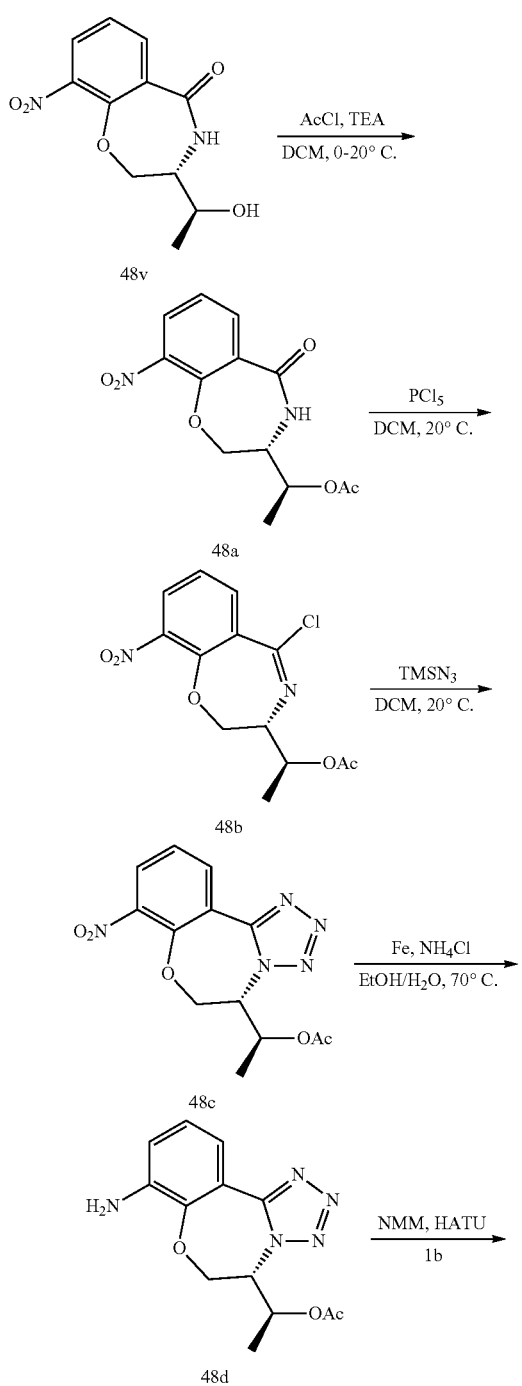

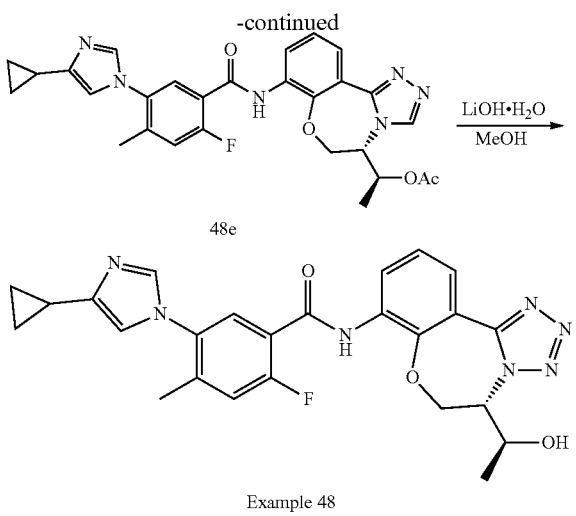

Example 48

(S)-1-((S)-9-nitro-5-oxo-2,3,4,5-tetrahydrobenzo[f][1,4]oxazepin-3-yl)ethyl acetate (48a)

To a solution of (S)-3-((S)-1-hydroxyethyl)-9-nitro-3,4-dihydrobenzo[f][1,4]oxazepin-5(2H)-one (48v) (187 mg, 741.41 umol) and TEA (375.12 mg, 3.71 mmol) in DCM (5 mL) at 0° C. was added acetyl chloride (215.34 mg, 2.74 mmol) dropwised under $N_2$. The mixture was stirred at 20° C. for 12 hr. TLC indicated one major new spot. The mixture was poured into water (10 mL), extracted with DCM (20 mL*3). The combined organic layers were washed with brine (10 mL), dried over $Na_2SO_4$, and filtered, the filtrate was concentrated. The residue was purified by prep-TLC to give 48a. MS mass calculated for $[M+1]^+$ ($C_{13}H_{14}N_2O_6$) requires m/z 295.1, LCMS found m/z 295.1.

(S)-1-((S)-5-chloro-9-nitro-2,3-dihydrobenzo[f][1,4]oxazepin-3-yl)ethyl acetate (48b)

To a solution of (S)-1-((S)-9-nitro-5-oxo-2,3,4,5-tetrahydrobenzo[f][1,4]oxazepin-3-yl)ethyl acetate (48a) (50 mg, 169.92 umol) in DCM (2 mL) was added $PCl_5$ (42.46 mg, 203.90 umol) at 20° C. The mixture was stirred at 20° C. for 2 hr. TLC (quenched by methanol, PE:EA=1:1) indicated one major new spot. The reaction mixture of 48b was used directly in the next step.

(S)-1-((S)-8-nitro-5,6-dihydrobenzo[f]tetrazolo[1,5-d][1,4]oxazepin-5-yl)ethyl acetate (48c)

To a solution of (S)-1-((S)-5-chloro-9-nitro-2,3-dihydrobenzo[f][1,4]oxazepin-3-yl)ethyl acetate (48b) in DCM (2 mL) was added $TMSN_3$ (78.11 mg, 677.95 umol, 89.16 uL) at 20° C. The mixture was stirred at 20° C. for 12 hr. LCMS showed one main peak with desired MS. The mixture was poured into $NaHCO_3$ (5 mL), and then water (10 mL) was added to the mixture. The mixture was extracted with dichloromethane (20 mL*3). The combined organic layers were washed with brine (10 mL), dried over $Na_2SO_4$, and filtered, the filtrate was concentrated. The residue was purified by prep-TLC to give 48c. $^1$H NMR (400 MHz, CHLOROFORM-d) δ=8.91 (dd, J=1.7, 8.2 Hz, 1H), 7.89 (dd, J=1.7, 7.9 Hz, 1H), 7.38 (t, J=8.1 Hz, 1H), 5.48 (quin, J=6.6 Hz, 1H), 5.10 (dd, J=2.9, 6.5 Hz, 1H), 5.07-5.01 (m, 1H), 4.33 (dd, J=1.2, 13.6 Hz, 1H), 1.93 (s, 3H), 1.49 (d, J=6.5 Hz, 3H).

(S)-1-((S)-8-amino-5,6-dihydrobenzo[f]tetrazolo[1,5-d][1,4]oxazepin-5-yl)ethyl acetate (48d)

A mixture of (S)-1-((S)-8-nitro-5,6-dihydrobenzo[f]tetrazolo[1,5-d][1,4]oxazepin-5-yl)ethyl acetate (48c) (30 mg, 93.96 umol), Fe (26.24 mg, 469.82 umol) and $NH_4Cl$ (50.26 mg, 939.64 umol) in EtOH (5 mL) and $H_2O$ (1 mL) was heated to 70° C. for 3h. LCMS showed one main peak with desired MS. The suspension was filtered through a Celite Pad, the Celite pad was rinsed with EtOH (10 mL), and the filtrate was concentrated. The residue was diluted with ethlyacetate (40 mL) and washed with water (10 mL*2). The organic layer was washed with brine (10 mL), dried over $Na_2SO_4$, and filtered, and the filtrate was concentrated. The residue was purified by prep-TLC to give 48d. $^1$H NMR (400 MHz, CHLOROFORM-d) δ=8.91 (dd, J=1.7, 8.2 Hz, 1H), 7.89 (dd, J=1.7, 7.9 Hz, 1H), 7.38 (t, J=8.1 Hz, 1H), 5.48 (quin, J=6.6 Hz, 1H), 5.10 (dd, J=2.9, 6.5 Hz, 1H), 5.07-5.01 (m, 1H), 4.33 (dd, J=1.2, 13.6 Hz, 1H), 1.93 (s, 3H), 1.49 (d, J=6.5 Hz, 3H).

(S)-1-((S)-8-(5-(4-cyclopropyl-1H-imidazol-1-yl)-2-fluoro-4-methylbenzamido)-5,6dihydrobenz-o[f]tetrazolo[1,5-d][1,4]oxazepin-5-yl)ethyl acetate (48e)

To a solution of 1b (14.84 mg, 57.04 umol) in DMF (0.5 mL) was added NMM (15.73 mg, 155.55 umol, 17.10 uL) and HATU (29.57 mg, 77.78 umol), followed by addition (S)-1-((S)-8-amino-5,6-dihydrobenzo[f]tetrazolo[1,5-d][1,4]oxazepin-5-yl)ethyl acetate (48d) (15 mg, 51.85 umol). The mixture was stirred at 40° C. for 2 hr. TLC indicated one major new spot. The mixture was poured into water (5 mL), extracted with ethlyacetate (10 mL*3). The combined organic layers were washed with brine (5 mL), dried over $Na_2SO_4$, and filtered, the filtrate was concentrated. The residue was purified by prep-TLC to give 48e (crude).

Synthesis of 5-(4-cyclopropyl-1H-imidazol-1-yl)-2-fluoro-N—((S)-5-((S)-1-hydroxyethyl)-5,6-dihydrobenzo-[f]tetrazolo[1,5-d][1,4]oxazepin-8-yl)-4-methylbenzamide (Example 48)

To a solution of (S)-1-((S)-8-(5-(4-cyclopropyl-1H-imidazol-1-yl)-2-fluoro-4-methylbenzamido)-5,6dihydrobenzo[f]tet-razolo[1,5-d][1,4]oxazepin-5-yl)ethyl acetate (48e) (40 mg, 75.25 umol) in MeOH (20 mL) and $H_2O$ (1 mL) was added $LiOH.H_2O$ (6.32 mg, 150.51 umol) at 20° C. under $N_2$. The mixture was stirred at 20° C. for 2 hr. TLC indicated the starting material was consumed and one new spot formed. The mixture was concentrated under reduced pressure. The residue was purified by prep-TLC to give Example 48. MS mass calculated for $[M+1]^+$ ($C_{25}H_{24}FN_7O_3$) requires m/z 490.2, LCMS found m/z 490.2; $^1$H NMR (400 MHz, CHLOROFORM-d) δ=9.28 (br d, J=15.9 Hz, 1H), 8.62 (br d, J=7.9 Hz, 1H), 8.33 (br d, J=7.9 Hz, 1H), 8.01 (br d, J=7.3 Hz, 1H), 7.40 (br s, 1H), 7.24 (br t, J=7.9 Hz, 1H), 7.13 (br d, J=12.6 Hz, 1H), 6.73 (s, 1H), 4.97 (br d, J=13.7 Hz, 1H), 4.89 (br s, 1H), 4.43-4.28 (m, 2H), 2.23 (s, 3H), 1.84 (br s, 1H), 1.41 (br d, J=6.0 Hz, 3H), 0.84 (br d, J=6.6 Hz, 2H), 0.77 (br s, 2H).

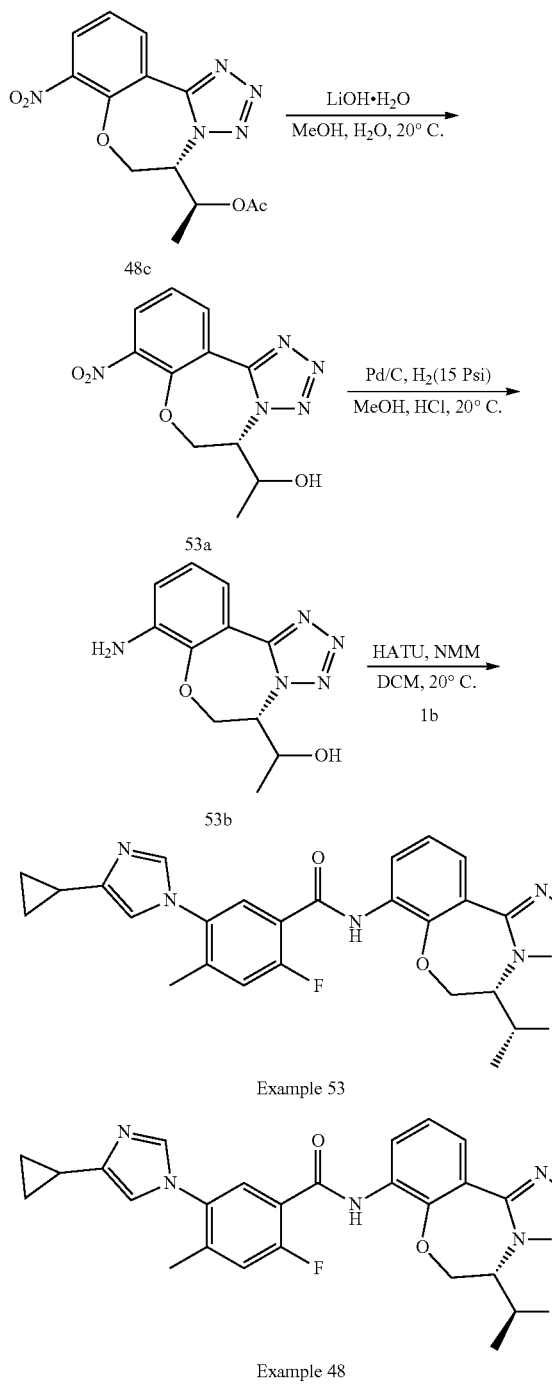

trated to give 53a. ¹H NMR (400 MHz, CHLOROFORM-d) δ=8.84-8.56 (m, 1H), 7.83 (br d, J=7.7 Hz, 1H), 7.39-7.19 (m, 1H), 5.06-4.80 (m, 2H), 4.66-4.23 (m, 1H), 4.03 (br d, J=12.1 Hz, 1H), 3.00-1.92 (m, 2H), 1.68-1.16 (m, 3H).

1-((S)-8-amino-5,6-dihydrobenzo[f]tetrazolo[1,5-d][1,4]oxazepin-5-yl)ethanol (53b)

To a solution of 1-((S)-8-nitro-5,6-dihydrobenzo[f]tetrazolo[1,5-d][1,4]oxazepin-5-yl)ethanol (53a) (20.00 mg, 72.14 umol, 1 eq) in MeOH (2 mL) and HCl (0.05 mL) was added Pd/c (10 mg, 72.14 umol, 10% purity) at 20° C. under H₂. The mixture was stirred at 20° C. for 1 hr. LCMS showed the reaction mixture was completed. The suspension was filtered through a Celite Pad, the Celite pad was rinsed with ethyl acetate (10 mL), and the filtrate was concentrated. The residue was diluted with ethyl acetate (20 mL) and washed with water (10 mL). The organic layer was washed with brine (10 mL), dried over Na₂SO₄, and filtered, the filtrate was concentrated. The residue was purified by prep-TLC (SiO₂, DCM:MeOH=10:1) to give 53b. MS mass calculated for [M+1]⁺ (C₁₁H₁₃N₅O₂) requires m/z 248.1, LCMS found m/z 248.1.

Synthesis of 5-(4-cyclopropyl-1H-imidazol-1-yl)-2-fluoro-N—((S)-5-((R)-1-hydroxyethyl)-5,6-dihydrobenzo[f]tetrazolo[1,5-d][1,4]oxazepin-8-yl)-4-methylbenzamide (Example 53)

To a solution of 1b (15.52 mg, 59.62 umol) in DMF (2 mL) was added in NMM (16.45 mg, 162.59 umol, 17.88 uL) and HATU (30.91 mg, 81.29 umol) at 20° C. under N₂. After stirring for 5 min, and 53b (13.40 mg, 54.20 umol) was added at 20° C. under N₂. The mixture was stirred at 20° C. for 2 hr. LCMS showed the reaction was completed. The mixture was poured into water (5 mL), extracted with ethlyacetate (10 mL*3). The combined organic layers were washed with brine (5 mL), dried over Na₂SO₄, and filtered, the filtrate was concentrated. The residue was purified by prep-HPLC to give Example 53 and Example 48. Example 53: MS mass calculated for [M+1]⁺ (C₂₅H₂₄FN₇O₃) requires m/z 490.3, LCMS found m/z 490.3; ¹H NMR (400 MHz, CHLOROFORM-d) δ=9.41 (br d, J=15.3 Hz, 1H), 8.76-8.67 (m, 2H), 8.30-8.23 (m, 1H), 8.17 (d, J=7.2 Hz, 1H), 7.33-7.29 (m, 2H), 6.91 (s, 1H), 4.92-4.80 (m, 2H), 4.71-4.45 (m, 1H), 4.23-4.09 (m, 1H), 2.34 (s, 3H), 2.12-2.03 (m, 1H), 1.66 (d, J=6.0 Hz, 3H), 1.20-1.14 (m, 2H), 1.00-0.93 (m, 2H).

Example S31

(R)-4-(4-cyclopropyl-1H-imidazol-1-yl)-N-(6-methyl-5,6-dihydrobenzo[f]tetrazolo[1,5-d][1,4]oxazepin-8-yl)picolinamide (Example 49) was synthesized according to the scheme provided below.

1-((S)-8-nitro-5,6-dihydrobenzo[f]tetrazolo[1,5-d][1,4]oxazepin-5-yl)ethanol (53a)

To a solution of (S)-1-((S)-8-nitro-5,6-dihydrobenzo[f]tetrazolo[1,5-d][1,4]oxazepin-5-yl)ethyl acetate (48c) (30 mg, 93.96 umol) in MeOH (5 mL) and H₂O (1 mL) was added LiOH.H₂O (7 mg, 166.80 umol) at 20° C. under N₂. The mixture was stirred at 20° C. for 2 hr. LCMS showed two peaks with desired MS. The mixture was concentrated under reduced pressure at 30° C. and was extracted with ethyl acetate (10 mL*3). The combined organic layers were dried over sodium sulfate, filtered, the filtrate was concen-

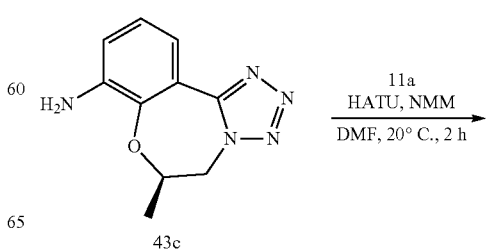

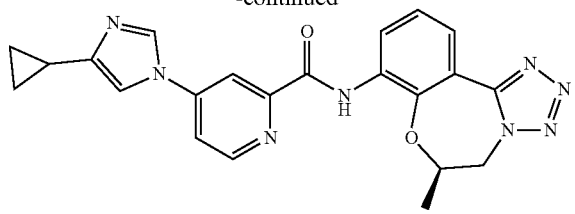

Example 49

Synthesis of (R)-4-(4-cyclopropyl-1H-imidazol-1-yl)-N-(6-methyl-5,6-dihydrobenzo[f]tetrazolo[1,5-d][1,4]oxazepin-8-yl)picolinamide (Example 49)

To a mixture of 11a (31.66 mg, 138.10 umol) in DMF (1 mL) was added NMM (37.25 mg, 368.28 umol), HATU (70.02 mg, 184.14 umol) and (R)-6-methyl-5,6-dihydrobenzo[f]tetrazolo[1,5-d][1,4]oxazepin-8-amine (43c) (20 mg, 92.07 umol) at 25° C. under $N_2$. The mixture was stirred at 25° C. for 1 h. LCMS showed the reaction was completed. The residue was poured into water (5 mL) and the mixture was extracted with DCM (2 mL*2). The combined organic layers were washed with brine (2 mL*2), dried with anhydrous $Na_2SO_4$, filtered and concentrated in vacuo. The residue was purified by prep-TLC (Petroleum ether/Ethyl acetate=3/1, $R_f$=0.5) to give Example 49. MS mass calculated for [M+H]$^+$ ($C_{22}H_{20}N_8O_2$) requires m/z 428.2, LCMS found m/z 429.2. $^1$H NMR (400 MHz, DMSO-d6) δ ppm 10.90 (s, 1H) 8.80 (d, J=5.73 Hz, 1H) 8.63 (d, J=8.16 Hz, 1H) 8.58 (s, 1H) 8.41 (s, 1H) 8.15 (d, J=8.38 Hz, 1H) 8.01 (d, J=5.73 Hz, 1H) 7.89 (s, 1H) 7.33-7.39 (m, 1H) 5.15 (d, J=13.89 Hz, 1H) 4.82 (dd, J=14.22, 9.15 Hz, 1H) 4.66-4.75 (m, 1H) 1.87 (s, 1H) 1.69 (d, J=6.17 Hz, 1H) 1.62-1.73 (m, 1H) 0.84 (d, J=7.72 Hz, 2H) 0.73 (d, J=2.87 Hz, 2H).

Example S32

4-(4-cyclopropyl-1H-imidazol-1-yl)-N-(5,6-dihydrobenzo[f]tetrazolo[1,5-d][1,4]oxazepin-8-yl)picolinamide (Example 50) was synthesized according to the scheme provided below.

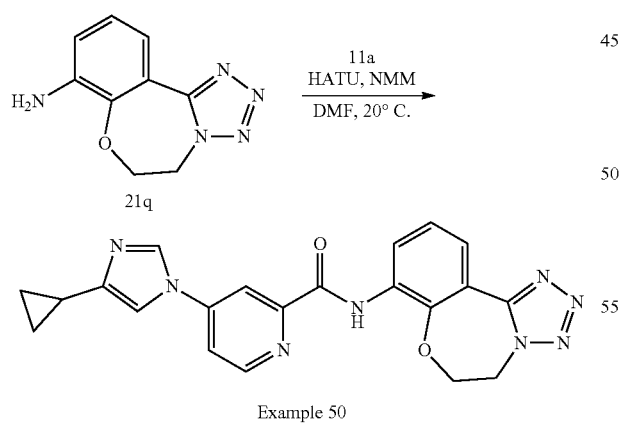

Example 50

Synthesis of 4-(4-cyclopropyl-1H-imidazol-1-yl)-N-(5,6-dihydrobenzo[f]tetrazolo[1,5-d][1,4]oxazepin-8-yl)picolinamide (Example 50)

To a solution of 4-(4-cyclopropyl-1H-imidazol-1-yl)picolinic acid (11a) (33.84 mg, 147.64 umol) in DMF (2 mL) was added NMM (39.82 mg, 393.70 umol) and stirred for 5 min. Then HATU (74.85 mg, 196.85 umol) and 5,6-dihydrobenzo[f]tetrazolo[1,5-d][1,4]oxazepin-8-amine (21q) (20 mg, 98.43 umol) were added at 20° C. under $N_2$. The mixture was stirred at 20° C. for 12 hr. The mixture was poured into water (5 mL), extracted with ethylacetate (10 mL*3). The combined organic layers were washed with brine (5 mL), dried over $Na_2SO_4$, and filtered, the filtrate was concentrated. The residue was purified by prep-HPLC (TFA condition column: Nano-micro Kromasil C 18 100*30 mm 5 um; mobile phase: [water (0.1% TFA)-ACN]; B %: 20%-40%, 10 min) to give Example 50. MS mass calculated for [M+1]$^+$ ($C_{21}H_{18}N_8O_2$) requires m/z 415.1, LCMS found m/z 415.1. $^1$H NMR (400 MHz, DMSO-d6) δ=10.74 (s, 1H), 9.18 (br s, 1H), 8.90 (d, J=5.4 Hz, 1H), 8.62 (d, J=6.8 Hz, 1H), 8.51 (d, J=2.0 Hz, 1H), 8.23 (dd, J=1.2, 8.1 Hz, 1H), 8.09 (td, J=3.0, 5.7 Hz, 2H), 7.36 (t, J=8.1 Hz, 1H), 5.05-4.99 (m, 2H), 4.81-4.76 (m, 2H), 1.97-1.89 (m, 1H), 0.98-0.90 (m, 2H), 0.84-0.76 (m, 2H).

Example S33

5-(4-cyclopropyl-1H-imidazol-1-yl)-2-fluoro-4-methyl-N-(1-methyl-5,6-dihydrobenzo[f]imidazo[1,5-d][1,4]oxazepin-8-yl)benzamide (Example 51) was synthesized according to the schemes provided below.

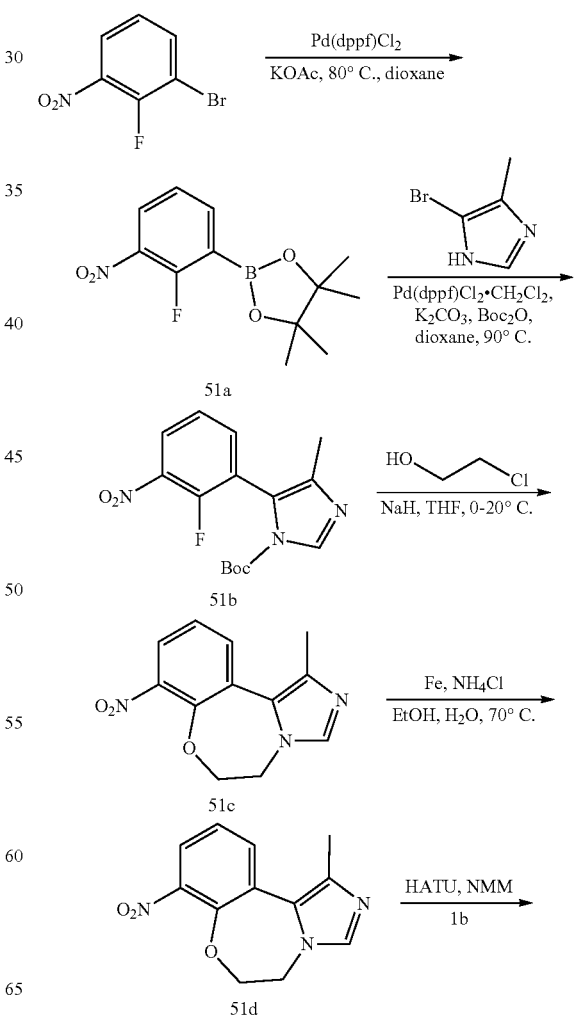

-continued

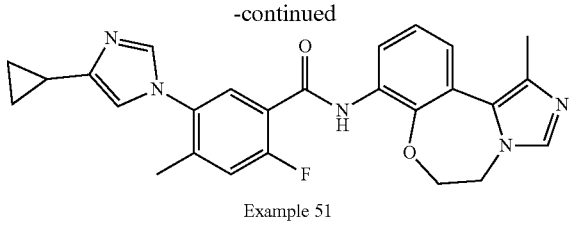

Example 51

2-(2-fluoro-3-nitrophenyl)-4,4,5,5-tetramethyl-1,3,2-dioxaborolane (51a)

To a mixture of 1-bromo-2-fluoro-3-nitrobenzene (1.36 mmol) in dioxane (10 mL) was added 4,4,5,5-tetramethyl-2-(4,4,5,5-tetramethyl-1,3,2-dioxaborolan-2-yl)-1,3,2-dioxaborolane (1.5 eq) and KOAc (2 eq), then Pd(dppf)Cl$_2$ (0.1 eq) under N$_2$. The mixture was stirred at 80° C. for 16 hours. The residue was poured into ice-water (10 mL) and the mixture was extracted with ethyl acetate (10 mL*2). The combined organic layers were washed with brine (10 mL), dried with anhydrous Na$_2$SO$_4$, filtered and concentrated in vacuo. The residue was purified by column chromatography (SiO$_2$, Petroleum ether/Ethyl acetate=15:1 to 10:1) to give 2-(2-fluoro-3-nitrophenyl)-4,4,5,5-tetramethyl-1,3,2-dioxaborolane (51a); $^1$H NMR (400 MHz, DMSO) δ 13.47 (br s, 1H), 8.03-6.96 (m, 4H), 2.20 (s, 3H), 1.94-1.77 (m, 1H), 0.80 (br s, 2H), 0.70 (br s, 2H).

Tert-butyl 5-(2-fluoro-3-nitrophenyl)-4-methyl-1H-imidazole-1-carboxylate (51b)

To a mixture of 5-bromo-4-methyl-1H-imidazole (200 mg, 1.24 mmol), 2-(2-fluoro-3-nitrophenyl)-4,4,5,5-tetramethyl-1,3,2-dioxaborolane (663.51 mg, 2.48 mmol) (51a) and Boc$_2$O (1.08 g, 4.97 mmol, 1.14 mL) in 1,4-dioxane (10 mL) was added Pd(dppf)Cl$_2$—CH$_2$Cl$_2$ (101.45 mg, 124.22 umol) and K$_2$CO$_3$ (343.37 mg, 2.48 mmol) at 25° C. under N$_2$. The mixture was stirred at 110° C. for 12 hours. The reaction mixture was filtered and the filtrate was concentrated in vacuo. The residue was diluted with H$_2$O (10 mL) and extracted with ethyl acetate (10 mL). The organic layer was washed with brine (8 mL*2), dried with anhydrous Na$_2$SO$_4$, filtered and concentrated under reduced pressure. The crude product was purified by prep-TLC (SiO$_2$, DCM:MeOH=10:1) to give tert-butyl 5-(2-fluoro-3-nitrophenyl)-4-methyl-1H-imidazole-1-carboxylate (51b). $^1$H NMR (400 MHz, CHLOROFORM-d) δ=8.21-8.13 (m, 1H), 8.06-7.98 (m, 1H), 7.89-7.81 (m, 1H), 7.40-7.29 (m, 3H), 2.51-2.41 (m, 3H), 1.66 (s, 9H).

Methyl-8-nitro-5,6-dihydrobenzo[f]imidazo[1,5-d][1,4]oxazepine (51c)

To a mixture of tert-butyl 5-(2-fluoro-3-nitrophenyl)-4-methyl-1H-imidazole-1-carboxylate (51b) (30 mg, 93.37 umol) and 2-chloroethanol (15.04 mg, 186.74 umol, 12.53 uL) in THF (2 mL) was added NaH (9.34 mg, 233.42 umol, 60% purity) at 0° C. under N$_2$. The mixture was stirred at 25° C. for 12 hours. LC-MS showed one main peak with desired mass. The reaction mixture was quenched by saturated NH$_4$Cl (10 mL) at 0° C. and poured into water (10 mL). Then the mixture was extracted with ethyl acetate (10 mL*2), the combined organic layers were washed with brine (10 mL), dried with anhydrous Na$_2$SO$_4$, filtered and concentrated in vacuo. The crude product was purified by prep-TLC (SiO$_2$, dichloromethane:methanol=10:1) to give 1-methyl-8-nitro-5,6-dihydrobenzo[f]imidazo[1,5-d][1,4]oxazepine (51c). MS mass calculated for [M+1]$^+$ (C$_{12}$H$_{11}$N$_3$O$_3$) requires m/z 246.1, LCMS found m/z 246.0. $^1$H NMR (400 MHz, CHLOROFORM-d) δ=7.81-7.76 (m, 1H), 7.75-7.69 (m, 1H), 7.63-7.59 (m, 1H), 7.37-7.31 (m, 1H), 4.75-4.71 (m, 2H), 4.24 (t, J=5.7 Hz, 2H), 2.41 (s, 3H).

Methyl-5,6-dihydrobenzo[f]imidazo[1,5-d][1,4]oxazepin-8-amine (51d)

To a mixture of 1-methyl-8-nitro-5,6-dihydrobenzo[f]imidazo[1,5-d][1,4]oxazepine (51c) (25 mg, 101.94 umol) in EtOH (5 mL) and H$_2$O (1 mL) was added Fe (28.47 mg, 509.72 umol) and NH$_4$Cl (54.53 mg, 1.02 mmol). The mixture was stirred at 70° C. for 2 hours. The reaction mixture was filtered and the filtrate was concentrated in vacuo. The crude product was purified by prep-TLC (SiO$_2$, DCM:MeOH=10:1) to give 1-Methyl-5,6-dihydrobenzo[f]imidazo[1,5-d][1,4]oxazepin-8-amine (51d); $^1$H NMR (400 MHz, CHLOROFORM-d) δ ppm 7.57-7.52 (m, 1H), 7.03-6.98 (m, 1H), 6.80-6.74 (m, 2H), 4.53-4.48 (m, 2H), 4.15-4.10 (m, 2H), 2.40-2.38 (m, 3H).

Synthesis of 5-(4-cyclopropyl-1H-imidazol-1-yl)-2-fluoro-4-methyl-N-(1-methyl-5,6-dihydrobenzo[f]imidazo[1,5-d][1,4]oxazepin-8-yl)benzamide (Example 51)

To a mixture of methyl-5,6-dihydrobenzo[f]imidazo[1,5-d][1,4]oxazepin-8-amine (51d) (5 mg, 23.23 umol) and 5-(4-cyclopropyl-1H-imidazol-1-yl)-2-fluoro-4-methylbenzoic acid (1b) (9.07 mg, 34.84 umol) in 1,4-dioxane (3 mL) was added HATU (13.25 mg, 34.84 umol) and NMM (9.40 mg, 92.91 umol, 10.22 uL) under N$_2$. The mixture was stirred at 25° C. for 24 hours. LCMS showed one main peak with desired mass. The reaction mixture was diluted with H$_2$O (8 mL) and extracted with Ethyl acetate (10 mL*2). The combined organic layers were washed with brine (10 mL*2), dried over anhydrous Na$_2$SO$_4$, filtered and concentrated under reduced pressure. The crude product was triturated with ethyl acetate (3 mL) at 25° C. and filtered, the filter cake was collected and dried in vacuo to give Example 51. MS mass calculated for [M+1]$^+$ (C$_{26}$H$_{24}$FN$_5$O$_2$) requires m/z 458.1, LCMS found m/z 458.1. $^1$H NMR (400 MHz, CHLOROFORM-d) δ=9.38-9.29 (m, 1H), 8.55-8.49 (m, 1H), 8.08 (d, J=7.3 Hz, 1H), 7.60-7.55 (m, 1H), 7.46 (s, 1H), 7.22-7.15 (m, 2H), 6.80 (s, 1H), 4.63 (t, J=5.5 Hz, 2H), 4.21 (t, J=5.5 Hz, 2H), 2.42 (s, 3H), 2.29 (s, 3H), 1.96-1.88 (m, 1H), 1.30-1.25 (m, 1H), 0.95-0.88 (m, 2H), 0.88-0.81 (m, 2H).

Example S34

(R)-4-(4-cyclopropyl-1H-imidazol-1-yl)-N-(6-methyl-5,6-dihydrobenzo[f][1,2,4]triazolo[4,3-d][1,4]oxazepin-8-yl)picolinamide (Example 52) was synthesized according to the scheme provided below.

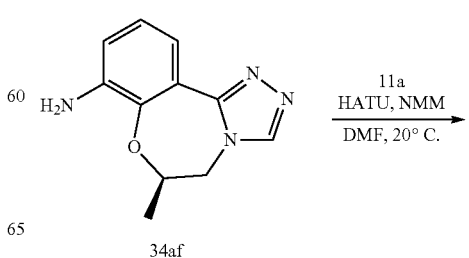

34af

-continued

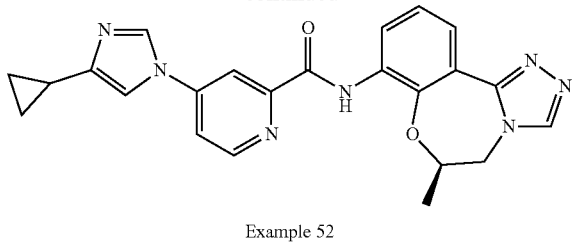

Example 52

Synthesis of (R)-4-(4-cyclopropyl-1H-imidazol-1-yl)-N-(6-methyl-5,6-dihydrobenzo[f][1,2,4]triazolo[4,3-d][1,4]oxazepin-8-yl)picolinamide (Example 52)

To a solution of 4-(4-cyclopropyl-1H-imidazol-1-yl)picolinic acid (11a) (7.00 mg, 30.52 umol) in DMF (1 mL) was added HATU (13.72 mg, 36.07 umol) and NMM (5.61 mg, 55.49 umol, 6.10 uL). Then (R)-6-methyl-5,6-dihydrobenzo[f][1,2,4]triazolo[4,3-d][1,4]oxazepin-8-amine (34af) (6 mg, 27.75 umol) was added to the mixture. The mixture was stirred at 20° C. for 16 hr. LCMS showed one main peak with desired MS. The mixture was purified by prep-HPLC (column: Nano-micro Kromasil C18 100*30 mm 5 um; mobile phase: [water (0.1% TFA)-ACN]; B %: 10%-40%, 10 min) to give Example 52. MS mass calculated for [M+H]+ ($C_{23}H_{21}N_7O_2$) requires m/z 428.2, LCMS found m/z 428.2. $^1$H NMR (400 MHz, METHANOL-$d_4$) δ ppm 9.41 (s, 1H) 8.88 (d, J=5.38 Hz, 1H) 8.61-8.70 (m, 2H) 8.51 (d, J=1.96 Hz, 1H) 8.06 (dd, J=8.19, 1.59 Hz, 1H) 7.94-8.02 (m, 2H) 7.25 (t, J=1.00 Hz, 1H) 4.61-4.76 (m, 2H) 4.39 (q, J=1.00 Hz, 1H) 1.98-2.10 (m, 1H) 1.72 (d, J=1.00 Hz, 3H) 1.07-1.20 (m, 2H) 0.87-0.96 (m, 2H).

Example S35

4-(4-cyclopropyl-1H-imidazol-1-yl)-N-(5,6-dihydrobenzo[f]tetrazolo[1,5-d][1,4]oxazepin-8-yl)-5-(4-methylpiperazin-1-yl)picolinamide (Example 54), (R)-4-(4-cyclopropyl-1H-imidazol-1-yl)-N-(5,6-dihydrobenzo[f]tetrazolo[1,5-d][1,4]oxazepin-8-yl)-5-(2-methylmorpholino)picolinamide (Example 55), (R)-4-(4-cyclopropyl-1H-imidazol-1-yl)-N-(5,6-dihydrobenzo[f]tetrazolo[1,5-d][1,4]oxazepin-8-yl)-5-(3-hydroxypyrrolidin-1-yl)picolinamide (Example 57), 5-(azetidin-1-yl)-4-(4-cyclopropyl-1H-imidazol-1-yl)-N-(5,6-dihydrobenzo[f]tetrazolo[1,5-d][1,4]oxazepin-8-yl)picolinamide (Example 58), 4-(4-cyclopropyl-1H-imidazol-1-yl)-N-(5,6-dihydrobenzo[f]tetrazolo[1,5-d][1,4]oxazepin-8-yl)-5-(dimethylamino)picolinamide (Example 60), (S)-4-(4-cyclopropyl-1H-imidazol-1-yl)-N-(5,6-dihydrobenzo[f]tetrazolo[1,5-d][1,4]oxazepin-8-yl)-5-(3-hydroxypyrrolidin-1-yl)picolinamide (Example 61), 5-((1R,4R)-2-oxa-5-azabicyclo[2.2.1]heptan-5-yl)-4-(4-cyclopropyl-1H-imidazol-1-yl)-N-(5,6-dihydrobenzo[f]tetrazolo[1,5-d][1,4]oxazepin-8-yl)picolinamide (Example 62), 4-(4-cyclopropyl-1H-imidazol-1-yl)-N-(5,6-dihydrobenzo[f]tetrazolo[1,5-d][1,4]oxazepin-8-yl)-5-(3-hydroxy-3-methylpyrrolidin-1-yl)picolinamide (Example 63), 5-((1S,4S)-2-oxa-5-azabicyclo[2.2.1]heptan-5-yl)-4-(4-cyclopropyl-1H-imidazol-1-yl)-N-(5,6-dihydrobenzo[f]tetrazolo[1,5-d][1,4]oxazepin-8-yl)picolinamide (Example 64), (S)-4-(4-cyclopropyl-1H-imidazol-1-yl)-N-(5,6-dihydrobenzo[f]tetrazolo[1,5-d][1,4]oxazepin-8-yl)-5-(3-methylmorpholino)picolinamide (Example 65), (S)-4-(4-cyclopropyl-1H-imidazol-1-yl)-N-(5,6-dihydrobenzo[f]tetrazolo[1,5-d][1,4]oxazepin-8-yl)-5-(2-methylmorpholino)picolinamide (Example 66), 4-(4-cyclopropyl-1H-imidazol-1-yl)-N-(5,6-dihydrobenzo[f]tetrazolo[1,5-d][1,4]oxazepin-8-yl)-5-(3-hydroxy-3-methylazetidin-1-yl)picolinamide (Example 67), and (R)-4-(4-cyclopropyl-1H-imidazol-1-yl)-N-(5,6-dihydrobenzo[f]tetrazolo[1,5-d][1,4]oxazepin-8-yl)-5-(3-methylmorpholino)picolinamide (Example 70) were synthesized according to the schemes provided below.

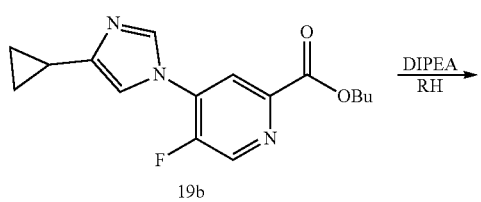

19b

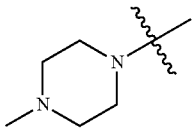

54a, R =

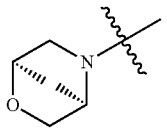

62a, R =

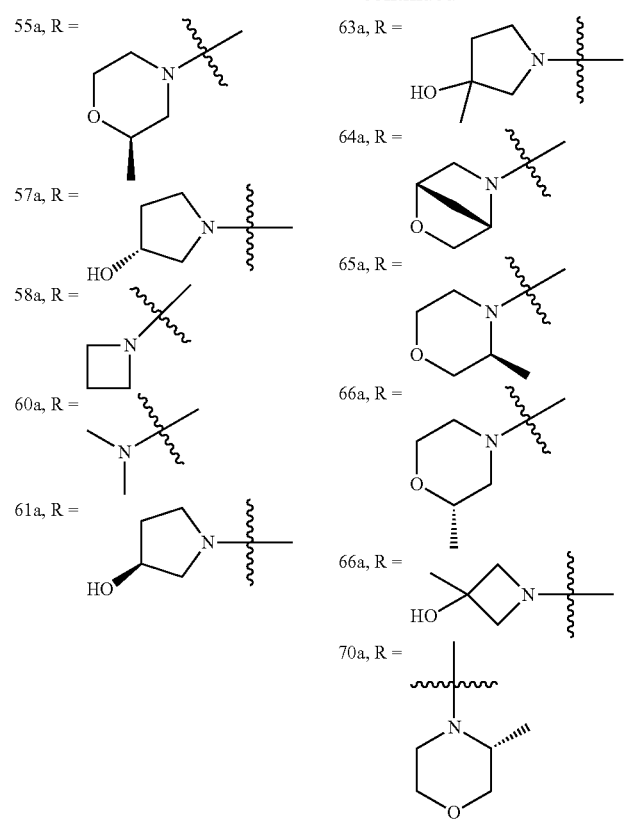
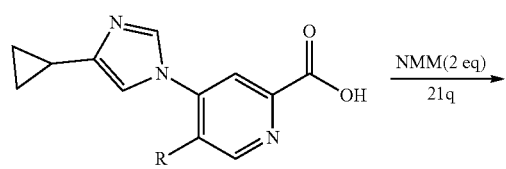

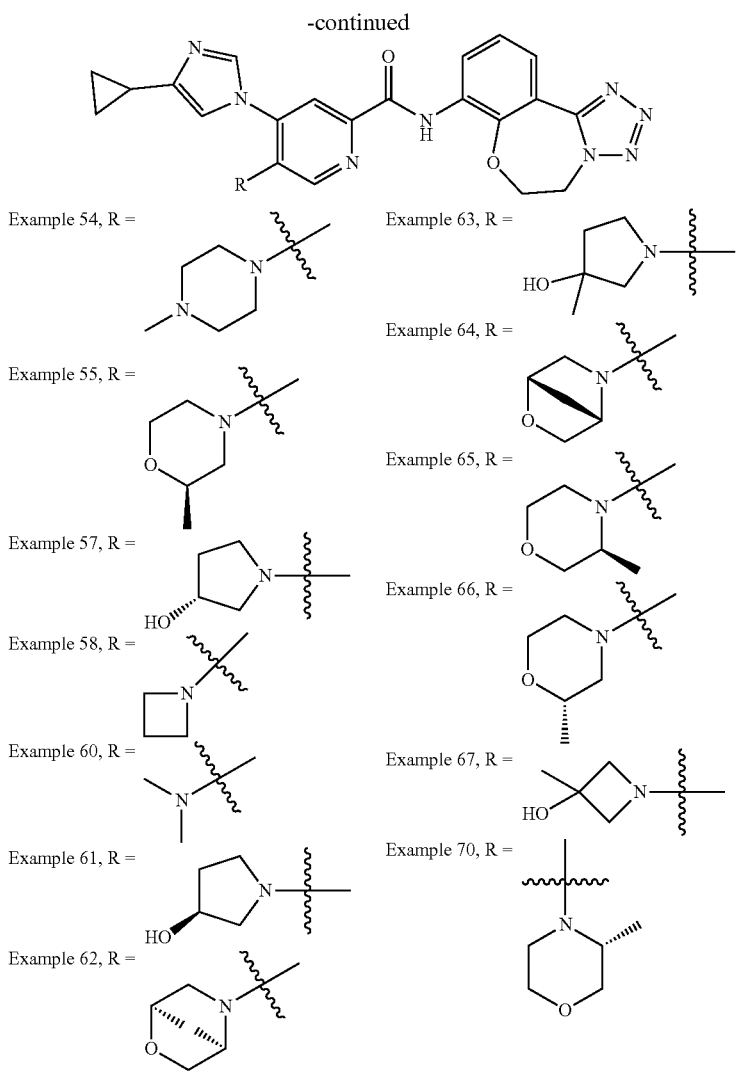

General Procedure for 54a, 55a, 57a, 58a, 60a, 61a, 63a, 66a, and 67a

To a mixture of butyl 4-(4-cyclopropyl-1H-imidazol-1-yl)-5-fluoropicolinate (19b) (100 mg, 329.67 umol) and amine (308.43 mg, 3.30 mmol) in $CH_3CN$ (5v) was added DIPEA (127.82 mg, 989.02 umol) at 25° C. under $N_2$. The mixture was stirred at 90° C. for 12 hours. The residue was poured into water and the mixture was extracted with ethyl acetate. The combined organic layers were washed with brine, dried with anhydrous $Na_2SO_4$, filtered and concentrated in vacuo. The residue was purified by prep-TLC (Petroleum ether/Ethyl acetate) to give a.

General Procedure for 62a and 64a

A mixture of butyl 4-(4-cyclopropyl-1H-imidazol-1-yl)-5-fluoropicolinate (19b) (100 mg, 329.67 umol), amine (223.50 mg, 1.65 mmol, HCl salt) and $K_2CO_3$ (318.94 mg, 2.31 mmol) in a sealed tube in DMF (5v) was stirred at 100° C. for 24 h. The residue was diluted with EtOAc and $H_2O$, and the phases were separated. The aqueous phase was extracted with EtOAc. The combined organic layers were washed with brine, dried over with $NaSO_4$, filtered and concentrated under reduced pressure to give a residue. The residue was purified by prep-TLC (Dichloromethane:Methanol=10:1) to give a.

General Procedure for 65a and 70a

Butyl 4-(4-cyclopropyl-1H-imidazol-1-yl)-5-fluoropicolinate (19b) (100 mg, 329.67 umol) and amine (500.18 mg, 4.95 mmol, 15 eq) were sealed in a glass tube, and stirred at 130° C. for 14 hr. The reaction mixture was diluted with ethyl acetate and $H_2O$ and the phases were separated. The aqueous layer was extracted with ethyl acetate. The combined organic layers were washed with brine, dried over with $NaSO_4$, filtered and concentrated under reduced pressure to give a residue. The residue was purified by prep-TLC (Petroleum ether:Ethyl acetate=0:1) to give a.

(b). A mixture of a (0.096 mmol) and $LiOH.H_2O$ (1.1 eq) in $THF/MeOH/H_2O$ (0.5 mL/0.5 mL/0.1 mL) was stirred at 20° C. for 4 hr. LCMS showed the reaction was completed and one main peak with desired m/z was detected. The mixture was concentrated under reduced pressure to give lithium salt b or the mixture was adjusted to pH 5-6 with 0.5M HCl solution and then concentrated to give b.

Synthesis of 4-(4-cyclopropyl-1H-imidazol-1-yl)-N-(5,6-dihydrobenzo[f]tetrazolo[1,5-d][1,4]oxazepin-8-yl)-5-(4-methylpiperazin-1-yl)picolinamide (Example 54)

To a solution of 4-(4-cyclopropyl-1H-imidazol-1-yl)-5-(4-methylpiperazin-1-yl)picolinic acid (54b) (50 mg, 152.73 umol) in DMF (3.5 mL) was added NMM (30.90 mg, 305.46 umol) and HATU (87.11 mg, 229.09 umol). After stirring for 5 min, 5,6-dihydrobenzo[f]tetrazolo[1,5-d][1,4]oxazepin-8-amine (21q) (46.55 mg, 229.09 umol, 1.5 eq) was added at 20° C. under $N_2$. The mixture was stirred at 20° C. for 12 hr. The reaction mixture was poured into water (4 mL), the mixture was filtered and the filter cake was washed with $H_2O$ (5 mL*2) and collected. The solid was dried in vacuo to give Example 54. MS mass calculated for $[M+1]^+$ ($C_{26}H_{28}N_{10}O_2$) requires m/z 513.3, LCMS found m/z 513.3. $^1$H NMR (400 MHz, DMSO-d6) δ=10.57 (s, 1H), 8.62 (dd, J=1.5, 8.0 Hz, 1H), 8.54 (s, 1H), 8.19 (dd, J=1.6, 8.2 Hz, 1H), 8.13 (d, J=1.1 Hz, 1H), 7.98 (s, 1H), 7.47 (d, J=1.1 Hz, 1H), 7.33 (t, J=8.1 Hz, 1H), 5.06-4.98 (m, 2H), 4.80-4.74 (m, 2H), 3.34-3.30 (m, 11H), 2.90-2.83 (m, 4H), 2.39 (br s, 4H), 2.20 (s, 3H), 1.93-1.85 (m, 1H), 0.87-0.80 (m, 2H), 0.75-0.68 (m, 2H).

Synthesis of (R)-4-(4-cyclopropyl-1H-imidazol-1-yl)-N-(5,6-dihydrobenzo[f]tetrazolo[1,5-d][1,4]oxazepin-8-yl)-5-(2-methylmorpholino)picolinamide (Example 55)

To a solution of (R)-4-(4-cyclopropyl-1H-imidazol-1-yl)-5-(2-methylmorpholino)picolinic acid (55b) (64 mg, 194.91 umol) in DMF (3 mL) was added NMM (39.43 mg, 389.81 umol) and HATU (111.16 mg, 292.36 umol). After stirring for 5 min, 5,6-dihydrobenzo[f]tetrazolo[1,5-d][1,4]oxazepin-8-amine (21q) (59.41 mg, 292.36 umol) was added at 20° C. under $N_2$. The mixture was stirring at 20° C. for 4h. The reaction mixture was poured into water (4 mL), and the mixture was filtered and the filter cake was washed with $H_2O$ (5 mL*2). The solid was collected and dried in vacuo to give Example 55. MS mass calculated for $[M+1]^+$ ($C_{26}H_{27}N_9O_3$) requires m/z 514.3, LCMS found m/z 514.3. $^1$H NMR (400 MHz, DMSO-d6) δ=10.56 (s, 1H), 8.61 (dd, J=1.3, 7.9 Hz, 1H), 8.51 (s, 1H), 8.18 (dd, J=1.3, 8.2 Hz, 1H), 8.12 (s, 1H), 7.98 (s, 1H), 7.49 (s, 1H), 7.32 (t, J=8.0 Hz, 1H), 5.07-4.98 (m, 2H), 4.81-4.73 (m, 2H), 3.79 (br d, J=11.0 Hz, 1H), 3.69-3.55 (m, 2H), 2.92-2.71 (m, 3H), 2.56 (br d, J=10.4 Hz, 1H), 1.95-1.84 (m, 1H), 1.02 (d, J=6.2 Hz, 3H), 0.88-0.79 (m, 2H), 0.74-0.67 (m, 2H).

Synthesis of (R)-4-(4-cyclopropyl-1H-imidazol-1-yl)-N-(5,6-dihydrobenzo[f]tetrazolo[1,5-d][1,4]oxazepin-8-yl)-5-(3-hydroxypyrrolidin-1-yl)picolinamide (Example 57)

To a mixture of (R)-4-(4-cyclopropyl-1H-imidazol-1-yl)-5-(3-hydroxypyrrolidin-1-yl)picolinic acid (47b) (33 mg, 104.98 umol, 1 eq) and HATU (59.88 mg, 157.47 umol, 1.5 eq) in DMF (2 mL) was added NMM (53.09 mg, 524.91 umol, 57.71 uL, 5 eq) and 5,6-dihydrobenzo[f]tetrazolo[1,5-d][1,4]oxazepin-8-amine (21q) (23.47 mg, 115.48 umol, 1.1 eq) under $N_2$. The mixture was stirred at 25° C. for 16 hours. LCMS showed desired mass was detected. The residue was poured into ethyl acetate (10 mL) and the mixture was washed with water (5 mL*3). The organic phase was washed with brine (10 mL), dried with anhydrous $Na_2SO_4$, filtered and concentrated in vacuo. The crude product was triturated with MeOH at 25° C. for 30 min and filtered, the filter cake was dried in vacuo to give (R)-4-(4-cyclopropyl-1H-imidazol-1-yl)-N-(5,6-dihydrobenzo[f]tetrazolo[1,5-d][1,4]oxazepin-8-yl)-5-(3-hydroxy pyrrolidin-1-yl)picolinamide (Example 57). MS mass calculated for $[M+1]^+$ ($C_{25}H_{25}N_9O_3$) requires m/z 500.2, LCMS found m/z 500.1; $^1$H NMR (400 MHz, DMSO-d6) δ 10.51 (s, 1H), 8.70 (dd, J=1.6, 8.1 Hz, 1H), 8.38 (s, 1H), 8.22 (dd, J=1.7, 8.1 Hz, 1H), 7.83-7.80 (m, 2H), 7.37 (t, J=8.1 Hz, 1H), 7.29 (d, J=1.2 Hz, 1H), 5.11-5.06 (m, 2H), 5.03 (d, J=3.7 Hz, 1H), 4.87-4.81 (m, 2H), 4.32 (br s, 1H), 3.30-3.20 (m, 2H), 2.89 (br d, J=10.5 Hz, 1H), 2.00-1.81 (m, 3H), 0.90-0.83 (m, 2H), 0.80-0.72 (m, 2H).

Synthesis of 5-(azetidin-1-yl)-4-(4-cyclopropyl-1H-imidazol-1-yl)-N-(5,6-dihydrobenzo[f]tetrazolo[1,5-d][1,4]oxaze-pin-8-yl)picolinamide (Example 58)

To a mixture of 5-(azetidin-1-yl)-4-(4-cyclopropyl-1H-imidazol-1-yl)picolinic acid (58b) (25 mg, 87.93 umol) in DMF (1 mL) was added HATU (40.12 mg, 105.52 umol), NMM (26.68 mg, 263.79 umol) and 5,6-dihydrobenzo[f]tetrazolo[1,5-d][1,4]oxazepin-8-amine (21q) (17.87 mg, 87.93 umol) at 25° C. under $N_2$. The mixture was stirred at 30° C. for 2 hours. LCMS showed the reaction was completed. The residue was poured into water (2 mL) and solid precipitated and the solid was collected by filtration. The solid was further triturated with MeOH (1 mL) at 25° C. for 10 min and filtered, the solid was dried in vacuo to give Example 58. MS mass calculated for $[M+H]^+$ ($C_{24}H_{23}N_9O_2$) requires m/z 469.20, LCMS found m/z 470.2. $^1$H NMR (400 MHz, DMSO-d6) δ ppm 10.46 (s, 1H) 8.63 (d, J=6.84 Hz, 1H) 8.16 (dd, J=8.16, 1.32 Hz, 1H) 8.07 (s, 1H) 7.76 (d, J=14.55 Hz, 1H) 7.29-7.35 (m, 1H) 7.21 (s, 1H) 4.97-5.05 (m, 2H) 4.77 (d, J=3.75 Hz, 2H) 3.75 (t, J=7.39 Hz, 2H) 2.23 (dt, J=14.99, 7.50 Hz, 2H) 1.86 (td, J=8.60, 4.19 Hz, 1H) 0.76-0.86 (m, 2H) 0.65-0.73 (m, 2H).

Synthesis of 4-(4-cyclopropyl-1H-imidazol-1-yl)-N-(5,6-dihydrobenzo[f]tetrazolo[1,5-d][1,4]oxazepin-8-yl)-5-(dimethylamino)picolinamide (Example 60)

To a mixture of 4-(4-cyclopropyl-1H-imidazol-1-yl)-5-(dimethylamino)picolinic acid (60b) (28 mg, 102.83 umol) and 5,6-dihydrobenzo[f]tetrazolo[1,5-d][1,4]oxazepin-8-amine (21q) (20.89 mg, 102.83 umol) in DMF (1 mL) was added HATU (46.92 mg, 123.39 umol) and NMM (31.20 mg, 308.48 umol) in one portion at 30° C. under $N_2$. The mixture was stirred at 30° C. for 2 hours. LCMS showed the reaction was completed. The residue was poured into water (2 mL) and the solid was collected by filtration, then triturated with MeOH (1 mL) for 10 min and filtered again. The filter cake was dried in vacuo to give Example 60. MS mass calculated for $[M+H]^+$ ($C_{23}H_{23}N_9O_2$) requires m/z 458.5, LCMS found m/z 458.2. $^1$H NMR (400 MHz, DMSO-d$_6$) δ ppm 10.52 (s, 1H) 8.62 (d, J=7.94 Hz, 1H) 8.48 (s, 1H) 8.13-8.18 (m, 1H) 7.96 (s, 1H) 7.89 (s, 1H) 7.35 (s, 1H) 7.31 (t, J=8.16 Hz, 1H) 4.98-5.03 (m, 2H) 4.74-4.78 (m, 2H) 2.64 (s, 6H) 1.87 (ddd, J=13.01, 8.27, 4.96 Hz, 2H) 0.78-0.83 (m, 2H) 0.67-0.72 (m, 2H).

Synthesis of (S)-4-(4-cyclopropyl-1H-imidazol-1-yl)-N-(5,6-dihydrobenzo[f]tetrazolo[1,5-d][1,4]oxazepin-8-yl)-5-(3-hydroxypyrrolidin-1-yl)picolinamide (Example 61)

To a mixture of (S)-4-(4-cyclopropyl-1H-imidazol-1-yl)-5-(3-hydroxypyrrolidin-1-yl)picolinic acid (61b) (39 mg, 124.07 umol) in DMF (2 mL) was added HATU (70.76 mg, 186.11 umol), NMM (62.75 mg, 620.35 umol, 68.20 uL) and 5,6-dihydrobenzo[f]tetrazolo[1,5-d][1,4]oxazepin-8-amine (21q) (27.73 mg, 136.48 umol) under $N_2$. The mixture was stirred at 25° C. for 16 hours. LCMS showed the starting material was consumed completely and desired mass was detected. TLC (Dichloromethane:Methanol=10:1, $R_F$=0.4) indicated one new spot formed. The reaction mixture was filtered and the filter cake was triturated with Methanol (2 mL) at 25° C. for 0.5 h.; The filter cake was washed with methanol (1 mL*2) and the solid was dried in vacuo to give Example 61. MS mass calculated for [M+1]$^+$ ($C_{25}H_{25}N_9O_3$) requires m/z, 499.21, LCMS found m/z 500.3 501.3; $^1$H NMR (400 MHz, DMSO-$d_6$) δ 10.52-10.39 (s, 1H) 8.69-8.59 (d, 1H) 8.37-8.28 (s, 1H) 8.23-8.14 (d, 1H) 7.81-7.71 (s, 2H) 7.36-7.29 (t, 1H) 7.26-7.21 (s, 1H) 5.07-5.00 (m, 2H) 5.00-4.96 (m, 1H) 4.82-4.75 (m, 2H) 4.31-4.25 (s, 1H) 3.24-3.15 (m, 2H) 2.86-2.81 (d, 1H) 1.95-1.77 (m, 3H) 0.86-0.79 (m, 2H) 0.74-0.67 (m, 2H).

Synthesis of 5-((1R,4R)-2-oxa-5-azabicyclo[2.2.1]
heptan-5-yl)-4-(4-cyclopropyl-1H-imidazol-1-yl)-N-
(5,6-dihydro-benzo[f]tetrazolo[1,5-d][1,4]oxazepin-
8-yl)picolinamide (Example 62)

To a solution of 5-((1R,4R)-2-oxa-5-azabicyclo[2.2.1]heptan-5-yl)-4-(4-cyclopropyl-1H-imidazol-1-yl)picolinic acid (62b) (17 mg, 52.09 umol) in DMF (1.5 mL) was added NMM (10.54 mg, 104.18 umol) and HATU (29.71 mg, 78.14 umol). After stirring for 5 min, 5,6-dihydrobenzo[f]tetrazolo[1,5-d][1,4]oxazepin-8-amine (21q) (15.88 mg, 78.14 umol) was added at 20° C. under $N_2$. The mixture was stirred at 20° C. for 12 hr. The reaction mixture was poured into water (4 mL) and the mixture filtered. The filter cake was washed with $H_2O$ (5 mL*2), the solid was collected and dried in vacuo to give Example 62. MS mass calculated for [M+1]$^+$ ($C_{26}H_{25}N_9O_3$) requires m/z 512.1, LCMS found m/z 512.1. $^1$H NMR (400 MHz, DMSO-d6) δ=8.65 (dd, J=1.5, 8.1 Hz, 1H), 8.45 (s, 1H), 8.17 (dd, J=1.6, 8.1 Hz, 1H), 7.84-7.77 (m, 2H), 7.32 (t, J=8.1 Hz, 1H), 7.24 (d, J=1.2 Hz, 1H), 5.07-4.98 (m, 2H), 4.82-4.74 (m, 2H), 4.55 (s, 1H), 4.34 (s, 1H), 3.84 (d, J=7.9 Hz, 1H), 3.72 (d, J=7.1 Hz, 1H), 2.95 (d, J=8.6 Hz, 1H), 2.79-2.72 (m, 1H), 1.91-1.80 (m, 3H), 0.87-0.78 (m, 2H), 0.74-0.66 (m, 2H).

Synthesis of 4-(4-cyclopropyl-1H-imidazol-1-yl)-N-
(5,6-dihydrobenzo[f]tetrazolo[1,5-d][1,4]oxazepin-
8-yl)-5-(3-hydroxy-3-methylpyrrolidin-1-yl)pi-
colinamide (Example 63)

To a solution of 4-(4-cyclopropyl-1H-imidazol-1-yl)-5-(3-hydroxy-3-methylpyrrolidin-1-yl)picolinic acid (63b) (10 mg, 30.45 umol) in DMF (1 mL) was added NMM (6.16 mg, 60.91 umol) and HATU (17.37 mg, 45.68 umol). After stirring for 5 min, 5,6-dihydrobenzo[f]tetrazolo[1,5-d][1,4]oxazepin-8-amine (21q) (9.28 mg, 45.68 umol) was added at 20° C. under $N_2$. The mixture was stirred at 20° C. for 12 hr. The reaction mixture was poured into water (4 mL), the mixture was filtered and the filter cake was washed with $H_2O$ (5 mL*2). The solid was collected and dried in vacuo to give Example 63. MS mass calculated for [M+1]$^+$ ($C_{26}H_{25}N_9O_3$) requires m/z 514.1, LCMS found m/z 514.1. $^1$H NMR (400 MHz, DMSO-d6) δ=10.44 (s, 1H), 8.63 (dd, J=1.5, 8.1 Hz, 1H), 8.29 (s, 1H), 8.15 (dd, J=1.5, 8.1 Hz, 1H), 7.74 (s, 2H), 7.30 (t, J=8.1 Hz, 1H), 7.22 (d, J=1.1 Hz, 1H), 5.01 (br d, J=4.5 Hz, 2H), 4.81 (s, 2H), 4.77 (br d, J=3.7 Hz, 2H), 3.22-3.15 (m, 1H), 3.01-2.93 (m, 2H), 2.92-2.85 (m, 2H), 1.90-1.70 (m, 4H), 1.23 (s, 3H), 0.81 (br dd, J=2.8, 8.3 Hz, 2H), 0.69 (br d, J=1.8 Hz, 2H).

Synthesis of 5-((1S,4S)-2-oxa-5-azabicyclo[2.2.1]
heptan-5-yl)-4-(4-cyclopropyl-1H-imidazol-1-yl)-N-
(5,6-dihydro-benzo[f]tetrazolo[1,5-d][1,4]oxazepin-
8-yl)picolinamide (Example 64)

To a solution of lithium 5-((1S,4S)-2-oxa-5-azabicyclo[2.2.1]heptan-5-yl)-4-(4-cyclopropyl-1H-imidazol-1-yl)picolinate (64b) (25 mg, 76.61 umol) in DMF (1 mL) was added HATU (43.69 mg, 114.91 umol) and NMM (15.50 mg, 153.21 umol, 16.84 uL), then 5,6-dihydrobenzo[f]tetrazolo[1,5-d][1,4]oxazepin-8-amine (21q) (15.57 mg, 76.61 umol) was added to the mixture. The mixture was stirred at 20° C. for 16 hr. LCMS showed the reaction was completed and one main peak with desired m/z (RT=1.065, m/z, 512.3, M+H) was detected. The mixture was added to $H_2O$ (3 mL) dropwised with stirring. Then the mixture was filtered, the filter cake was washed with $H_2O$ (20 mL) and dried in vacuo to give Example 64. MS mass calculated for [M+H]$^+$ ($C_{26}H_{25}N_9O_3$) requires m/z 512.2, LCMS found m/z 512.3. $^1$H NMR (400 MHz, CHLOROFORM-d) δ ppm 10.43 (s, 1H) 8.80 (d, J=6.85 Hz, 1H) 8.30-8.40 (m, 1H) 8.18 (s, 1H) 8.03 (s, 1H) 7.58 (s, 1H) 7.31 (t, J=8.13 Hz, 1H) 7.28-7.28 (m, 1H) 6.90 (s, 1H) 4.95-5.06 (m, 2H) 4.70-4.81 (m, 2H) 4.52-4.60 (m, 1H) 4.12 (s, 1H) 3.96-4.05 (m, 1H) 3.81-3.91 (m, 1H) 3.07 (br d, J=9.29 Hz, 1H) 2.92-2.92 (m, 1H) 2.88-2.94 (m, 1H) 1.93-2.03 (m, 1H) 1.86-1.93 (m, 1H) 0.88-0.97 (m, 2H) 0.79-0.84 (m, 2H).

Synthesis of (S)-4-(4-cyclopropyl-1H-imidazol-1-
yl)-N-(5,6-dihydrobenzo[f]tetrazolo[1,5-d][1,4]
oxazepin-8-yl)-5-(3-methylmorpholino)picolinamide
(Example 65)

To a solution of lithium (S)-4-(4-cyclopropyl-1H-imidazol-1-yl)-5-(3-methylmorpholino)picolinate (65b) (35 mg, 104.70 umol) in DMF (1 mL) was added HATU (59.71 mg, 157.05 umol) and NMM (21.18 mg, 209.39 umol, 23.02 uL), then 5,6-dihydrobenzo[f]tetrazolo[1,5-d][1,4]oxazepin-8-amine (21q) (21.27 mg, 104.70 umol) was added to the mixture. The mixture was stirred at 20° C. for 16 hr. LCMS showed the reaction was completed and one main peak with desired MS was detected. The mixture was added dropwise into $H_2O$ (3 mL) with stirring and the mixture was filtered. The filter cake was washed with $H_2O$ (20 mL) and MeOH (2 mL), then was dried in vacuo to give Example 65. MS mass calculated for [M+H]$^+$ ($C_{26}H_{27}N_9O_3$) requires m/z 514.2, LCMS found m/z 514.3. $^1$H NMR (400 MHz, CHLOROFORM-d) δ ppm 10.56-10.69 (m, 1H) 8.84 (br d, J=7.58 Hz, 1H) 8.45-8.57 (m, 1H) 8.33-8.42 (m, 1H) 8.12-8.26 (m, 2H) 7.30-7.43 (m, 2H) 4.98-5.13 (m, 2H) 4.80 (br s, 2H) 3.74-4.00 (m, 3H) 3.52 (br dd, J=10.76, 4.89 Hz, 1H) 3.17 (br d, J=6.97 Hz, 2H) 2.94 (br s, 1H) 1.91-2.04 (m, 1H) 1.08 (br d, J=5.87 Hz, 3H) 0.94-1.03 (m, 2H) 0.90 (br s, 2H).

Synthesis of (S)-4-(4-cyclopropyl-1H-imidazol-1-
yl)-N-(5,6-dihydrobenzo[f]tetrazolo[1,5-d][1,4]
oxazepin-8-yl)-5-(2-methylmorpholino)picolinamide
(Example 66)

To a solution of (S)-4-(4-cyclopropyl-1H-imidazol-1-yl)-5-(2-methylmorpholino)picolinic acid (66b) (30 mg, 89.74 umol) in DMF (1 mL) was added HATU (46.53 mg, 122.37 umol) and NMM (16.50 mg, 163.16 umol, 17.94 uL). After stirring for 5 minutes, 5,6-dihydrobenzo[f]tetrazolo[1,5-d]

[1,4]oxazepin-8-amine (21q) (16.58 mg, 81.58 umol) was added at 20° C. under N$_2$. The mixture was stirring at 20° C. for 8 hours. LCMS showed starting material was consumed completely and one main peak with desired mass was detected. The reaction mixture was poured into deionized water (5 mL) and the mixture was filtered and the filter cake was collected and dried in vacuo. The filter cake was further triturated with deionized water (5 mL) at 20° C. for 5 minutes, then filtered, the filter cake was dried in vacuo to give Example 66. MS mass calculated for [M+1]$^+$ (C$_{26}$H$_{27}$N$_9$O$_3$) requires m/z 514.5, LCMS found m/z 514.1. $^1$H NMR (400 MHz, CHLOROFORM-d) δ=10.59-10.52 (m, 1H), 8.84-8.77 (m, 1H), 8.38 (s, 1H), 8.35 (br d, J=7.8 Hz, 1H), 8.10 (s, 1H), 7.98 (s, 1H), 7.32 (br t, J=8.1 Hz, 1H), 7.19-7.13 (m, 1H), 5.04-4.97 (m, 2H), 4.78-4.71 (m, 2H), 3.96-3.89 (m, 1H), 3.80-3.68 (m, 2H), 2.97-2.87 (m, 1H), 2.87-2.79 (m, 2H), 2.64-2.56 (m, 1H), 1.98-1.89 (m, 1H), 1.21-1.12 (m, 3H), 0.97-0.90 (m, 2H), 0.87-0.79 (m, 2H).

Synthesis of 4-(4-cyclopropyl-1H-imidazol-1-yl)-N-(5,6-dihydrobenzo[f]tetrazolo[1,5-d][1,4]oxazepin-8-yl)-5-(3-hydroxy-3-methylazetidin-1-yl)picolinamide (Example 67)

To a solution of 4-(4-cyclopropyl-1H-imidazol-1-yl)-5-(3-hydroxy-3-methylazetidin-1-yl)picolinic acid (67b) (40 mg, 124.89 umol) in DMF (1 mL) was added HATU (64.76 mg, 170.31 umol), NMM (22.97 mg, 227.08 umol, 24.97 uL). After stirring for 5 minutes, 5,6-dihydrobenzo[f]tetrazolo[1,5-d][1,4]oxazepin-8-amine (21q) (23.07 mg, 113.54 umol) was added at 20° C. under N$_2$. The mixture was stirred at 20° C. for 6 hours. LC-MS showed one main peak with desired MS was detected. The reaction was concentrated in vacuo. The residue was purified by prep-HPLC (neutral condition, column: Waters Xbridge 150*25 5u; mobile phase: [water (10 mM NH$_4$HCO$_3$)-ACN]; B %: 20%-50%, 10 min) to give Example 67. MS mass calculated for [M+1]$^+$ (C$_{25}$H$_{25}$N$_9$O$_3$) requires m/z 500.2, LCMS found m/z 500.3. $^1$H NMR (400 MHz, DMSO-d$_6$) δ=10.48-10.45 (m, 1H), 8.65-8.61 (m, 1H), 8.19-8.14 (m, 1H), 8.13-8.09 (m, 1H), 7.81-7.78 (m, 1H), 7.76-7.73 (m, 1H), 7.34-7.28 (m, 1H), 7.23-7.20 (m, 1H), 5.59-5.56 (m, 1H), 5.04-4.99 (m, 2H), 4.80 (s, 2H), 3.64-3.60 (m, 2H), 3.59-3.55 (m, 2H), 1.90-1.82 (m, 1H), 1.40-1.32 (m, 3H), 0.81 (br s, 2H), 0.74-0.66 (m, 2H).

Synthesis of (R)-4-(4-cyclopropyl-1H-imidazol-1-yl)-N-(5,6-dihydrobenzo[f]tetrazolo[1,5-d][1,4]oxazepin-8-yl)-5-(3-methylmorpholino)picolinamide (Example 70)

To a solution of (R)-4-(4-cyclopropyl-1H-imidazol-1-yl)-5-(3-methylmorpholino)picolinic acid (70b) (30 mg, 89.74 umol) in DMF (2 mL) was added HATU (51.18 mg, 134.61 umol) and NMM (18.15 mg, 179.48 umol, 19.73 uL), and then 5,6-dihydrobenzo[f]tetrazolo[1,5-d][1,4]oxazepin-8-amine (21q) (18.24 mg, 89.74 umol). The mixture was stirred at 20° C. for 4 hr. LCMS showed one main peak with desired MS was detected. The reaction mixture was concentrated under reduced pressure. The residue was diluted with water (5 mL) and extracted with EtOAc (5 mL*3). The combined organic layers were washed with brine (10 mL*2), dried over sodium sulfate, filtered and concentrated under reduced pressure to give crude product. The crude was purified by prep-HPLC (TFA condition: column: Nano-Micro UniSil 5-100 C18 ULTRA 100*250 mm 5 um; mobile phase: [water (0.1% TFA)-ACN]; B %: 28%-43%, 10 min) to give Example 70; MS mass calculated for [M+H]$^+$ (C$_{26}$H$_{27}$N$_9$O$_3$) requires m/z 514.22, MS found m/z 514.2; $^1$H NMR (400 MHz, CHLOROFORM-d) δ ppm 10.51 (s, 1H), 9.14 (br s, 1H), 8.77 (br d, J=7.9 Hz, 1H), 8.58 (s, 1H), 8.33 (br d, J=8.2 Hz, 1H), 8.18 (s, 1H), 7.31 (t, J=8.2 Hz, 1H), 7.24 (s, 1H), 5.28 (br s, 3H), 5.00 (br d, J=4.2 Hz, 2H), 4.78-4.72 (m, 2H), 3.83 (br d, J=7.5 Hz, 3H), 3.50 (br dd, J=5.7, 11.5 Hz, 1H), 3.16-3.04 (m, 2H), 3.01-2.90 (m, 1H), 2.12-2.02 (m, 1H), 1.19-1.12 (m, 2H), 1.02 (d, J=6.4 Hz, 3H), 0.94 (br d, J=4.4 Hz, 2H).

(R)-butyl 4-(4-cyclopropyl-1H-imidazol-1-yl)-5-(2-methylmorpholino)picolinate (55a)

$^1$H NMR (400 MHz, METHANOL-d4) δ=8.43 (s, 1H), 8.08 (d, J=1.3 Hz, 1H), 7.97 (s, 1H), 7.34 (d, J=0.9 Hz, 1H), 4.38 (t, J=6.7 Hz, 2H), 3.87-3.62 (m, 3H), 2.94-2.77 (m, 3H), 2.55 (dd, J=10.0, 12.0 Hz, 1H), 1.97-1.73 (m, 3H), 1.47 (qd, J=7.5, 15.0 Hz, 2H), 1.08 (d, J=6.2 Hz, 3H), 0.98 (t, J=7.4 Hz, 2H), 0.94-0.88 (m, 2H), 0.77-0.72 (m, 2H).

(R)-butyl 4-(4-cyclopropyl-1H-imidazol-1-yl)-5-(3-hydroxypyrrolidin-1-yl)picolinate (57a)

MS mass calculated for [M+1]$^+$ (C$_{20}$H$_{26}$N$_4$O$_3$) requires m/z 371.2, LCMS found m/z 371.3.

Butyl 4-(4-cyclopropyl-1H-imidazol-1-yl)-5-(dimethylamino)picolinate (60a)

$^1$H NMR (400 MHz, CHLOROFORM-d) δ ppm 8.44 (s, 1H) 7.87 (s, 1H) 7.75 (d, J=1.32 Hz, 1H) 7.01 (d, J=1.32 Hz, 1H) 4.40 (t, J=6.84 Hz, 2H) 2.70 (s, 6H) 1.88-1.97 (m, 1H) 1.75-1.84 (m, 2H) 1.42-1.52 (m, 2H) 0.98 (t, J=7.39 Hz, 3H) 0.88-0.95 (m, 2H) 0.81-0.87 (m, 2H).

(S)-butyl 4-(4-cyclopropyl-1H-imidazol-1-yl)-5-(3-hydroxypyrrolidin-1-yl)picolinate (61a)

MS mass calculated for [M+1]$^+$ (C$_{20}$H$_{26}$N$_4$O$_3$) requires m/z, 370.2, LCMS found m/z 371.3 372.2; $^1$H NMR (400 MHz, CHLOROFORM-d) δ 8.37-8.25 (s, 1H) 7.88-7.80 (s, 1H) 7.61-7.49 (s, 1H) 6.95-6.85 (s, 1H) 4.57-4.48 (s, 1H) 4.42-4.30 (s, 2H) 3.55-3.41 (t, 1H) 3.32-3.19 (m, 2H) 2.03-3.94 (m, 1H) 1.06-2.06 (m, 2H) 1.86-1.95 (m, 2H) 1.74-1.82 (m, 2H) 1.50-1.61 (m, 1H) 1.40-1.49 (m, 2H) 1.22-1.36 (m, 2H) 0.94-1.01 (m, 3H) 0.88-0.93 (m, 2H) 0.79-0.85 (m, 2H).

Butyl 5-((1R,4R)-2-oxa-5-azabicyclo[2.2.1]heptan-5-yl)-4-(4-cyclopropyl-1H-imidazol-1-yl)picolinate (62a)

$^1$H NMR (400 MHz, CHLOROFORM-d) δ=8.27 (s, 1H), 7.86 (s, 1H), 7.53 (d, J=1.2 Hz, 1H), 6.86 (d, J=1.2 Hz, 1H), 4.52 (s, 1H), 4.44-4.33 (m, 2H), 4.11 (s, 1H), 3.95 (d, J=8.1 Hz, 1H), 3.83 (dd, J=1.3, 8.1 Hz, 1H), 3.03 (dd, J=1.6, 9.9 Hz, 1H), 2.89 (d, J=9.9 Hz, 1H), 1.98-1.86 (m, 3H), 1.83-1.74 (m, 2H), 1.46 (qd, J=7.5, 15.1 Hz, 2H), 0.97 (t, J=7.4 Hz, 3H), 0.95-0.89 (m, 2H), 0.83-0.78 (m, 2H).

Butyl 4-(4-cyclopropyl-1H-imidazol-1-yl)-5-(3-hydroxy-3-methylpyrrolidin-1-yl)picolinate (63a)

$^1$H NMR (400 MHz, CHLOROFORM-d) δ=8.27 (s, 1H), 7.81 (s, 1H), 7.52 (d, J=1.2 Hz, 1H), 6.86 (d, J=1.2 Hz, 1H), 4.37 (t, J=6.8 Hz, 2H), 3.47 (dt, J=7.0, 9.8 Hz, 1H), 3.20 (dt,

J=2.6, 9.0 Hz, 1H), 3.12-2.98 (m, 2H), 2.00-1.83 (m, 4H), 1.82-1.73 (m, 2H), 1.50-1.39 (m, 5H), 0.97 (t, J=7.4 Hz, 3H), 0.93-0.87 (m, 2H), 0.82-0.77 (m, 2H).

Butyl 5-((1S,4S)-2-oxa-5-azabicyclo[2.2.1]heptan-5-yl)-4-(4-cyclopropyl-1H-imidazol-1-yl)picolinate (64a)

MS mass calculated for [M+1]$^+$ ($C_{21}H_{26}N_4O_3$) requires m/z 383.2, LCMS found m/z 383.0; $^1$H NMR (400 MHz, CHLOROFORM-d) δ ppm 8.26 (s, 1H) 7.87 (s, 1H) 7.52 (s, 1H) 6.81-6.91 (m, 1H) 4.52 (s, 1H) 4.39 (t, J=1.00 Hz, 2H) 4.11 (s, 1H) 4.12 (s, 1H) 3.95 (d, J=8.16 Hz, 1H) 3.83 (dd, J=7.94, 1.10 Hz, 1H) 3.02 (dd, J=9.92, 1.54 Hz, 1H) 2.89 (d, J=1.00 Hz, 1H) 1.85-2.01 (m, 3H) 1.72-1.83 (m, 2H) 1.58-1.66 (m, 1H) 1.39-1.53 (m, 2H) 0.99 (t, J=1.00 Hz, 3H) 0.88-0.94 (m, 2H) 0.78-0.84 (m, 2H).

(S)-butyl 4-(4-cyclopropyl-1H-imidazol-1-yl)-5-(3-methylmorpholino)picolinate (65a)

MS mass calculated for [M+H]$^+$ ($C_{16}H_{18}FN_3O_2$) requires m/z 385.2, LCMS found m/z 385.1; $^1$H NMR (400 MHz, CHLOROFORM-d) δ ppm 8.51 (s, 1H) 8.01 (s, 1H) 7.95 (s, 1H) 7.15 (s, 1H) 4.38-4.49 (m, 2H) 3.69-3.88 (m, 3H) 3.39-3.51 (m, 1H) 3.11-3.20 (m, 1H) 3.00-3.08 (m, 1H) 2.80-2.89 (m, 1H) 1.88-1.98 (m, 1H) 1.81 (m, 2H) 1.41-1.51 (m, 2H) 1.22-1.31 (m, 1H) 1.19-1.26 (m, 1H) 1.10-1.10 (m, 1H) 0.96-1.05 (m, 6H) 0.91-0.95 (m, 1H) 0.90-0.96 (m, 1H) 0.89-0.95 (m, 1H) 0.79-0.88 (m, 2H).

(S)-butyl 4-(4-cyclopropyl-1H-imidazol-1-yl)-5-(2-methylmorpholino)picolinate (66a)

$^1$H NMR (400 MHz, CHLOROFORM-d) δ=8.47-8.44 (m, 1H), 7.94-7.91 (m, 1H), 7.90-7.88 (m, 1H), 7.11 (d, J=0.9 Hz, 1H), 4.45-4.39 (m, 2H), 3.90 (dd, J=1.7, 11.8 Hz, 1H), 3.75-3.64 (m, 2H), 2.93-2.85 (m, 1H), 2.81-2.76 (m, 2H), 2.61-2.53 (m, 1H), 1.96-1.89 (m, 1H), 1.80 (quin, J=7.3 Hz, 2H), 1.52-1.41 (m, 2H), 1.15 (d, J=6.4 Hz, 3H), 1.01-0.95 (m, 3H), 0.94-0.90 (m, 2H), 0.84-0.79 (m, 2H).

Butyl 4-(4-cyclopropyl-1H-imidazol-1-yl)-5-(3-hydroxy-3-methylazetidin-1-yl)picolinate (67a)

$^1$H NMR (400 MHz, CHLOROFORM-d) δ=8.05-8.00 (m, 1H), 7.81 (s, 1H), 7.49 (d, J=0.9 Hz, 1H), 6.84 (d, J=1.1 Hz, 1H), 4.37 (t, J=6.8 Hz, 2H), 3.76 (d, J=8.4 Hz, 2H), 3.66 (d, J=8.8 Hz, 2H), 1.93-1.85 (m, 1H), 1.81-1.73 (m, 2H), 1.54 (s, 3H), 1.45 (qd, J=7.5, 15.1 Hz, 2H), 0.96 (t, J=7.4 Hz, 3H), 0.93-0.87 (m, 2H), 0.81-0.76 (m, 2H).

(R)-butyl 4-(4-cyclopropyl-1H-imidazol-1-yl)-5-(3-methylmorpholino)picolinate (70a)

MS mass calculated for [M+H]$^+$ ($C_{21}H_{28}N_4O_3$) requires m/z 385.22, MS found m/z 385.2; $^1$HNMR (400 MHz, CHLOROFORM-d) δ ppm 8.50 (s, 1H), 8.03-7.92 (m, 2H), 7.15 (s, 1H), 4.48-4.36 (m, 2H), 3.86-3.69 (m, 3H), 3.44 (dd, J=5.2, 11.4 Hz, 1H), 3.18-2.99 (m, 2H), 2.84 (ddd, J=2.9, 5.7, 11.9 Hz, 1H), 1.97-1.89 (m, 1H), 1.81 (quin, J=7.2 Hz, 2H), 1.62 (s, 1H), 1.47 (sxt, J=7.5 Hz, 2H), 1.02-0.96 (m, 6H), 0.95-0.90 (m, 2H), 0.85-0.81 (m, 2H).

4-(4-cyclopropyl-1H-imidazol-1-yl)-5-(4-methylpiperazin-1-yl)picolinic acid (54b)

MS mass calculated for [M+1]$^+$ ($C_{17}H_{21}N_5O_2$) requires m/z, 328.2, LCMS found m/z 328.2.

(R)-4-(4-cyclopropyl-1H-imidazol-1-yl)-5-(2-methylmorpholino)picolinic acid (55b)

MS mass calculated for [M+1]$^+$ ($C_{17}H_{20}N_4O_3$) requires m/z, 329.2, LCMS found m/z 329.2.

(R)-4-(4-cyclopropyl-1H-imidazol-1-yl)-5-(3-hydroxypyrrolidin-1-yl)picolinic acid (57b)

MS mass calculated for [M+1]$^+$ ($C_{16}H_{18}N_4O_3$) requires m/z, 315.1, LCMS found m/z 315.2; $^1$H NMR (400 MHz, DMSO-d6) δ 7.99 (br s, 1H), 7.70 (s, 1H), 7.59 (s, 1H), 7.17 (s, 1H), 4.22 (br s, 1H), 3.19 (br d, J=8.9 Hz, 1H), 3.04 (br s, 2H), 2.74-2.65 (m, 1H), 1.91-1.80 (m, 2H), 1.76 (br s, 1H), 0.84-0.77 (m, 2H), 0.73-0.64 (m, 2H).

5-(azetidin-1-yl)-4-(4-cyclopropyl-1H-imidazol-1-yl)picolinic acid (58b)

$^1$H NMR (400 MHz, DMSO-d$_6$) δ ppm 7.75 (s, 1H) 7.67 (s, 1H) 7.58 (s, 1H) 7.13 (s, 1H) 3.50-3.63 (m, 1H) 3.57 (t, J=7.28 Hz, 3H) 2.15 (quin, J=7.33 Hz, 2H) 1.83 (ddd, J=13.45, 8.49, 5.18 Hz, 1H) 0.75-0.82 (m, 2H) 0.59-0.70 (m, 2H).

5-((1R,4R)-2-oxa-5-azabicyclo[2.2.1]heptan-5-yl)-4-(4-cyclopropyl-1H-imidazol-1-yl)picolinic acid (62b)

MS mass calculated for [M+1]$^+$ ($C_{17}H_{18}N_4O_3$) requires m/z, 327.2, LCMS found m/z 327.2.

4-(4-cyclopropyl-1H-imidazol-1-yl)-5-(3-hydroxy-3-methylpyrrolidin-1-yl)picolinic acid (63b)

MS mass calculated for [M+1]$^+$ ($C_{17}H_{20}N_4O_3$) requires m/z, 329.2, LCMS found m/z 329.2.

Lithium 5-((1S,4S)-2-oxa-5-azabicyclo[2.2.1]heptan-5-yl)-4-(4-cyclopropyl-1H-imidazol-1-yl)picolinate (64b)

MS mass calculated for [M+H]$^+$ ($C_{17}H_{17}LiN_4O_3$) requires m/z 327.1, LCMS found m/z 327.2.

Lithium (S)-4-(4-cyclopropyl-1H-imidazol-1-yl)-5-(3-methylmorpholino)picolinate (65b)

MS mass calculated for [M+H]$^+$ ($C_{17}H_{19}LiN_4O_3$) requires m/z 329.1, LCMS found m/z 329.2.

(S)-4-(4-cyclopropyl-1H-imidazol-1-yl)-5-(2-methylmorpholino)picolinic acid (66b)

MS mass calculated for [M+1]$^+$ ($C_{17}H_{20}N_4O_3$) requires m/z 329.4, LCMS found m/z 329.1.

(R)-4-(4-cyclopropyl-1H-imidazol-1-yl)-5-(3-methylmorpholino)picolinic acid (70b)

MS mass calculated for [M-Li—H]+ ($C_{17}H_{20}N_4O_3$) requires m/z 327.15, MS found m/z 327.0.

Example S36

4-(4-cyclopropyl-1H-imidazol-1-yl)-N-(5,6-dihydrobenzo[f][1,2,4]triazolo[4,3-d][1,4]oxazepin-8-yl)picolinamide (Example 56) was synthesized according to the scheme provided below.

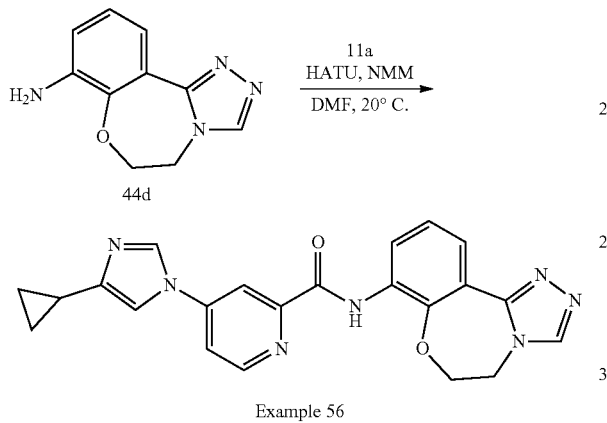

Synthesis of 4-(4-cyclopropyl-1H-imidazol-1-yl)-N-(5,6-dihydrobenzo[f][1,2,4]triazolo[4,3-d][1,4]oxazepin-8-yl)picolinamide (Example 56)

To a solution of 11a (23 mg, 100.33 umol) in DMF (1 mL) was added HATU (45.78 mg, 120.40 umol), NMM (30.45 mg, 301.00 umol) and 5,6-dihydrobenzo[f][1,2,4]triazolo[4,3-d][1,4]oxazepin-8-amine (44d) (20.29 mg, 100.33 umol) at 25° C. The mixture was stirred at 25° C. for 2 h. LCMS showed the reaction was completed. To the mixture was added H₂O (1 mL). Solid precipitated and the mixture was filtered to give crude product. The crude product was purified by prep-HPLC (column: Welch Ultimate AQ-C18 150*30 mm*5 um; mobile phase: [water (0.1% TFA)-ACN]; B %: 15%-45%, 12 min) to give Example 56. MS mass calculated for [M+H]+ ($C_{22}H_{19}N_7O_2$) requires m/z 414.4, LCMS found m/z 414.1. ¹H NMR (400 MHz, DMSO-d6) δ ppm 10.70 (s, 1H) 10.66-10.74 (m, 1H) 9.02 (s, 1H) 8.84 (d, J=5.5 Hz, 1H) 8.68 (s, 1H) 8.53 (dd, J=7.8, 1.4 Hz, 1H) 8.47 (d, J=2.2 Hz, 1H) 8.23 (dd, J=8.3, 1.7 Hz, 1H) 8.03 (dd, J=5.7, 2.4 Hz, 1H) 7.23 (t, J=8.0 Hz, 1H) 4.65 (dd, J=5.0, 2.8 Hz, 2H) 4.54-4.62 (m, 2H) 1.91 (ddd, J=13.2, 8.2, 4.9 Hz, 1H) 0.86-0.94 (m, 2H) 0.70-0.82 (m, 2H).

Example S37

4-(4-cyclopropyl-1H-imidazol-1-yl)-N-(5,6-dihydrobenzo[f]tetrazolo[1,5-d][1,4]oxazepin-8-yl)-5-isopropoxypicolinamide (Example 68) was prepared according to the schemes provided below.

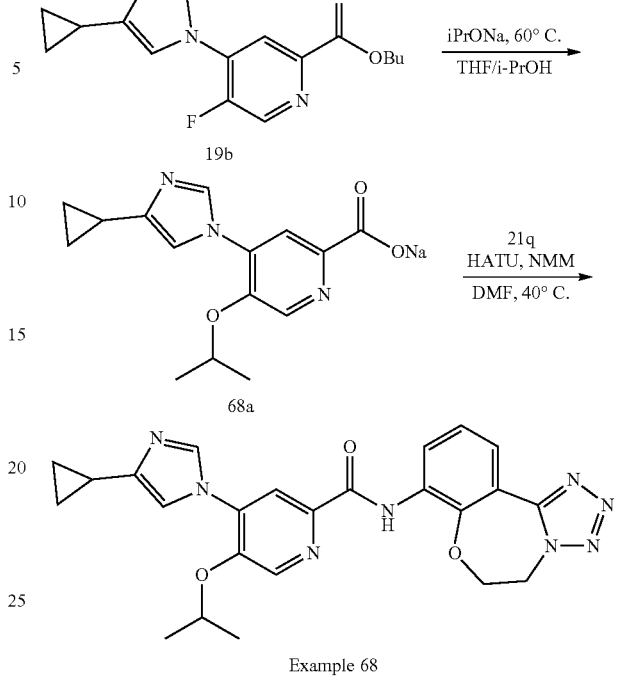

Example 68

Sodium 4-(4-cyclopropyl-1H-imidazol-1-yl)-5-isopropoxypicolinate (68a)

To a solution of butyl 4-(4-cyclopropyl-1H-imidazol-1-yl)-5-fluoropicolinate (19b) (500 mg, 1.65 mmol) in i-PrOH (16 mL) was added the solution of isopropoxysodium (0.3 M, 24.73 mL) in THF/i-PrOH (2:1). The mixture was stirred at 60° C. for 14 hr. LCMS showed the reaction was completed and one main peak with desired MS was detected. The reaction mixture was concentrated under reduced pressure and then purified by prep-HPLC (column: Xtimate C18 10μ 250 mm*50 mm; mobile phase: [water (0.04% HCl)-ACN]; B %: 1%-20%, 20 min) to give 68a. MS mass calculated for [M+H]+ ($C_{15}H_{16}NaN_3O_3$) requires m/z 288.1, LCMS found m/z 287.9. ¹H NMR (400 MHz, METHANOL-d4) δ ppm 9.38 (d, J=1.00 Hz, 1H) 8.79 (d, J=1.00 Hz, 1H) 8.45 (d, J=1.00 Hz, 1H) 7.81 (d, J=1.00 Hz, 1H) 5.11-5.23 (m, 1H) 2.00-2.15 (m, 1H) 1.41-1.52 (m, 6H) 1.09-1.23 (m, 2H) 0.83-1.00 (m, 2H).

Synthesis of 4-(4-cyclopropyl-1H-imidazol-1-yl)-N-(5,6-dihydrobenzo[f]tetrazolo[1,5-d][1,4]oxazepin-8-yl)-5-isopropoxypicolinamide (Example 68)

To a solution of sodium 4-(4-cyclopropyl-1H-imidazol-1-yl)-5-isopropoxypicolinate (68a) (45.66 mg, 147.64 umol) in DMF (1 mL) was added HATU (42.10 mg, 110.73 umol) and NMM (29.87 mg, 295.28 umol, 32.46 uL). Then 5,6-dihydrobenzo[f]tetrazolo[1,5-d][1,4]oxazepin-8-amine (21q) (15 mg, 73.82 umol) was added. The mixture was stirred at 40° C. for 16 h. TLC indicated the reaction was completed and one main spot formed. The residue was diluted with EtOAc (10 mL) and H₂O (10 mL) and then extracted with EtOAc (10 mL*2). The combined organic layers were washed with brine (10 mL), dried over Na₂SO₄, filtered and concentrated under reduced pressure to give a residue. The residue was purified by prep-TLC (SiO₂, ethyl acetate:methanol=10:1) to give 4-(4-cyclopropyl-1H-imidazol-1-yl)-N-(5,6-dihydrobenzo[f]tetrazolo[1,5-d][1,4]oxazepin-8-yl)-5-isopropoxypicolinamide (Example 68). MS mass calculated for [M+H]$^+$ ($C_{24}H_{24}N_8O_3$) requires m/z 473.2, LCMS found m/z 473.1; $^1$H NMR (400 MHz, CHLOROFORM-d) δ ppm 10.55 (br s, 1H) 8.81 (dd, J=7.95, 1.47 Hz, 1H) 8.43 (s, 1H) 8.36 (dd, J=8.13, 1.53 Hz, 1H) 8.24 (s, 1H) 8.13 (d, J=0.98 Hz, 1H) 7.33 (t, J=1.00 Hz, 1H) 7.20 (d, J=0.86 Hz, 1H) 5.01 (t, J=1.00 Hz, 2H) 4.83-4.91 (m, 1H) 4.75 (t, J=1.00 Hz, 2H) 1.90-1.98 (m, 1H) 1.49 (d, J=5.99 Hz, 6H) 0.89-0.95 (m, 2H) 0.84-0.89 (m, 2H).

Example S38

(R)-4-(4-cyclopropyl-1H-imidazol-1-yl)-5-isopropoxy-N-(5-methyl-5,6-dihydrobenzo[f]tetrazolo[1,5-d][1,4]oxazepin-8-yl)picolinamide (Example 69) was synthesized according to the scheme provided below.

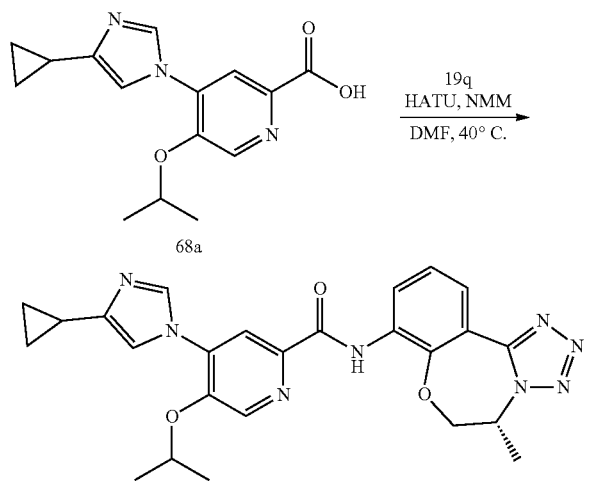

Synthesis of (R)-4-(4-cyclopropyl-1H-imidazol-1-yl)-5-isopropoxy-N-(5-methyl-5,6-dihydrobenzo[f]tetrazolo[1,5-d][1,4]oxazepin-8-yl)picolinamide (Example 69)

To a solution of sodium 4-(4-cyclopropyl-1H-imidazol-1-yl)-5-isopropoxypicolinate (68a) (32.30 mg, 104.42 umol) in DMF (1 mL) was added HATU (43.31 mg, 113.91 umol) and NMM (38.40 mg, 379.69 umol, 41.74 uL). Then (R)-5-methyl-5,6-dihydrobenzo[f]tetrazolo[1,5-d][1,4]oxazepin-8-amine (19q) (20.62 mg, 94.92 umol) was added. The mixture was stirred at 40° C. for 6h. TLC indicated the reaction was completed and one new spot formed. The residue was diluted with EtOAc (10 mL) and H$_2$O (10 mL) and then extracted with EtOAc (10 mL*2). The combined organic layers were washed with brine (10 mL), dried over Na$_2$SO$_4$, filtered and concentrated under reduced pressure to give a residue. The residue was purified by prep-TLC (SiO$_2$, petroleum ether:ethyl acetate=0:1) to give (R)-4-(4-cyclopropyl-1H-imidazol-1-yl)-5-isopropoxy-N-(5-methyl-5,6-dihydrobenzo[f]tetrazolo[1,5-d][1,4]oxazepin-8-yl)-picolinamide (Example 69). MS mass calculated for [M+H]$^+$ ($C_{25}H_{26}N_8O_3$) requires m/z 487.2, LCMS found m/z 487.3; $^1$H NMR (400 MHz, CHLOROFORM-d) δ ppm 10.43 (s, 1H) 8.80 (d, J=6.85 Hz, 1H) 8.30-8.40 (m, 1H) 8.18 (s, 1H) 8.03 (s, 1H) 7.58 (s, 1H) 7.31 (t, J=8.13 Hz, 1H) 7.28-7.28 (m, 1H) 6.90 (s, 1H) 4.95-5.06 (m, 2H) 4.70-4.81 (m, 2H) 4.52-4.60 (m, 1H) 4.12 (s, 1H) 3.96-4.05 (m, 1H) 3.81-3.91 (m, 1H) 3.07 (br d, J=9.29 Hz, 1H) 2.92-2.92 (m, 1H) 2.88-2.94 (m, 1H) 1.93-2.03 (m, 1H) 1.86-1.93 (m, 1H) 0.88-0.97 (m, 2H) 0.79-0.84 (m, 2H).

Example S39

(S)-4-(4-cyclopropyl-1H-imidazol-1-yl)-5-isopropoxy-N-(5-methyl-5,6-dihydrobenzo[f]tetrazolo[1,5-d][1,4]oxazepin-8-yl)picolinamide (Example 71) was synthesized according to the schemes provided below.

(S)-5-methyl-5,6-dihydrobenzo[f][1,2,4]triazolo[4,3-d][1,4]oxazepin-8-amine (71a)

A mixture of (S)-5-methyl-8-nitro-5,6-dihydrobenzo[f][1,2,4]triazolo[4,3-d][1,4]oxazepine (71p) (100 mg, 404.51 umol), Pd/C (499.36 mg, 469.24 umol, 10%) and HCl (12 M, 3.37 uL) in THF (3 mL) was degassed and purged with H$_2$ for 3 times, and then the mixture was stirred at 20° C. for 6 hours under H$_2$ (15 psi). LCMS showed one main peak with desired MS was detected. The reaction mixture was filtered and the filtrate was concentrated under reduced pressure to give crude (S)-5-methyl-5,6-dihydrobenzo[f][1,2,4]triazolo[4,3-d][1,4]oxazepin-8-amine (71a) which was used directly without further purification. MS mass calculated for [M+1]$^+$ ($C_{11}H_{12}N_4O$) requires m/z 217.2, LCMS found m/z 217.9; $^1$H NMR (400 MHz, CHLOROFORM-d) δ=7.99-7.92 (m, 1H), 7.09-7.01 (m, 1H), 6.93-6.85 (m, 1H), 5.22-5.12 (m, 1H), 4.61-4.53 (m, 1H), 4.38-4.30 (m, 1H), 1.76 (d, J=6.8 Hz, 3H).

Synthesis of (S)-4-(4-cyclopropyl-1H-imidazol-1-yl)-5-isopropoxy-N-(5-methyl-5,6-dihydrobenzo[f][1,2,4]triazolo[4,3-d][1,4]oxazepin-8-yl)picolinamide (Example 71)

To a solution of (S)-5-methyl-5,6-dihydrobenzo[f][1,2,4]triazolo[4,3-d][1,4]oxazepin-8-amine (71a) (13.23 mg, 60.90 umol) in DMF (2 mL) was added HATU (34.74 mg, 91.35 umol) and NMM (24.64 mg, 243.60 umol, 26.78 uL). After stirring for 5 minutes, 4-(4-cyclopropyl-1H-imidazol-1-yl)-5-isopropoxypicolinic acid (68a) (37.67 mg, 121.80 umol) was added at 40° C. The resulting mixture was stirred at 40° C. for 6 hours. The reaction mixture was diluted with H$_2$O (5 mL) and extracted with ethyl acetate (10 mL). The organic layer was washed with brine (5 mL*2), dried over anhydrous Na$_2$SO$_4$, filtered and concentrated under reduced pressure to give a residue. The residue was purified by prep-TLC (SiO$_2$, Ethyl acetate:Methanol=10:1) to give Example 71. $^1$H NMR (400 MHz, CHLOROFORM-d) δ=10.63-10.60 (m, 1H), 8.88-8.85 (m, 1H), 8.51 (s, 1H), 8.43-8.39 (m, 1H), 8.32-8.29 (m, 1H), 8.22-8.18 (m, 1H), 7.44-7.33 (m, 1H), 5.37-5.27 (m, 1H), 5.01-4.75 (m, 2H), 4.64-4.55 (m, 1H), 2.04-1.96 (m, 1H), 1.92-1.88 (m, 3H), 1.59-1.53 (m, 6H), 1.05-0.97 (m, 2H), 0.96-0.89 (m, 2H).

Example S40

5-(4-cyclopropyl-1H-imidazol-1-yl)-2-fluoro-4-methyl-N-(5H-spiro[benzo[f]tetrazolo[1,5-d][1,4]oxazepine-6,1'-cyclobutan]-8-yl)benzamide (Example 72) was synthesized according to the schemes provided below.

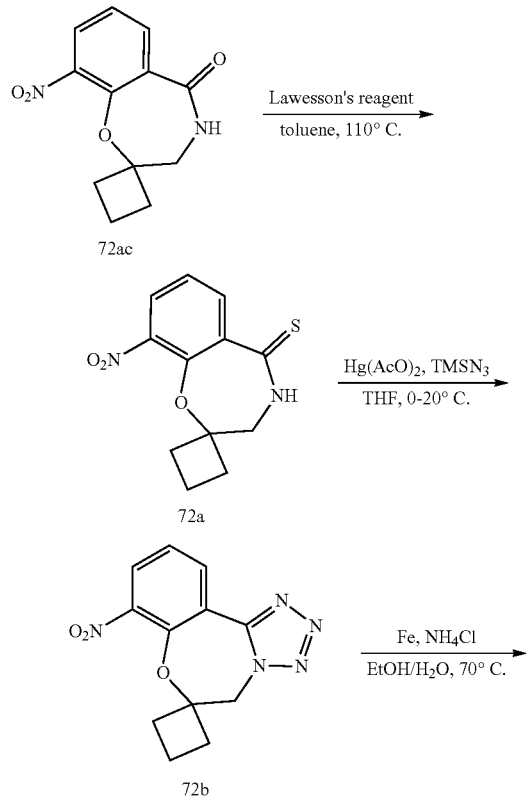

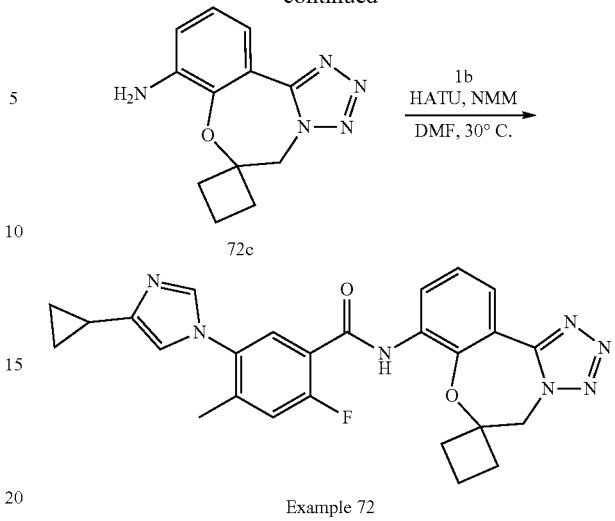

Example 72

9-nitro-3H-spiro[benzo[f][1,4]oxazepine-2,1'-cyclobutane]-5(4H)-thione (72a)

To a solution of 9-nitro-3H-spiro[benzo[f][1,4]oxazepine-2,1'-cyclobutan]-5(4H)-one (72ac) (380 mg, 1.53 mmol) in toluene (20 mL) was added Lawesson's reagent (371.50 mg, 918.49 umol) at 20° C. under N$_2$. The mixture was heated to 110° C. and stirred for 6 hours. TLC (petroleum ether:ethyl acetate=1:1, R$_f$=0.5) showed the starting material was consumed and one main spot with lower polarity was detected. LCMS showed one main peak with desired MS. The reaction mixture was concentrated in vacuo. The residue was diluted with water (5 mL) and extracted with EtOAc (5 mL*3), and the combined organic layers were washed with brine (10 mL*2), dried over Na$_2$SO$_4$, filtered and concentrated. The residue was purified by flash silica gel chromatography (SiO$_2$, Petroleum ether:Ethyl acetate from 40:1 to 3:1) to give 72a. $^1$H NMR (400 MHz, CHLOROFORM-d) δ=8.76 (br s, 1H), 8.25 (dd, J=1.7, 7.9 Hz, 1H), 7.80 (dd, J=1.7, 8.1 Hz, 1H), 7.25-7.22 (m, 1H), 3.58 (d, J=6.4 Hz, 2H), 2.65-2.56 (m, 2H), 2.17 (tdd, J=2.9, 8.2, 10.7 Hz, 2H), 1.97-1.87 (m, 1H), 1.54-1.47 (m, 1H).

8-nitro-5H-spiro[benzo[f]tetrazolo[1,5-d][1,4]oxazepine-6,1'-cyclobutane] (72b)

To a solution of 9-nitro-3H-spiro[benzo[f][1,4]oxazepine-2,1'-cyclobutane]-5(4H)-thione (72a) (100 mg, 378.36 umol) in THF (5 mL) was added Hg(OAc)$_2$ (144.69 mg, 454.03 umol) and TMSN$_3$ (87.18 mg, 756.72 umol) at 20° C. and the mixture was stirred for 4 hours. TLC (Petroleum ether:Ethyl acetate=3:1, R$_f$=0.5) showed starting material was consumed and one main spot was detected. Saturated NaHCO$_3$ solution was added into the reaction mixture. The mixture was concentrated under reduced pressure to remove solvent. The residue was diluted with water (5 mL) and extracted with EtOAc (5 mL*3). The combined organic layers were washed with brine (10 mL*2), dried over sodium sulfate, filtered and concentrated under reduced pressure to give 8-nitro-5H-spiro[benzo[f]tetrazolo[1,5-d][1,4]oxazepine-6,1'-cyclobutane] (72b). $^1$H NMR (400 MHz, CHLOROFORM-d) δ=8.78 (dd, J=1.5, 8.1 Hz, 1H), 7.91-7.85 (m, 1H), 7.36 (t, J=8.0 Hz, 1H), 4.98 (s, 2H), 2.55-2.42 (m, 2H), 2.14-2.09 (m, 2H), 1.89-1.83 (m, 2H).

211

5H-spiro[benzo[f]tetrazolo[1,5-d][1,4]oxazepine-6,1'-cyclobutan]-8-amine (72c)

To a solution of 8-nitro-5H-spiro[benzo[f]tetrazolo[1,5-d][1,4]oxazepine-6,1'-cyclobutane] (72b) (20 mg, 73.19 umol) in EtOH (5 mL) and H$_2$O (1 mL) was added Fe (20.44 mg, 365.97 umol) and NH$_4$Cl (39.15 mg, 731.94 umol) at 20° C. Then the mixture was heated to 70° C. and stirred for 2 hours. The reaction mixture was filtered through a Celite pad, the Celite pad was rinsed with EtOH (10 mL) and EtOAc (10 mL). The filtrate was concentrated and the residue was purified by prep-TLC (SiO$_2$, PE:EtOAc=1:2, R$_f$=0.4) to give 5H-spiro[benzo[f]tetrazolo[1,5-d][1,4]oxazepine-6,1'-cyclobutan]-8-amine (72c).

Synthesis of 5-(4-cyclopropyl-1H-imidazol-1-yl)-2-fluoro-4-methyl-N-(5H-spiro[benzo[f]tetrazolo[1,5-d][1,4]oxazepine-6,1'-cyclobutan]-8-yl)benzamide (Example 72)

To a solution of 5-(4-cyclopropyl-1H-imidazol-1-yl)-2-fluoro-4-methylbenzoic acid (1b) (23.08 mg, 61.66 umol, TFA) in DMF (4 mL) was added HATU (35.17 mg, 92.49 umol) and NMM (24.95 mg, 246.65 umol, 27.12 uL) at 30° C. Then 5H-spiro[benzo[f]tetrazolo[1,5-d][1,4]oxazepine-6,1'-cyclobutan]-8-amine (72c) (15 mg, 61.66 umol) was added and the mixture was stirred for 12 hours. LCMS showed one main peak with desired MS. TLC (DCM:MeOH=10:1, R$_f$=0.7) indicated one main new spot with lower polarity. The reaction mixture was concentrated. The residue was diluted with water (5 mL) and extracted with EtOAc (5 mL*3). The combined organic layers were washed with brine (3 mL*2), dried over sodium sulfate, filtered and concentrated under reduced pressure to give a residue. The residue was purified by prep-HPLC (neutral condition: column: Waters Xbridge 150*25 5u; mobile phase: [water (10 mM NH$_4$HCO$_3$)-ACN]; B %: 35%-65%, 7 min) and lyophilized to afford Example 72. MS mass calculated for [M+1]$^+$ (C$_{26}$H$_{24}$FN$_7$O$_2$) requires m/z 486.20, LCMS found m/z 486.3; $^1$H NMR (400 MHz, CHLOROFORM-d) δ=9.54 (br d, J=16.5 Hz, 1H), 8.81 (d, J=7.9 Hz, 1H), 8.30 (d, J=8.2 Hz, 1H), 8.13 (d, J=7.5 Hz, 1H), 7.46 (s, 1H), 7.32-7.28 (m, 1H), 7.23 (d, J=12.8 Hz, 1H), 6.81 (s, 1H), 4.97 (s, 2H), 2.45-2.34 (m, 2H), 2.31 (s, 3H), 2.21-2.01 (m, 4H), 1.97-1.87 (m, 2H), 0.94-0.88 (m, 2H), 0.87-0.82 (m, 2H).

Example S41

4-(4-cyclopropyl-1H-imidazol-1-yl)-N-(5,6-dihydrobenzo[f][1,2,4]triazolo[4,3-d][1,4]oxazepin-8-yl)-5-isopropoxypicolinamide (Example 73) was synthesized according to the scheme provided below.

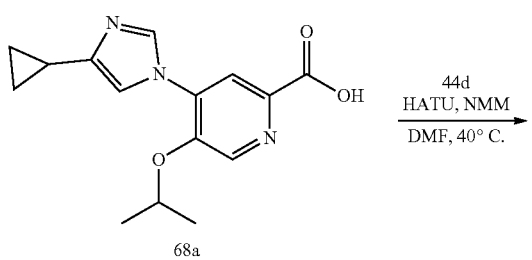

68a

212

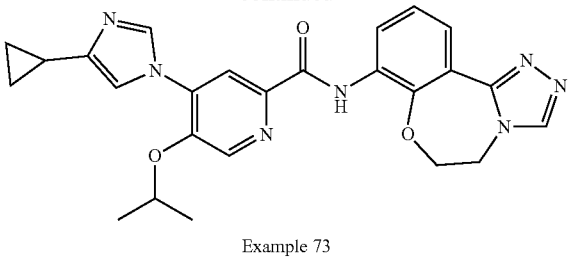

Example 73

Synthesis of 4-(4-cyclopropyl-1H-imidazol-1-yl)-N-(5,6-dihydrobenzo[f][1,2,4]triazolo[4,3-d][1,4]oxazepin-8-yl)-5-isopropoxypicolinamide (Example 73)

To a solution of 4-(4-cyclopropyl-1H-imidazol-1-yl)-5-isopropoxypicolinic acid (68a) (23.55 mg, 76.15 umol) in DMF (1.5 mL) was added HATU (39.49 mg, 103.85 umol) and NMM (28.01 mg, 276.92 umol, 30.45 uL). Then 5,6-dihydrobenzo[f][1,2,4]triazolo[4,3-d][1,4]oxazepin-8-amine (44d) (14 mg, 69.23 umol) was added to the mixture. The mixture was stirred at 40° C. for 6 hours. LCMS showed one main peak with desired mass was detected. The reaction mixture was diluted with H$_2$O (5 mL) and extracted with ethyl acetate (10 mL). The combined organic layers were washed with brine (5 mL*2), dried over anhydrous Na$_2$SO$_4$, filtered and concentrated under reduced pressure to give a residue. The residue was purified by prep-HPLC (neutral condition, column: Xamide 150*30 mm 5 um; mobile phase: [water (10 mM NH$_4$HCO$_3$)-ACN]; B %: 30%-50%, 7 min) to give Example 73. MS mass calculated for [M+1]$^+$ (C$_{25}$H$_{25}$N$_7$O$_3$) requires m/z 472.5, LCMS found m/z 472.3. $^1$H NMR (400 MHz, CHLOROFORM-d) δ=10.52 (s, 1H), 8.70 (br d, J=7.9 Hz, 1H), 8.45-8.39 (m, 2H), 8.25 (d, J=10.4 Hz, 2H), 8.12 (s, 1H), 7.25-7.18 (m, 1H), 7.05-7.05 (m, 1H), 4.91-4.80 (m, 1H), 4.73-4.67 (m, 2H), 4.57 (br d, J=4.0 Hz, 2H), 1.98-1.89 (m, 1H), 1.48 (d, J=6.2 Hz, 6H), 0.96-0.89 (m, 2H), 0.88-0.82 (m, 2H).

Example S42

N-(1-bromo-5,6-dihydrobenzo[f]imidazo[1,5-d][1,4]oxazepin-8-yl)-5-(4-cyclopropyl-1H-imidazol-1-yl)-2-fluoro-4-methylbenzamide (Example 74) was synthesized according to the schemes provided below.

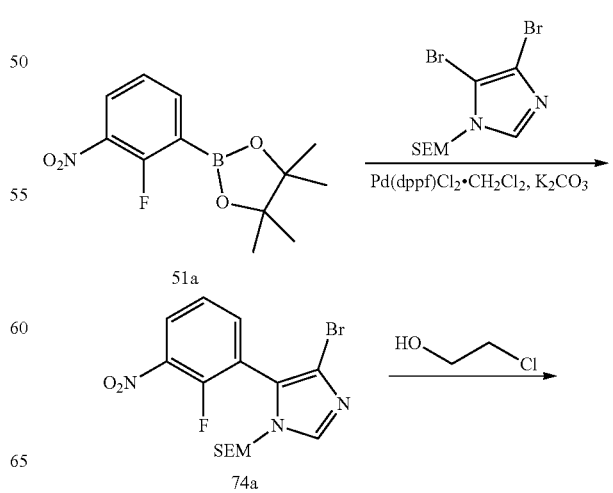

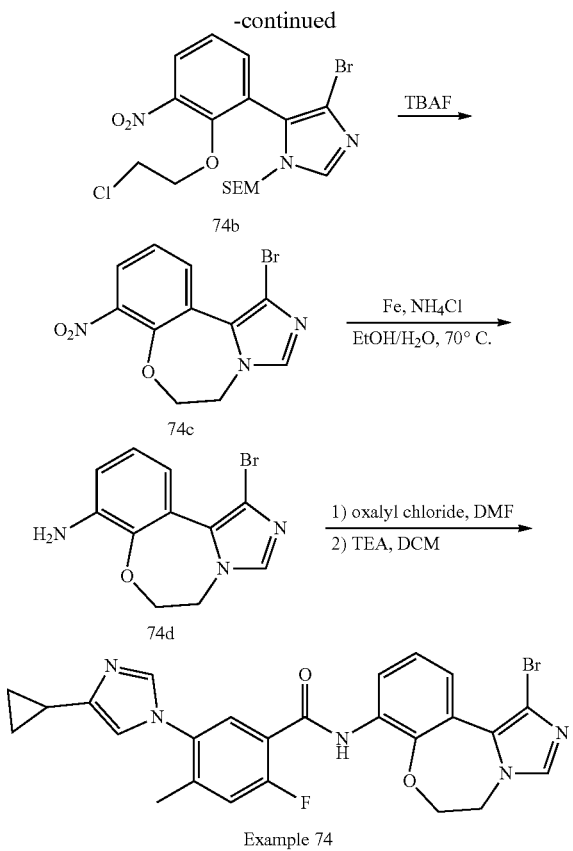

Example 74

4-bromo-5-(2-fluoro-3-nitrophenyl)-1-((2-(trimethylsilyl)ethoxy)methyl)-1H-imidazole (74a)

To a mixture of 2-(2-fluoro-3-nitrophenyl)-4,4,5,5-tetramethyl-1,3,2-dioxaborolane (51a) (476.94 mg, 1.79 mmol) and 4,5-dibromo-1-((2-(trimethylsilyl)ethoxy)methyl)-1H-imidazole (530 mg, 1.49 mmol) in dioxane (12 mL) was added $K_2CO_3$ (617.06 mg, 4.46 mmol) and Pd(dppf)Cl$_2$ CH$_2$Cl$_2$ (121.53 mg, 148.82 umol) under N$_2$. The mixture was stirred at 90° C. for 16 hours. The reaction mixture was concentrated under reduced pressure to remove most of the dioxane, the residue was poured into water (10 mL) and extracted with ethyl acetate (20 mL*3). The combined organic layers were washed with brine (15 mL*2), and dried with anhydrous Na$_2$SO$_4$, filtered and concentrated in vacuo. The residue was purified by column chromatography (SiO$_2$, Petroleum ether:Ethyl acetate=50:1 to 5:1) to give 74a. MS mass calculated for [M+1]$^+$ (C$_{15}$H$_{19}$BrFN$_3$O$_3$Si) requires m/z, 415.1/417.1, LCMS found m/z 416.1/418.1.

4-bromo-5-(2-(2-chloroethoxy)-3-nitrophenyl)-1-((2-(trimethylsilyl)ethoxy)methyl)-1H-imidazole (74b)

To a mixture of 4-bromo-5-(2-fluoro-3-nitrophenyl)-1-((2-(trimethylsilyl)ethoxy)methyl)-1H-imidazole (74a) (100 mg, 240.20 umol) and NaH (24.02 mg, 600.50 umol, 60% purity) in THF (4 mL) was added 4-bromo-5-(2-(2-chloroethoxy)-3-nitrophenyl)-1-((2-(trimethylsilyl)ethoxy)methyl)-1H-imidazole (29.01 mg, 360.30 umol) under N$_2$. The mixture was stirred at 0° C. for 30 min, then warmed to 25° C. and stirred for 2.5h. LCMS showed the starting material was consumed completely and desired mass was detected. The reaction mixture was quenched by addition of H$_2$O (2 mL). Then the reaction mixture was diluted with water (5 mL) and extracted with ethyl acetate (15 mL*3). The combined organic layers were washed with brine (15 mL*3), dried with anhydrous Na$_2$SO$_4$, filtered and concentrated in vacuo. The residue was purified by prep-TLC (petroleum ether:ethyl acetate=1:1 R$_f$=0.6) to give 74b. MS mass calculated for [M+1]$^+$ (C$_{17}$H$_{23}$BrClN$_3$O$_4$Si) requires m/z, 475.03, LCMS found m/z 476.1 478.1; $^1$H NMR (400 MHz, CHLOROFORM-d) δ 7.97 (d, J=8.31 Hz, 1H) 7.71 (s, 1H) 7.65 (d, J=7.82 Hz, 1H) 7.41 (t, J=7.83 Hz, 1H) 5.30-5.17 (m, 2H) 4.26-4.19 (m, 1H) 3.72-3.64 (m, 2H) 3.53-3.46 (m, 1H) 3.36-3.24 (m, 2H) 0.77-0.69 (m, 2H) −0.08 (s, 9H).

1-bromo-8-nitro-5,6-dihydrobenzo[f]imidazo[1,5-d][1,4]oxazepine (74c)

To a mixture of 4-bromo-5-(2-(2-chloroethoxy)-3-nitrophenyl)-1-((2-(trimethylsilyl)ethoxy)methyl)-1H-imidazole (74b) (100 mg, 209.72 umol) in THF (2 mL) was added TBAF (1 M, 1.26 mL) under N$_2$. The mixture was stirred at 50° C. for 16 hr. The reaction mixture was poured into water (5 mL) and extracted with ethyl acetate (10 mL*3). The combined organic layers were washed with brine (10 mL*2), dried with anhydrous Na$_2$SO$_4$, filtered and concentrated in vacuo. The residue was purified by prep-TLC (Dichloromethane:Methanol=10:1) to give 74c. $^1$H NMR (400 MHz, CHLOROFORM-d) δ 7.99 (d, J=7.89 Hz, 1H) 7.85 (d, J=8.33 Hz, 1H) 7.64 (s, 1H) 7.41-7.35 (m, 1H) 4.77 (t, J=5.92 Hz, 2H) 4.27 (t, J=5.92 Hz, 2H).

1-bromo-5,6-dihydrobenzo[f]imidazo[1,5-d][1,4]oxazepin-8-amine (74d)

To a mixture of 1-bromo-8-nitro-5,6-dihydrobenzo[f]imidazo[1,5-d][1,4]oxazepine (74c) (15 mg, 48.37 umol) in EtOH (1 mL) and H$_2$O (0.2 mL) was added NH$_4$Cl (25.87 mg, 483.71 umol) and Fe (13.51 mg, 241.85 umol) under N$_2$. The mixture was stirred at 70° C. for 2 hours. LCMS showed desired MS. The reaction mixture was filtered, and the filtrate was added water (2 mL) and extracted with ethyl acetate (5 mL*3). The combined organic layers were washed with water (5 mL*2), brine (5 mL*2), dried with anhydrous Na$_2$SO$_4$ and concentrated in vacuo. The residue was purified by prep-TLC (SiO$_2$, dichloromethane:methanol=10:1) to give 74d. MS mass calculated for [M+1]$^+$ (C$_{11}$H$_{10}$BrN$_3$O) requires m/z, 279.00, LCMS found m/z 280.1 282.1.

Synthesis of N-(1-bromo-5,6-dihydrobenzo[f]imidazo[1,5-d][1,4]oxazepin-8-yl)-5-(4-cyclopropyl-1H-imidazol-1-yl)-2-fluoro-4-methylbenzamide (Example 74)

To a mixture of 5-(4-cyclopropyl-1H-imidazol-1-yl)-2-fluoro-4-methylbenzoic acid (1b) (50 mg, 192.11 umol) in DCM (2 mL) was added DMF (1.68 mg, 23.05 umol, 1.77 uL) and oxalyl chloride (29.26 mg, 230.54 umol, 20.18 uL) under N$_2$. The mixture was stirred at 25° C. for 2 hours. The reaction mixture was concentrated under reduced pressure to give a solid. To a mixture of 1-bromo-5,6-dihydrobenzo[f]imidazo[1,5-d][1,4]oxazepin-8-amine (74d) (9.5 mg, 33.91 umol, 1 eq) and TEA (10.30 mg, 101.74 umol, 14.16 uL, 3 eq) in DCM (0.7 mL) was added the prepared above acyl chloride (37.81 mg, 135.66 umol, 4 eq) in portions under N$_2$. The mixture was stirred at 25° C. for 4 hours The reaction mixture was washed with saturated sodium bicarbonate solution (2 mL), the aqueous phase was extracted with ethyl acetate (5 mL*3). The combined organic layers were washed with water (5 mL*2), brine (5 mL*2), dried with anhydrous Na$_2$SO$_4$ and concentrated in vacuo. The residue was purified by prep-TLC (SiO$_2$, DCM:MeOH=10:1) to give Example 74. MS mass calculated for [M+1]$^+$ (C$_{25}$H$_{21}$BrFN$_5$O$_2$) requires m/z, 521.1/523.1, LCMS found m/z 522.1/524.1 $^1$H NMR (400 MHz, CHLOROFORM-d) δ 9.29 (br d, J=15.66 Hz, 1H) 8.56 (d, J=8.38 Hz, 1H) 8.08 (d, J=7.28 Hz, 1H) 7.59 (s, 1H) 7.54 (dd, J=7.83, 1.43 Hz, 1H) 7.45 (s, 1H) 7.30 (t, J=8.05 Hz, 1H) 7.18 (d, J=12.13 Hz, 1H) 6.80 (s, 1H) 4.66 (t, J=5.73 Hz, 2H) 4.24 (t, J=5.73 Hz, 2H) 2.29 (s, 3H) 1.95-1.88 (m, 1H) 0.94-0.88 (m, 2H) 0.86-0.82 (m, 2H).

Example S43

4-(4-cyclopropyl-1H-imidazol-1-yl)-N—((R)-5-methyl-5,6-dihydrobenzo[f]tetrazolo[1,5-d][1,4]oxazepin-8-yl)-5-((R)-2-methylmorpholino)picolinamide (Example 75) was synthesized according to the scheme provided below.

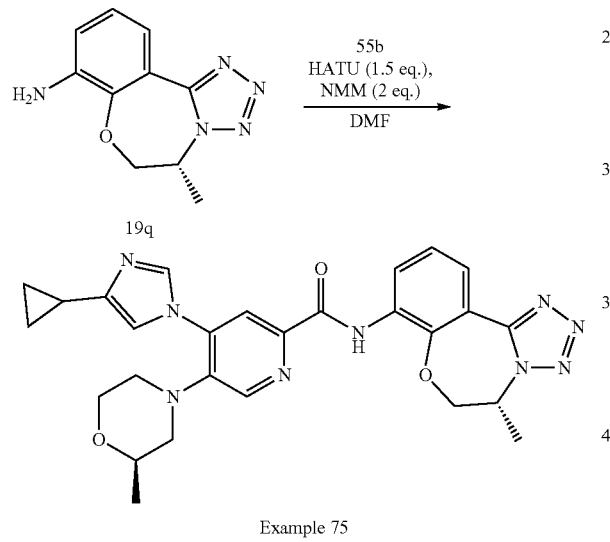

Example 75

Synthesis of 4-(4-cyclopropyl-1H-imidazol-1-yl)-N—((R)-5-methyl-5,6-dihydrobenzo[f]tetrazolo[1,5-d][1,4]oxazepin-8-yl)-5-((R)-2-methylmorpholino) picolinamide (Example 75)

To a solution of lithium (R)-4-(4-cyclopropyl-1H-imidazol-1-yl)-5-(2-methylmorpholino)picolinate (55b) (36.93 mg, 110.48 umol) in DMF (1 mL) was added HATU (42.01 mg, 110.48 umol) and NMM (18.63 mg, 184.14 umol, 20.25 uL). Then (R)-5-methyl-5,6-dihydrobenzo[f]tetrazolo[1,5-d][1,4]oxazepin-8-amine (19q) (20 mg, 92.07 umol) was added to the mixture. The mixture was stirred at 40° C. for 4 hr. LCMS showed one main peak with desired MS. The reaction mixture was concentrated under reduced pressure. The residue was diluted with water (5 mL) and extracted with EtOAc (5 mL*3). The combined organic layers were washed with brine (10 mL*2), dried over Na$_2$SO$_4$, filtered and concentrated under reduced pressure to give a residue which was purified by prep-HPLC (TFA condition, column: Welch Ultimate AQ-C18 150*30 mm*5 um; mobile phase: [water (0.1% TFA)-ACN]; B %: 25%-55%, 12 min) to give Example 75. MS mass calculated for [M+H]$^+$ (C$_{27}$H$_{29}$N$_9$O$_3$) requires m/z 528.24, MS found m/z 528.30; $^1$H NMR (400 MHz, CHLOROFORM-d) δ=10.47 (s, 1H), 9.08 (br s, 1H), 8.74 (br d, J=7.7 Hz, 1H), 8.53 (s, 1H), 8.31 (d, J=8.2 Hz, 1H), 8.13 (br s, 1H), 7.33-7.28 (m, 1H), 7.25 (s, 1H), 5.28-5.20 (m, 1H), 4.71 (dd, J=4.3, 13.1 Hz, 1H), 4.51 (br d, J=12.6 Hz, 1H), 3.93 (br d, J=11.0 Hz, 1H), 3.78-3.69 (m, 2H), 3.04-2.95 (m, 1H), 2.86 (br d, J=11.5 Hz, 1H), 2.79-2.68 (m, 2H), 2.07 (br s, 1H), 1.82 (d, J=6.8 Hz, 3H), 1.22-1.12 (m, 5H), 0.93 (br d, J=4.6 Hz, 2H).

Example S44

4-(4-cyclopropyl-1H-imidazol-1-yl)-N—((S)-5-methyl-5,6-dihydrobenzo[f]tetrazolo[1,5-d][1,4]oxazepin-8-yl)-5-((R)-2-methylmorpholino)picolinamide (Example 76) was synthesized according to the scheme provided below.

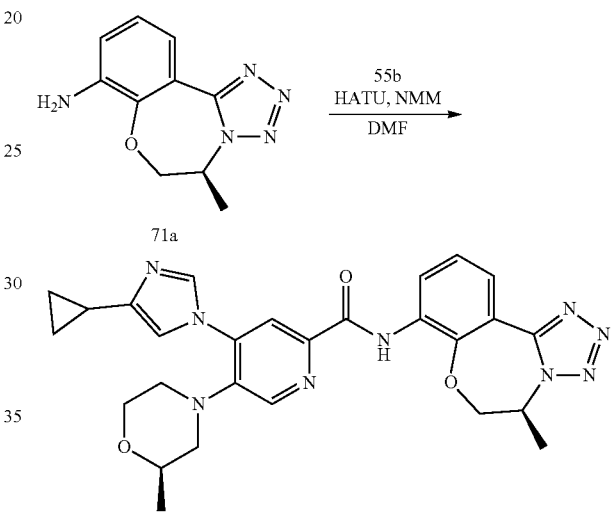

Example 76

Synthesis of 4-(4-cyclopropyl-1H-imidazol-1-yl)-N—((S)-5-methyl-5,6-dihydrobenzo[f]tetrazolo[1,5-d][1,4]oxazepin-8-yl)-5-((R)-2-methylmorpholino) picolinamide (Example 76)

To a solution of (R)-4-(4-cyclopropyl-1H-imidazol-1-yl)-5-(2-methylmorpholino)picolinic acid (55b) (20 mg, 92.07 umol) in DMF (1 mL) was added HATU (52.51 mg, 138.10 umol) and NMM (18.63 mg, 184.14 umol, 20.24 uL). After that, (S)-5-methyl-5,6-dihydrobenzo[f][1,2,4]triazolo[4,3-d][1,4]oxazepin-8-amine (71a) (36.93 mg, 110.48 umol) was added to the mixture. The mixture was stirred at 40° C. for 6 hours. LCMS showed one main peak with desired mass. The reaction was concentrated in vacuo. The residue was purified by prep-HPLC (TFA condition, column: Nano-Micro UniSil 5-100 C18 ULTRA 100*250 mm 5 um; mobile phase: [water (0.1% TFA)-ACN]; B %: 20%-50%, 10 min) to give Example 76. MS mass calculated for [M+1]$^+$ (C$_{27}$H$_{29}$N$_9$O$_3$) requires m/z 528.6, LCMS found m/z 528.3. $^1$H NMR (400 MHz, CHLOROFORM-d) δ=10.48 (s, 1H), 9.04 (s, 1H), 8.78-8.73 (m, 1H), 8.53 (s, 1H), 8.33 (dd, J=1.4, 8.0 Hz, 1H), 8.16 (s, 1H), 7.30 (t, J=8.2 Hz, 1H), 7.24 (s, 1H), 5.29-5.20 (m, 1H), 4.70 (dd, J=4.5, 13.1 Hz, 1H), 4.55-4.48 (m, 1H), 3.93 (br d, J=10.4 Hz, 1H), 3.79-3.68 (m, 2H), 2.99 (dt, J=2.8, 11.6 Hz, 1H), 2.86 (br d, J=11.2 Hz, 1H), 2.79-2.66 (m, 2H), 2.11-2.02 (m, 1H), 1.83 (d, J=6.8 Hz, 3H), 1.22-1.17 (m, 3H), 1.17-1.17 (m, 1H), 1.17-1.12 (m, 1H), 0.96-0.90 (m, 2H).

Example S45

4-(4-cyclopropyl-1H-imidazol-1-yl)-5-((R)-3-hydroxy-pyrrolidin-1-yl)-N—((R)-5-methyl-5,6-dihydrobenzo[f]tetrazolo[1,5-d][1,4]oxazepin-8-yl)picolinamide (Example 77) was synthesized according to the scheme provided below.

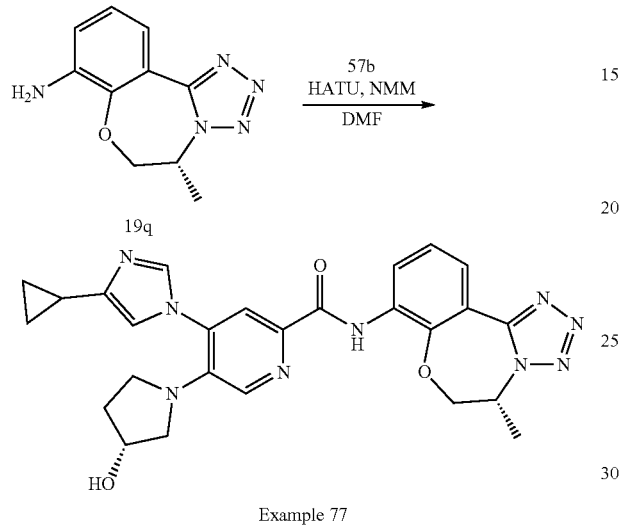

Example 77

Synthesis of 4-(4-cyclopropyl-1H-imidazol-1-yl)-5-((R)-3-hydroxypyrrolidin-1-yl)-N—((R)-5-methyl-5,6-dihydrobenzo[f]tetrazolo[1,5-d][1,4]oxazepin-8-yl)picolinamide (Example 77)

To a mixture of (R)-4-(4-cyclopropyl-1H-imidazol-1-yl)-5-(3-hydroxypyrrolidin-1-yl)picolinic acid (57b) (47.03 mg, 149.61 umol) and HATU (87.52 mg, 230.17 umol) in DMF (1 mL) was added NMM (58.20 mg, 575.44 umol, 63.26 uL) and (R)-5-methyl-5,6-dihydrobenzo[f]tetrazolo[1,5-d][1,4]oxazepin-8-amine (19q) (25 mg, 115.09 umol) under $N_2$. The mixture was stirred at 40° C. for 5 hours. The reaction mixture was diluted with ethyl acetate (10 mL) and washed with water (10 mL*2). The organic phase was washed with brine (10 mL*2), dried with anhydrous $Na_2SO_4$, filtered and concentrated in vacuo. The residue was purified by prep-TLC ($SiO_2$, DCM:MeOH=10:1) to give Example 77. MS mass calculated for [M+1]$^+$ ($C_{26}H_{27}N_9O_3$) requires m/z 514.2, LCMS found m/z 514.2; $^1$H NMR (400 MHz, DMSO-d6) δ 10.42 (s, 1H), 8.64 (dd, J=1.5, 8.1 Hz, 1H), 8.33 (s, 1H), 8.17 (dd, J=1.5, 8.1 Hz, 1H), 7.76 (s, 2H), 7.32 (t, J=8.1 Hz, 1H), 7.24 (d, J=1.1 Hz, 1H), 5.39-5.26 (m, 1H), 5.00 (br s, 1H), 4.81-4.72 (m, 1H), 4.68-4.61 (m, 1H), 4.27 (br s, 1H), 3.25-3.15 (m, 3H), 2.83 (br d, J=11.0 Hz, 1H), 1.95-1.77 (m, 3H), 1.67 (d, J=6.8 Hz, 3H), 0.87-0.79 (m, 2H), 0.75-0.65 (m, 2H).

Example S46

4-(4-cyclopropyl-1H-imidazol-1-yl)-5-((R)-3-hydroxy-pyrrolidin-1-yl)-N—((S)-5-methyl-5,6-dihydrobenzo[f]tetrazolo[1,5-d][1,4]oxazepin-8-yl)picolinamide (Example 78) was synthesized according to the scheme provided below.

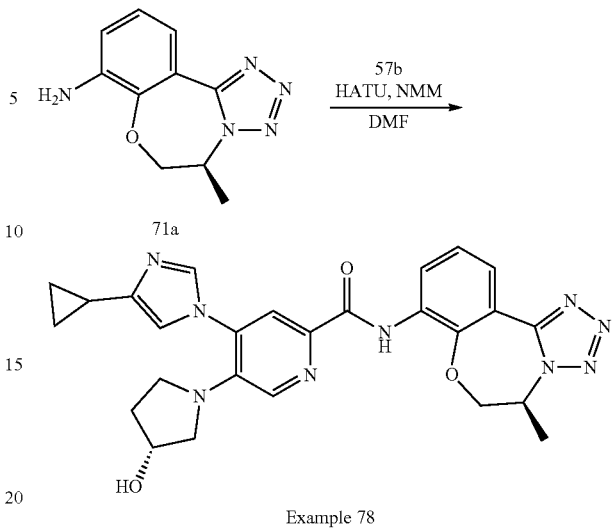

Example 78

Synthesis of 4-(4-cyclopropyl-1H-imidazol-1-yl)-5-((R)-3-hydroxypyrrolidin-1-yl)-N—((S)-5-methyl-5,6-dihydrobenzo[f]tetrazolo[1,5-d][1,4]oxazepin-8-yl)picolinamide (Example 78)

To a mixture of (R)-4-(4-cyclopropyl-1H-imidazol-1-yl)-5-(3-hydroxypyrrolidin-1-yl)picolinic acid (57b) (65.12 mg, 207.16 umol) in DMF (1 mL) was added HATU (105.02 mg, 276.21 umol), NMM (69.85 mg, 690.52 umol) and (S)-5-methyl-5,6-dihydrobenzo[f]tetrazolo[1,5-d][1,4]oxazepin-8-amine (71a) (30 mg, 138.10 umol) under $N_2$. The mixture was stirred at 40° C. for 2 hours. LCMS showed desired mass. The reaction mixture was poured into water (5 mL) and the mixture was extracted with ethyl acetate (10 mL*3). The combined organic layers were washed with water (10 mL*2), brine (10 mL*2), dried with anhydrous $Na_2SO_4$, filtered and concentrated in vacuo. The residue was purified by prep-TLC ($SiO_2$, Dichloromethane:Methanol=10:1) to give Example 78. MS mass calculated for [M+1]$^+$ ($C_{26}H_{27}N_9O_3$) requires m/z, 513.22, LCMS found m/z 514.2 $^1$H NMR (400 MHz, DMSO-d$_6$) δ 10.41 (s, 1H) 8.63 (dd, J=7.82, 1.47 Hz, 1H) 8.32 (s, 1H) 8.16 (dd, J=8.07, 1.71 Hz, 1H) 7.75 (s, 2H) 7.31 (t, J=8.31 Hz, 1H) 7.23 (d, J=0.98 Hz, 1H) 5.35-5.24 (m, 1H) 4.97 (d, J=3.91 Hz, 1H) 4.78-4.70 (m, 1H) 4.67-4.60 (m, 1H) 4.26 (br s, 1H) 3.23-3.14 (m, 2H) 2.82 (br d, J=10.76 Hz, 1H) 1.91-1.76 (m, 3H) 1.66 (d, J=6.85 Hz, 3H) 0.79-0.84 (m, 2H) 0.74-0.65 (m, 2H).

BIOLOGICAL EXAMPLES

Example B1. RBC Kinase Assay Protocol

Base Reaction buffer: 20 mM Hepes (pH 7.5), 10 mM MgCl2, 1 mM EGTA, 0.02% Brij35, 0.02 mg/ml BSA, 0.1 mM Na3VO4, 2 mM DTT, and 1% DMSO were used for the assay.

Myelin base protein (MPB) was prepared in freshly prepared Base Reaction Buffer. 20 ng of ASK1 kinase was delivered into the substrate solution and gently mixed. Compounds in DMSO were delivered into the kinase reaction mixture (final DMSO concentration 1%). Commercially available 33P-ATP was delivered into the reaction mixture to initiate the reaction. The kinase reaction was incubated for 120 min. at room temperature. Reactions were spotted onto P81 ion exchange paper (Whatman #3698-915). Filters were washed extensively in 0.75% Phosphoric acid. Radioactivity on filters was read, and $IC_{50}$ values were determined. The $IC_{50}$ values of certain compounds are provided in the table below (Table 2).

TABLE 2

| Example | IC50 (uM) |
|---|---|
| 1 | 0.0058 |
| 2 | 0.0091 |
| 3 | 0.0057 |
| 4 | 0.0057 |
| 5 | 0.0058 |
| 6 | 0.0077 |
| 7 | 0.0085 |
| 8 | 0.0117 |
| 9 | 0.0056 |
| 10 | 0.0005 |
| 11 | 0.0054 |
| 12 | 0.0047 |
| 13 | 0.0052 |
| 14 | 0.0042 |
| 15 | 0.0058 |
| 16 | 0.0052 |
| 17 | 0.0109 |
| 18 | 0.0116 |
| 19 | 0.0022 |
| 20 | 0.0060 |
| 21 | 0.0060 |
| 22 | 0.0006 |
| 23 | 0.0009 |
| 24 | 0.0062 |
| 25 | 0.0033 |
| 26 | 0.0080 |
| 27 | 0.0068 |
| 28 | 0.0045 |
| 29 | 0.0041 |
| 30 | 0.0045 |
| 31 | 0.0057 |
| 32 | 0.0031 |
| 33 | 0.0041 |
| 34 | 0.0041 |
| 35 | 0.0025 |
| 36 | 0.0056 |
| 37 | 0.0005 |
| 38 | 0.0006 |
| 39 | 0.0055 |
| 40 | 0.0005 |
| 41 | 0.0057 |
| 42 | 0.0168 |
| 43 | 0.0009 |
| 44 | 0.0156 |
| 45 | 0.0053 |
| 46 | 0.0151 |
| 47 | 0.0068 |
| 48 | 0.0051 |
| 49 | 0.0247 |
| 50 | 0.0039 |
| 51 | 0.3070 |
| 52 | 0.0059 |
| 53 | 0.0064 |
| 54 | 0.0059 |
| 55 | 0.0021 |
| 56 | 0.0352 |
| 57 | 0.0047 |
| 58 | 0.0032 |
| 59 | 0.0042 |
| 60 | 0.0069 |
| 61 | 0.0035 |
| 62 | 0.0051 |
| 63 | 0.0027 |
| 64 | 0.0039 |
| 65 | 0.0033 |
| 66 | 0.0060 |
| 67 | 0.0026 |
| 68 | 0.0018 |
| 69 | 0.0041 |

TABLE 2-continued

| Example | IC50 (uM) |
|---|---|
| 70 | 0.0022 |
| 71 | 0.0053 |
| 72 | 0.0116 |
| 73 | 0.0058 |
| 74 | 0.0398 |
| 75 | 0.0040 |
| 76 | 0.0032 |
| 77 | 0.0047 |
| 78 | 0.0047 |
| 79 | 0.0066 |
| 80 | 0.0057 |
| 81 | 0.0057 |

The disclosures of all publications, patents, patent applications and published patent applications referred to herein by an identifying citation are hereby incorporated herein by reference in their entirety.

Although aspects of the foregoing invention have been described in some detail by way of illustration and example for purposes of clarity of understanding, it is apparent to those skilled in the art that certain changes and modifications will be practiced. Therefore, the description and examples should not be construed as limiting the scope of the invention.

The invention claimed is:

1. A compound of formula (IA):

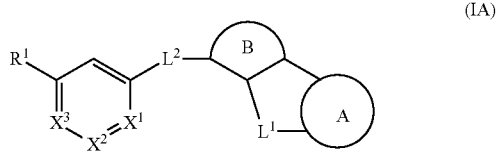

(IA)

or a pharmaceutically acceptable salt thereof, wherein:
ring A is a triazole, a tetrazole, or an imidazole optionally substituted with halo or $C_1$-$C_6$ alkyl;
ring B is phenyl or 6 membered heteroaryl containing 1-2 ring nitrogen atoms;
$L^1$ is

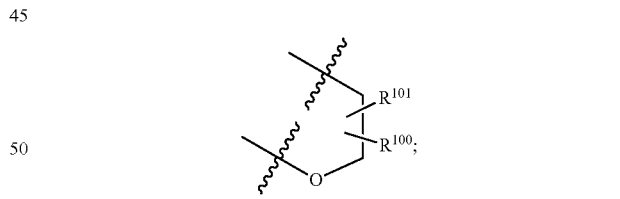

$R^{100}$ and $R^{101}$ are independently H; $C_1$-$C_6$ alkyl optionally substituted with 1-3 hydroxyl or halo; halo; $C_3$-$C_5$ cycloalkyl optionally substituted with 1-3 $C_1$-$C_6$ alkyl, hydroxyl, or halo; 4- to 5-membered heterocyclyl optionally substituted with 1-3 $C_1$-$C_6$ alkyl, hydroxyl, or halo; or 5-membered heteroaryl optionally substituted with 1-3 $C_1$-$C_6$ alkyl, hydroxyl, or halo;
or $R^{100}$ and $R^{101}$ are taken together with the carbon atom or carbon atoms to which they are attached to form a $C_3$-$C_5$ cycloalkyl;
$L^2$ is —CO—NH—;
$R^1$ is $C_3$-$C_8$ cycloalkyl, 6-membered aryl, 5- to 6-membered heteroaryl, or 4- to 6-membered heterocyclyl, each of which is optionally substituted with 1-2 $C_1$-$C_6$ alkyl or with one $C_3$-$C_6$ cycloalkyl which is optionally substituted with 1-2 substituents selected from the group consisting of $C_1$-$C_6$ alkyl, $C_2$-$C_6$ alkenyl, and $C_2$-$C_6$ alkynyl; —$CONR^{11}R^{12}$; or —$SO_2NR^{11}R^{12}$;

$R^{11}$ and $R^{12}$ are independently selected from the group consisting of hydrogen, $C_1$-$C_6$ alkyl, and $C_3$-$C_8$ cycloalkyl;

or $R^{11}$ and $R^{12}$ are taken together with the nitrogen atom to which they are attached to form a 4- to 7-membered heterocyclyl;

$X^1$ is $CR^2$ or N;
$X^2$ is $CR^2$;
$X^3$ is $CR^2$;

each $R^2$ is independently hydrogen; $C_1$-$C_6$ alkyl optionally substituted with 1-3 halo, —$CF_3$, —$OCF_3$, hydroxy, —CN or —$N(R^3)(R^4)$; $C_1$-$C_6$ alkoxy optionally substituted with 1-3 halo, —$CF_3$, —$OCF_3$, hydroxy, —CN or —$N(R^3)(R^4)$; $C_3$-$C_8$ cycloalkyl optionally substituted with 1-3 halo, $C_1$-$C_6$ alkyl, —$CF_3$, —$OCF_3$, hydroxy, —CN or —$N(R^3)(R^4)$; 6-membered aryl optionally substituted with 1-3 halo, $C_1$-$C_6$ alkyl, —$CF_3$, —$OCF_3$, hydroxy, —CN or —$N(R^3)(R^4)$; 5- to 10-membered heteroaryl optionally substituted with 1-3 halo, $C_1$-$C_6$ alkyl, —$CF_3$, —$OCF_3$, hydroxy, —CN or —$N(R^3)(R^4)$; 4-10 membered heterocyclyl optionally substituted with 1-3 halo, $C_1$-$C_6$ alkyl, —$CF_3$, —$OCF_3$, hydroxy, —CN or —$N(R^3)(R^4)$; or halo; and $R^3$ and $R^4$ are independently hydrogen; $C_1$-$C_6$ alkyl optionally substituted with 1-3 halo, —$CF_3$, —$OCF_3$, hydroxyl, or —CN; $C_3$-$C_8$ cycloalkyl optionally substituted with 1-3 halo, $C_1$-$C_6$ alkyl, —$CF_3$, —$OCF_3$, hydroxyl, or —CN; 6-membered aryl optionally substituted with 1-3 halo, $C_1$-$C_6$ alkyl, —$CF_3$, —$OCF_3$, hydroxyl, or —CN; 5- to 10-membered heteroaryl optionally substituted with 1-3 halo, $C_1$-$C_6$ alkyl, —$CF_3$, —$OCF_3$, hydroxyl, or —CN; or 5- to 10-membered heterocyclyl optionally substituted with 1-3 halo, $C_1$-$C_6$ alkyl, —$CF_3$, —$OCF_3$, hydroxyl, or —CN;

or $R^3$ and $R^4$ are taken together with the nitrogen atom or with the intervening atoms to which they are attached to form a 4- to 10-membered heterocyclyl optionally substituted with 1-3 halo, $C_1$-$C_6$ alkyl, —$CF_3$, —$OCF_3$, hydroxyl, or —CN.

2. The compound of claim 1, or a pharmaceutically acceptable salt thereof, wherein:
ring B is phenyl.

3. The compound of claim 1, or a pharmaceutically acceptable salt thereof, wherein:
ring A is

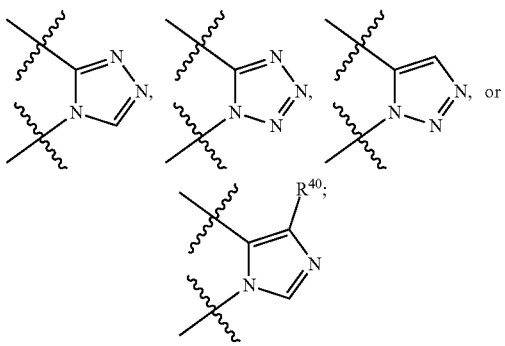

and
$R^{40}$ is H, $C_1$-$C_6$ alkyl, or halo.

4. The compound of claim 1, or a pharmaceutically acceptable salt thereof, wherein:
$R^{100}$ and $R^{101}$ are independently H; $C_1$-$C_6$ alkyl optionally substituted with 1-3 hydroxyl or halo; halo; or $C_3$-$C_5$ cycloalkyl optionally substituted with 1-3 $C_1$-$C_6$ alkyl, hydroxyl, or halo;

or $R^{100}$ and $R^{101}$ are taken together with the carbon atom or carbon atoms to which they are attached to form a $C_3$-$C_5$ cycloalkyl.

5. The compound of claim 1, or a pharmaceutically acceptable salt thereof, wherein:
$L^1$ is —O—$CH_2$—$CH_2$—, —O—$CH_2$—CH(Me)-, —O—$CH_2$—C(Me)$_2$-, —O—CH(Me)-$CH_2$—, —O—$CH_2$—CH($CH_2OH$)—, —O—$CH_2$—CH($CH_2F$)—,

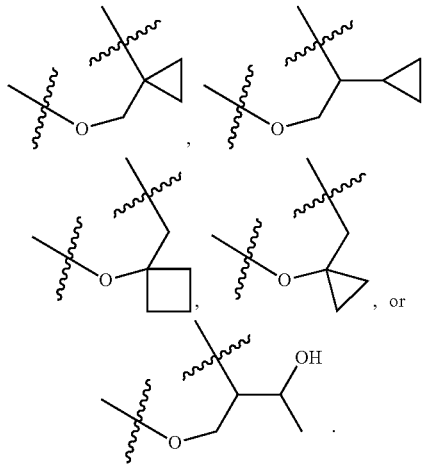

6. The compound of claim 1, or a pharmaceutically acceptable salt thereof, wherein:
$R^1$ is 5- to 6-membered heteroaryl, which is optionally substituted with 1-2 $C_1$-$C_6$ alkyl or with one $C_3$-$C_6$ cycloalkyl which is optionally substituted with 1-2 substituents selected from the group consisting of $C_1$-$C_6$ alkyl, $C_2$-$C_6$ alkenyl, and $C_2$-$C_6$ alkynyl; —$CONR^{11}R^{12}$; or —$SO_2NR^{11}R^{12}$.

7. The compound of claim 6, or a pharmaceutically acceptable salt thereof, wherein:
$R^1$ is

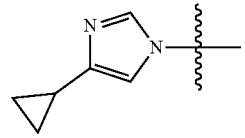

8. The compound of claim 1, or a pharmaceutically acceptable salt thereof, wherein:
each $R^2$ is independently hydrogen; $C_1$-$C_6$ alkyl optionally substituted with 1-3 halo, —$CF_3$, —$OCF_3$, hydroxyl, —CN or —$N(R^3)(R^4)$; $C_1$-$C_6$ alkoxy optionally substituted with 1-3 halo, —$CF_3$, —$OCF_3$, hydroxyl, —CN or —$N(R^3)(R^4)$; 4- to 10-membered heterocyclyl optionally substituted with 1-3 halo, $C_1$-$C_6$ alkyl, —$CF_3$, —$OCF_3$, hydroxyl, —CN or —$N(R^3)(R^4)$; or halo; and R³ and R⁴ are independently selected from the group consisting of hydrogen; $C_1$-$C_6$ alkyl optionally substituted with 1-3 halo, —$CF_3$, —$OCF_3$, hydroxyl, or —CN; $C_3$-$C_8$ cycloalkyl optionally substituted with 1-3 halo, $C_1$-$C_6$ alkyl, —$CF_3$, —$OCF_3$, hydroxyl, or —CN; 6-membered aryl optionally substituted with 1-3 halo, $C_1$-$C_6$ alkyl, —$CF_3$, —$OCF_3$, hydroxyl, or —CN; 5- to 10-membered heteroaryl optionally substituted with 1-3 halo, $C_1$-$C_6$ alkyl, —$CF_3$, —$OCF_3$, hydroxyl, or —CN; or 5- to 10-membered heterocyclyl optionally substituted with 1-3 halo, $C_1$-$C_6$ alkyl, —$CF_3$, —$OCF_3$, hydroxyl, or —CN;

or R³ and R⁴ are taken together with the nitrogen atom or with the intervening atoms to which they are attached to form a 4- to 10-membered heterocyclyl optionally substituted with 1-3 halo, $C_1$-$C_6$ alkyl, —$CF_3$, —$OCF_3$, hydroxyl, or —CN.

9. The compound of claim 1, or a pharmaceutically acceptable salt thereof, wherein:
$X^1$ is N or $CR^2$; and
$R^2$ is halo.

10. The compound of claim 1, or a pharmaceutically acceptable salt thereof, wherein:
$X^2$ is CH.

11. The compound of claim 1, or a pharmaceutically acceptable salt thereof, wherein:
$X^3$ is $CR^2$; and
$R^2$ is hydrogen; $C_1$-$C_6$ alkyl optionally substituted with 1-2 halo or hydroxyl; $C_1$-$C_6$ alkoxy optionally substituted with 1-2 halo or hydroxyl; 4-10 membered heterocyclyl optionally substituted with 1-2 $C_1$-$C_6$ alkyl or hydroxyl; —O—R³; or —N(R³)(R⁴); and
R³ and R⁴ are independently hydrogen or $C_1$-$C_6$ alkyl;
or R³ and R⁴ are taken together with the nitrogen atom or with the intervening atoms to which they are attached to form a 4- to 7-membered heterocyclyl optionally substituted with 1-2 $C_1$-$C_6$ alkyl or hydroxyl.

12. The compound of claim 11, or a pharmaceutically acceptable salt thereof, wherein:
$X^3$ is $CR^2$; and
$R^2$ is H, —$CH_3$, —$OCH(CH_3)_2$, —$N(CH_3)_2$,

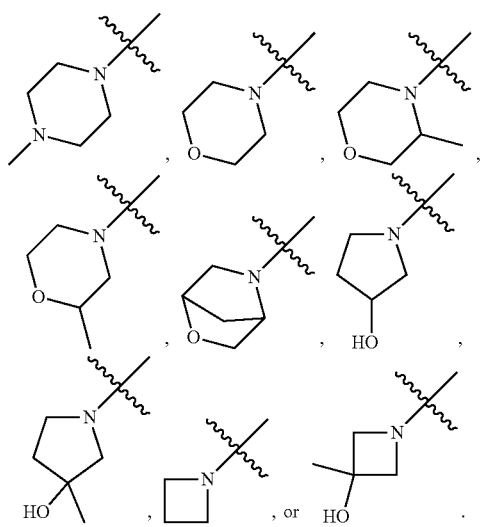

13. The compound of claim 1, or a pharmaceutically acceptable salt thereof, which is of formula (5A) or (5B):

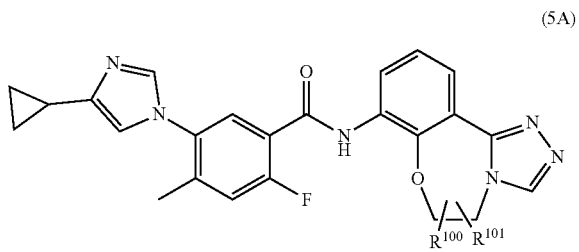
(5A)

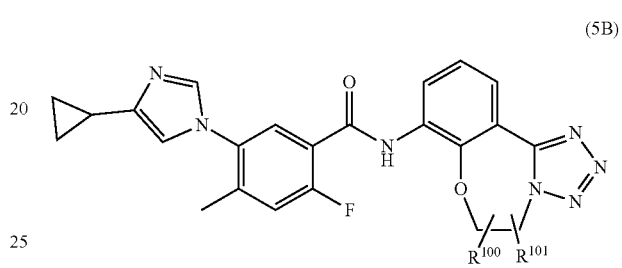
(5B)

wherein:
$R^{100}$ and $R^{101}$ are independently H; $C_1$-$C_6$ alkyl optionally substituted with 1-3 hydroxyl or halo; halo; $C_3$-$C_5$ cycloalkyl optionally substituted with 1-3 $C_1$-$C_6$ alkyl, hydroxyl, or halo; 4- to 5-membered heterocyclyl optionally substituted with 1-3 $C_1$-$C_6$ alkyl, hydroxyl, or halo; or 5-membered heteroaryl optionally substituted with 1-3 $C_1$-$C_6$ alkyl, hydroxyl, or halo;
or $R^{100}$ and $R^{101}$ are taken together with the carbon atom or carbon atoms to which they are attached to form a $C_3$-$C_5$ cycloalkyl.

14. A compound selected from the group consisting of:

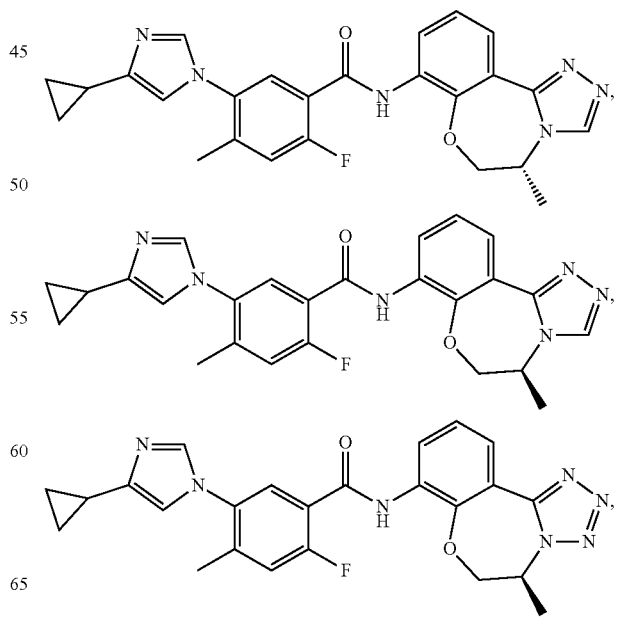

225
-continued
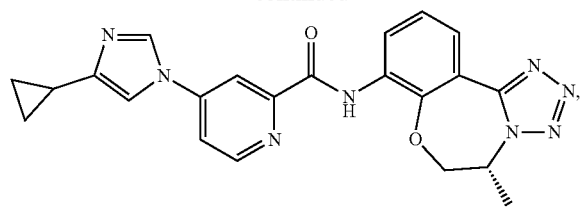
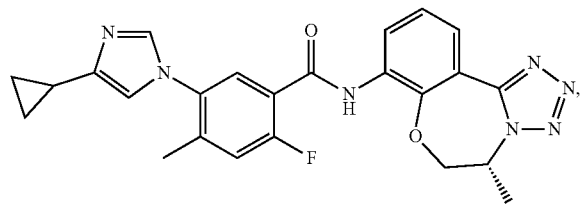
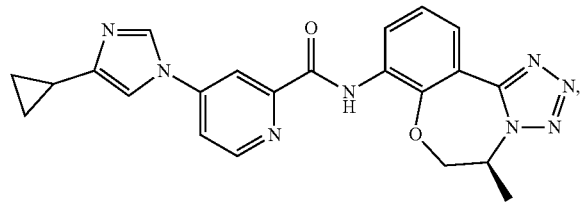
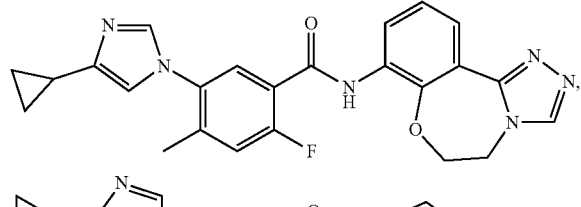
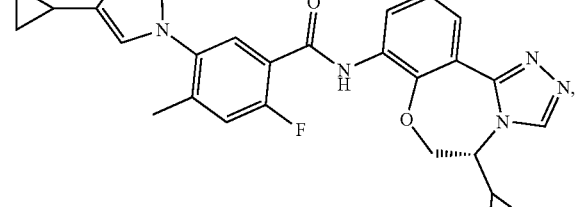
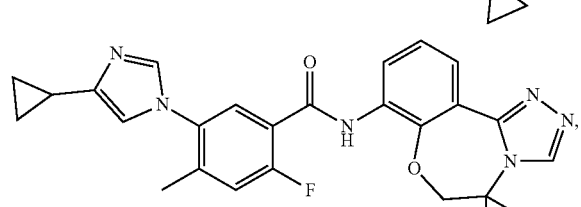
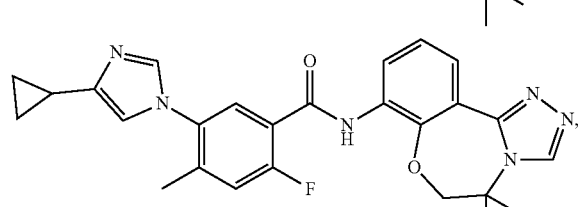
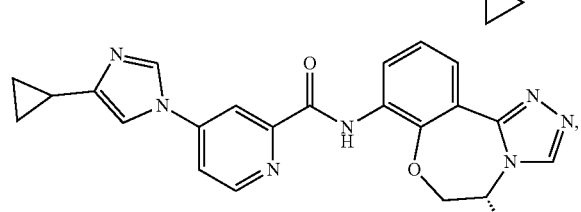
226
-continued
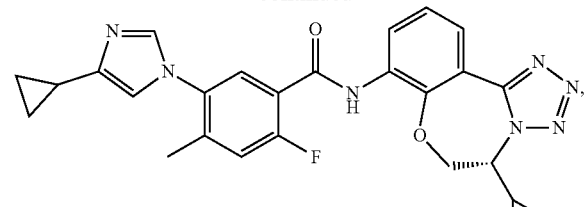
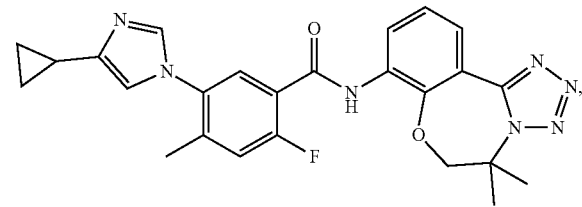
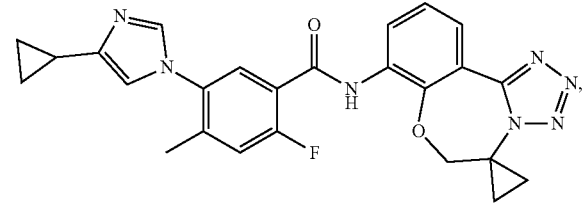
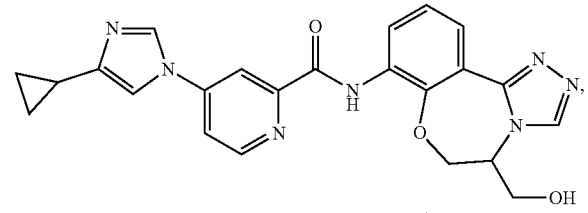
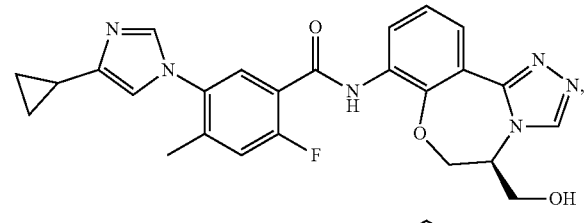
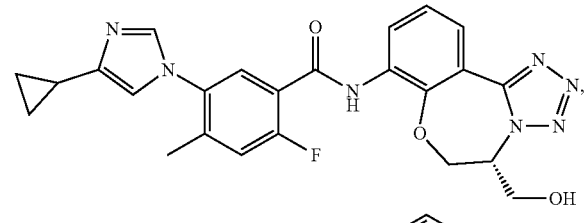
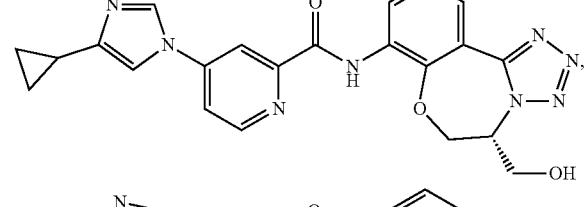
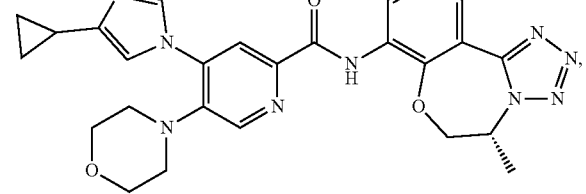

227
228

229
-continued
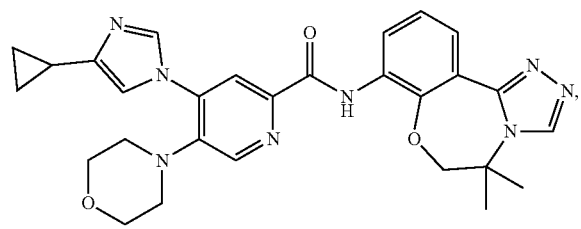
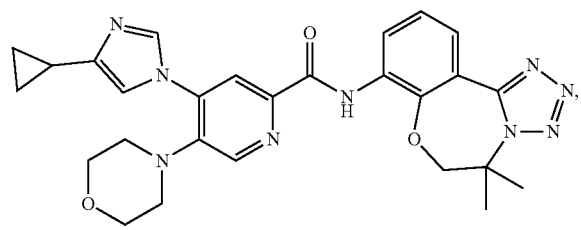
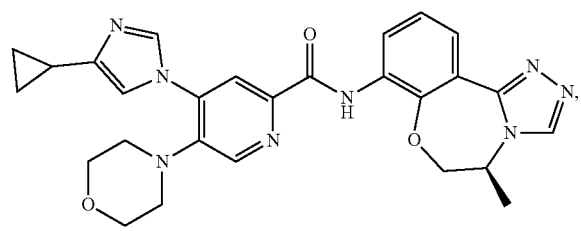
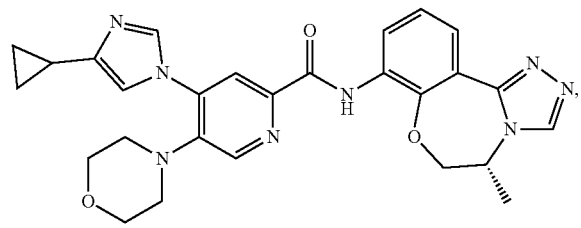
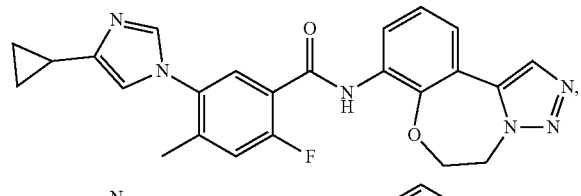
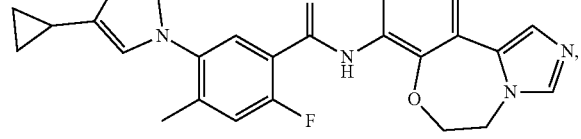
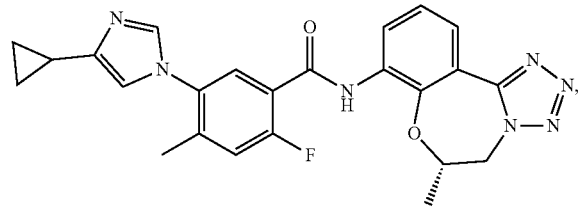
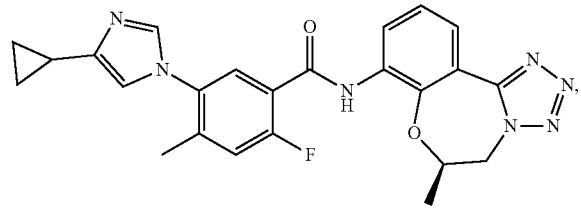
230
-continued
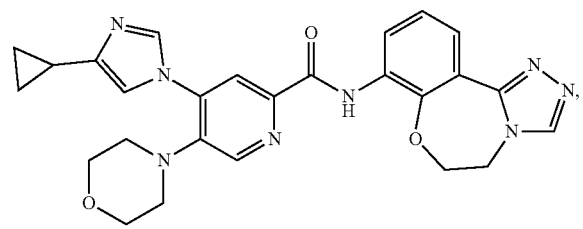
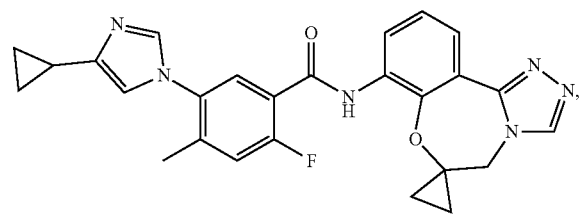
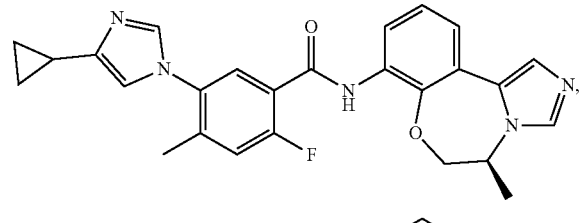
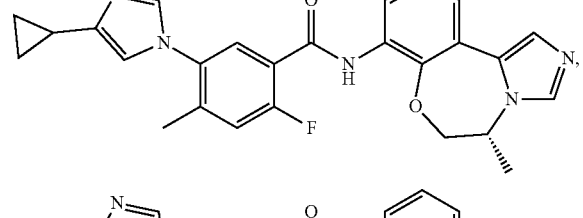
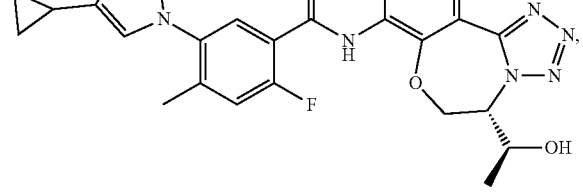
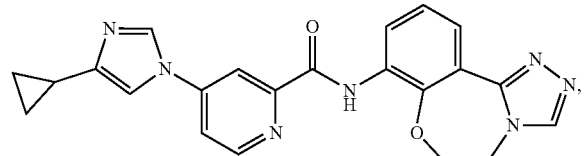
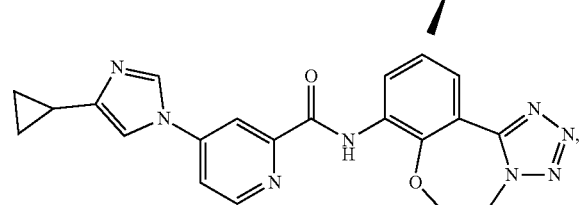
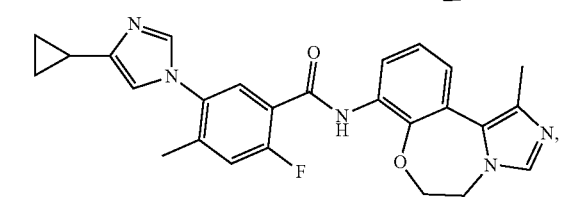

231
-continued
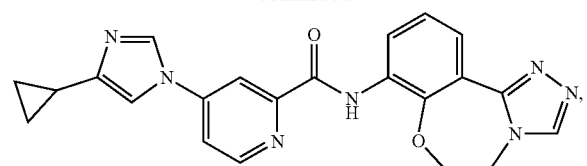
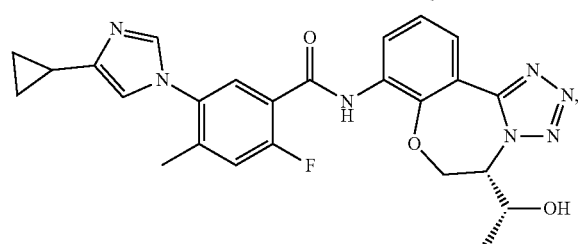
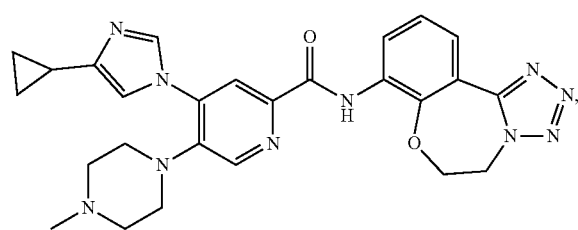
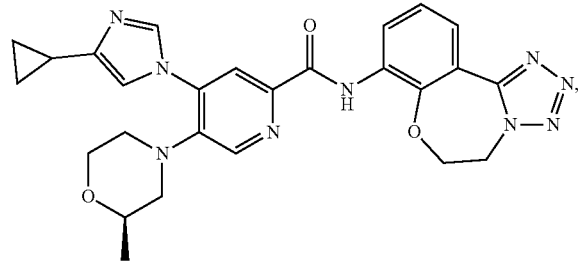
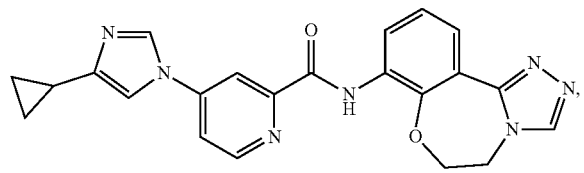
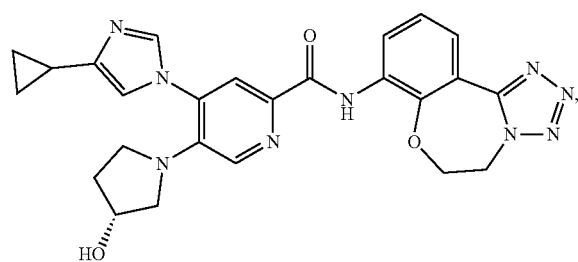
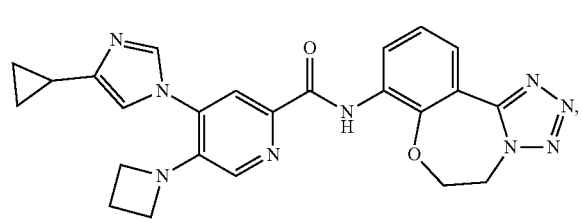
232
-continued
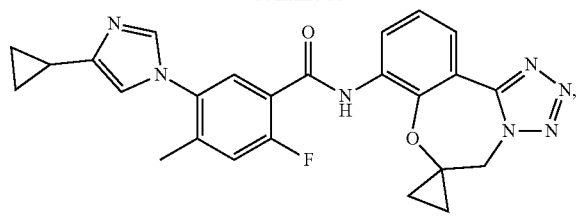
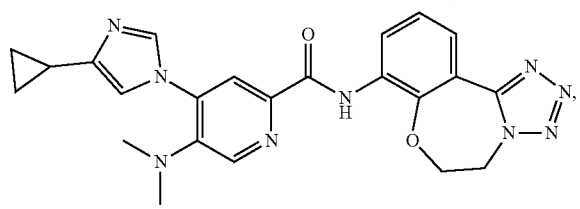
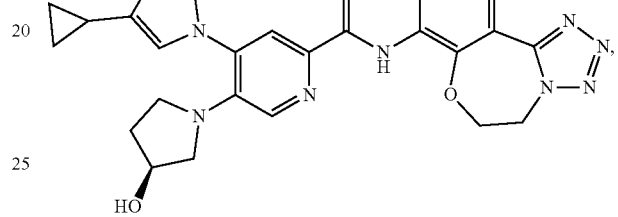
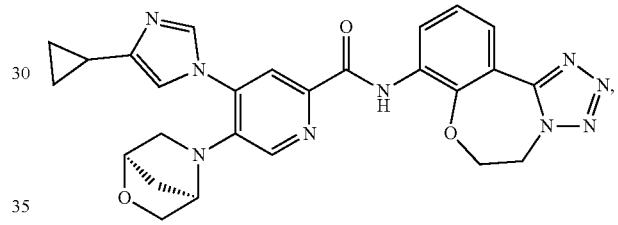
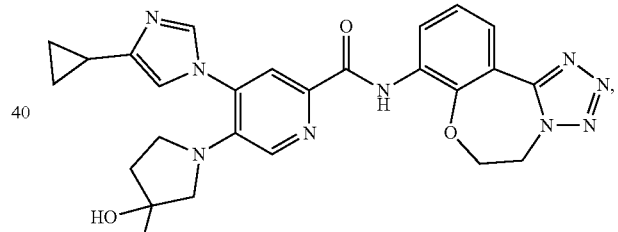
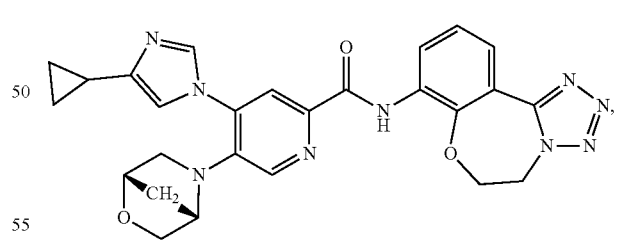
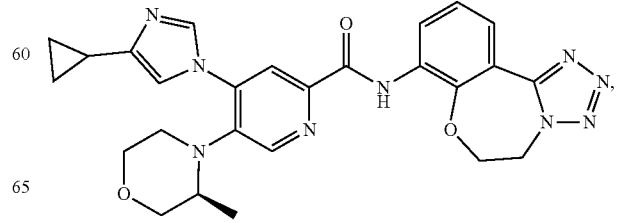

233
-continued
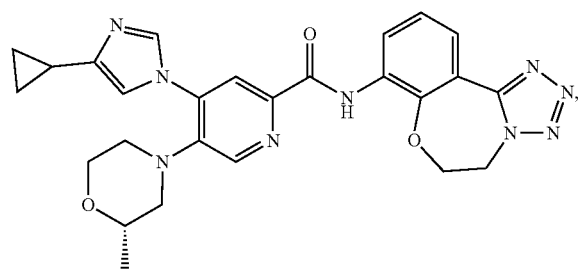
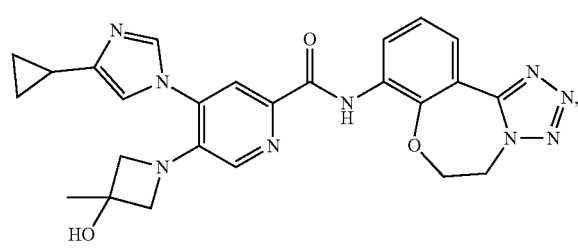
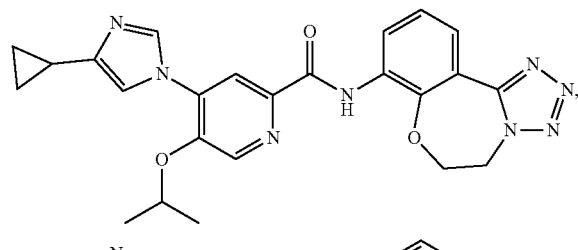
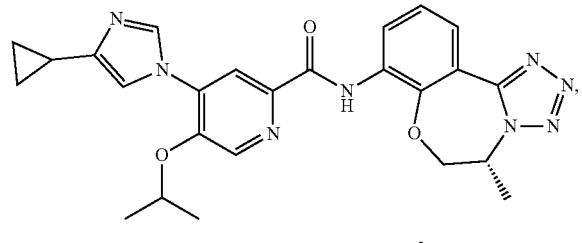
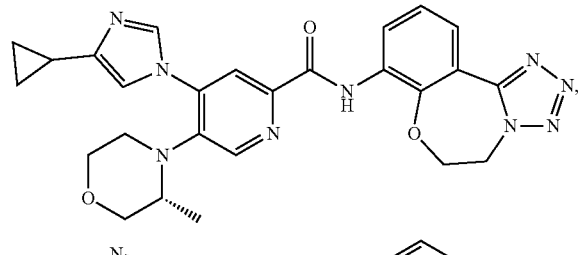
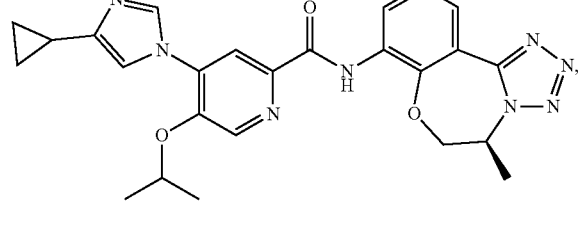
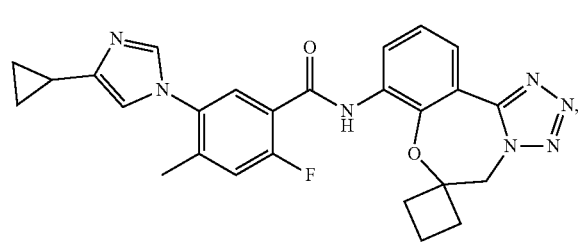
234
-continued
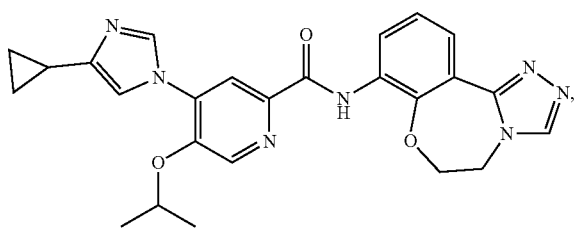
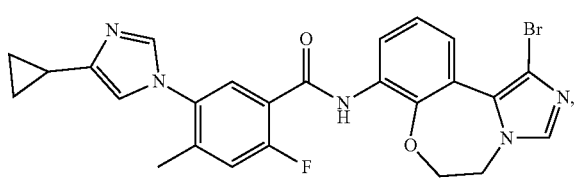
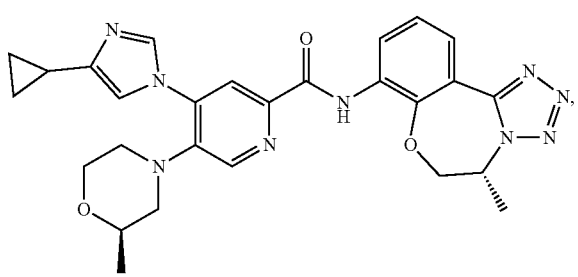
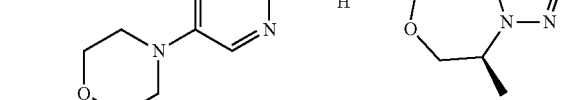
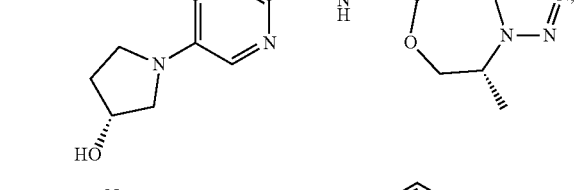
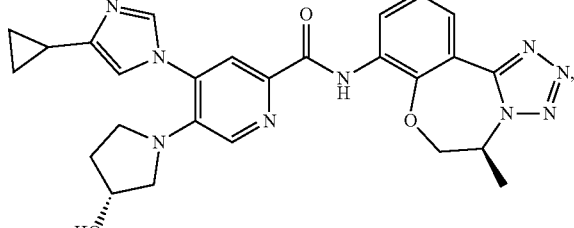
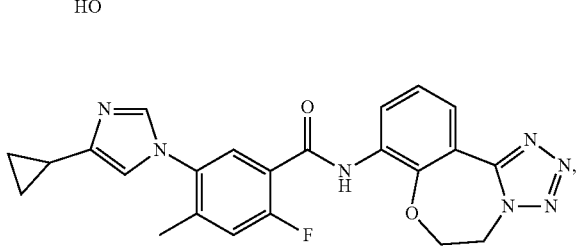

235
-continued

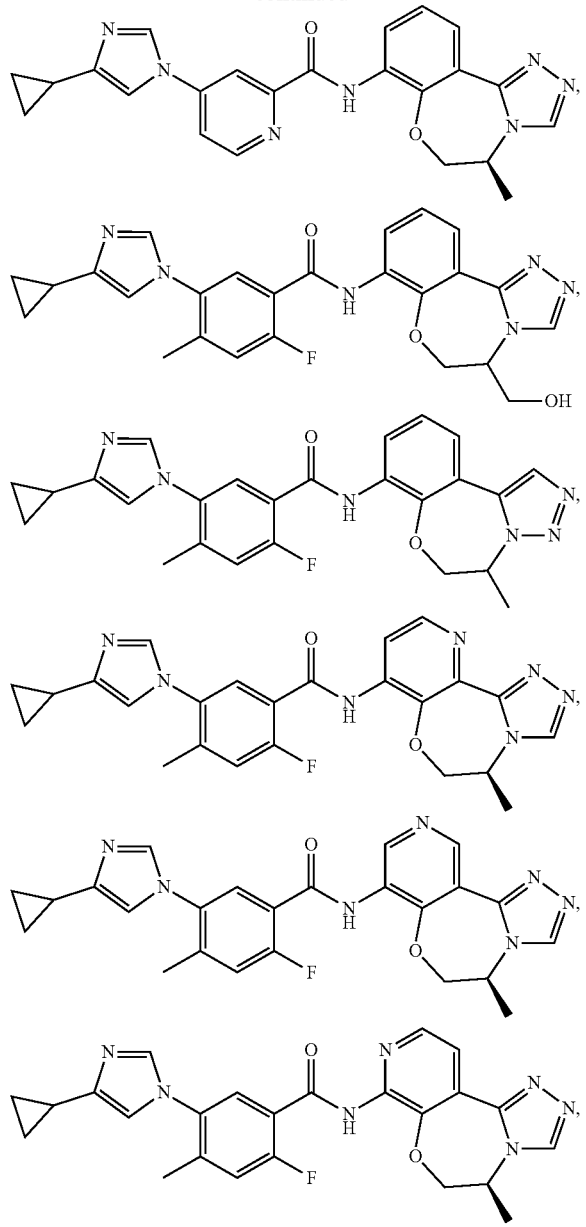

236
-continued

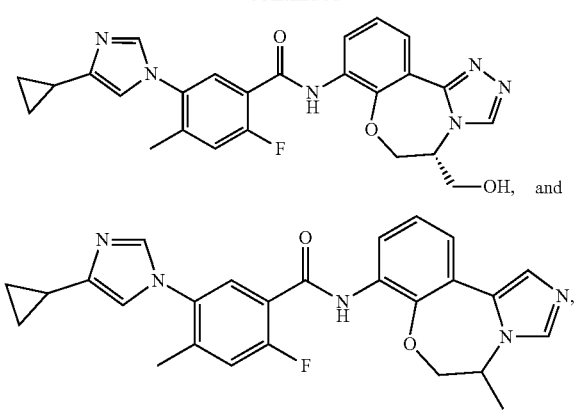

or a pharmaceutically acceptable salt thereof.

15. A pharmaceutical composition comprising the compound of claim 1, or a pharmaceutically acceptable salt thereof, and at least one pharmaceutically acceptable excipient.

16. A method of inhibiting ASK1, comprising contacting ASK1 with an effective amount of the compound of claim 1, or a pharmaceutically acceptable salt thereof.

17. A method of treating a disorder which is mediated by ASK1, comprising administering to a patient in need thereof a therapeutically effective amount of the compound of claim 1, or a pharmaceutically acceptable salt thereof, wherein the disorder which is mediated by ASK1 is pulmonary arterial hypertension (PAH), diabetic kidney disease, heart failure, or nonalcoholic steatohepatitis (NASH).

18. The method of claim 17, wherein the disorder is NASH.

19. The method of claim 17, comprising administering to the patient in need thereof a therapeutically effective amount of the compound of claim 14, or a pharmaceutically acceptable salt thereof.

20. The method of claim 18, comprising administering to the patient in need thereof a therapeutically effective amount of the compound of claim 14, or a pharmaceutically acceptable salt thereof.

* * * * *